(12) United States Patent
Sporbert et al.

(10) Patent No.: US 8,021,147 B2
(45) Date of Patent: Sep. 20, 2011

(54) METHOD AND SYSTEM FOR COMPREHENSIVE EVALUATION OF ORTHODONTIC CARE USING UNIFIED WORKSTATION

(75) Inventors: Peer Sporbert, Berlin (DE); Markus Kaufmann, Berlin (DE); Rohit Sachdeva, Plano, TX (US); Claudia Strauss, Berlin (DE); Doke Evan Roberts, Lucas, TX (US)

(73) Assignee: Orametrix, Inc., Richardson, TX (US)

( * ) Notice: Subject to any disclaimer, the term of this patent is extended or adjusted under 35 U.S.C. 154(b) by 1135 days.

(21) Appl. No.: 11/133,996

(22) Filed: May 20, 2005

(65) Prior Publication Data

US 2005/0271996 A1 Dec. 8, 2005

Related U.S. Application Data

(63) Continuation-in-part of application No. 10/620,231, filed on Jul. 14, 2003, now Pat. No. 7,156,655, which is a continuation-in-part of application No. 10/428,461, filed on May 2, 2003, now Pat. No. 7,717,708, which is a continuation-in-part of application No. 09/834,412, filed on Apr. 13, 2001, now Pat. No. 6,632,089.

(51) Int. Cl.
*A61C 3/00* (2006.01)

(52) U.S. Cl. ......................................................... 433/24

(58) Field of Classification Search .................... 433/24, 433/25, 72, 213
See application file for complete search history.

(56) References Cited

U.S. PATENT DOCUMENTS

| 5,882,192 | A | * | 3/1999 | Bergersen | 433/2 |
| 6,632,089 | B2 | * | 10/2003 | Rubbert et al. | 433/24 |
| 6,739,869 | B1 | * | 5/2004 | Taub et al. | 433/24 |
| 7,156,655 | B2 | * | 1/2007 | Sachdeva et al. | 433/24 |

* cited by examiner

*Primary Examiner* — Ralph Lewis
(74) *Attorney, Agent, or Firm* — Jasvantrai C. Shah

(57) ABSTRACT

A method and system for orthodontic treatment planning, evaluation and quality measurement is provided comprising a workstation having computing platform, a graphical user interface, a processor and a computer storage medium containing digitized records pertaining to a patient. The digitized records include image and other types of data. The computer storage medium further includes a set of software instructions providing graphical user interface tools for providing a user with access to the digitized records for planning orthodontic treatment of a patient. Also provided are reference databases for aiding in the decision process during treatment selection, treatment planning and treatment delivery and progress monitoring and evaluation. Also provided are parameter or criteria measurement techniques and generally acceptable thresholds, which can be updated through learning process and through acquisition of patient data. Once the treatment is planned, the virtual dentition model of the patient in the proposed treatment set-up or the target state is evaluated using several virtual model evaluation features and criteria.

14 Claims, 89 Drawing Sheets

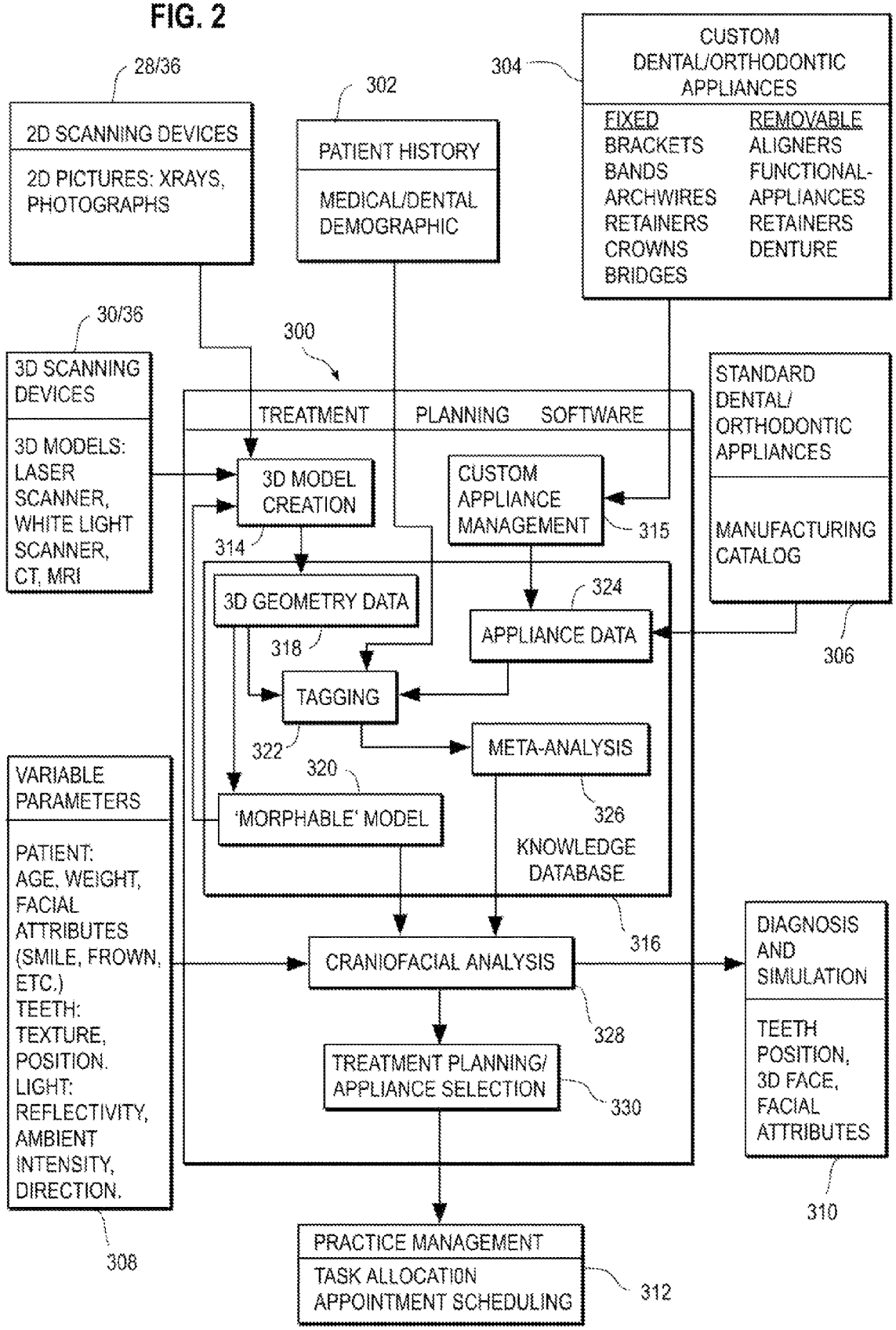

FIG. 3

[Screenshot of SureSmile 3.6 software interface showing Case Management / Digital Treatment Planning tab with Treatment Strategy view]

Callouts:
- 450: Patient Information tab area
- 452: OraScan / Digital Impression tabs
- 454: Case Management tab
- 456: Digital Treatment Planning tab
- 458: Treatment Strategy
- 460: Order Information / Treatment Strategy list (Midline and Aesthetic Occlusal Plane; Occlusal Plane and AP Positions; Reference Tooth; Alignment 2D – 3D; Mandible Space Management; Maxilla Space Management; Space Management (Mandible and Maxilla))
- 461: Order Information
- 462: 3D/3T Matrix table with columns Vertical, Sagittal, Transverse and rows Soft Tissue, Skeletal, Dental
- 464: Diagnosis and Problem Classification text area
- 466: (matrix area)
- 468: Treatment Strategy text area

FIG. 3A

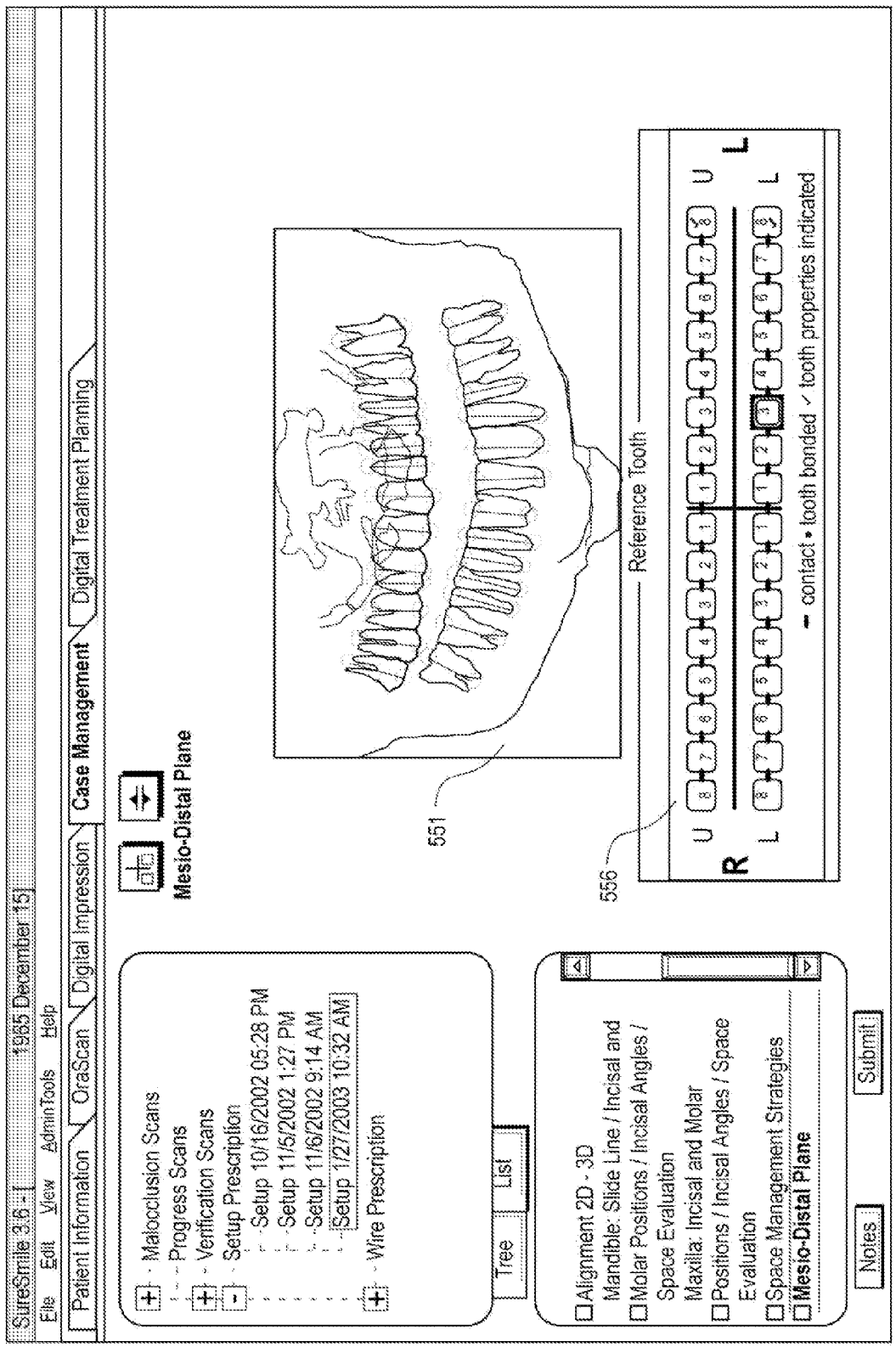

| | |
|---|---|
| TREATMENT EFFICIENCY | ~940 |
| TREATMENT EFFECTIVENESS | ~950 |
| PATIENT CONNECTEDNESS TO TREATMENT | ~960 |
| TIMELINESS OF TREATMENT | ~970 |
| TREATMENT SAFETY | ~980 |
| TREATMENT EQUITABILITY | ~990 |

FIG. 40

| | |
|---|---|
| ALIGNMENT | ~1010 |
| MARGINAL RIDGES | ~1012 |
| BUCCOLINGUAL INCLINATION | ~1014 |
| OCCLUSAL RELATIONSHIP | ~1016 |
| OCCLUSAL CONTACTS | ~1018 |
| OVERJET | ~1020 |
| INTERPROXIMAL CONTACTS | ~1022 |
| VERTICAL ALIGNMENT OF BUCCAL CUSP TIPS | ~1024 |
| VERTICAL ALIGNMENT OF FRONT | ~1026 |
| ANGULATION OF FRONT | ~1028 |

FIG. 43

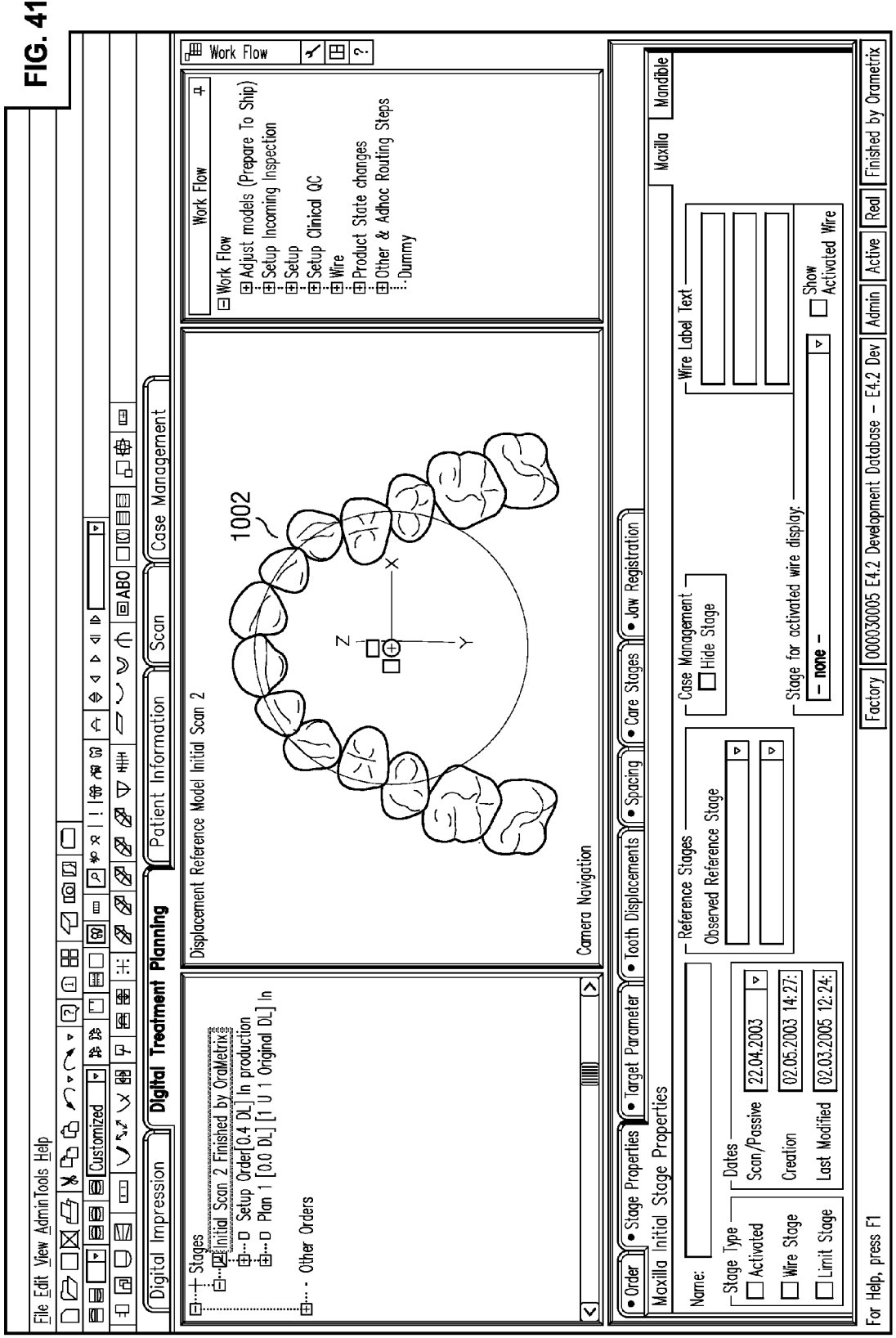

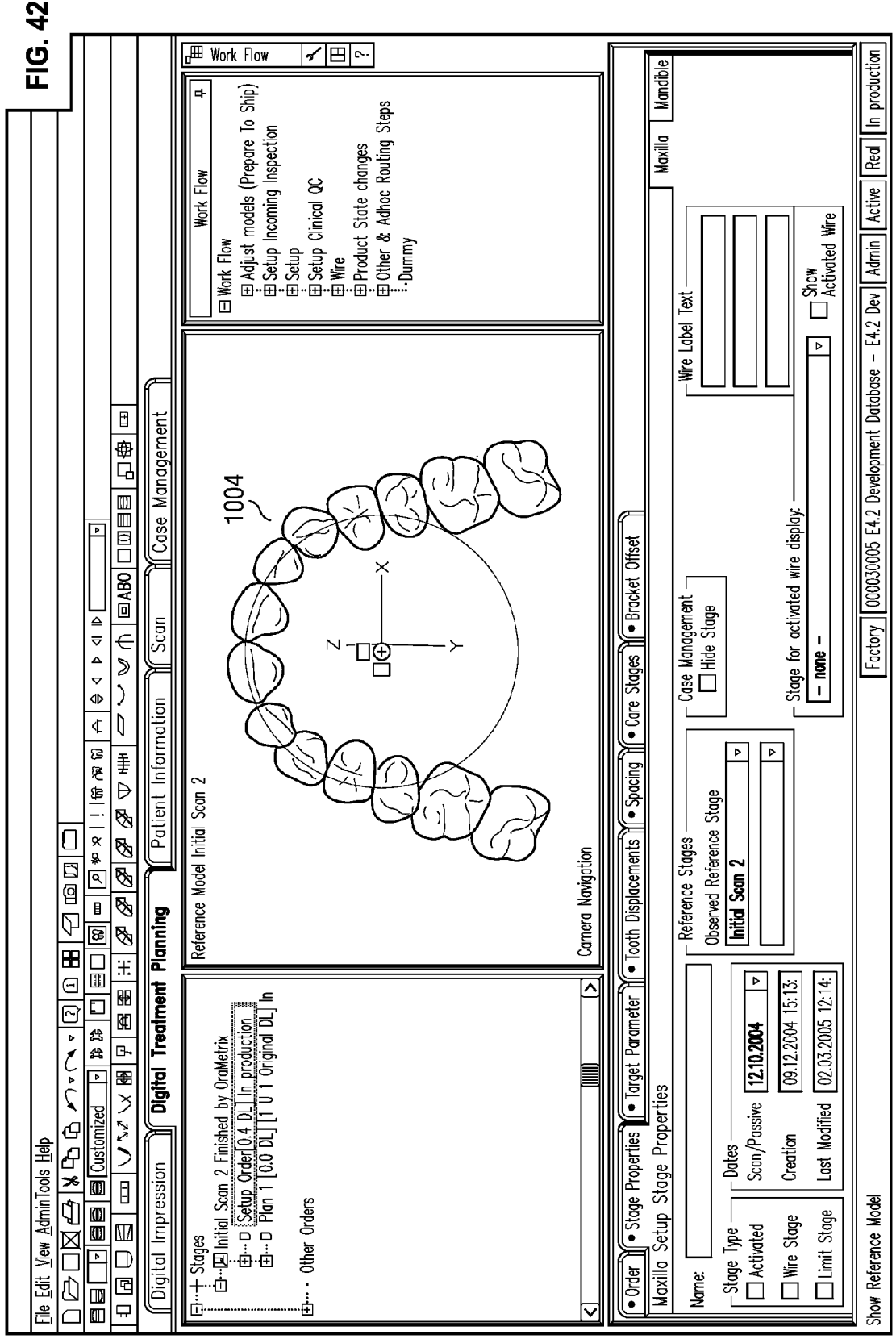

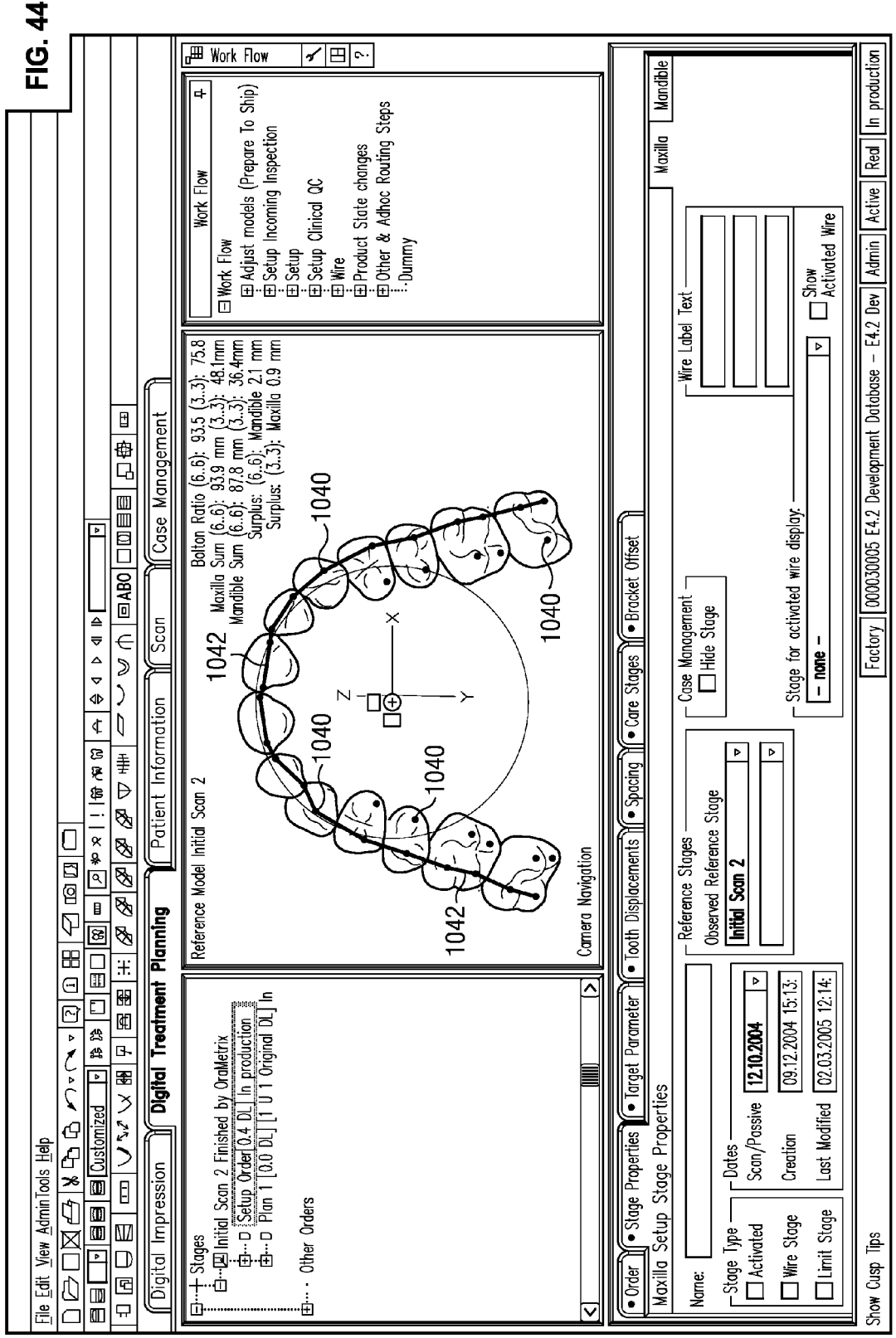

| DIRECTED DISTANCE BETWEEN TWO POINTS | —1100 |
| --- | --- |
| DIRECTED DISTANCE BETWEEN A POINT AND AN OBJECT | —1110 |
| SHORTEST DIRECTED DISTANCE BETWEEN TWO OBJECTS | —1120 |
| SHORTEST DISTANCE BETWEEN TWO OBJECTS | —1130 |
| DEEPEST PENETRATION BETWEEN TWO OBJECTS | —1140 |
| DISTANCE/PENETRATION BETWEEN TWO OBJECTS | —1150 |

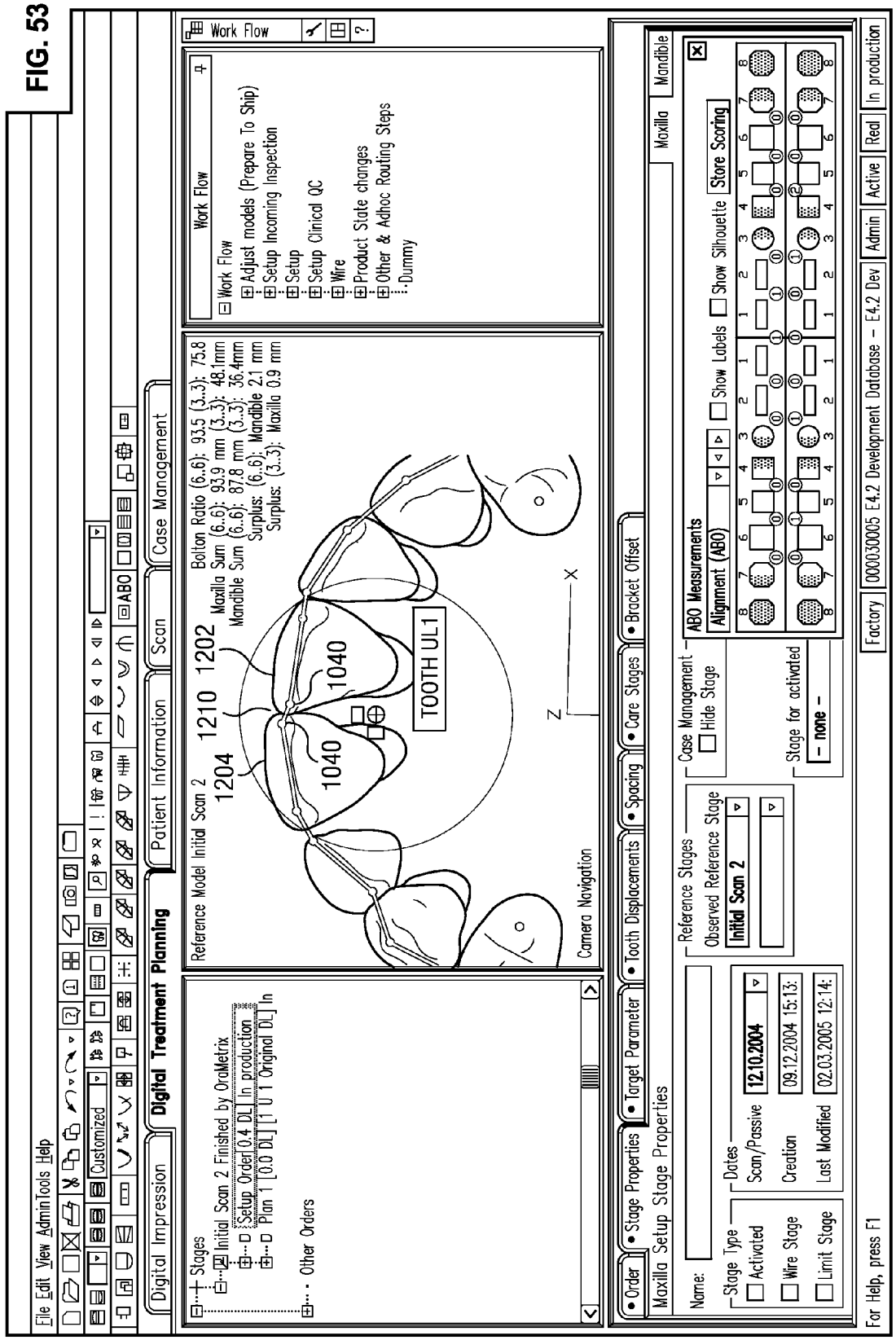

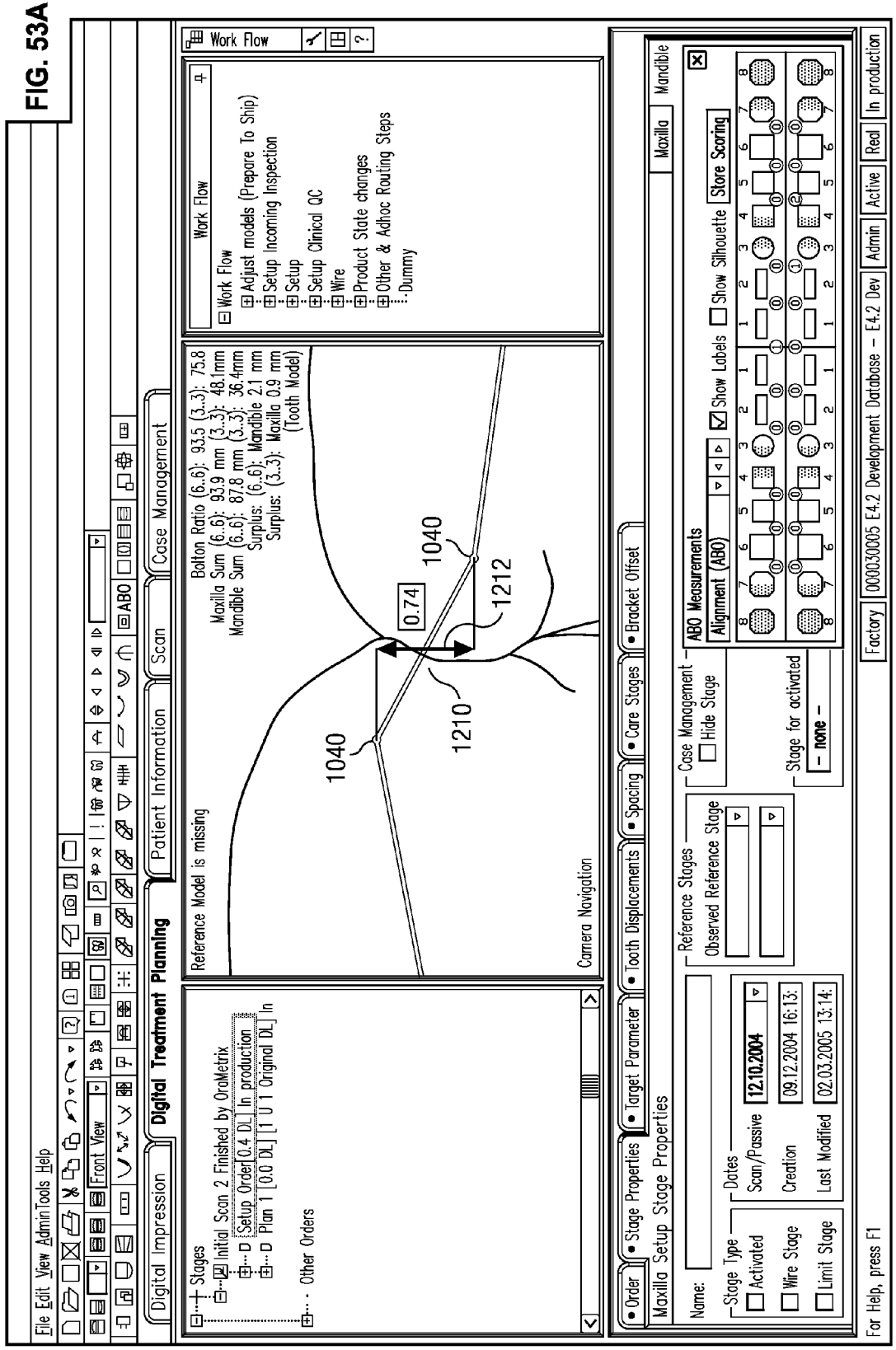

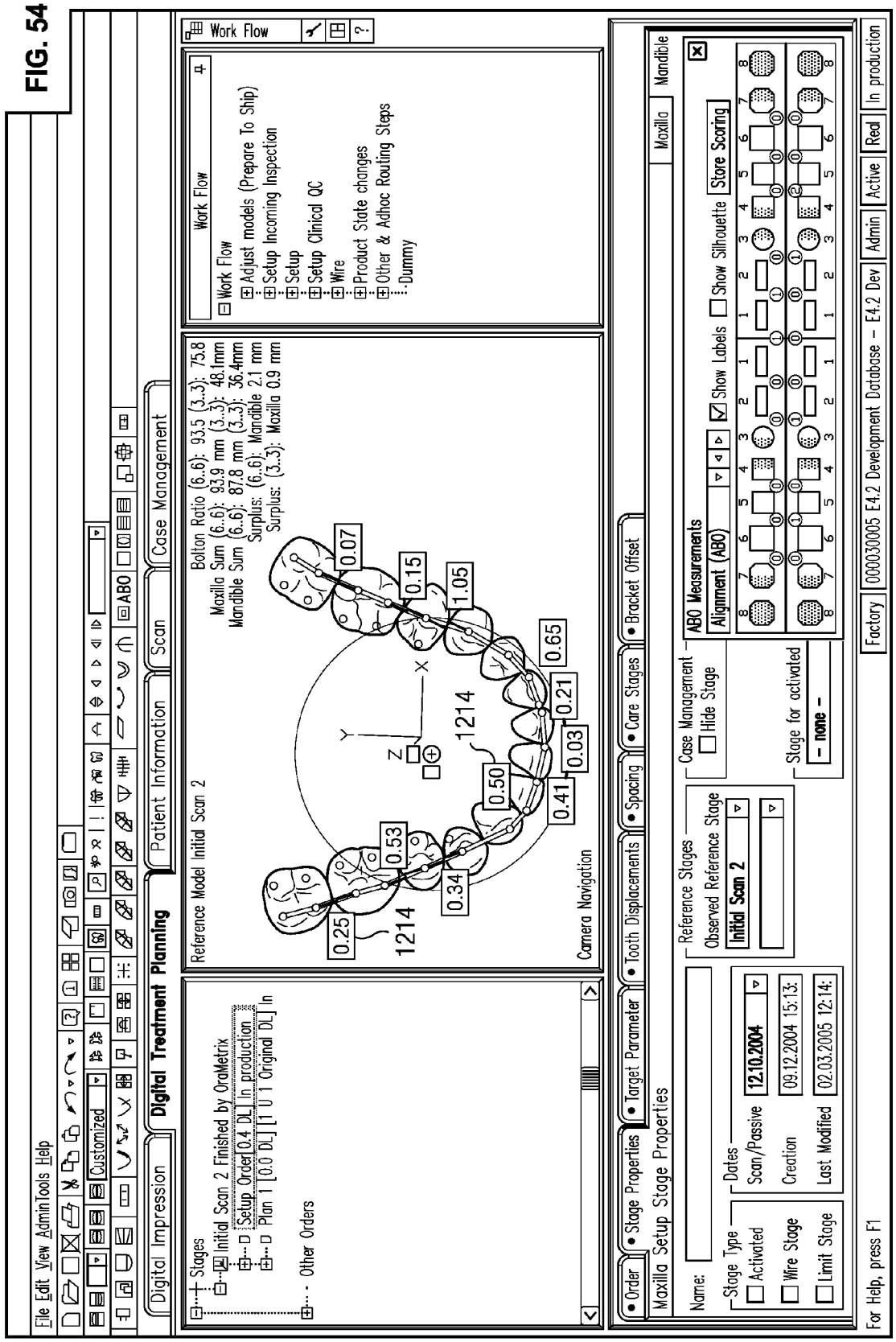

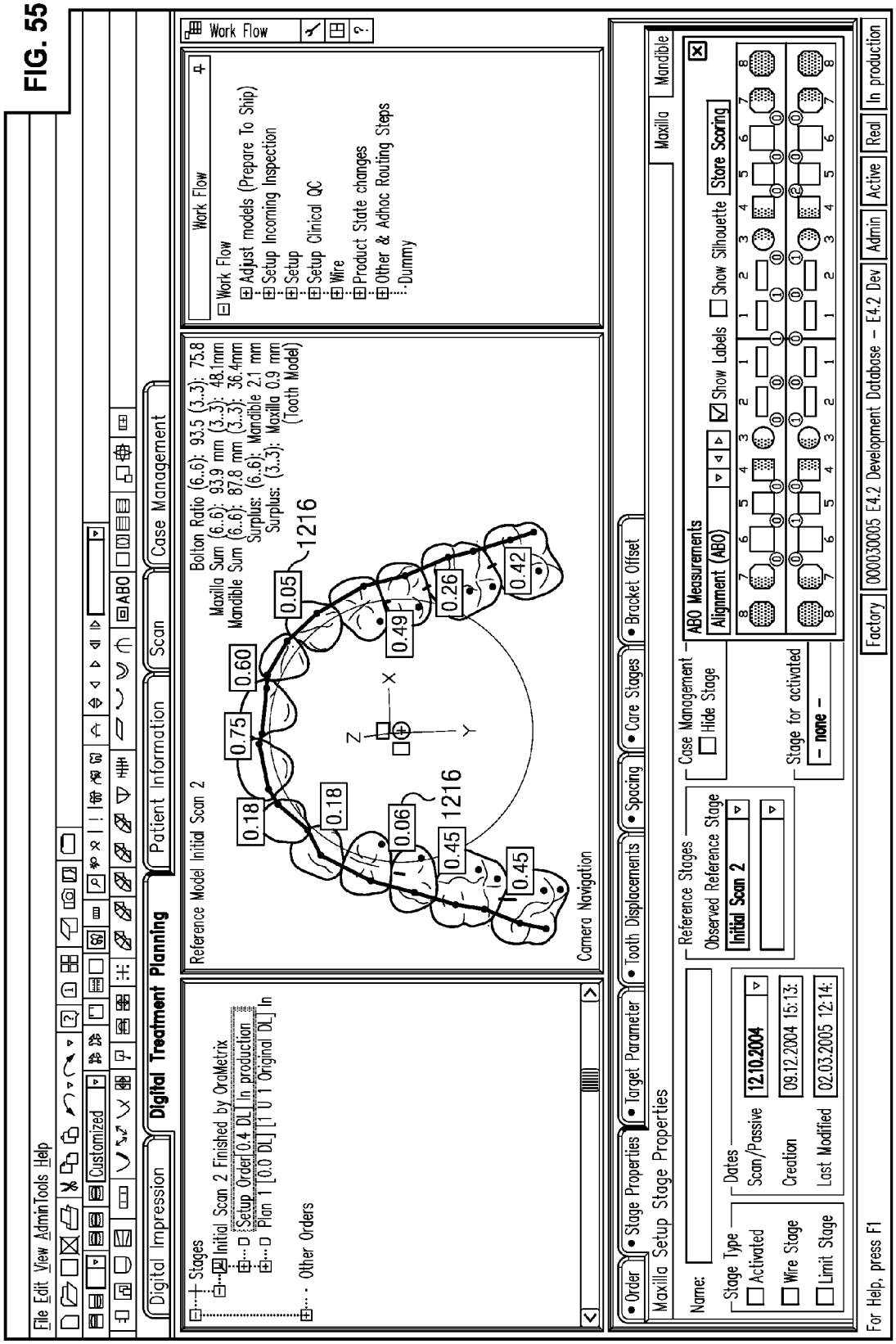

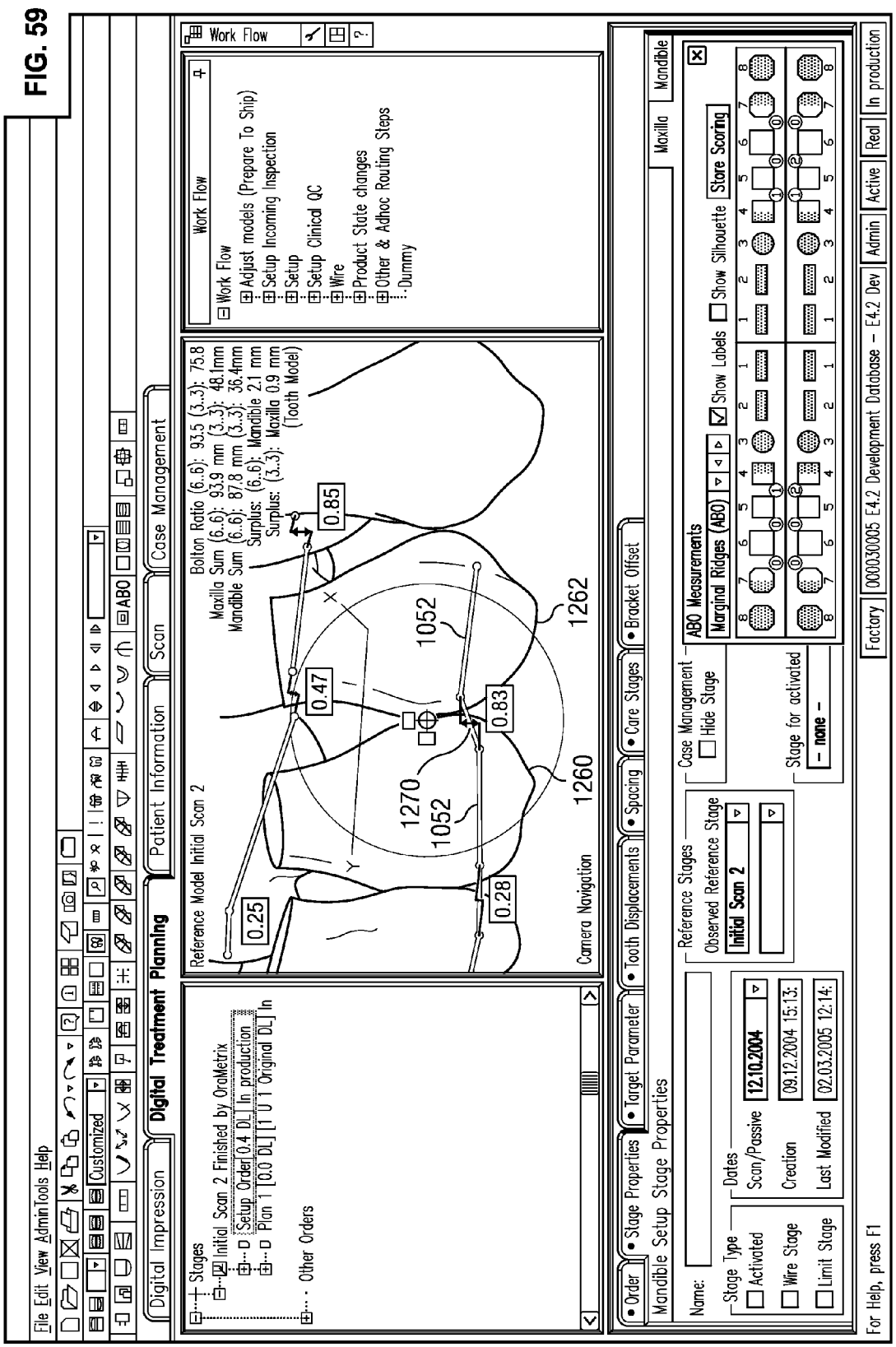

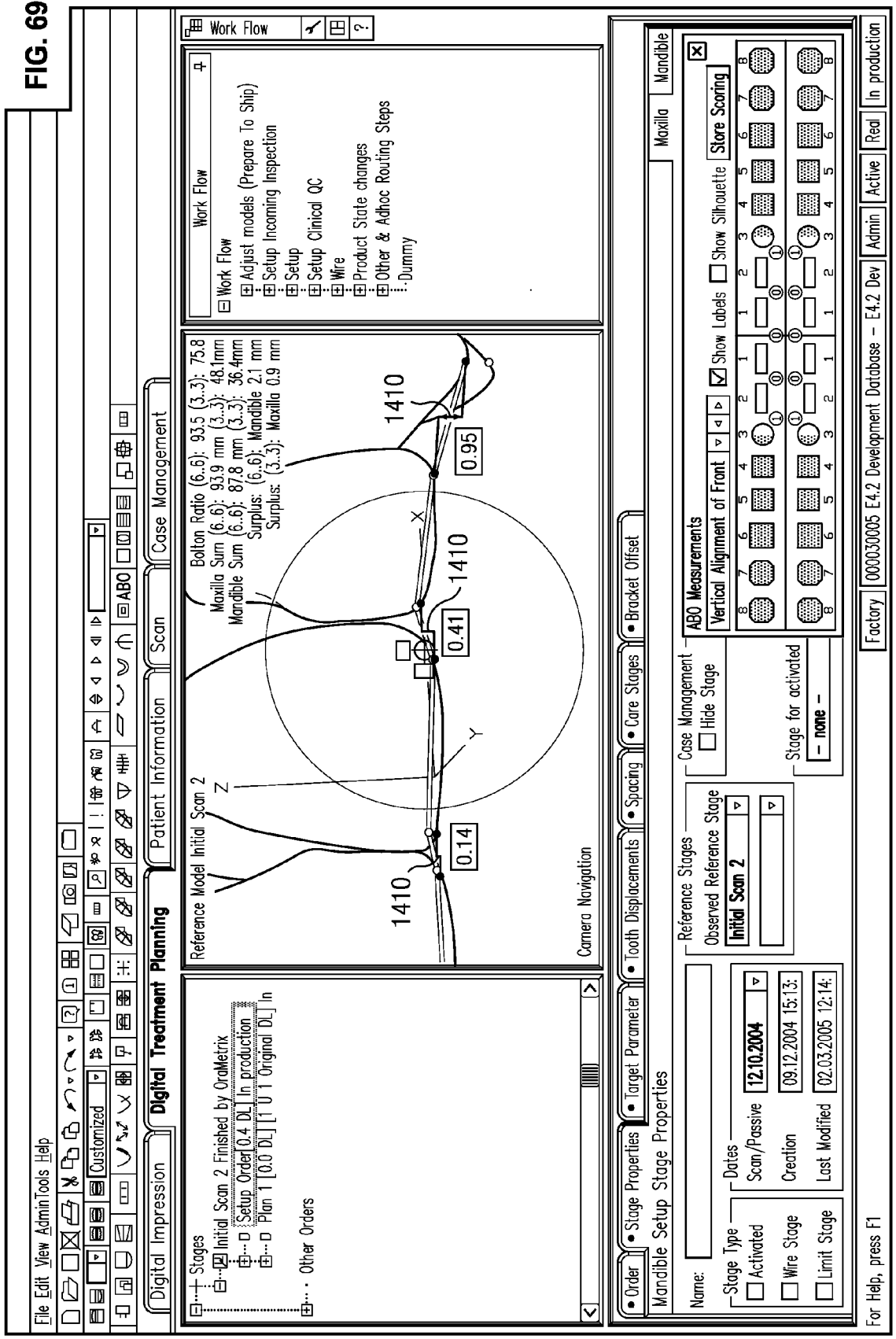

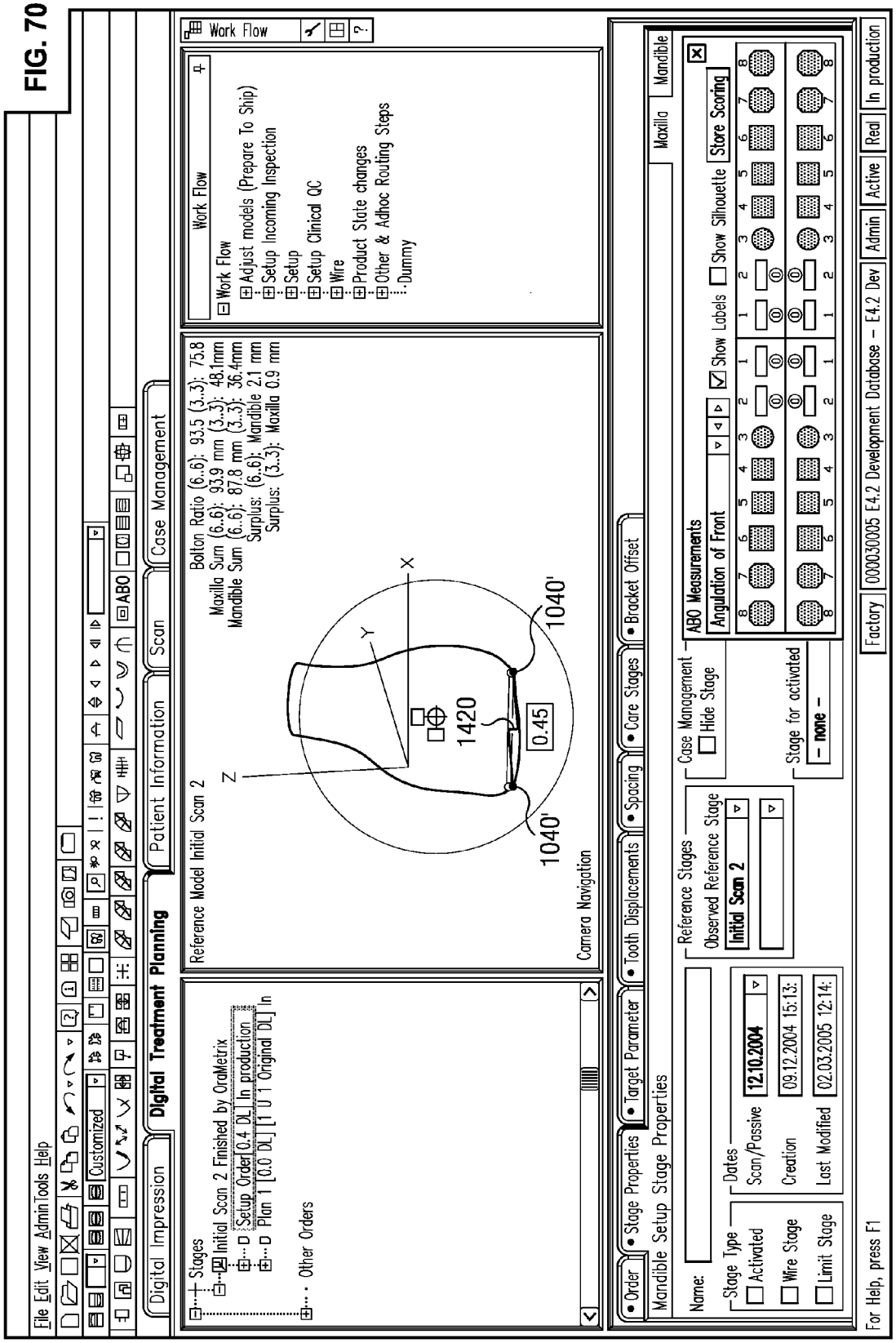

METHOD AND SYSTEM FOR COMPREHENSIVE EVALUATION OF ORTHODONTIC CARE USING UNIFIED WORKSTATION

RELATED APPLICATIONS

This is a continuation-in-part of application Ser. No. 10/620,231 filed Jul. 14, 2003 now U.S. Pat. No. 7,156,655, which is a continuation-in-part of application Ser. No. 10/428,461 filed May 2, 2003 now U.S. Pat. No. 7,717,708, which is a continuation-in-part of application Ser. No. 09/834,412, filed Apr. 13, 2001, now issued as U.S. Pat. No. 6,632,089. The entire contents of each of the above applications and issued patent are incorporated by reference herein.

BACKGROUND OF THE INVENTION

A. Field of the Invention

This invention relates to the field of computerized techniques for orthodontic treatment planning for human patients. More particularly, the invention is directed to a method and system for a comprehensive evaluation of total care of orthodontic patients comprising evaluation of available treatment options, evaluation of a proposed treatment plan, as well as evaluation of the progress during the course of the treatment, thereby helping the practitioner or the user in making treatment adjustments if necessary for finding a desired treatment plan or during the course of the treatment. An interactive workstation and associated computerized techniques for facilitating integration of various tasks performed in planning and evaluation of treatment for orthodontic patients is disclosed.

B. Description of Related Art

The traditional process of diagnosis and treatment planning for a patient with orthodontic problems or disease typically consists of the practitioner obtaining clinical history, medical history, dental history, and orthodontic history of the patient supplemented by 2D photographs, 2D radiographic images, CT scans, 2D and 3D scanned images, ultrasonic scanned images, and in general non-invasive and sometimes invasive images, plus video, audio, and a variety of communication records. Additionally, physical models, such as made from plaster of paris, of the patient's teeth are created from the impressions taken of the patient's upper and lower jaws. Such models are manually converted into teeth drawings by projecting teeth on drawing paper. Thus, there is a large volume of images and data involved in the diagnosis and treatment planning process. Furthermore, the information may require conversion from one form to another and selective reduction before it could become useful. There are some computerized tools available to aid the practitioner in these data conversion and reduction steps, for example to convert cephalometric x-rays (i.e., 2 dimensional x-ray photographs showing a lateral view of the head and jaws, including teeth) into points of interest with respect to soft tissue, hard tissue, etc., but they are limited in their functionalities and scope. Even then, there is a fairly substantial amount of manual work involved in these steps.

Additionally, a number of measurements, e.g., available space between teeth, are also often done manually. Generally, these steps are time consuming and prone to inherent inaccuracies. Furthermore, the practitioner has to contend with the biological interdependencies within the patient, which introduces constraints eliminating certain treatment options that would otherwise be acceptable, between the soft tissue, the hard tissue, and the teeth. There is lack of an integrated platform which a practitioner could utilize to filter-out non-practicable treatment options.

Consequently, the practitioner is left to mental visualization, chance process to select the treatment course that would supposedly work. Furthermore, the diagnosis process is some-what ad-hoc and the effectiveness of the treatment depends heavily upon the practitioner's level of experience. Often, due to the complexities of the detailed steps and the time consuming nature of them, some practitioners take a shortcut, relying predominantly on their intuition to select a treatment plan. For example, the diagnosis and treatment planning is often done by the practitioner on a sheet of acetate placed over the X-rays. All of these factors frequently contribute towards trial and error, hit-and-miss, lengthy and inefficient treatment plans that require numerous mid-course adjustments. While at the beginning of treatment things generally run well as all teeth start to move at least into the right direction, at the end of treatment a lot of time is lost by adaptations and corrections required due to the fact that the end result has not been properly planned at any point of time. By and large, this approach lacks reliability, reproducibility and precision. More over, there is no comprehensive way available to a practitioner to stage and simulate the treatment process in advance of the actual implementation to avoid the often hidden pitfalls. And the patient has no choice and does not know that treatment time could be significantly reduced if proper planning was done.

In recent years, computer-based approaches have been proposed for aiding orthodontists in their practice. However, these approaches are limited to diagnosis and treatment planning of craniofacial structures, including the straightening of teeth. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein. Also see imaging and diagnostic software and other related products marketed by Dolphin Imaging, 6641 Independence Avenue, Canoga Park, Calif. 91303-2944.

A method for generation of a 3D model of the dentition from an in-vivo scan of the patient, and interactive computer-based treatment planning for orthodontic patients, is described in published PCT patent application of OraMetrix, Inc., the assignee of this invention, publication no. WO 01/80761, the contents of which are incorporated by reference herein.

Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc. (EMBS) Conf.*, Vol. 20, Hong Kong, October 1998, pp. 563-566; and M. Yamany, A. A. Farag, David Tasman, A. G. Farman, "A 3-D Reconstruction System for the Human Jaw Using a Sequence of Optical Images," *IEEE Transactions on Medical Imaging*, Vol. 19, No. 5, May 2000, pp. 538-547. The contents of these references are incorporated by reference herein.

The technical literature further includes a body of literature describing the creation of 3D models of faces from photographs, and computerized facial animation and morphable modeling of faces. See, e.g., Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of* 3D *Faces*, Computer Graphics Proceedings SIGGRAPH '99 (August 1999). The contents of these references are incorporated by reference herein.

However, a comprehensive evaluation of total care of orthodontic patients comprising evaluation of available treatment options, evaluation of a proposed treatment plan, as well as evaluation of the progress during the course of the treatment, in terms of the overall quality of treatment, by and large, remains subjective, cumbersome, not reproducible, error prone and limited in scope. Generally the evaluation is done at either the beginning of the treatment or at the end of the treatment; and lacks continuous monitoring and improvement of the treatment as and when needed.

PAR Index, reported by Richmond S, Shaw W C, O'Brien K D et al., "The development of PAR Index (Peer Assessment rating): reliability and validity," *Eur J Orthod* 1992; 14: 125-40, offers an approach to evaluating the degree or severity of mal-occlusion of a patient. The evaluation is primarily useful in performing diagnosis of an orthodontic patient. The evaluation is done by inspection of the dentition of a patient and general observation regarding the patient's condition. The evaluation utilizes 2D photographs of the patient's dentition. The process generally comprises evaluation of the occlusal contact points, degree of over jet or over byte, malocclusion classification, etc. The evaluation is manual and subject to judgment and error.

The American Board of Orthodontics (ABO) has introduced an Objective Grading System (OGS) for evaluating the results of an orthodontic treatment once it is completed. OGS evaluates the dental casts and panoramic radiographs using eight criteria; namely, alignment, marginal ridges, buccolingual inclination, occlusal relationships, occlusal contacts, overjet, interproximal contacts, and root angulation; and a method of scoring teh adequacy. (a) Alignment refers to an assessment of tooth alignment. In the anterior region, the incisal edges and lingual surfaces of the maxillary anterior teeth and the incisal edges and labial-incisal surfaces of the mandibular anterior teeth are chosen to assess anterior alignment. These are not only the functioning areas of these teeth, but they also influence esthetics if they are not arranged in proper relationship. In the maxillary posterior region, the mesiodistal central groove of the premolars and molars is used to assess adequacy of alignment. In the mandibular arch, the buccal cusps of the premolars and molars are used to assess proper alignment. (b) Marginal ridges are used to assess proper vertical positioning of the posterior teeth. In patients with no restorations, minimal attrition, and no periodontal bone loss, the marginal ridges of adjacent teeth should be at the same level. If the marginal ridges are at the same relative height, the cementoenamel junctions will be at the same level. In a periodontally healthy individual, this will result in flat bone level between adjacent teeth. In addition, if marginal ridges are at the same height, it will be easier to establish proper occlusal contacts, since some marginal ridges provide contact areas for opposing cusps. (c) Buccolingual inclination is used to assess the buccolingual angulation of the posterior teeth. In order to establish proper occlusion in maximum intercuspation and avoid balancing interferences, there should not be a significant difference between the heights of the buccal and lingual cusps of the maxillary and mandibular molars and premolars. (d) Occlusal relationship is used to assess the relative anteroposterior position of the maxillary and mandibular posterior teeth. The buccal cusps of the maxillary molars, premolars, and canines must align within 1 mm of the interproximal embrasures of the mandibular posterior teeth. The mesiobuccal cusp of the maxillary first molar must align within 1 mm of the buccal groove of the mandibular first molar. (e) Occlusal contacts are measured to assess the adequacy of the posterior occlusion. Again, a major objective of orthodontic treatment is to establish maximum intercuspation of opposing teeth. Therefore, the functioning cusps are used to assess the adequacy of this criterion; i.e., the buccal cusps of the mandibular molars and premolars, and the lingual cusps of the maxillary molars and premolars. If cusp form is small or diminutive, that cusp is not scored. (f) Overjet is used to assess the relative transverse relationship of the posterior teeth, and the anteroposterior relationship of the anterior teeth. In the posterior region, the mandibular buccal cusps and maxillary lingual cusps are used to determine proper position within the fossae of the opposing arch. In the anterior region, the mandibular incisal edges should be in contact with the lingual surfaces of the maxillary anterior teeth. (g) Interproximal contacts are used to determine if all spaces within the dental arch have been closed. Persistent spaces between teeth after orthodontic therapy are not only unesthetic, but can lead to food impaction. (h) Root angulation is used to assess how well the roots of the teeth have been positioned relative to one another. Although the panoramic radiograph is not the perfect record for evaluating root angulation, it is probably the best means possible for making this assessment. If roots are properly angulated, then sufficient bone will be present between adjacent roots, which could be important if the patient were susceptible to periodontal bone loss at some point in time. If roots are dilacerated, then they are not graded. As mentioned earlier, the OGS requires dental casts and its application is limited to evaluating the post-treatment results. The OGS in its present form cannot be used to evaluate the effectiveness of a proposed orthodontic treatment and the adjustments thereto in order to realize a desired treatment plan prior to actually embarking upon execution of the treatment plan. The ABO has developed an orthodontic measuring gauge to assist in the manual measurement of parameters related to the OGS criteria from the dental cast and the panoramic radiograph. Although the measuring gauge introduces a degree of consistency in the measurements when performed by different people, the evaluation is still limited in scope to two-dimensional analysis.

The Institute of Medicine's Committee on Quality of Health Care in America, in a year 2001 report on "Crossing the Quality Chasm: A New Health System for the 21st Century," has suggested that a comprehensive quality management system should include measures of: (a) treatment efficiency, (b) treatment effectiveness, (c) Patient connectedness to treatment, (d) timeliness of treatment, (e) treatment safety and (f) treatment equitability. However, to-date there dose not exist a comprehensive system or a set of measuring tools in the field of orthodontics that would enable a practitioner to evaluate these six dimensions of the quality of care while planning and throughout delivery of treatment to orthodontic patients.

What is lacking in the art is a an integrated treatment evaluation and quality measurement approach in the field of orthodontics that is either automatic or semi-automatic, objective, reproducible, reliable, accurate and enables measurements in two-dimensions or three-dimensions. In addition what is lacking in the art is an evaluation and measurement process in orthodontics that enables total quality improvement of the treatment planning and delivery process through periodic feedback. What is further lacking in the art is a treatment evaluation process that enables continuous learning from the patients' responses to different treatment approaches, thereby enabling establishments of improved benchmarks for standard of care. The present invention discloses solutions to these and other problems of treatment evaluation and is directed to an effective, computer-based, integrated and interactive orthodontic treatment planning and evaluation system that provides the necessary tools to allow the orthodontist to quickly and efficiently design and evaluate the treatment plan and delivery for a patient.

SUMMARY OF THE INVENTION

In a first aspect of the invention, an orthodontic treatment planning, evaluation and quality measurement system is provided comprising a workstation having computing platform, a graphical user interface, a processor and a computer storage medium containing digitized records pertaining to a patient. The digitized records include image data. The computer storage medium further includes a set of software instructions providing graphical user interface tools for providing a user with access to the digitized records for planning orthodontic treatment of a patient. Also provided are reference databases for aiding in the decision process during treatment selection, treatment planning and treatment delivery and progress monitoring and evaluation. Also provided are parameter or criteria measurement techniques and generally acceptable thresholds, which can be updated through learning process and through acquisition of patient data. The thresholds can be adjusted by users as desired and from the perspective of the patient needs. The set of instructions include:

(a) instructions for evaluating high-level criteria comprising (i) treatment efficiency, (ii) treatment effectiveness, (iii) patient connectedness to treatment, (iv) timeliness of treatment, (v) treatment safety, and (vi) treatment equitability for a comprehensive orthodontic treatment evaluation and quality measurement process. Each high level criterion may comprise plurality of sub-criteria. Basically, the evaluation process is performed as follows: each criterion is measured and compared against a threshold in order to determine whether its performance is acceptable or not. In the event that the performance of a particular criterion is unacceptable or rejected, a root-cause analysis is performed if applicable; and the corrective actions taken or planned accordingly.

In another aspect of the invention the treatment efficiency is evaluated while selecting the type of treatment and planning the treatment for an orthodontic patient and during the execution of the treatment. The treatment efficiency is evaluated from the perspective of (i) productivity of the people delivering the treatment, (ii) cost and availability of materials required for the treatment, (iii) suitability of the treatment method for the patient, and the estimated time duration for the treatment, (iv) reliability and cost contributions towards the treatment of the patient from the equipment necessary for creating and delivering the treatment, (v) the cost contribution and other criteria attributable to the environment in which the treatment is delivered, etc.

In another aspect of the invention, the treatment effectiveness is evaluated. Treatment effectiveness is measured against known clinical standards and benchmarks, and taking this information into account, the treatment is planned by the practitioner in accordance with the patient's needs. The treatment itself can be staged when that is a desired option.

In another aspect of the invention, the patient connectedness to the treatment is evaluated. The patient connectedness criterion includes sub-criteria such as matching treatment results with the patient expectations, care of service, e.g., timeliness of response from the practice to the queries from the patient, patient comfort and patient overall satisfaction. Other factors may contribute towards a patient's connectedness towards a particular treatment.

In another aspect of the invention, the timeliness of the treatment is evaluated. The timeliness criterion includes sub-criteria such as appointment intervals, length of appointments, time spent waiting in the reception area, difference between the estimated treatment time and the actual treatment time.

In another aspect of the invention, the treatment safety is evaluated. In order to assess the safety of a treatment, it is examined against the historical database which catalogues the occurrences of the adverse events related to the treatment as well as the successful events. The adverse events are further classified according to the number of episodes causing discomfort or pain to the patient, the nature of pain, decalcification of teeth, root resorption, gingivitis, periodontitis, etc. The adverse events are also classified as follows: (a) iatrogenic event where the problem is caused by the practitioner's mistake, e.g., inadvertently causing the fracture of the jaw bone of the patient; (b) idiopathic event where there is no known cause for the problem; however the patient is sensitive to the treatment; and (c) idiosyncratic event which develops a new response within the patient which was never recorded before in the history of the treatment.

In another aspect of the invention, the treatment equitability is evaluated. The treatment equitability criterion comprises factors such as whether or not same standard of care is offered to all patients, matching of patient profile against the treatment needs of the patient, against established clinical pathways, and between offerings from different orthodontic practices.

According to a preferred embodiment of the invention, different ways to measure the evaluation criteria disclosed herein have been integrated into a comprehensive and unified system.

In another aspect of the invention, 'alert system' is built into the integrated system based upon the patient's initial condition or history, whereby the alert system would raise a flag to the practitioner if a certain aspect of the treatment would be problematic for the patient.

In another embodiment of the invention, the integrated system is linked with other databases and key search engines such as Medline, and other resources such as doctors, hospitals and universities through Internet or other communication media. As new information is gathered from patients, the databases are updated, and the benchmarks revised accordingly.

Treatment can be planned solely in line with the practitioner's diagnosis of the patient's problems, or the patient's needs, or a combination of both.

The treatment evaluation can be performed in the beginning while planning the treatment, during the treatment and at the end of the treatment.

The integrated system is optimized to yield best clinical pathways; and it refreshes existing clinical pathways as the experience is gained from the treatment of new patients.

The integrated system utilizes both internal and external data resources. The data may be image based, audio, text etc.

The measurements may be distance based or based upon volume. The measurements may be two-dimensional or three-dimensional. Three-dimensional coordinate systems providing local and global references can be used for such measurements. The evaluation process comprises analysis of 3D shapes, forms and contours of three-dimensional virtual images derived from CT scan, craneo-facial X-rays, scanning of dentition, etc. Such analysis can be used to analyze root shapes, bone structure, tissue, etc.

The measurement thresholds and grading can be set from experience; and changed as new data become available. Furthermore, the measurement thresholds and grading can be individualized as desired.

Root cause analysis depends upon the problem to be investigated. For example, if in a certain patient's case the treatment is taking longer than anticipated, a root cause analysis may reveal that one or more brackets prematurely came off from the patient's teeth due to defective base; so a proper corrective action can be undertaken.

In another embodiment of the invention, the integrated system provides a closed-loop or a feedback loop unified system for treatment planning, treatment monitoring and treatment evaluation and quality measurement.

In another aspect of the invention, the thresholds can be set at single or range of values.

In another embodiment of the invention, a database of cases is created to find a suitable response that would match a patient's condition.

In another aspect of the invention, the treatment evaluation approach described herein can as well be used to evaluate denture set-ups, crowns, bridges, and in general any prostethic or restorative dental element. The user can select the extent and type of evaluation to be performed from the types of evaluations described earlier for the orthodontic treatment.

In another aspect of the preferred embodiment, once the treatment is planned, the virtual dentition model of the patient in the proposed treatment set-up or the target state is evaluated using several virtual model evaluation features and criteria such as: (a) alignment, (b) marginal ridges, (c) buccolingual inclination, (d) occlusal relationship, (e) occlusal contacts, (f) overjet, (g) interproximal contacts, (h) vertical alignment of buccal cusp tips, (i) vertical alignment of front, and (j) angulation of front. The virtual model evaluation features utilize certain tooth features and distance or penetration measurements involving these tooth features for evaluating the quality of the planned treatment.

In another aspect of the invention, measurement types needed to support the virtual model evaluation features, namely, (a) distance between two points, (b) distance between a point and an object, (c) shortest directed distance between two objects, (d) shortest distance between two objects, (e) deepest penetration between two objects, and (f) distance or penetration between two objects.

In another aspect of the invention, according to a preferred embodiment of the invention, an orthodontic coordinate system is disclosed which enables measurement of the orthodontic parameters in a meaningful and consistent manner. For every tooth, its own reference system is assigned that is applicable in any position of the tooth. The position of theses reference systems coincides in any tooth position with the subjectively found rotation axes, which means buccolabial and mesiodistal alignment. The coordinate (reference) systems can be thought of as lying at the location of the tooth axis of every tooth with their origins in one plane. Within this plane a monotonously curved plane (virtual) tooth arc is defined, so that one axis of the systems coincides with the tangent at the arc at the respective position (at its origin) and one with the normal to the arc at that position. The origin of the reference systems always falls on one point of the arc. In this way rotation axes for angular displacement and torque are always in agreement with a buccolabial or a mesiodistal view of the jaw. That means the axes are oriented themselves by the jaw, not by the single tooth. The virtual (tooth) arc or virtual tooth jaw (VTJ) consists of an even polynomial of higher order. That means the VTJ is symmetrical in regard of the jaw halves.

In another aspect of the invention, the alignment evaluation is performed comprising measuring the distance between: (a) the anterior incisor cusp tips; (b) the anterior incisor contact points; (c) buccal upper central groves; and (d) buccal lower cusp tips; and comparing the results against specified thresholds and grading the outcome.

In another aspect of the invention, the marginal ridges evaluation is performed comprising measuring the vertical distance between the marginal ridges of the adjacent teeth; and comparing the results against specified thresholds and grading the outcome.

In another aspect of the invention, the buccolingual inclination evaluation is performed comprising measuring the orthogonal distance between the plane touching one or two cusp tips of the measured tooth and touching one cusp tip of the opposite tooth; and comparing the results against specified thresholds and grading the outcome.

In another aspect of the invention, the occlusal relationship evaluation is performed comprising measuring the directed distance (in mesio-distal direction) between the upper jaw mesial, labial cusp tip and the buccal groove of the lower jaw posterior; and comparing the results against specified thresholds and grading the outcome.

In another aspect of the invention, the occlusal contacts evaluation is performed comprising measuring the vertical distance of a cusp tip on a virtual tooth and the surface of the opposite virtual tooth; and comparing the results against specified thresholds and grading the outcome.

In another aspect of the invention, the overjet evaluation is performed comprising measuring the overjet in two different ways: (a) in the anterior area, the shortest distance in the in-out-direction between the posterior of the virtual upper jaw and the anterior of the virtual lower-jaw; and (b) in the posterior area, the mesio-distal distance of the lower-jaw labial cusp tip and the upper jaw central groove line connecting the central groove points. The results are then compared against specified thresholds and the outcome is graded.

In another aspect of the invention, the interproximal contacts evaluation is performed comprising measuring the interproximal contacts between the adjoining teeth; and comparing the results against specified thresholds and grading the outcome.

In another aspect of the invention, the vertical alignment of buccal cusp tips evaluation is performed comprising measuring the vertical distance of the (labial) cusp tips of the virtual canines and the virtual posterior teeth; and comparing the results against specified thresholds and grading the outcome.

In another aspect of the invention, the vertical alignment of front evaluation is performed comprising measuring the vertical distance between the "corrected cusp tips", that is the cusp tips moved to the edge of the tooth when necessary, of two virtual adjacent teeth.

In another aspect of the invention, the angulation of front evaluation is performed comprising measuring the vertical distance between the two "corrected" cusp tips of the same virtual tooth.

In yet another aspect of the invention, a computerized method of planning and evaluating treatment for an orthodontic patient is disclosed, comprising the steps of:

(a) providing an orthodontic treatment planning workstation comprising a computing platform having a graphical user interface, a processor and a computer storage medium containing digitized records pertaining to a patient, the digitized records including image data, and a set of software instructions providing graphical user interface tools for providing a user with access to the digitized records and for planning orthodontic treatment of a patient;

(b) selecting a treatment plan;

(c) generating a proposed set-up for treating the patient in accordance with the selected treatment plan, the proposed set-up comprising a proposed three-dimensional position of the dentition of the patient in a post-treatment condition;

(d) conducting an evaluation of the proposed set-up, the evaluation prompted by computer instructions providing a series of predetermined steps for guiding a user to interactively evaluate the proposed set-up, wherein the predetermined steps comprise steps for checking (a) vertical alignment of buccal cusp tips; (b) vertical alignment of front, and (c) checking angulation of front;

(e) monitoring progress of said treatment; and (f) evaluating said progress of said treatment.

The proposed set-up can be transmitted over a communications medium to a remote workstation comprising the computer instructions providing a series of predetermined steps for guiding a user to interactively evaluate the proposed set-up. The computer instructions further comprise instructions which allow a user to modify the proposed set-up during one or more of the predetermined steps, and wherein modifications made in any one of the one predetermined steps are carried over to subsequent steps in the series of predetermined steps. Indeed the computer instructions further comprise instructions which allow a user to navigate through the series of predetermined steps in any order desired by the user. The series of predetermined steps further comprise the following evaluation steps of the proposed set-up:

1. checking alignment;
2. checking marginal ridges;
3. checking buccolingual inclination;
4. checking occlusal relationship;
5. checking occlusal contacts;
6. checking overjet; and
7. checking interproximal contacts.

BRIEF DESCRIPTION OF THE DRAWINGS

Presently preferred embodiments of the invention are described below in reference to the appended drawings, wherein like reference numerals refer to like elements in the various views, and in which:

FIG. 2 is a more detailed block diagram of the treatment planning software executed by the workstation of FIG. 1.

FIGS. 3-39 and 39A illustrate screen shots from the workstation of FIG. 1, showing various treatment planning features that are provided by the treatment planning software of FIG. 2 in a presently preferred embodiment.

FIG. 40 shows a list of high-level criteria comprising for a comprehensive orthodontic treatment evaluation and quality measurement process integrated into the treatment planning and evaluation system according to the preferred embodiment of the invention.

FIG. 41 provides a screen shot depicting virtual maxilla teeth of a patient in malocclusion state.

FIG. 42 provides a screen shot depicting virtual maxilla teeth of the patient in a set-up or target state after planning the treatment.

FIG. 43 provides a list of the virtual model evaluation criteria according to the preferred embodiment of the invention.

FIG. 44 shows virtual maxilla teeth of a patient and cusp tips.

FIG. 53 shows a screen shot depicting the distance between the virtual maxilla incisor cusp tips.

FIG. 53A shows a screen shot depicting an enlarged view of the distance between the virtual maxilla incisor cusp tips.

FIG. 54 shows a screen shot depicting cusp tip distance measurements for all virtual mandible or lower teeth.

FIG. 55 shows a screen shot depicting cusp tip distance measurements for all virtual maxilla or upper teeth.

FIGS. 68 and 69 show vertical alignment of front.

FIG. 70 shows angulation of front.

DETAILED DESCRIPTION OF PREFERRED EMBODIMENTS

Before describing the integrated treatment planning, evaluation and quality measurement features and approach of this invention in detail, an overview of a unified workstation will be set forth initially. The workstation, in a preferred embodiment, provides software features that create two dimensional and/or three-dimensional virtual patient models on a computer, which can be used for purposes of treatment planning, evaluation and quality measurement in accordance with a presently preferred embodiment.

Many of the details and computer user interface tools which a practitioner may use in adjusting tooth position, designing appliance shape and location, managing space between teeth, and arriving at a finish tooth position using interaction with a computer storing and displaying a virtual model of teeth are set forth in the prior application Ser. No. 09/834,412 filed Apr. 13, 2001, now issued as U.S. Pat. No. 6,632,089, and in published OraMetrix patent application WO 01/80761, the contents of each of which are incorporated by reference herein. Other suites of tools and functions are possible and within the scope of the invention. Such details will therefore be omitted from the present discussion.

General Description

A unified workstation environment and computer system for diagnosis, treatment planning and evaluation and quality measurement, and delivery of therapeutics, especially adapted for treatment of craniofacial structures, is described below. In one possible example, the system is particularly useful in diagnosis and planning and evaluating treatment of an orthodontic patient. Persons skilled in the art will understand that the invention, in its broader aspects, is applicable to other craniofacial disorders or conditions requiring surgery, prosthodontic treatment, restorative treatment, etc.

Figure 1:
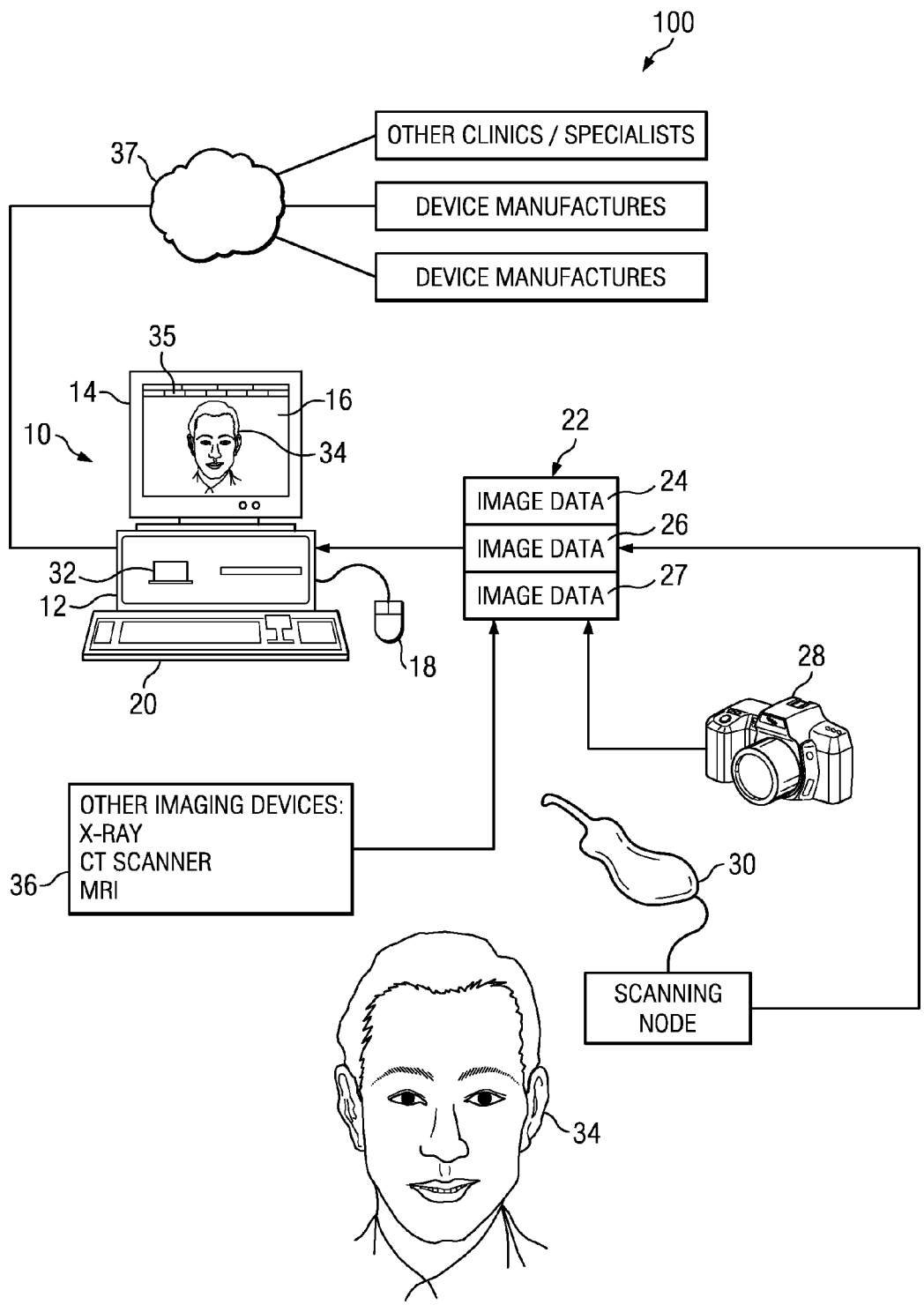
FIG. 1 is block diagram of a system for creating a three-dimensional virtual patient model and for diagnosis and planning treatment of the patient.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning and evaluating treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions and reference databases or digital libraries stored on a machine-readable storage medium. The instructions and reference databases may be stored in the memory 22 accessible to the general-purpose computer system 10. The machine-readable medium storing the instructions and reference databases may alternatively be a hard disk memory 32 for the computer system 10, external memory devices, or may be resident on a file server on a network connected to the computer system, the details of which are not important. The set of instructions and reference databases, described in more detail below, comprise instructions and reference databases for causing the general computer system 10 to perform several functions related to the generation and use of the virtual patient model in diagnostics, therapeutics and treatment planning, evaluation and quality measurement.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data includes intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as a 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is capable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in an dynamic format (i.e., during movement of anatomical structures relative to each other, such as chewing, occlusion, growth, etc.). To facilitate such modeling and simulations, teeth may be modeled as independent, individually moveable three dimensional virtual objects, using the techniques described in the above-referenced OraMetrix published PCT application, WO 01/80761.

The workstation environment provided by this invention provides a powerful system and for purposes of diagnosis, treatment planning and evaluation and quality measurement, and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial position, which might be pre-treatment position or position at any other time during treatment, to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, now issued as U.S. Pat. No. 6,648,640, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents. Alternatively, the initial and final tooth positions can be used to derive data sets representing intermediate tooth positions, which are used to fabricate transparent aligning shells or aligners for moving teeth to the final position, as described in the above-referenced Chisti et al. patents. The data can also be used to place brackets and design a customized archwire as described in the previously cited application Ser. No. 09/835,039, now issued as U.S. Pat. No. 6,648,640.

To facilitate sharing of the virtual patient model among specialists and device manufacturers, the system 100 includes software routines and appropriate hardware devices for transmitting the virtual patient model or some subset thereof, and a proposed set-up for treatment of the patient, over a computer network. The treatment plan developed in the workstation could be either evaluated locally, on the workstation itself, or else at a remote workstation (such as at an appliance manufacture site or site of practitioners that perform evaluations for a service). In this latter situation, the same interactive treatment planning software is installed at the remote site, along with the evaluation instructions for evaluation of the set-up, as described herein.

The workstation's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored and evaluated by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing subsystems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including 2D X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed before hand to the patient and changes made depending on the patient input.

With the above general description in mind, additional details of presently preferred components and aspects of the inventive system and the software modules will be described next.

Capture of Image Information

The image data regarding the patient's dentition can be obtained through a variety of means including via scanning of the dentition of the patient via the hand-held 3D-scanner 30 described in the published OraMetrix PCT application WO 01/80761, referenced previously. If this approach is used, it may be beneficial to apply a thin layer of non-toxic, opaque and reflective substance to the teeth prior to scanning to insure adequate data capture by the hand-held scanner. A suitable opaquing substance is described in the patent application of Nancy Butcher et al. Ser. No. 10/099,042 filed Mar. 14, 2002, entitled "Method for Wet-Field Scanning," now issued as U.S. Pat. No. 6,854,973 the contents of which are incorporated by reference herein. In operation, the scanner captures a sequence of overlapping images of the dentition of the patient as the scanner is held by the hand and moved about the oral cavity. The set of images can be obtained in only a few minutes. Each image is converted to a set of X, Y and Z coordinate positions comprising a cloud of points representing the surface of the dentition. The point clouds from each image are registered to each other to find a best fit to the data. The resulting registered point cloud is then stored in the memory as a virtual three-dimensional object. The construction, calibration and operation of the scanner, and the manner of converting scanned data to point clouds and registering three-dimensional point clouds to form a three-dimensional object is described at length in the published PCT application of OraMetrix WO 01/80761, referenced earlier and therefore omitted from the present discussion for the sake of brevity. Other types of scanners or coordinate measuring instruments could also be used.

Treatment Planning

The computer or workstation 10 (FIG. 1) that includes the software for generating the patient model preferably includes interactive treatment planning software that allows the user to simulate various possible treatments for the patient on the workstation and visualize the results of proposed treatments on the user interface by seeing their effect on the visual appearance of the patient, especially their smile. The interactive treatment planning preferably provides suitable tools and icons that allow the user to vary parameters affecting the patient. Such parameters would include parameters that can be changed so as to simulate change in the age of the patient, and parameters that allow the user to adjust the color, texture, position and orientation of the teeth, individually and as a group. The user manipulates the tools for these parameters and thereby generates various virtual patient models with different features and smiles. The patient models are displayed on the user interface of the workstation where they can be shared with the patient directly. Alternatively, the workstation can be coupled to a color printer. The user would simply print out hard copies of the screen shots showing the virtual patient model.

The manner in which the software is written to provide tools allowing for simulation of various parameters can vary widely and is not considered especially critical. One possibility is a Windows-based system in which a series of icons are displayed, each icon associated with a parameter. The user clicks on the icon, and a set of windows are displayed allowing the user to enter new information directing a change in some aspect of the model. The tools could also include slide bars, or other features that are displayed to the user and tied to specific features of the patient's anatomy. Treatment planning icons for moving teeth are disclosed in the published PCT application of OraMetrix, Inc., WO 01/80761, which gives some idea of the types of icons and graphical user interface tools that could be used directly or adapted to simulate various parameters.

Once the user has modified the virtual patient model to achieve the patient's desired feature and smile, it is possible to automatically back-solve for the teeth, jaw and skull movement or correction necessary to achieve this result. In particular, the tooth movement necessary can be determined by isolating the teeth in the virtual patient model, treating this tooth finish position as the final position in the interactive treatment planning described in the published OraMetrix PCT application, WO 01/80761, designing the bracket placement and virtual arch wire necessary to move teeth to that position, and then fabricating the wire and bracket placement trays, templates or jigs to correctly place the brackets at the desired location. The desired jaw movement can be determined by comparing the jaw position in the virtual patient model's finish position with the jaw position in the virtual patient model in the original condition, and using various implant devices or surgical techniques to change the shape or position of the jaw to achieve the desired position.

The virtual patient model as described herein provides a common set of data that is useable in a variety of orthodontic or other treatment regimes. For example, the initial and final (target) digital data sets of the patient's tooth positions can be relayed to a manufacturer of customized transparent removable aligning shells for manufacture of a series of aligning devices, as taught in the Chisti et al. patents cited previously. Alternatively, the tooth positions may be used to derive customized bracket prescriptions for use with a flat planar archwire.

The choice of which treatment modality, and whether to use any additional treatment or therapeutic approaches (including surgery) will depend on the patient in consultation with the treating physician. The integrated environment proposed herein provides essentially a platform for a variety of possible treatment regimes. Further, the creation and display of the virtual patient model provides for new opportunities in patient diagnosis and sharing of patient information across multiple specialties in real time over communications networks.

FIG. 2 is a block diagram of an integrated workstation environment for creation of the virtual patient model and diagnosis, treatment planning and delivery of therapeutics. The workstation environment shown in block diagram form in FIG. 2 may incorporate many of the hardware aspects shown in FIG. 1, including scanning or imaging devices 28/36 for capturing two dimensional images, such as a color digital camera or X-Ray machine. The workstation environment will preferably include scanning or imaging devices 30/36 for capturing three dimensional images and creating 3D models of the patient, including one or more of the following: laser scanners for scanning a plaster model of the teeth, optical scanner such as the OraMetrix hand-held scanner 30 referenced in FIG. 1, CT scanner or MRI. In some instances, the scanning devices may be located at other facilities, in which case the 3D scans are obtained at another location and the 3D data is supplied to the workstation 10 (FIG. 1) over a suitable communications channel (Internet) or via a disk sent in the mail.

The workstation includes a memory storing machine readable instructions comprising an integrated treatment planning and model manipulation software program indicated generally at 300. The treatment planning instructions and tools can be used for initial treatment planning and evaluation as well as for monitoring treatment progress and evaluation thereof. The treatment planning instructions 300 will be described in further detail below. The treatment planning software uses additional software modules. A patient history module 302 contains user interface screens and appropriate prompts to obtain and record a complete patient medical and dental history, along with pertinent demographic data for the patient.

A module 304 contains instructions for designing custom dental and orthodontic appliances. These appliances could include both fixed appliances, e.g., brackets, bands, archwires, crowns and bridges, surgical splints, surgical archwires, surgical fixation plates, laminates, implants, as well as removable appliances including aligning shells, retainers and partial or full dentures. In one possible embodiment, the module 304 may be located and executed at the site of a vendor of custom orthodontic applicants. The vendor would receive an order for a custom appliance specifically to fit an individual patient. Module 34 would process this order and containing instruction for designing the appliance to fit the individual morphology and condition of the patient. The vendor would take the appliance design, manufacture the appliance in accordance with the design, and then ship the custom appliance to the practitioner. Examples of how the appliance design module 304 might be implemented include the appliance design software developed by OraMetrix and described in the published PCT patent application cited previously, the customized bracket, jig and wire appliance design software of Ormco described in the issued Andreiko patents (see, e.g., U.S. Pat. No. 5,431,562) and in the published patent application of Chapoulaud, U.S. patent publication No. 2002/

002841, the techniques of Chisti et al., U.S. Pat. Nos. 6,227,850 and 6,217,325, all incorporated by reference herein.

The treatment planning software 300 also obtains information on standard ("off the shelf") dental or appliances from a module 306, which stores manufacturer catalogs of such appliances, including 3D virtual models of the individual appliances.

The treatment planning software includes a module 308 that allows the user to input selections as to variable parameters that affect the visual appearance of the patient, as input to a craniofacial analysis module 328 described below. The variable parameters include patient factors: age, weight, sex, facial attributes (smile, frown, etc.). The variable parameters also include parameters affecting the teeth, including texture (color), position, spacing, occlusion, etc. The variable parameters further include various illumination parameters, including reflectivity of the skin, ambient light intensity, and light direction.

The treatment planning software further uses a diagnosis and simulation module 310 that displays diagnosis data graphically and/or in report format. This diagnosis data includes teeth position, 3D face and smile appearance, and various facial attributes.

The software further includes third party practice management software 312. Information about treatment planes generated by the craniofacial analysis module 328 is input to the practice management software 312. Based on the treatment plan, this software generates the most productive scheduling of appointments for the patient. The practice management software 312 also generates reports, provides insurance and benefit tracking, and supports electronic claims filing with the patient's insurance company. Preferably, the practice management software provides a flexible scheduling of patient appointments based on progress of treatment of the patient's craniofacial anatomical structures. The progress of treatment is obtained from periodically obtaining updated three-dimensional information regarding the progress of treatment of the craniofacial features of the patient. For example, the patient is periodically rescanned during the course of treatment. A new virtual patient model is created. Depending on the progress of treatment (e.g., movement of the teeth to target positions) the patient may be scheduled for more or less frequent visits depending on their progress.

Referring again generally to the treatment planning software 300, the software includes a 3D model generation module 314 that uses as input the 2D and 3D scanning devices. A 3D virtual model of the patient is created by module 314.

The system further includes a custom appliance management module 315. This module provides appliance specifications and 3D geometry data to the vendor site for the purpose of providing necessary input for the design and manufacture of custom appliances, such as custom orthodontic appliances, for the patient. This module also provides updates to an appliance data module 324 for storing custom appliance data within the database. The module 324 is responsible for managing the database of all the appliances, including custom appliances.

The 3D virtual patient model is supplied to a knowledge database 316. The knowledge database includes 3D Geometry data file 316 that stores the 3D geometry data of the virtual patient model. This data is supplied to a tagging module 322 and a morphable model module 320. The morphable model module 320 includes instructions for creating a morphable model from various 3D model samples, using the techniques for example set forth in the article of Blantz et al., *A Morphable Model for The Synthesis of 3D Faces*, Computer Graphics Proceedings SIGGRAPH '99 (August 1999).

The tagging module 322 includes instructions for tagging or placing pieces of information regarding the virtual patient model into each patient record, which is used for statistical procedures. In particular, the tagged information is supplied to a meta-analysis module 326. The meta-analysis module implements a set of statistical procedures designed to accumulate experimental and correlational results across independent studies that address a related set of research questions. Meta-analysis uses the summary statistics from individual studies as the data points. A key assumption of this analysis is that each study provides a different estimate of the underlying relationship. By accumulating results across studies, one can gain a more accurate representation of the relation than is provided by the individual study estimators. In one example, the software will use previous patient cases/studies to help in the craniofacial analysis module 328. For example, surgery cases for "lip and chin" will be one set of independent studies, whereas jaw surgery to correctly position the upper and lower jaw will be another. An orthodontist trying to align the upper and lower jaw will do a meta-analysis with the module 326 in order to see how this treatment will affect the patient's lip and chin.

The output of the morphable model from module 320 and the meta-analysis from module 326 is provided to a craniofacial analysis module 328. This module takes as input, patient information and the patient 3D virtual model to generate diagnosis and simulation data. Based on one or more simulation results, this module 328, and/or module 330 generates a treatment plan and appliance selection. User involvement is contemplated in modules 328 and 330. In particular, the user may interact with the patient information and the morphable model, and vary the parameters 308, to simulate different possible treatments and outcomes to arrive at a final or target treatment objective for the patient. The craniofacial analysis module 328 may include some or all of the treatment planning features described at length in the published PCT application of OraMetrix, Inc. cited previously.

The software instructions included in the craniofacial analysis module 326 preferably includes a set of instructions providing the user with user interface tools (e.g., icons), for visually studying on the user interface 316 the interaction of the craniofacial anatomical structures and their relationship to the external, visual appearance of the patient. For example, tools may provide a chewing simulation. Alternatively, the tools may provide a smile function in which the face is morphed to smile, showing the position of the teeth, gums, lips and other structures. These tools simulate changes in the anatomical position or shape of craniofacial anatomical structures (teeth, lips, skin, etc.) and show the effect of such changes on the visual appearance of the patient. As another example, the tools may include tools for modifying the shape or position of one or more bones of the upper and lower jaws, and show how those modifications affect the patient's appearance and smile.

After the patient simulations have been completed and the patient and physician are satisfied, the resulting data set of teeth position, jaw position, etc. are stored by the diagnosis and simulation module 310 of FIG. 2. This module 310 preferably includes a routine for storing a three-dimensional representation of said patient's craniofacial structures (e.g., teeth) in a format suitable for use by a manufacturer of orthodontic appliances. Each manufacturer may have a unique format needed for use by the manufacturer, and the routine takes that into consideration in storing the data. For example, a manufacturer may require 3D digital models of the teeth in initial and final positions in the form of triangle surfaces, along with archwire and bracket prescription data.

It is contemplated that the creation and usage of the virtual model may occur at the patient care site. In particular, the treating physician or orthodontist will access the scan and photographic data, create the virtual model there-from, and perform the treatment planning and simulation described herein in their own office. Once the treatment plan is arrived at, the treating physician can export the virtual patient model or some subset of data to appliance manufacturers or specialists, as indicated in FIG. 1.

Alternatively, the virtual patient model may be created at a remote location. In this latter example, a third party, such as an appliance manufacturer, may be the entity that creates the virtual patient model and makes it available to the treating physician. In this example, the treating physician will have access to the scanners, X-Ray, digital camera, or other imaging device, obtain the required data from the patient, and forward such data to the third party. The third party executes the instructions to create, visualize and manipulate the virtual patient model. This model can be transmitted to the treating physician for their review and usage. Then, either the third party could create a proposed treatment for review and approval by the treating physician, or the treating physician could create the treatment plan. The plan is then transmitted to one or more appliance manufacturers for fabrication of therapeutic devices (e.g., brackets and wires, aligning shells, maxillary expansion devices, etc.)

A treatment plan created from the virtual patient model described herein may be one in which only one type of appliances, e.g. fixed of removable, is used during the entire course of the treatment. For example, the treatment plan may be one in which brackets and wires are the type of appliance that is used. Or, alternatively, the treatment plan may be one in which removable aligning shells are the type of appliance that is used.

On the other hand, the treatment plan might be such that it is a hybrid plan requiring the use of different types of appliances during the course of the treatment. In the hybrid orthodontic treatment plan, a variety of scenarios are possible. In one type of hybrid treatment plan, different types of appliances might be used at different times during the course of the treatment. For example, patient may start out with brackets and wires and shift at some point during treatment to an approach based on removable aligning shells. In another type of hybrid treatment plan, different types of appliances might be used simultaneously, for example in different portions of the mouth, for example brackets and wires could be used for certain teeth and transparent aligning shells uses for a different set of teeth. A hybrid treatment plan may be chosen right from the beginning, or it may be introduced dynamically at any stage during the treatment course.

To develop a hybrid treatment plan, the treatment planning software will preferably include features of the appliance design and treatment planning software of the manufacturers of the appliances that are used in the hybrid treatment. As one example, the treatment planning software may include the wire and bracket features of the OraMetrix treatment planning software described in the published application WO 01/80761, as well as the treatment planning software described in the Align Technologies patents to Chisti et al., U.S. Pat. Nos. 5,975,893 and 6,227,850. The software would thus allow the user to simulate treatment with brackets and wires for part of the tooth movement to reach a particular milestone, and also design the configuration of intermediate tooth positions and configuration of removable aligning shells for the remainder of tooth movement. Alternatively, the shape of the aligning shells could be determined automatically via the treatment planning software from the tooth configuration at which the shells are first introduced to the patient and the final tooth position in accordance with the teachings of the Chisti et al. patents.

Referring now to FIG. 3, a screen shot from the graphical user interface of the workstation of FIG. 1 is shown. The workstation includes a computer memory that stores, and makes available to the practitioner, records in the form of digital data pertaining to some or all of the following: the patient's clinical history, medical history, dental history, and orthodontic history as well as 2D photographs, 2D radio graphic images, CT scans, 2D and 3D scanned images, ultrasonic scanned images, and in general, non-invasive and sometimes invasive images, plus video, audio, and a variety of communication records, such notes, records of office visits, patient letters or communications, etc. All records and images are digitized. The records and images are made available through suitable user interface icons which cause display of the images and records on the user interface. The images can be combined or superimposed to create a virtual patient model that includes surface features (soft tissue) of the patient in one possible embodiment.

The workstation also further maintains a comprehensive set of computer instructions providing tools in the form of icons, screen displays, windows, functions and features, accessible through the user interface of the workstation to assist the practitioner in planning the treatment. Various types of tools are contemplated; numerous examples are set forth herein.

Figure 3A:
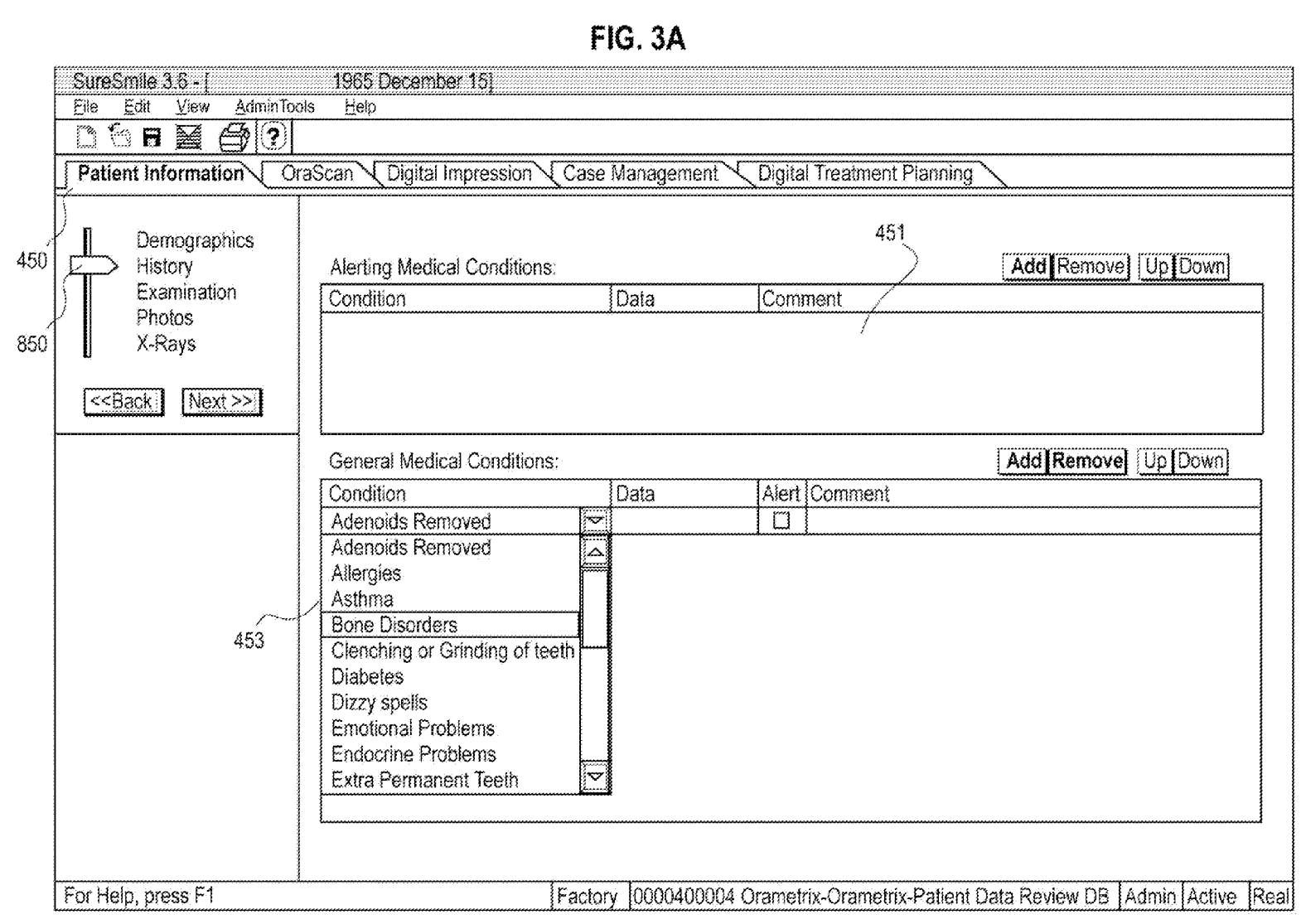

In FIG. 3, a set of tabs 450, 452, 454, 456 and 458 are provided. The tab 450 is a patient information tab which provides suitable screen displays for entering a variety of patient information, such as their name and address, dental and clinical history, insurance information, diagnostic information, names of other treating or consulting practitioners, etc. Tab 450 will be discussed in further detail below in conjunction with FIGS. 3A and 3B and FIGS. 36-39A. The tab 452 is a tab whereby the user accesses scan or other image data and accesses instructions and menus for scanning the patient with an in-vivo intra-oral scanner such as described in the previously cited OraMetrix PCT application. Tab 454 is a tab by which the user accesses the digital 3D impression of the teeth, obtained from the scanning of the patient. Tab 456 is a case management tab and includes a number of specific available screen displays and menus which are shown in the menu 460 in the lower left of the Figure. The case management tab, and its various features, is described at length in the following discussion. Additionally, there is a digital treatment planning tab 458 which provides further menus, tools and displays by which the practitioner may further move teeth and design the shape and configuration of a customized orthodontic appliance. An example of the types of menus and tools that are available in the tab 458 is the OraMetrix treatment planning software described in application Ser. No. 09/834,412, filed Apr. 13, 2001. However, it is possible to provide, in the workstation, a suite of treatment planning software from different appliance manufacturers in which case the user could access the treatment planning software for whatever appliance manufacturer the practitioner wished to use for treatment of the patient. In this situation, it may be necessary to format the tooth data in a format compatible with the appliance design and treatment planning software so as to ensure compatibility between the various systems that may be installed on the workstation.

In FIG. 3, the user has selected a "treatment strategy" icon 461, which causes the display 462 to appear. In this display, there is a field 464 for the user to enter high level diagnosis and problem classification information, for example in the form of text. A field 466 is provided which provides a matrix format by which the conditions relevant to the patient's soft tissue, skeletal, and dental anatomy are entered, each with respect to vertical, sagittal, and transverse positions, again in text form. The display also includes a treatment strategy field 468 where the user will indicate the general, high level approach to treatment, such as any proposed extractions, appliance type, stages of treatment, etc. These fields 464, 466 and 468, along with displayed image data for the patient, assist the practitioner in identifying the constraints pertinent to the treatment planning.

FIG. 3A shows the patient information tab 450, with the slide bar 850 moved next to "history". The screen display shown in FIG. 21A appears, with a field 451 for which the user can enter alerting medical conditions, such as AIDS or HIV infection, epilepsy, allergy conditions, tuberculosis, etc., along with any explanatory data or comment. In field 453, the user is provided with tools to enter general medical condition regarding the patient by clicking on the drop-down menu as shown, and entering any appropriate data or commentary, as shown.

In FIG. 3B, the user has moved the slide bar 850 to the "Examination" icon, which causes the display shown in FIG. 3B to appear. This screen allows the user to enter dental examination data in field 455, a tooth chart 457 where the user clicks on a particular tooth and enters tooth data in fields 459, 461 and 463 as indicated.

After the user has entered the information into the fields 464, 466, 488 shown in FIG. 3, the user clicks on one of the other icons in the field 460 to continue the process of case management and initial treatment planning. At this point the information entered into the fields of FIG. 3 is stored in the computer memory of the workstation.

Figure 4:
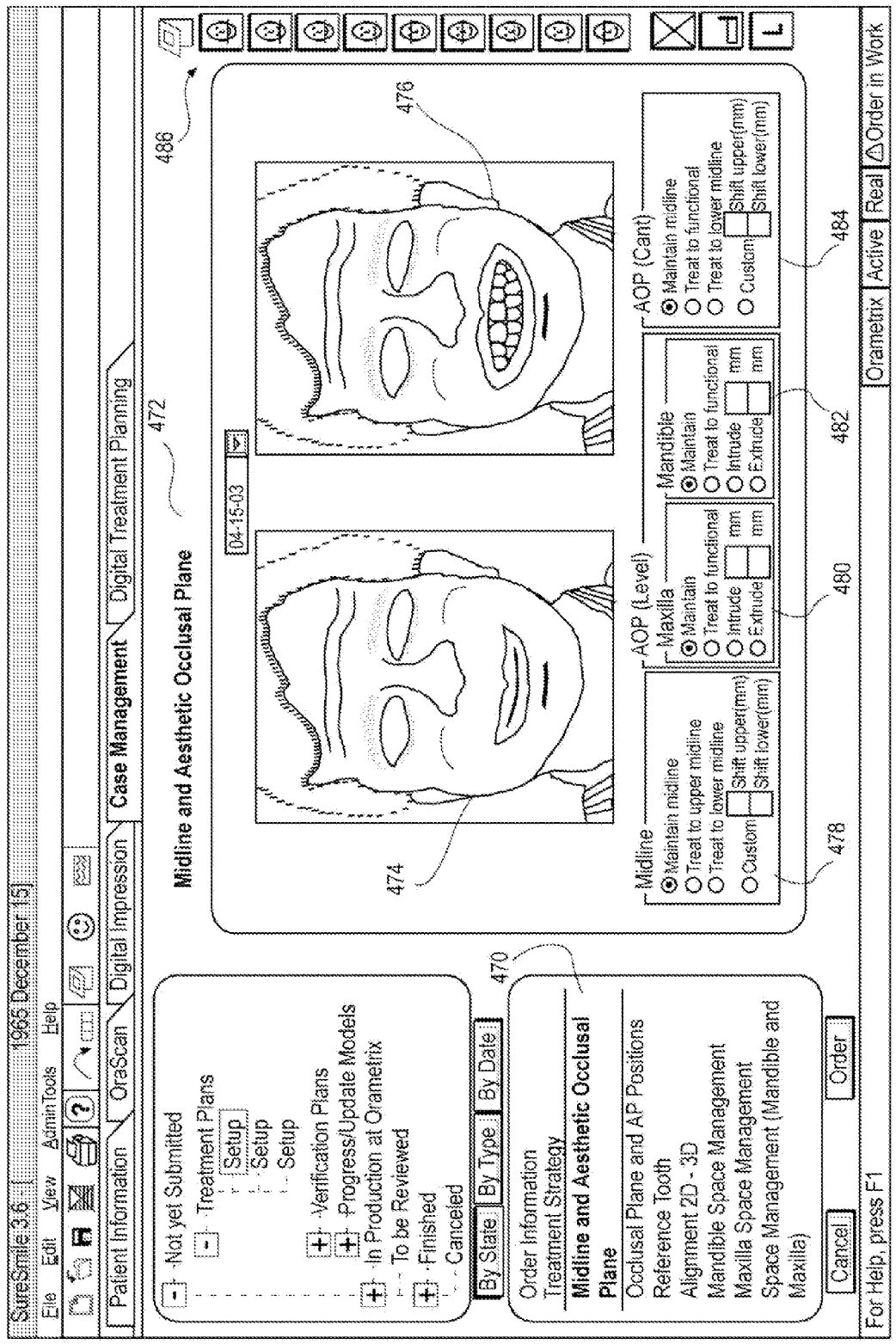

In FIG. 4, the user has now selected a "Midline and Aesthetic Occlusal Plane" icon 470, which causes the screen display 472 to appear. The user uses this screen to evaluate and define both vertical and horizontal lines of references such as soft tissue midline, interpupilliary line, etc and also define the dental midlines for the upper and lower dentition and the aesthetic occlusal planes for both the upper and lower arches and cant of the occlusal planes. These midlines and occlusal planes are designed relative to the face, which here is a global reference. These lines are useful references for where you want the patient's teeth to move.

When screen display 472 is activated, the workstation displays a pair of two-dimensional color photographs of the patient, shown as a photo 474 with the patient's mouth closed, and a photo 476 with the patient smiling. The display includes a field 478 where the patient can maintain the midline that the user marks on the images, as described below, or activate one of the other tabs indicating treat to upper midline, treat to lower midline, or provide a custom midline. The midline is entered using the tools 486 on the right hand side of the screen A region 480 is provided for the Aesthetic Occlusal Plane (occlusal plane for the front teeth), which the user can indicate or mark on the images of the patient using the tools 486 on the right hand side of the screen. The user marks an Aesthetic Occlusal Plane (AOP) for both the maxilla and mandible dentition, and the user is provided with fields 480 and 482 for customization of these planes (technically, lines in two dimensions). A tab 484 is provided to create a customized canted AOP with various tabs as shown. Thus, the tools provide the user to mark, among other things, a midline and maxilla and mandible levels and cant of an aesthetic occlusal plane.

The display of FIG. 4 includes a set of tools 486 in the form of icons which, when selected, allow the user to mark on the images various vertical and horizontal lines. For example, the user can mark an upper occlusal plane on the photographs of the upper arch of the patient, a lower occlusal plane (line) in the lower arch of the patient, and marking various positions in the upper and lower occlusal planes, e.g., marking a posterior position of the upper or lower occlusal plane (line in 2D); marking a functional position of the upper or lower occlusal plane; and marking an aesthetic position of the upper or lower occlusal plane.

Figure 5:
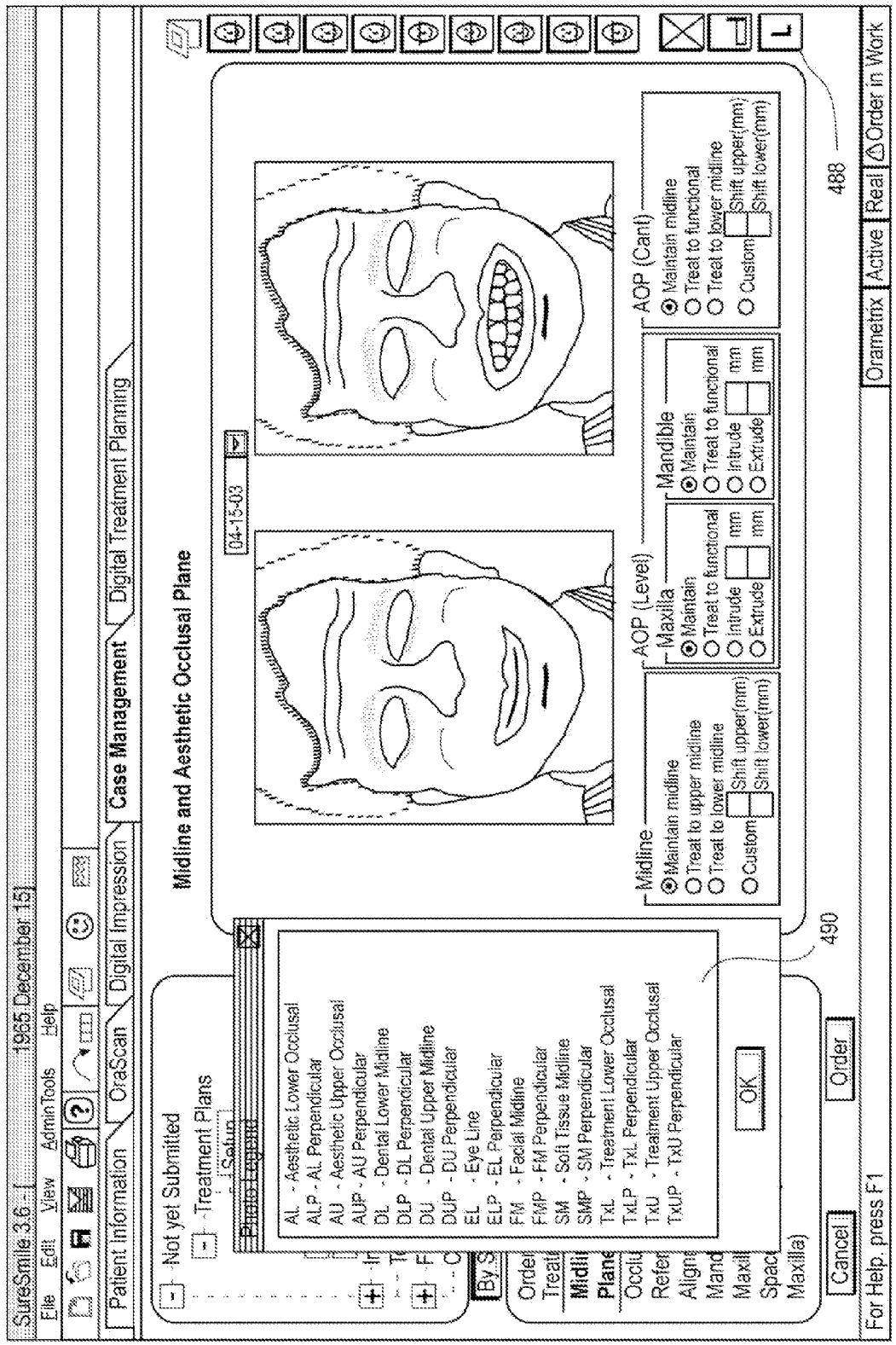

As shown in FIG. 5[, when the user activates the legend "L" icon 488, a window 490 pops up and a legend appears that explains the acronyms for various lines and midlines that the user may mark on the images.

Figure 6:
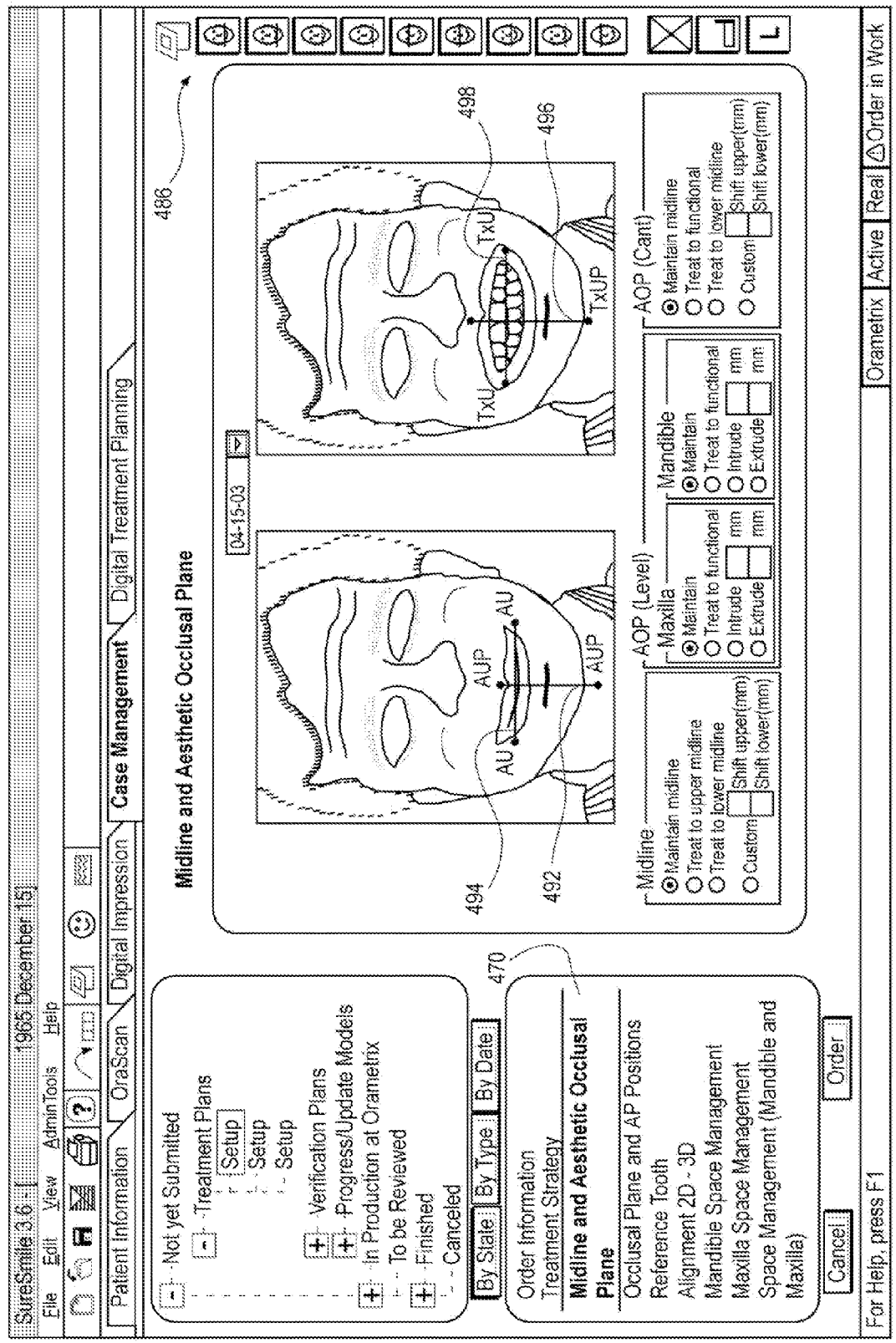

As shown in FIG. 6, the user has activated various icons 486 and has drawn on the virtual model of the patient an aesthetic upper occlusal plane ("AU") 494 and a aesthetic upper perpendicular line ("AUP") 492 in the left-hand image, and a treatment upper occlusal plane ("TxU") 498 and a treatment upper perpendicular line ("TxUP") 496. The lines 492, 494, 496 and 498 are all user specified in terms of their location. The location is selected by using the workstation mouse, moving the cursor to the location where the user wishes to draw the midlines and occlusal planes, and clicking the mouse.

Figure 7:
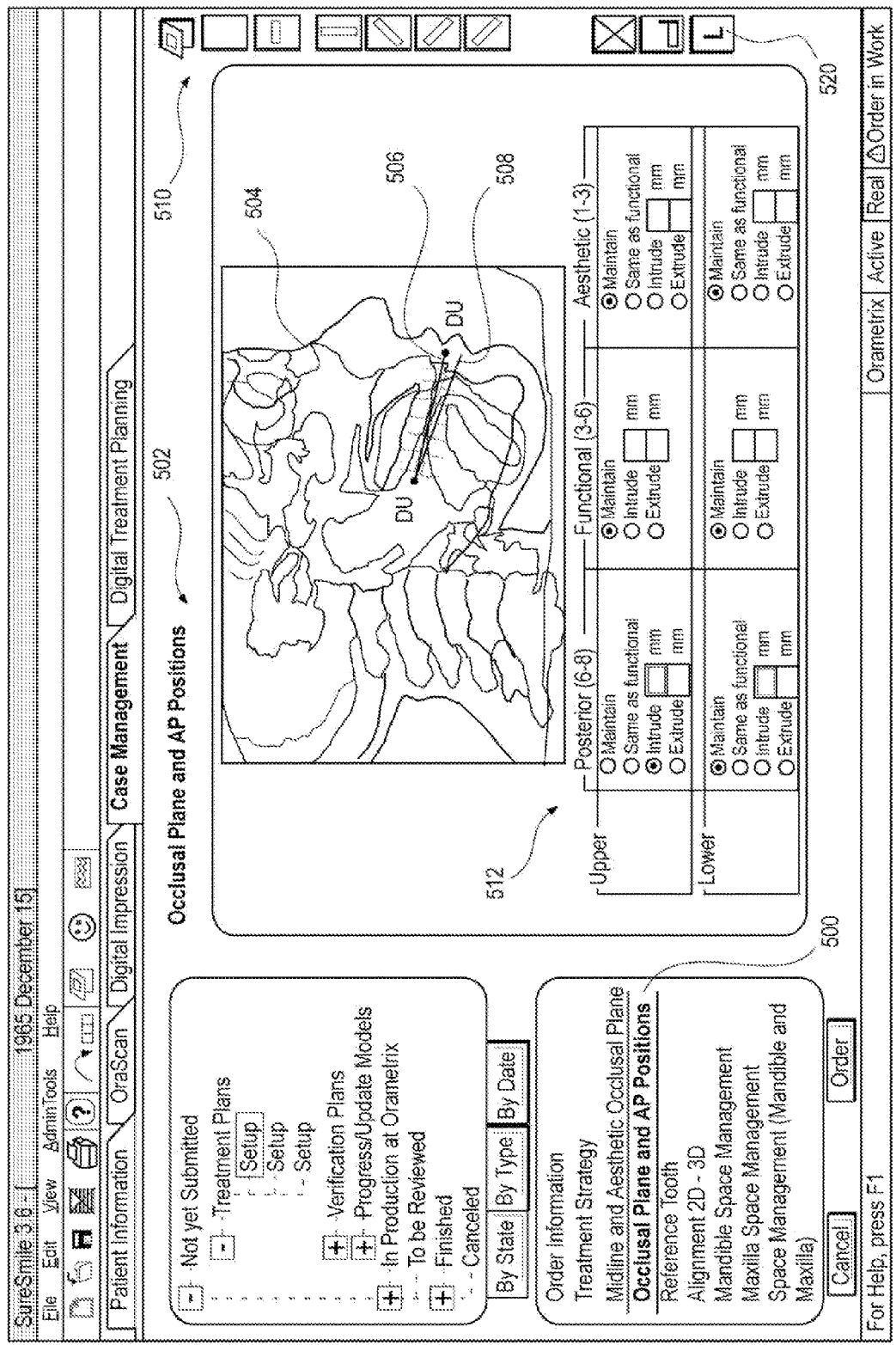
Figure 38:
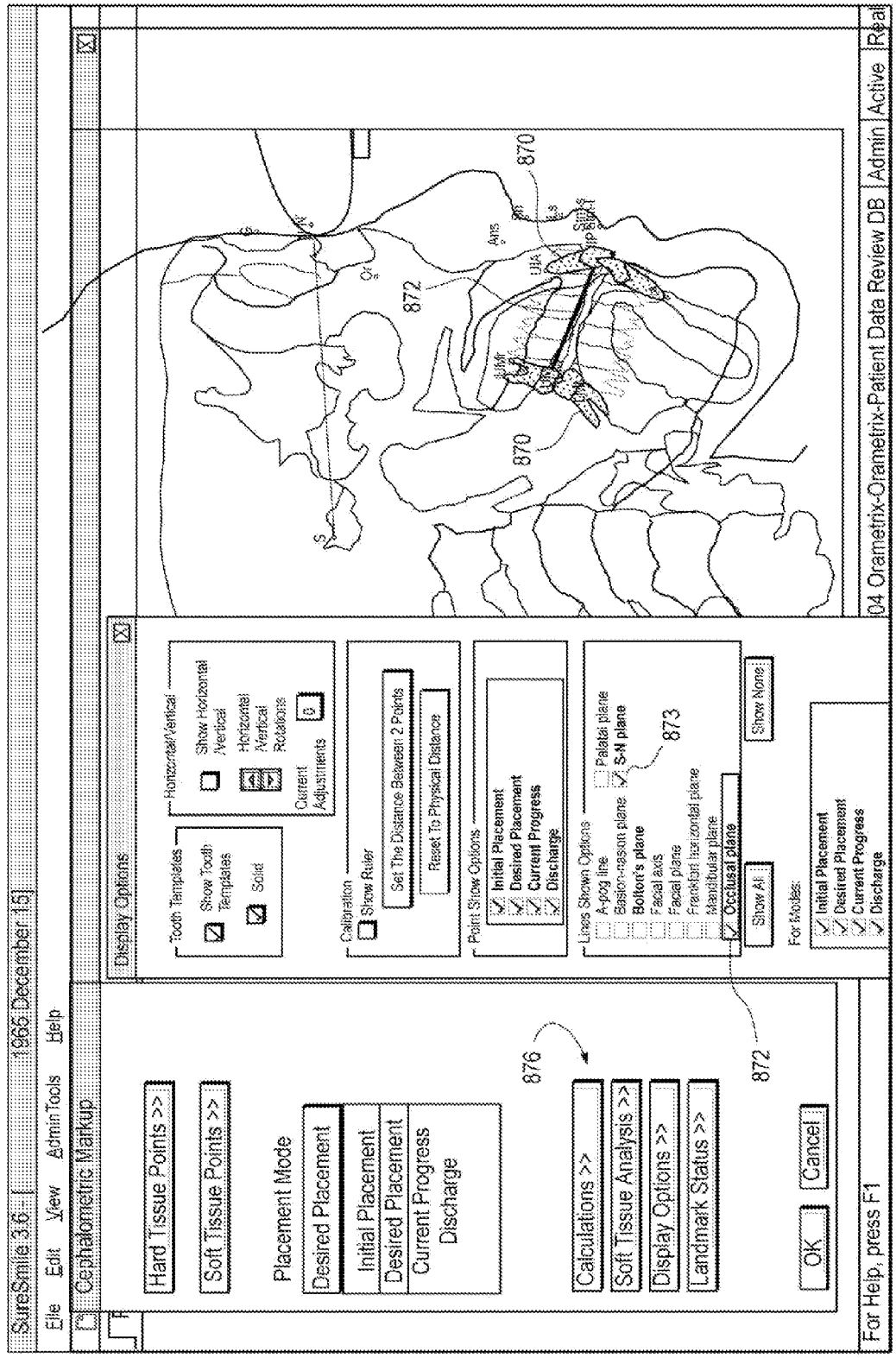

Referring now to FIG. 7, after the user has proceeded to mark the location of midlines and occlusal planes, the user clicks on the icon 500, at which point the "Occlusal Plane and AP (Anterior, Posterior) Positions" screen display 502 appears. The display 504 shows other aspects of the patient virtual model, here a two-dimensional lateral x-ray view of the face, including teeth and jaws. Shown on the display 504 are two of the occlusal planes (line in 2 dimensions) the user has previously entered from the screen display of FIG. 6: a normal occlusal plane ("NO") 506, and a Treatment Occlusal Plane Upper (TxOU) 508, indicating the occlusal plane to which the teeth are designed to be aligned with as a result of treatment of the patient. These lines can be segmented into three separate lines, one for the posterior, functional and aesthetic. The screen display includes a set of icons 510 providing tools for the user to mark various occlusal planes and locations thereof in two dimensions, as well as a Legend icon 520. The display also includes a region 512 whereby the user can modify the location of the aesthetic occlusal plane (front teeth, teeth 1-3), a functional occlusal plane (teeth 3-6), and a posterior occlusal plane (rear teeth, teeth 6-8), for both the upper and lower jaws. The axis of cant of the occlusal plane can be changed by rotating around a predetermined center or fulcrum of rotation. Also, the AP position and inclinations and the vertical relations of the incisors with respect to the occlusal plane can be represented by animating teeth as shown in FIGS. 38, 39A. The desired position of the incisors can be planned. The position of the incisors also drives the change in the position of the soft tissue, e.g. lips. Any changes can be compared against a normative database of positions of various craniofacial structures. A complete 2D cephalometric analysis is thus possible.

Figure 8:
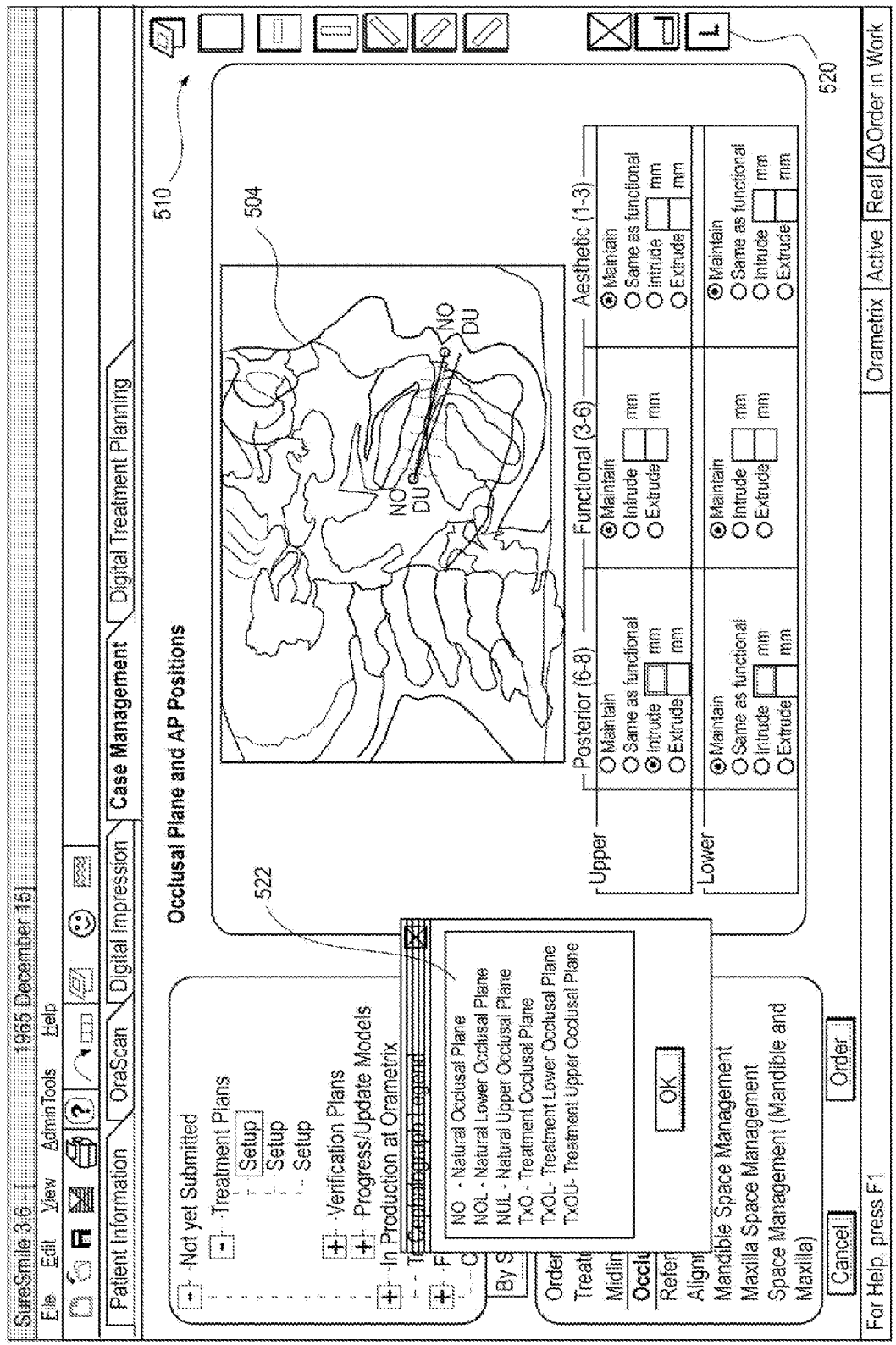

As shown in FIG. 8, when the activates the legend icon 520, the window 522 pops up and provides a legend for the acronyms which accompany the occlusal planes that are shown on the x-ray image 504. The various occlusal planes 522 are accessed by activating the icons 510 at the right hand side of the screen display, and using the mouse to indicate their location on the image 504.

Figure 9:
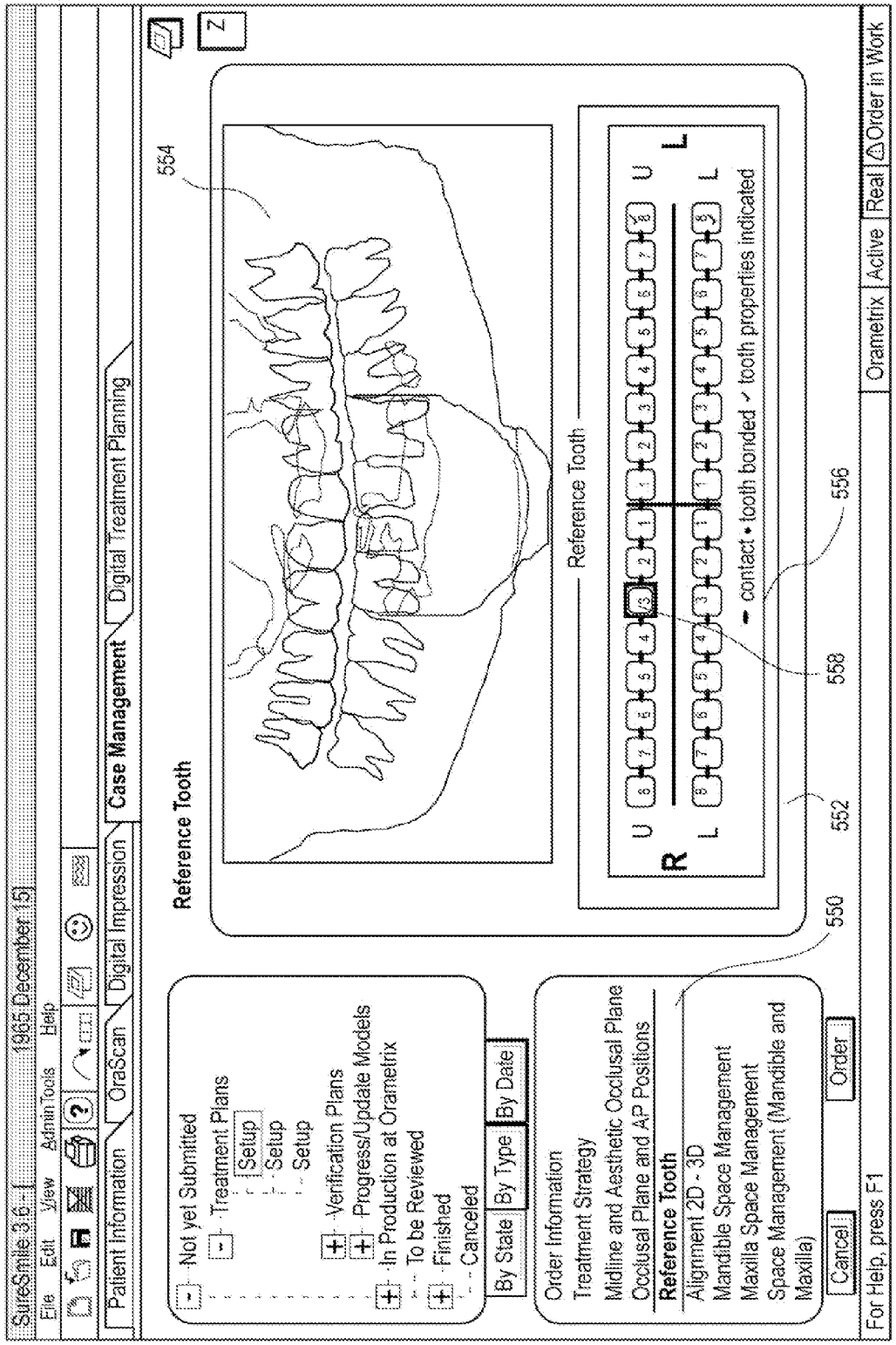

Referring to FIG. 9, the user has finished marking the midline, the occlusal plane(s) and making any anterior/posterior adjustments, and proceeded activate the "Reference Tooth" icon 550. This action causes the display 552 to appear.

The display 552 includes a reference tooth selection field 556. The display also changes to show a panoramic X-ray 554 to appear, showing all of the patient's teeth to appear in a line, along with associated soft tissue and surrounding bone structures. The user makes a judgment decision as to which tooth or teeth should be moved the least (or not at all), and selects this tooth (or teeth) to be the reference tooth or teeth. This action is completed by the user moving the mouse cursor to the tooth or teeth in the field 556 and clicking the tooth they wish to select as the reference tooth. Here, the user has selected tooth 3 on the upper right hand side as the reference tooth, as indicated at 558. Any changes in crown position in two dimensions or root positions are seen and transferred into the three-dimensional data sets.

FIG. 9A shows a screen display with the display showing a flattened 3D x-ray of the teeth flattened such that all the teeth lie in a two dimensional line, with each tooth having a tooth axis indicated by a line segment having one end terminating at the cusp or tip of the tooth and the other end of the line segment terminating at the end of the tooth root. This screen is displayed simultaneously with the field 556 showing the reference tooth selected. The user, having inspected the axes of the teeth and their relationship to other teeth via the X-ray, may select a different reference tooth by simply clicking on a different tooth in the field 556. Typically, the user will select a reference tooth in which the axis of the tooth does not move during the course of treatment, and the displays of FIG. 9 and FIG. 9A facilitates that selection. The screen display of FIG. 9A facilitates the measurement of the tooth axes to make the reference tooth selection.

Figure 10:
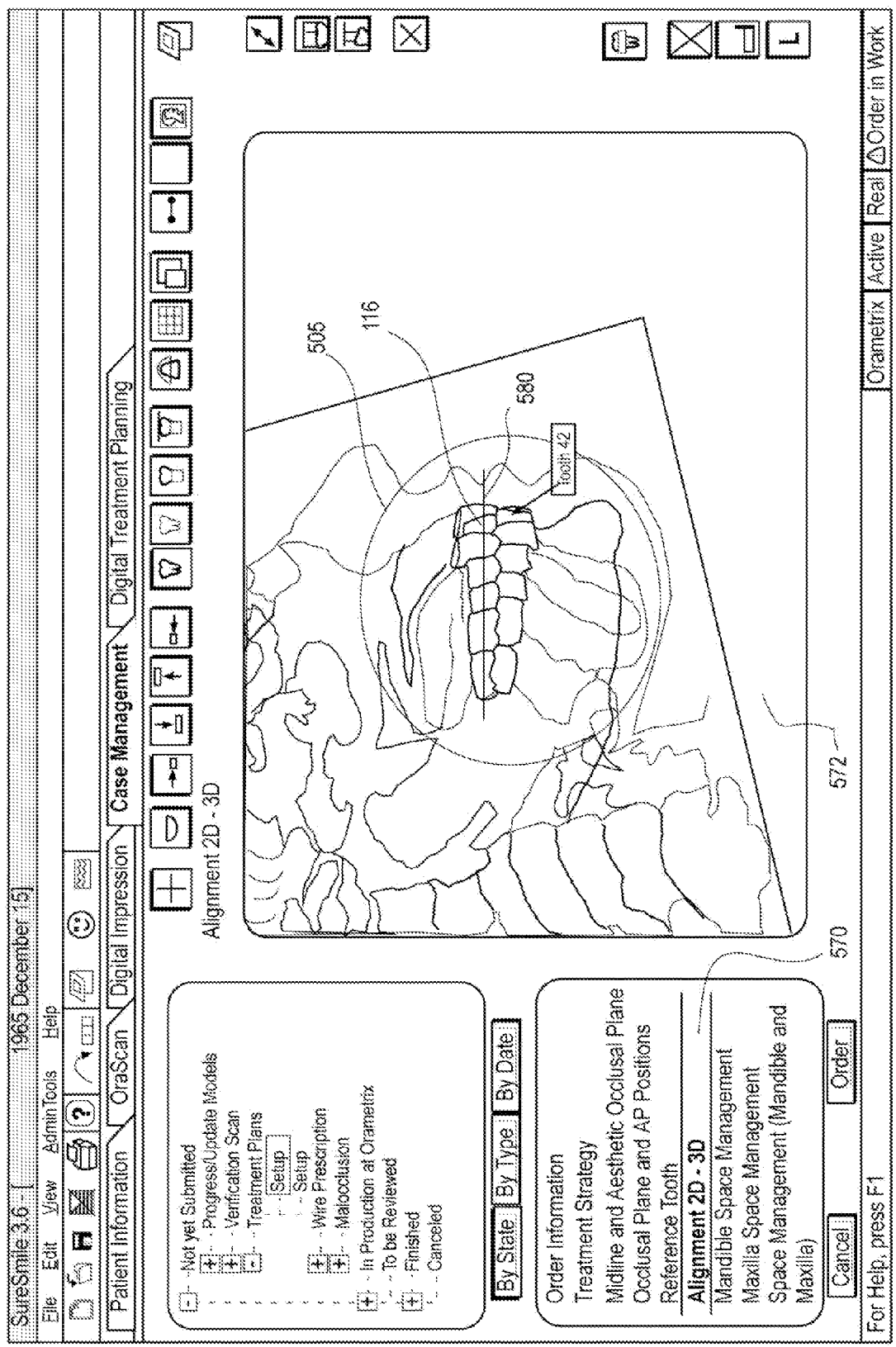

The treatment planning process continues by using the graphical user interface to align two-dimensional images of the patient, e.g. x-rays, with three-dimensional virtual teeth models. In this manner, the user progresses from two-dimensional treatment planning to three-dimensional treatment planning. One possible embodiment is shown in FIGS. 10-13. In FIG. 10, the user has selected the "Alignment 2D-3D" icon 570, which causes the screen display 572 to appear. In this display, a 3D virtual model of the teeth 116 appears on the display, superimposed over a two dimensional X-ray photograph 505. The 3D model of teeth 116 is created by suitable scanning techniques, such as in-vivo scan of the dentition or a scan of a model of the dentition, as described previously. After the scan is obtained, the teeth are separated from the surrounding structures and represented in the computer as individual, individually moveable, virtual tooth objects. The display includes navigation and other icons by which the user can rotate the model 116 in any desired orientation, show only one or both arches, select or deselect for display gingival tissue, occlusal planes, etc. The 3D tooth models are scaled so that they coincide in size with the size of the teeth in the 2D image. The superposition shown in FIG. 10 could be either performed manually, or possibly automatically with suitable pattern matching algorithms to identify tooth objects in the 2D image and align the 3D tooth objects with the teeth in the 2D image.

In FIG. 10, the functional occlusal plane 508 is displayed together with the teeth and the x-ray. Whereas in FIG. 6, the upper occlusal plane was shown as merely a line, in FIG. 10 the occlusal plane 508 is represented in two dimensions but it actually is also represented in three dimensions in FIG. 25. Thus, the original 2D representation is transferred to a surface in three dimensions. The user is able to view the arrangement of the teeth relative to the bone in any orientation, such as front perspective or side perspective.

The arrangement in FIG. 10 facilitates the user understanding the relationship of the 3D teeth with respect to the soft tissues as well as bone. The 3D plan of the teeth can be oriented relative to the occlusal plane 580 that the user has defined.

Figure 10A:
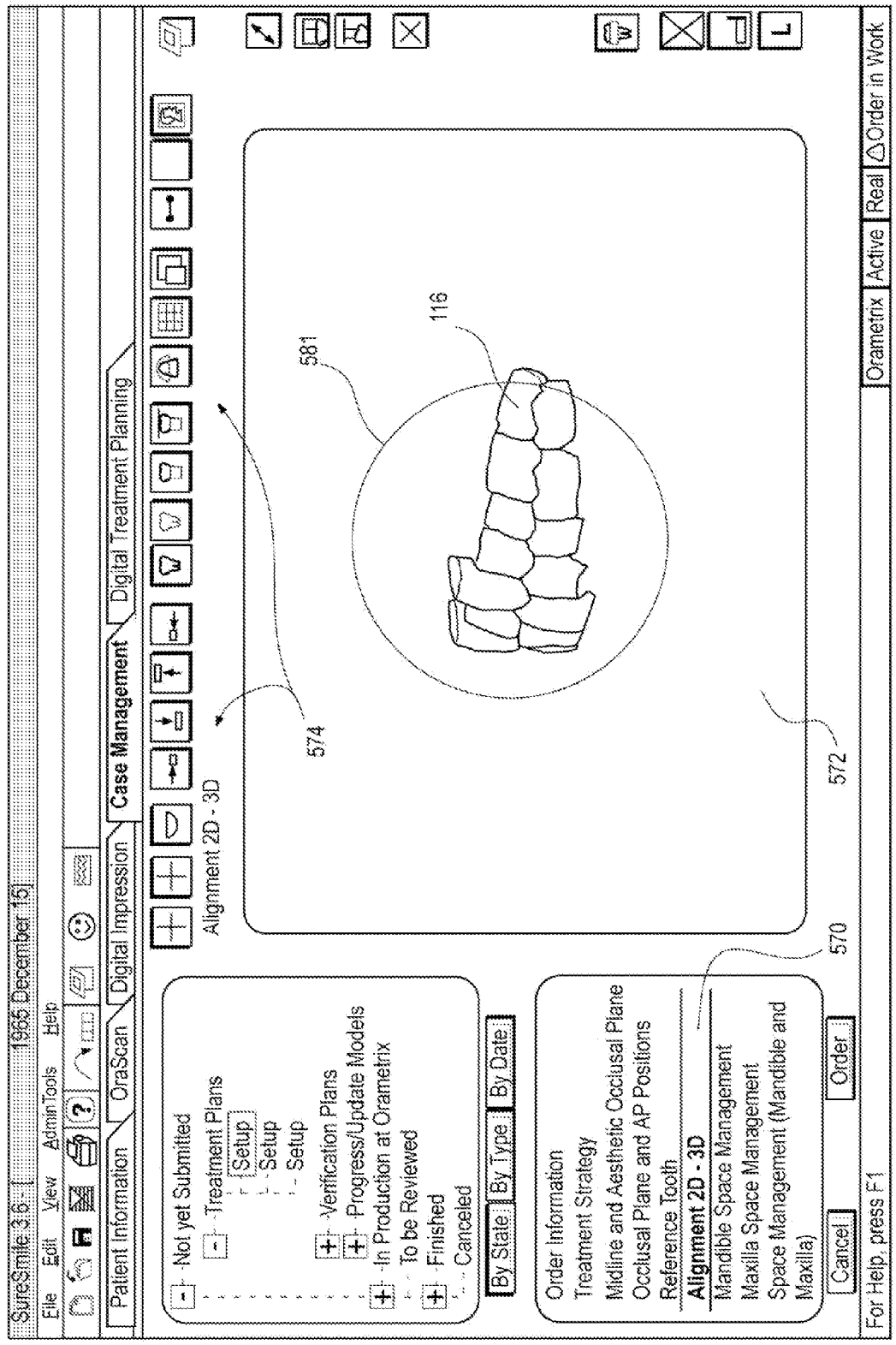

In FIG. 10A, the user has activated icons 574 for display of both arches and a midline plane 581.

Figure 11:
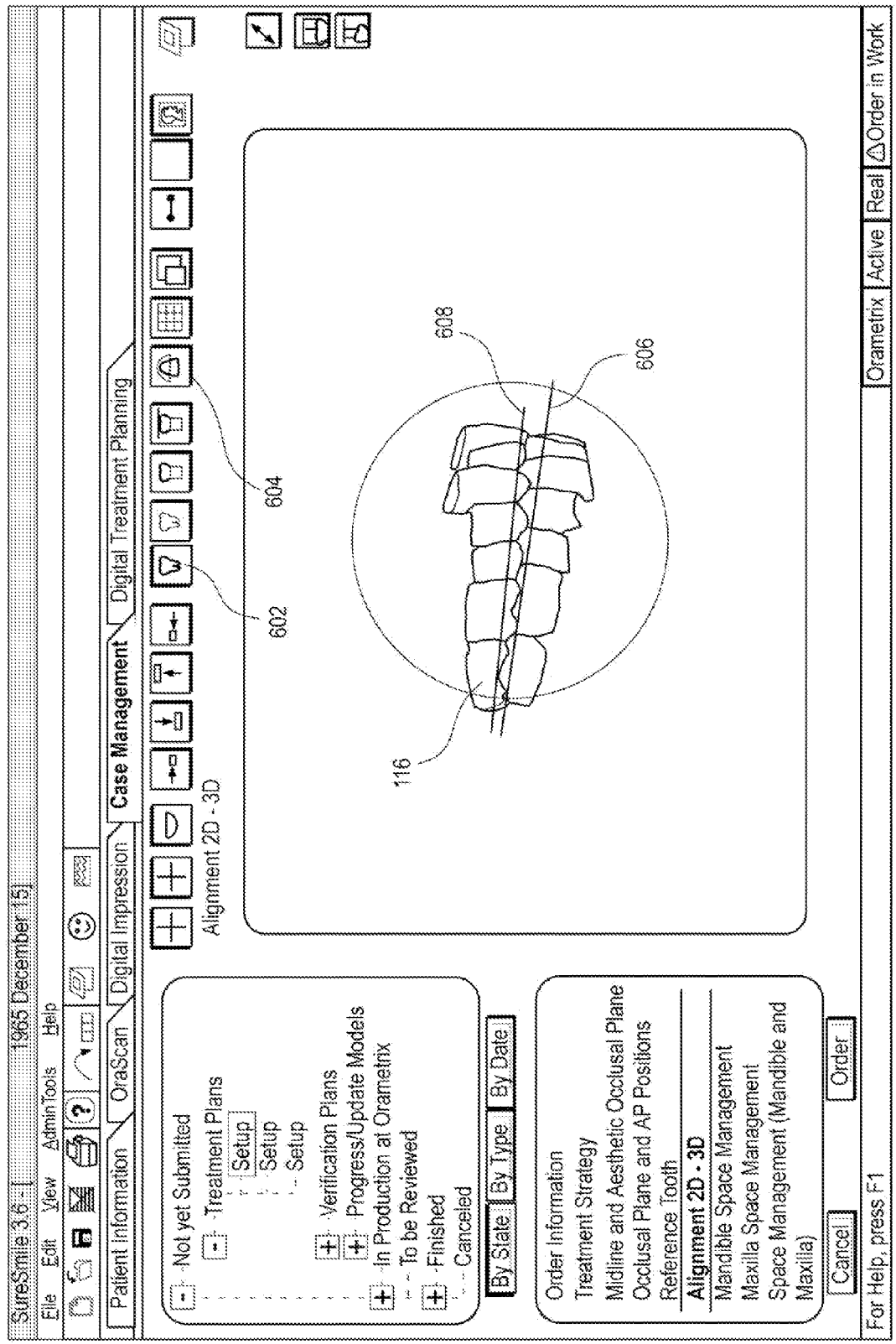

In FIG. 11, the user has selected for display both the upper and lower arches by activation of icon 602, and treatment occlusal planes 606 and 608 for the upper and lower arches. The occlusal planes 606 and 608 are activated by selecting the icon 604. Note that in FIG. 11, the occlusal planes are rendered and displayed in three dimensions as a three-dimensional surface, whereas, initially in FIG. 6, the midline and occlusal planes were rendered in two dimensions. The three dimensionality of the planes 606 and 608 is hard to see in FIG. 11, but becomes more apparent when the model of the teeth is rotated or viewed from an orientation that is not so closely in line with the planes 606 and 608.

Figure 12:
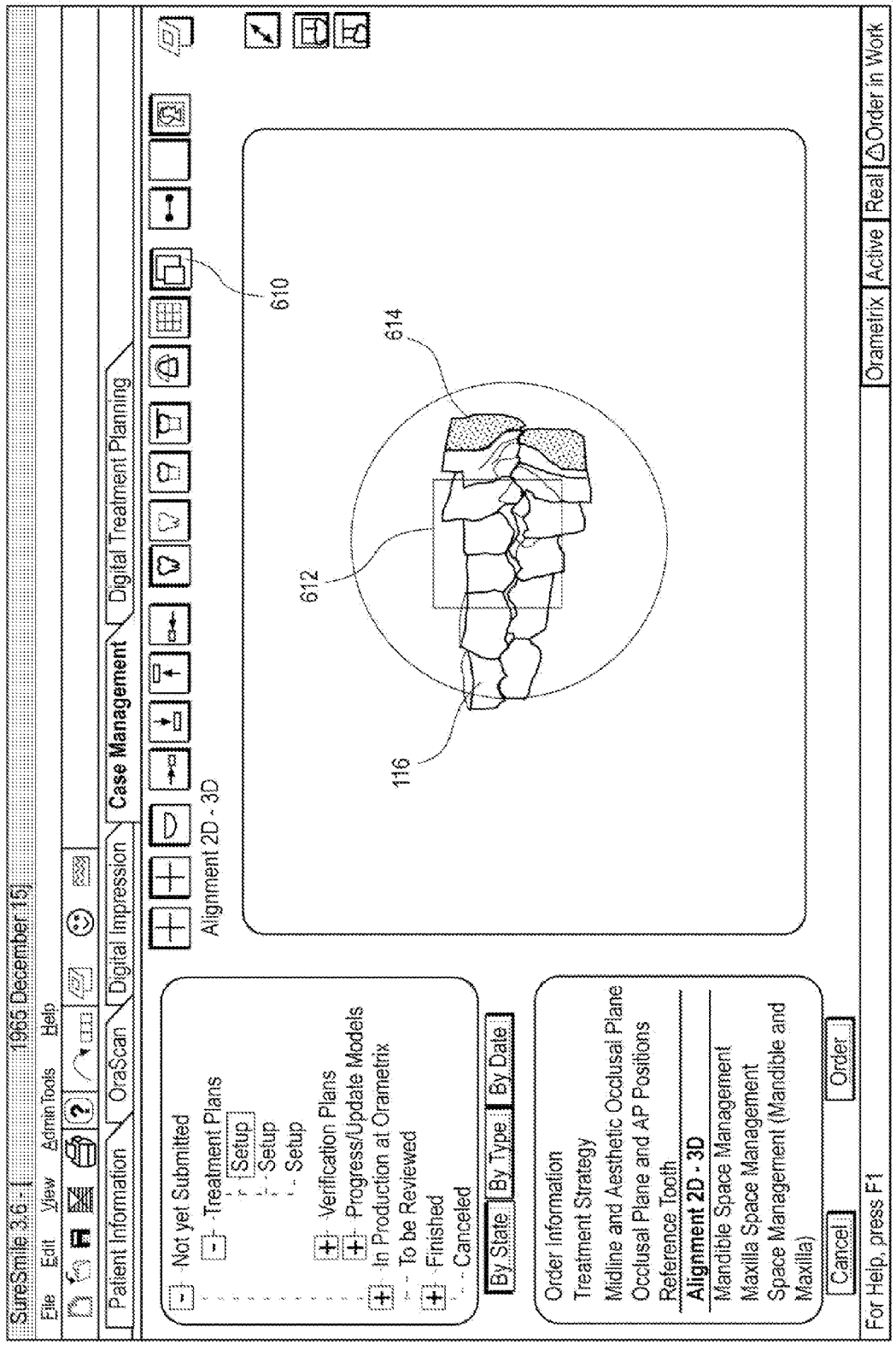

In FIG. 12, the user has activated icon 610 which causes a mid-sagittal clipping plane 612 to appear. The location where the clipping plane 612 intersects the front teeth in the upper and lower arches is shown by the shaded areas 614. The clipping plane can be moved over the arch to view the teeth in any cross-sectional view, using navigation icons. The view shown in FIG. 12 allows the user to judge subjectively the relationship between the upper and lower incisors, and compare that with the 2D views, for example, from a 2D X-ray.

Figure 13:
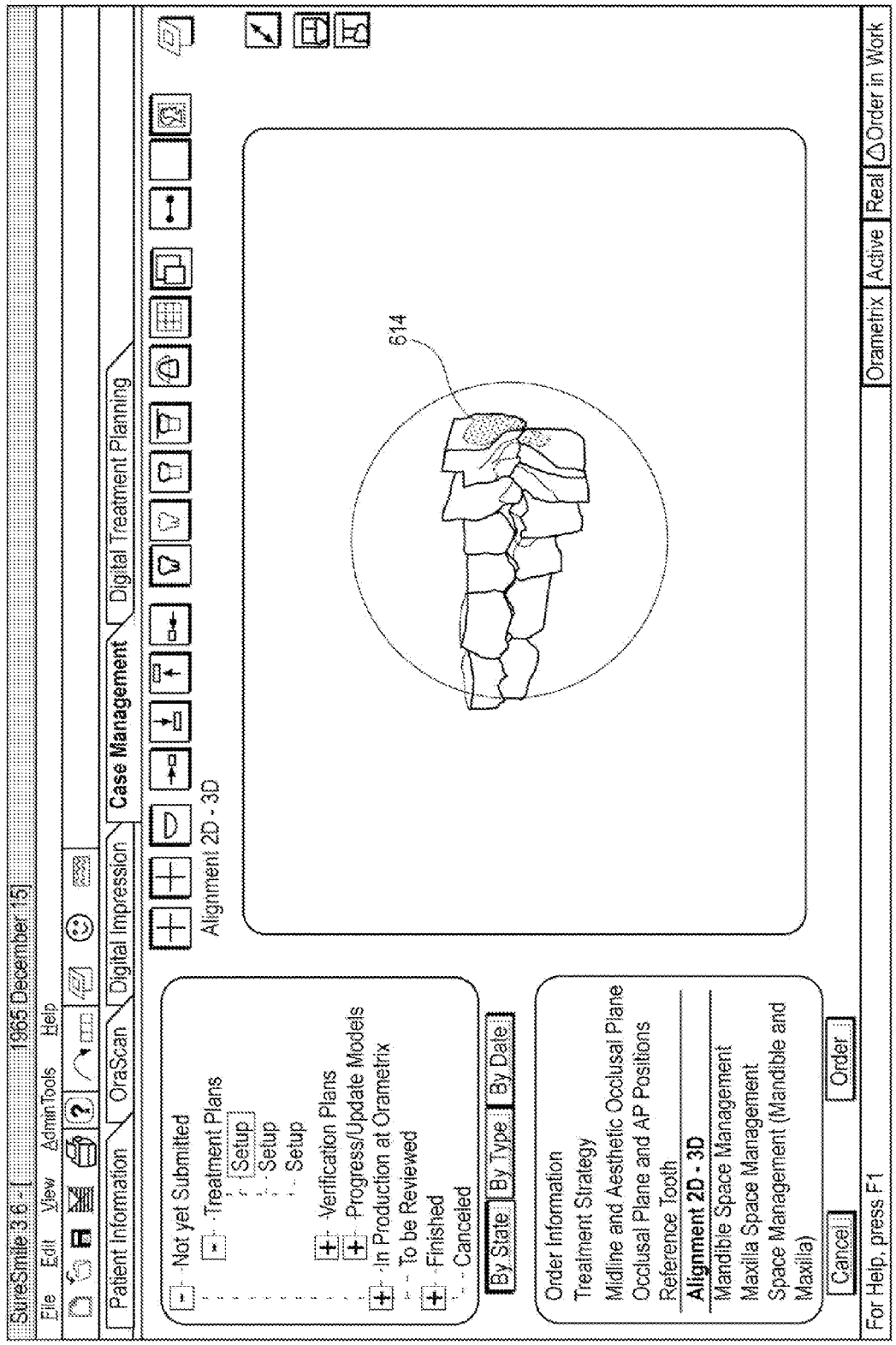

As shown in FIG. 13, the user can adjust the position of the clipping plane and thereby change the location at which the plane intersects the upper and lower arches, as will be appreciated from a comparison of the shaded areas 614 in FIG. 13 with the areas 614 in FIG. 12. The user adjusts the position of the upper and lower incisors in the clipping plane illustration to match the position that was determined in the 2D lateral view in FIG. 39.

Figure 14:
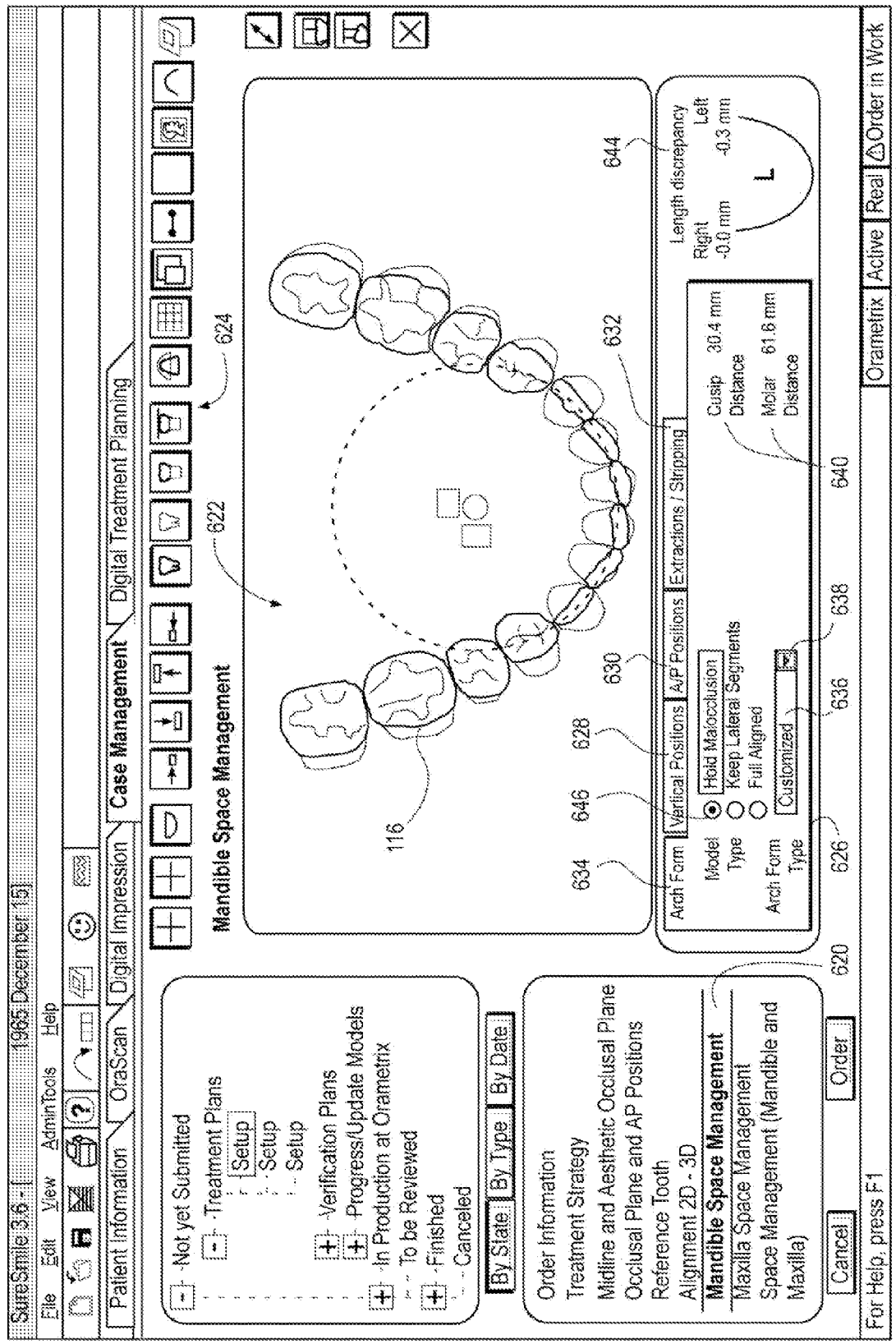

When the user is satisfied with the 2D-3D aligning step, the user proceeds to additional tasks, including space evaluation, and space management tasks by which the user first evaluates how much space is needed to align the teeth and then how he wishes to manage the space. The user further proceeds with the design of a desired arch form. This is done for both arches, typically the mandible first and then the maxilla. However, at any time the user can view both arches together by activating a hide/display icon. To proceed to these tasks, in the illustrated embodiment, the user selects a mandible space management icon 620, as shown in FIG. 14, which causes the screen display 622 to appear. The screen display 622 includes a plurality of icons 624 which are used for hiding and displaying various aspects of the virtual patient model, soft tissue, occlusal planes, and other features of the software. The central region of the display 622 is used to display the 3D virtual teeth 116. The display 622 also includes a lower region 626, where the user can activate an Arch Form tab 636, as shown, or other tabs, including a Vertical Positions tab 628, a AP positions tab 630, and an Extractions and Stripping tab 632. The arch form tab 634 includes an area indicating that the user has selected a customized arch form. However, by activating the drop down icon 638, the user can scroll through and select pre-defined arch form types that are stored in the workstation, and adapt tooth position to standard arch forms. At all times, the user is able to interactively move any tooth or teeth on the graphical user interface relative to the desired arch form, by clicking the tooth to select the tooth and then dragging the tooth with the mouse to a new position.

Space analysis can be dynamically evaluated by affecting the following parameters: midline, arch form, AP position, tooth position, the reference tooth, tooth size, spatial distribution of the teeth in the arch and by appliance prescription, either selectively or in tandem. Furthermore, space management can be effectuated by simulation of interproximal reduction, buildup of the tooth, extraction, distal and mesial tooth movement, expansion of the jaw, axial inclination angle change, rotation change, overjet and overbite change, appliance choice, adjustment of inter-arch relationship, or selectively maintaining crowding.

The tab 634 further includes measurement tools 640 which provide cuspid distance measurements and inter-molar distance measurements for the current tooth positions displayed on the screen. The user can also set points anywhere on the virtual model and activate an icon to get a distance measurement, or invoke a graph tool as described elsewhere. FIG. 14 also shows a display 644 that provides an arch length discrepancy measurement (in terms of mm) which indicates, given the current virtual tooth positions, whether there is sufficient length in the arch (positive values) or whether some interproximal reduction, tooth rotation, extraction, distal movement of the molars, uprighting of the molars, changing of the torque of the teeth, changing the AP position of the incisors, expanding the arch form, maintaining selective crowding, adjusting the level of the occlusal plane or the midline, axial inclination of teeth, overjet or overbite or other action is required to fit the teeth in the arch (negative values). The left-right balance in the arch length discrepancy can be changed by interactively selecting the midline and moving the midline either to the right or left.

Figure 15:
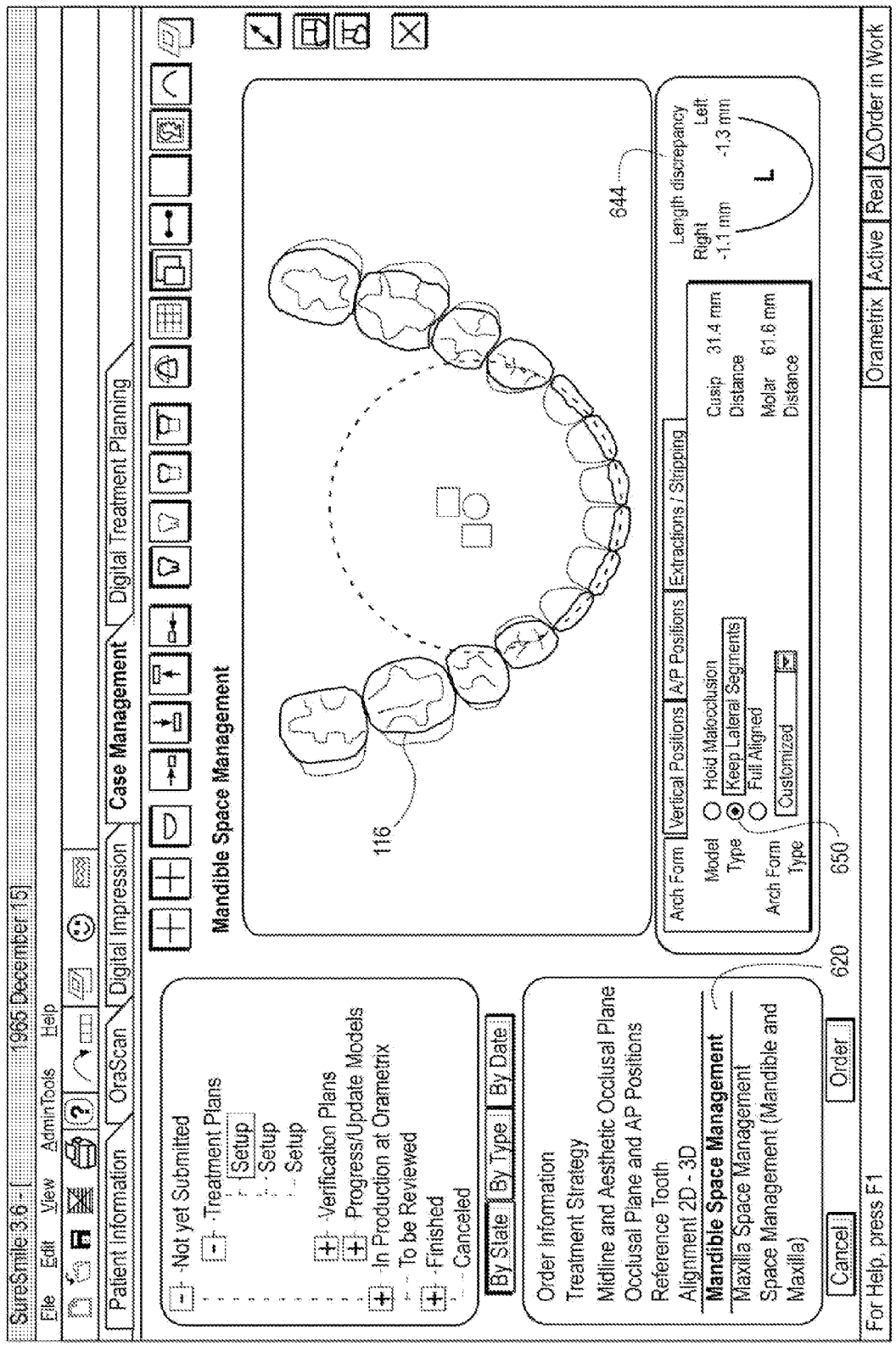

In FIG. 14[, the present malocclusion is seen. The user has indicated that they wish to hold the malocclusion as indicated at 646. In FIG. 15, the keep lateral segments tab 650 has been activated. This feature immobilizes the lateral segments (premolars and molars) and allows for the alignment to occur only through the change in the arch form anteriorly. The user can define the incisor position based on the lower incisor and where it was initially. The user can hold the buccal segment (basically holding the lateral segments) then impose no movement and you allow for full alignment of the anterior teeth. What this has done is tell the practitioner how much space is needed in the arch length and at the same time the display provides the inter-molar and inter-cuspid width based upon holding the posterior teeth fixed. In other words, as the user changes the constraints in terms of tooth mobility, the user is provided instantaneous measurements in terms of arch length and the new positions of the teeth that are allowed to move. The user can selectively immobilize teeth or allow their free movement in three planes of space, either individually or in groups.

The teeth are moved to a more ideal position. This action changed the cuspid distance from FIG. 14, but did not change the molar distance. The length discrepancy tool 644 indicates that the right and left arch length has increased from the previous values, which would require some interproximal reduction, extraction, or some other action to fit the teeth to the arch length.

Figure 16:
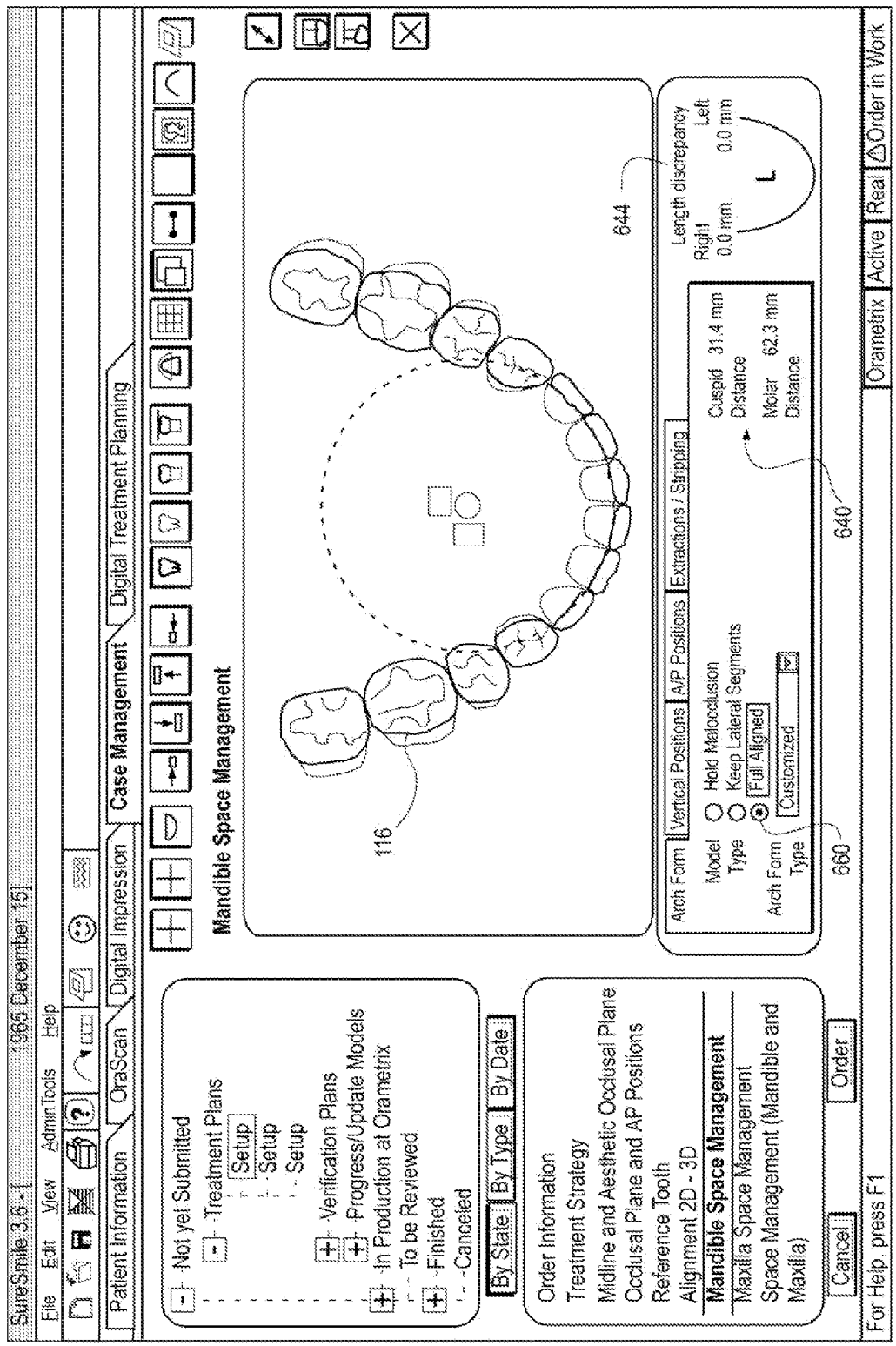

In FIG. 16, the user has selected "full aligned", as indicated at 660. Both the cuspid distance and the molar distance have changed, as indicated by the measurement tools 640. The length discrepancy, as indicated by the display 644, has now returned to zero, indicating that the arch form is "good". "Fully aligned" allows free movement of all the teeth along the pre-selected arch form. If some arch length discrepancy remained, the user could simulate a change in arch form, midline, occlusal plane, rotation of teeth about their axis, extraction etc. to rectify the situation. If the user wants to customize the shape of the arch form they activate the slide line tab, discussed later.

Figure 17:
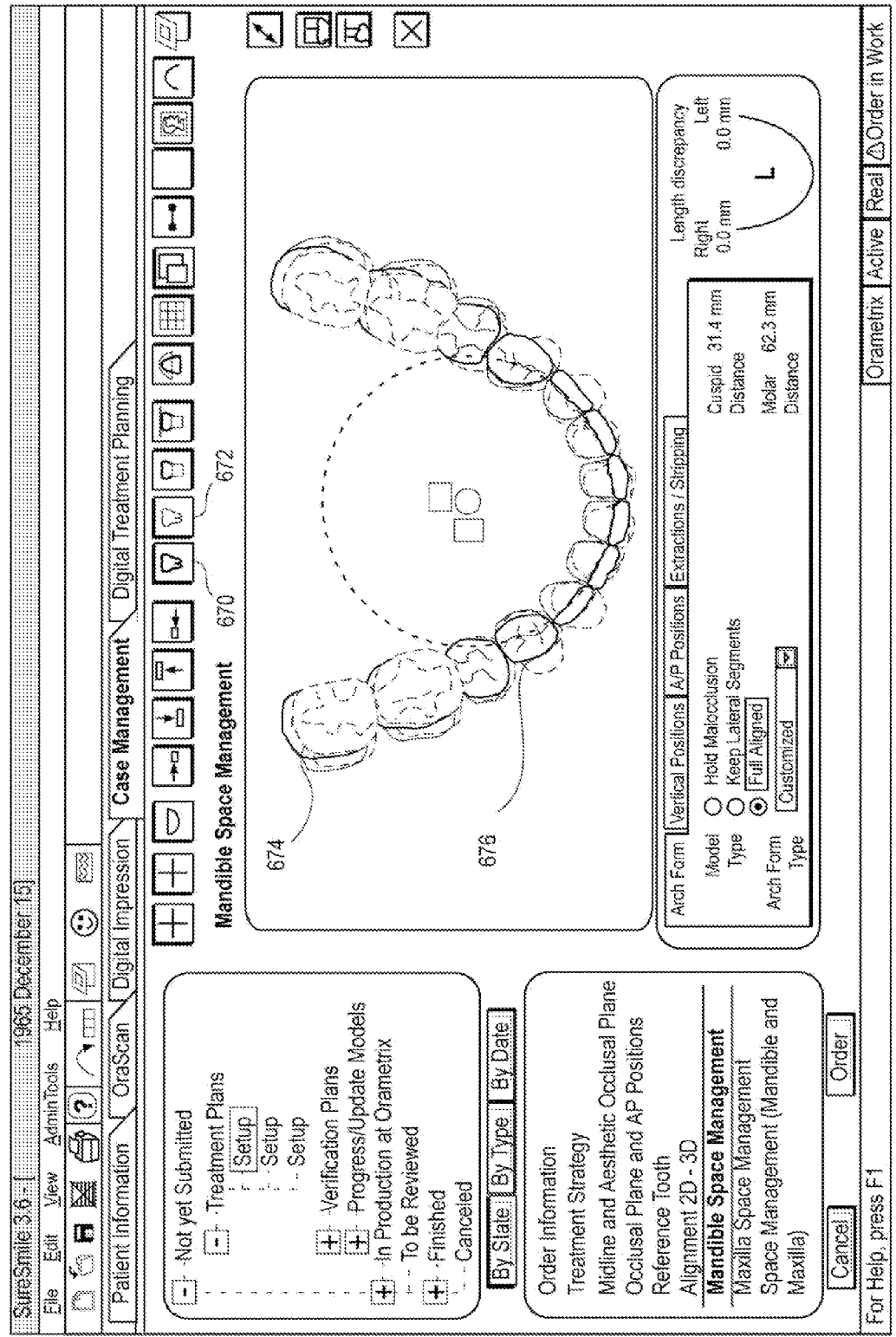

In FIG. 17, the user has activated icons 670 and 672, which causes the display to show both the original position of the teeth (areas with dark shading indicated at 674) and the new position as a result of the mandible space management exercise (white areas, indicated at 676). This color coding helps the user visualize the tooth movement that will occur in accordance with the proposed treatment plan. This feature of reference back to the original malocclusion is available at any time and in any plane, both in 3D or 2D images or combination.

Figure 18:
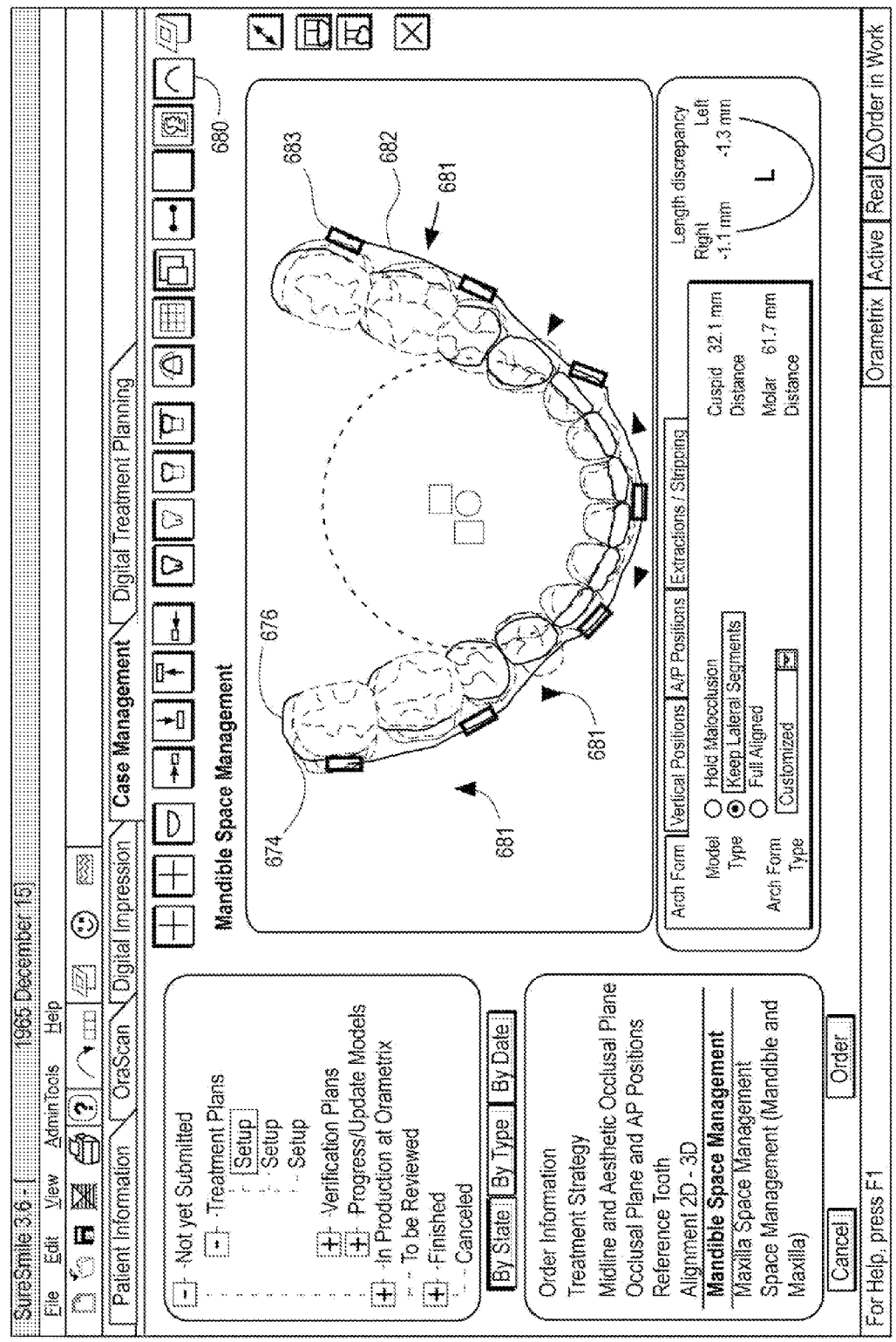

In FIG. 18, the user has activated icon 680 which causes a slide line 682 to appear. The slide line can positioned at different levels, such as the bracket level, the level of the cusp tips, or the level of the interproximal contact points.

Arch length discrepancy can be defined at various levels, including contact points, cusp tips and at the level of brackets, based upon the location of the slide line that is chosen. Then, the effect of bracket prescription on the dentition is also modeled in defining the position of the teeth in the arch, thus providing the clinician with a method of understanding the effects of his appliances on arch length inadequacy.

The slide line 682 is a tool that assists the user in changing the shape of the arch form. The slide line 680 includes anchor points 683 spaced along the length of the slide line 682, which are affixed to labial surfaces of the teeth in the positions shown, The slide line 682 also includes points 681 equidistantly spaced from the anchor points, which the user manipulates to cause the slide line to bow out or in relative to the teeth, and thereby change the shape of the arch form. For example the user would click on one of the points 681 and drag the point 681 out away from the slide line, which would cause the slide line to bow outwardly towards the point 681. The clamping or anchor points can be moved by the user anywhere along the slide line. The slide line (as was the case with the midline) allows for designing asymmetric arch forms. Whenever the user wishes to compare the proposed arch form with the original tooth position, they activate an icon at the top of the screen and the original tooth position is also shown, with the difference in position shown in a contrasting color.

Figure 18A:
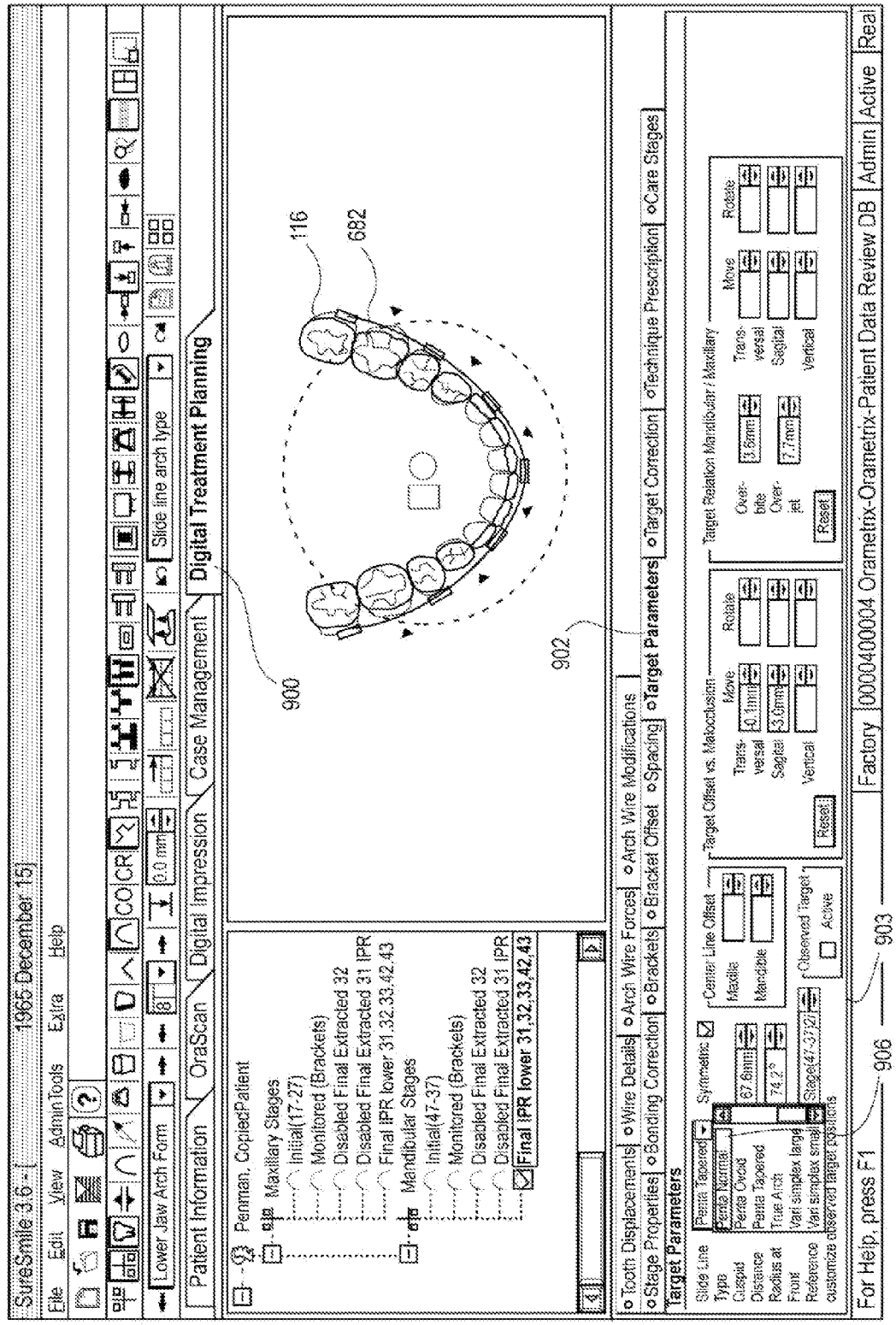

FIG. 18A shows a screen display when the treatment planning icon 900 is actuated. This icon takes the user to addition treatment planning software which enables a user to further define the shape of the arch form, move teeth relative to each other, and design customized appliances. Many of the features shown in the display of FIG. 18A are described in the published PCT application WO 01/8076, and therefore will not be repeated here. The user has highlighted the "TARGET PARAMETER" icon 902, which allows the user to customize the configuration of the desired target arch form. Here, in area 906, the user can scroll through a series of available general arch form types. In field 903, the user is provided with various tools to make the arch form symmetric (or not symmetric), enter in values for transverse, sagittal or vertical movement, or change the relation of the overbite or overjet. As shown in FIG. 36A, the slide line feature 682 is also displayed, which the user can use as described previously to change the shape of the arch using the slide line features.

Figure 19:
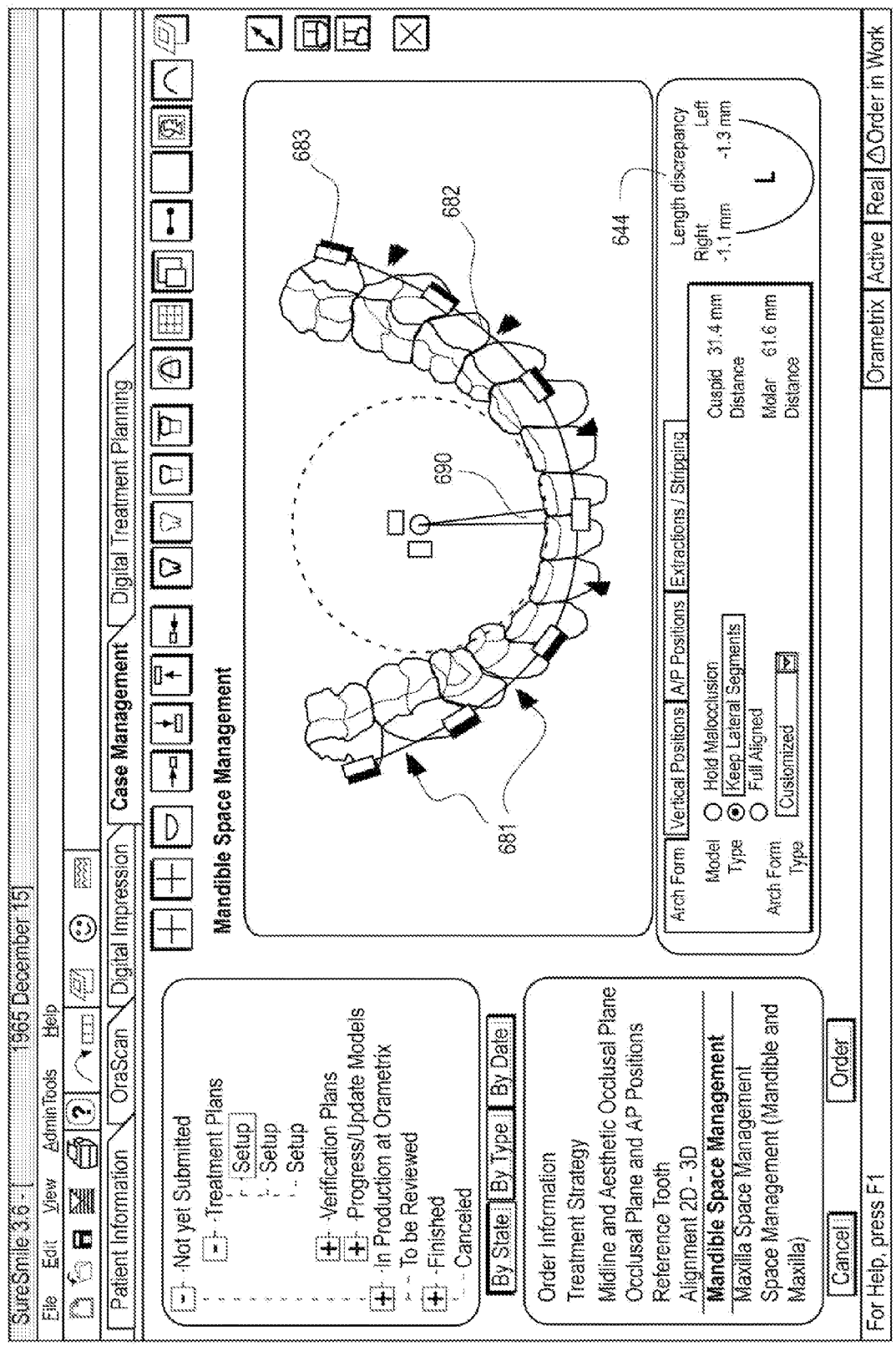

In FIG. 19, the user has activated an icon to show a midline plane 690 to appear. By interactively moving the midline (using click and drag technique), the user can change the orientation of the midline relative to the teeth in the arch and thereby change the right/left values shown in the length discrepancy icon 644. The midline is shifted slightly to the patient's right. The lateral segments are held fixed while the midline shift is only carried out by the anterior teeth. If "full aligned" had been checked the all the teeth would move along the slide line to accommodate the new position of the midline. Note also in this Figure that the new position of the teeth can be measured against the original as indicated by the lightly speckled pattern of the posterior teeth, which indicates little movement of the lateral teeth from the malocclusion position (the difference in position indicated by the dark or shaded spots on the teeth).

Figure 19A:
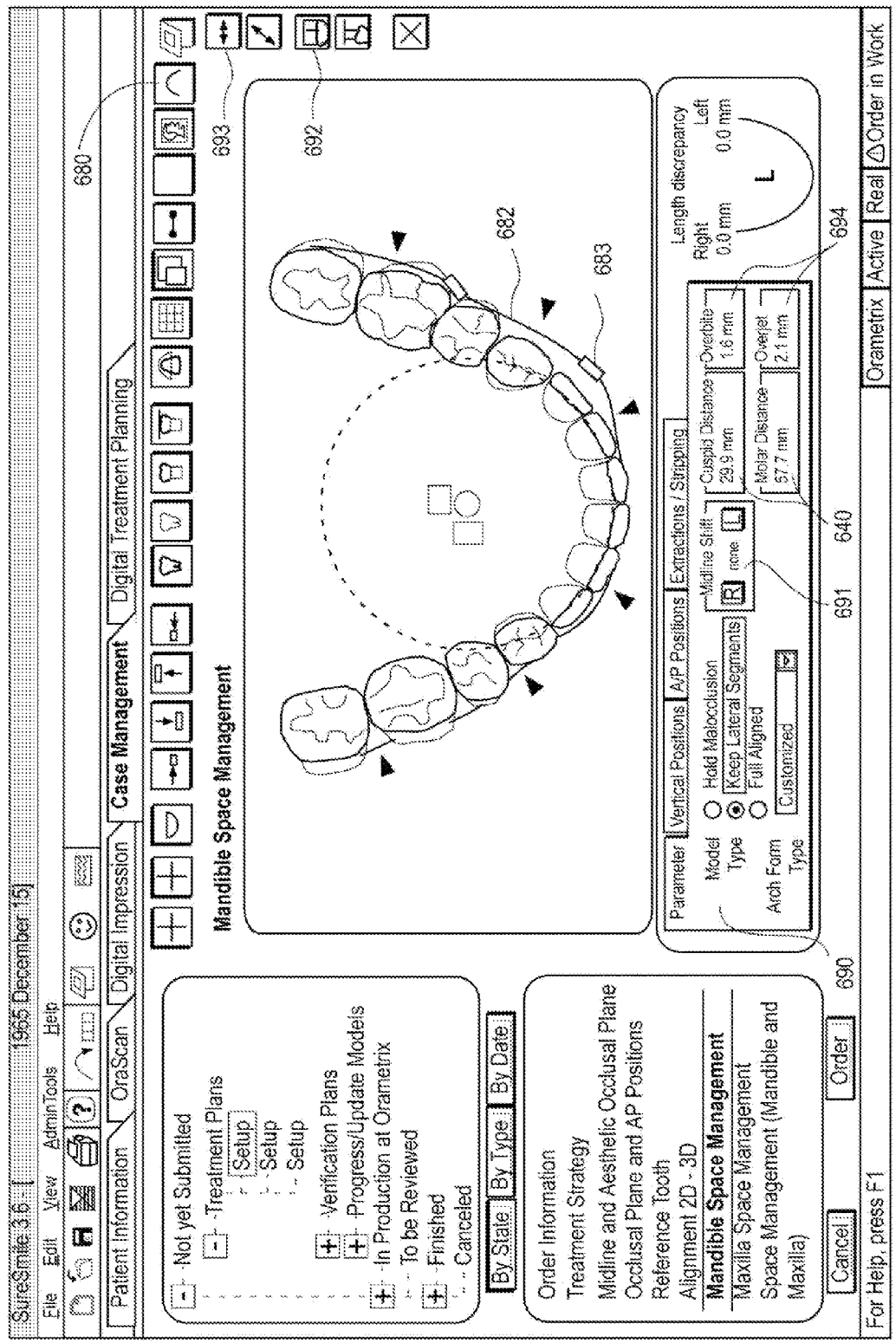

In FIG. 19A, the user has selected a parameter tab 690, which includes icons 691 for midline shift (left or right), the measurement tools providing cuspid and intermolar distance, and a tool 694 indicating the amount of over bite and overjet, given the current configuration. This data is obtainable since the position of the upper arch relative to the lower arch is known in the in the computer, and the position of the incisors in both arches is known in three-dimensional space. Thus, the display allows the user to interactively move the teeth and immediately realize the effect of tooth movement on overbite and overjet. You can also adjust overjet and overbite parameters to see their effect on the arch length inadequacy.

By activating icon 692, the user can manage the spacing between teeth by having all spacing between teeth to be equal. By activating icon 693, the user invokes a collision detection algorithm that prevents the user from moving teeth in a manner such that a tooth collides with another tooth, either in the same arch or in the opposing arch. The software allows for interproximal reduction by morphing the tooth shape to match the available space, using a simple morphing algorithm that shrinks the tooth in two or three dimensions.

Figure 20:
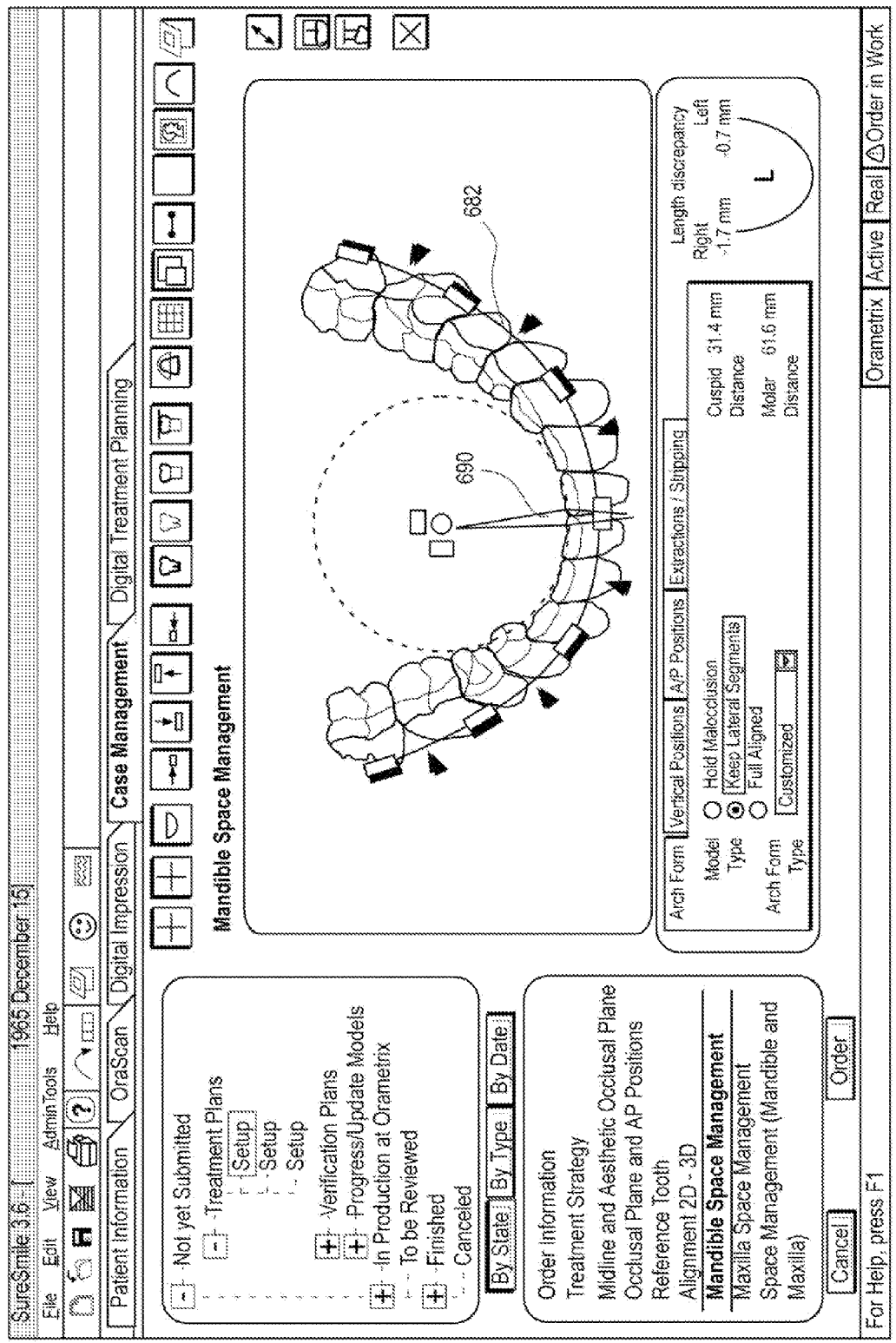

In FIG. 20 the user has invoked the simulation of the midline plane 690. By movement of the midline plane left or right they can correct the length discrepancy (left or right) for the arch.

Figure 21:
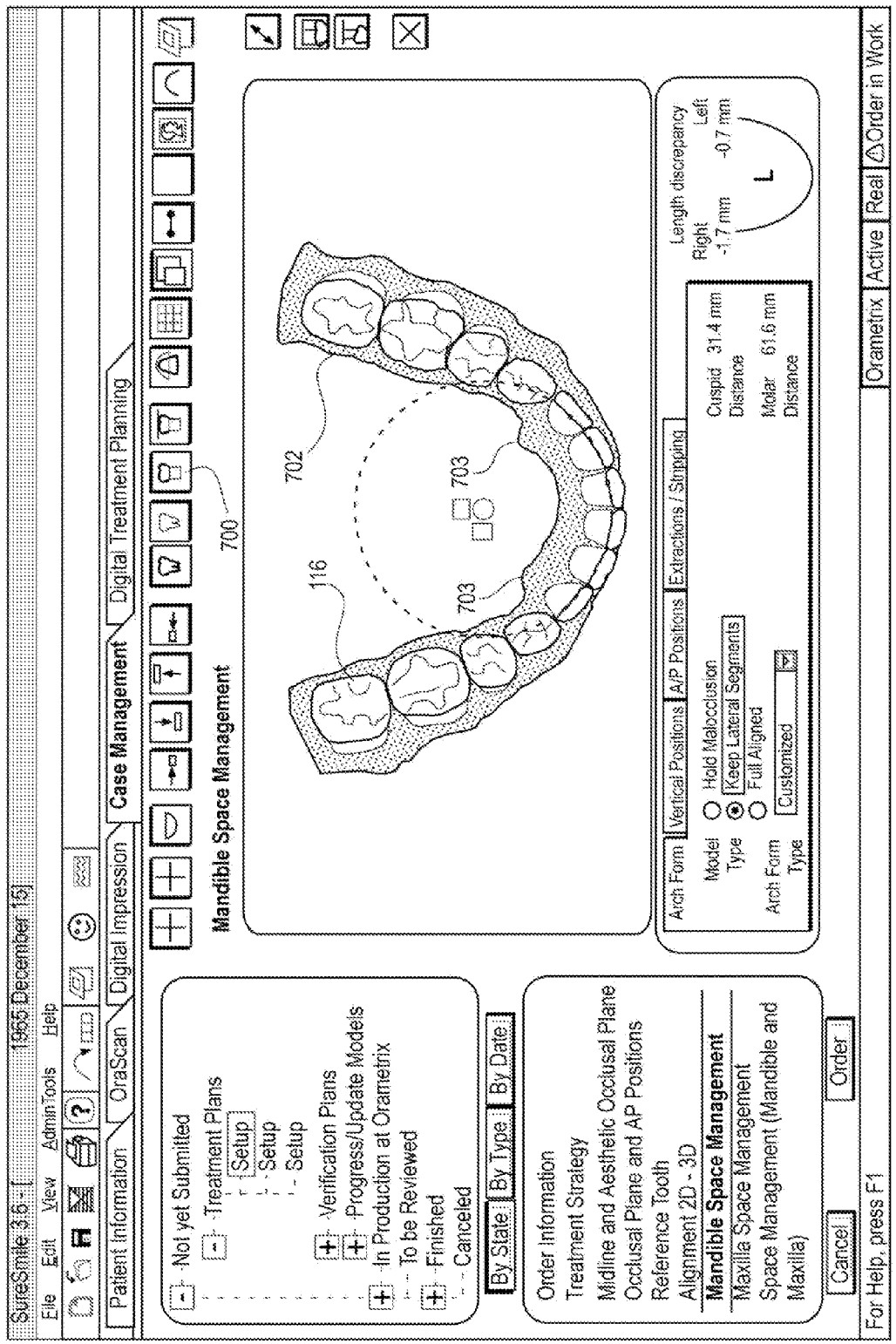
Figure 21A:
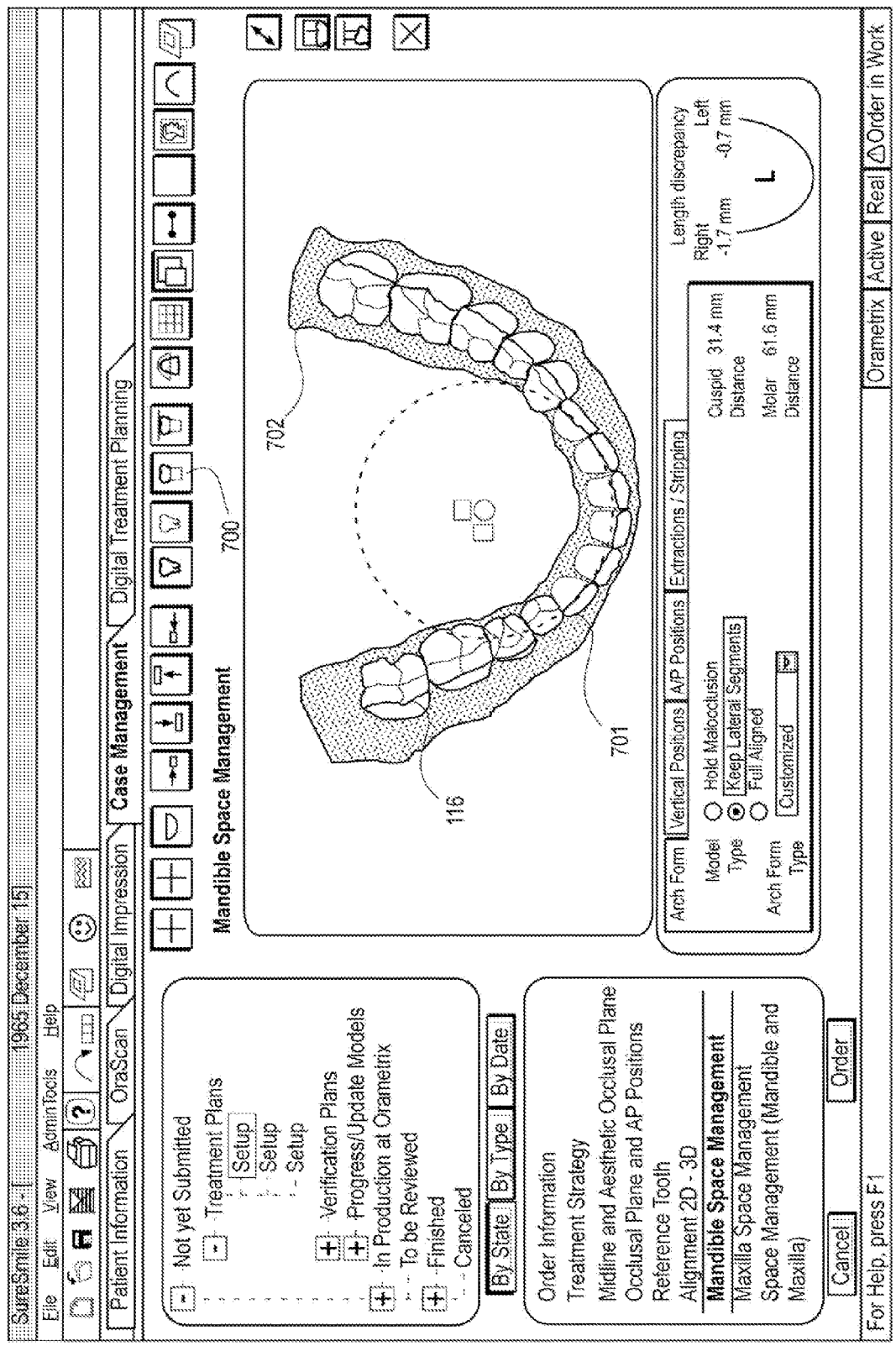

In FIGS. 21 and 21A, the user has activated a gingival display icon 700 which causes the display to show both the 3D virtual teeth 116 and a 3D model of the gingival tissue 702. This icon can be activated at any time in the space planning screen. The model 702 of the gingival tissue can be obtained from a scan of the patient's mouth with an intra-oral 3D scanner as described previously, or it could be obtained from a scan of a physical model of the patient. The gingival tissue 702 is separated from the scan data of the teeth 116 so that the two types of objects can be modeled as separate 3D objects and thus displayed either alone or together. In FIG. 20, the proposed treatment indicates substantial bumps 703 on the lingual side of the teeth. The gingival tissue is morphed to show the effect of tooth movement to this position on the gingival tissue. Since gingival tissue closely follows the underlying bone, the bumps 703 may indicate that the proposed tooth movement is incompatible with the patient's mandible bone structure. This could be confirmed for example by zooming in on the location of the bumps 703, invoking the display of underlying bone structure from an X-ray or CT scan stored in the workstation, and examining the superposition of the virtual tooth over the underlying bone. In FIG. 21A, the user has moved tooth 701 slightly and the gingival tissue 702 "morphs" to follow the position of the tooth.

Figure 22:
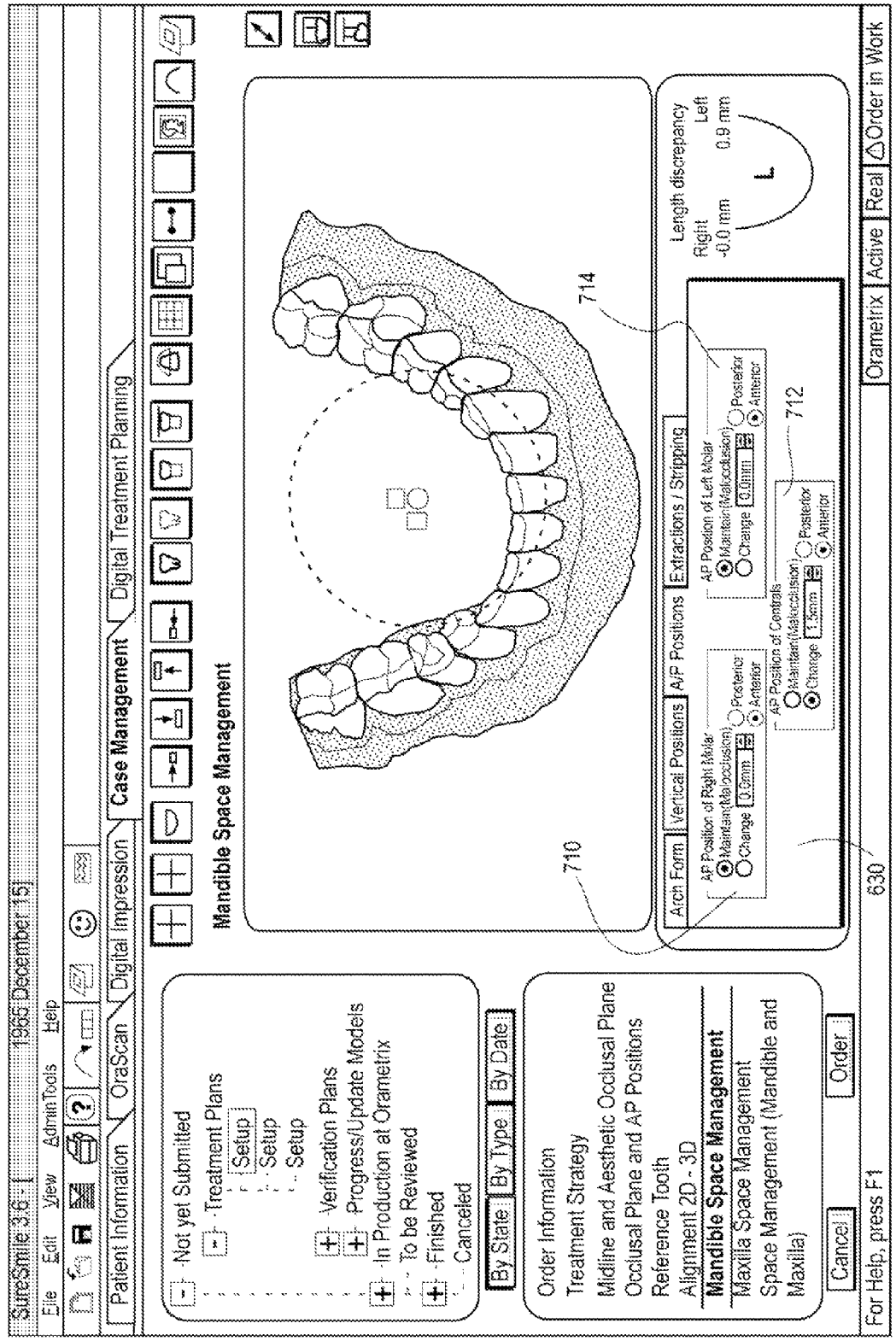

In FIG. 22, the user has activated navigation icons on the display to rotate the model of teeth+gingival tissue to a new orientation. The user has also activated the AP positions tab 630, which allows the user to constrain either a singular movement of teeth or a group movement of teeth in the AP direction. The display shows a field 710 which allows the user to either maintain or interactively change the AP position of the right molar, a field 712 that allows the user to interactively change the AP position of the central incisors, and a field 714 that allows the user to interactively change or maintain the AP position of the left molar. As shown in FIG. 22, the user has interactively changed the anterior position of the central teeth by an amount of 1.5 mm, and the change is simulated by moving the central teeth anterior wise by 1.5 mm and keeping the back teeth fixed and showing the new position on the screen display. The 1.5 mm movement may not be sufficient given the 0.9 mm arch length inadequacy remaining.

Figure 23:
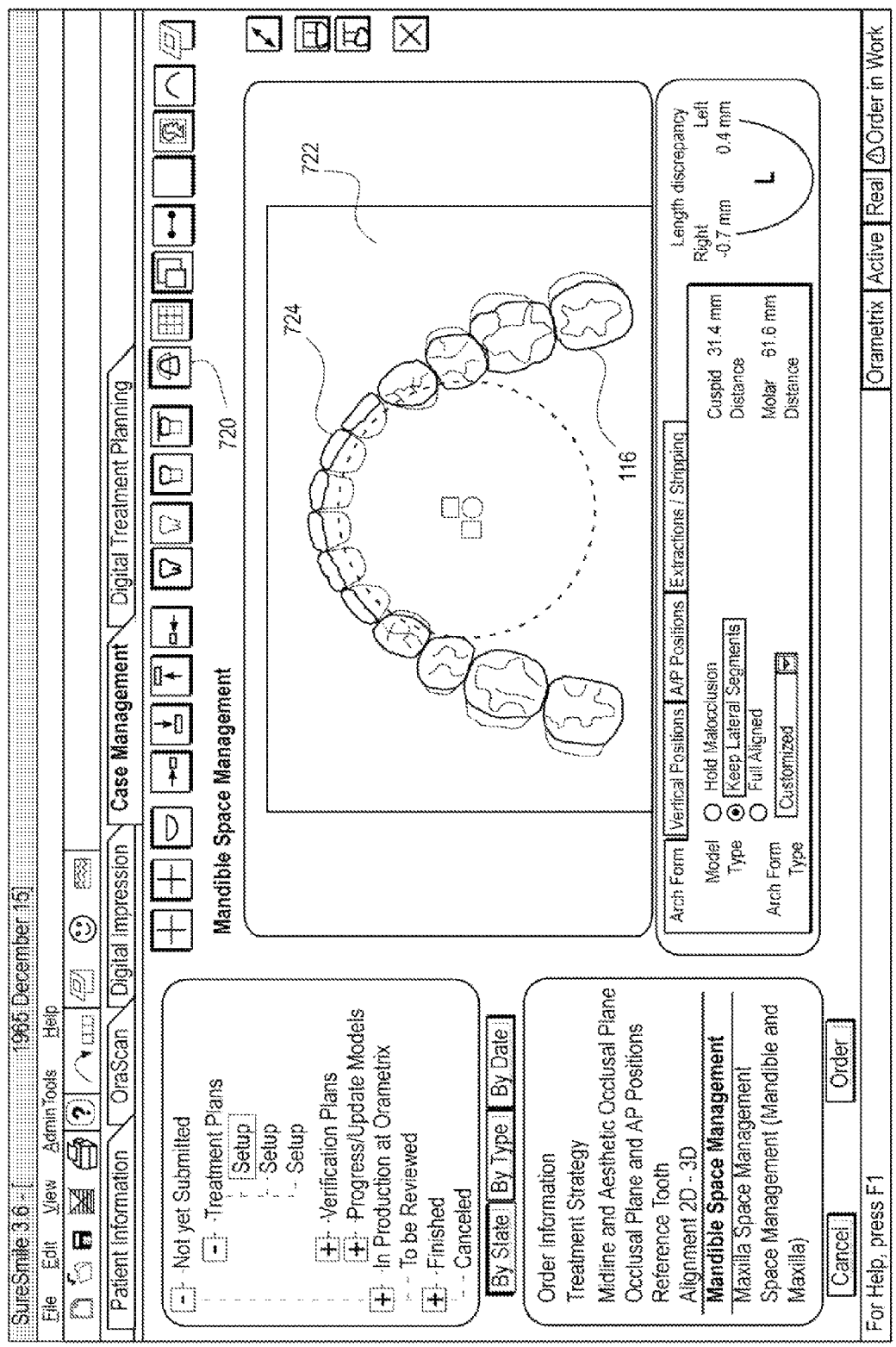

In FIG. 23, the user has selected an icon 720 that causes the display to show an occlusal plane 722, along with the position of the teeth 116 in a proposed arrangement. The areas where the occlusal plane intersects the teeth 116 are shown as white areas 724 of the teeth.

Figure 24:
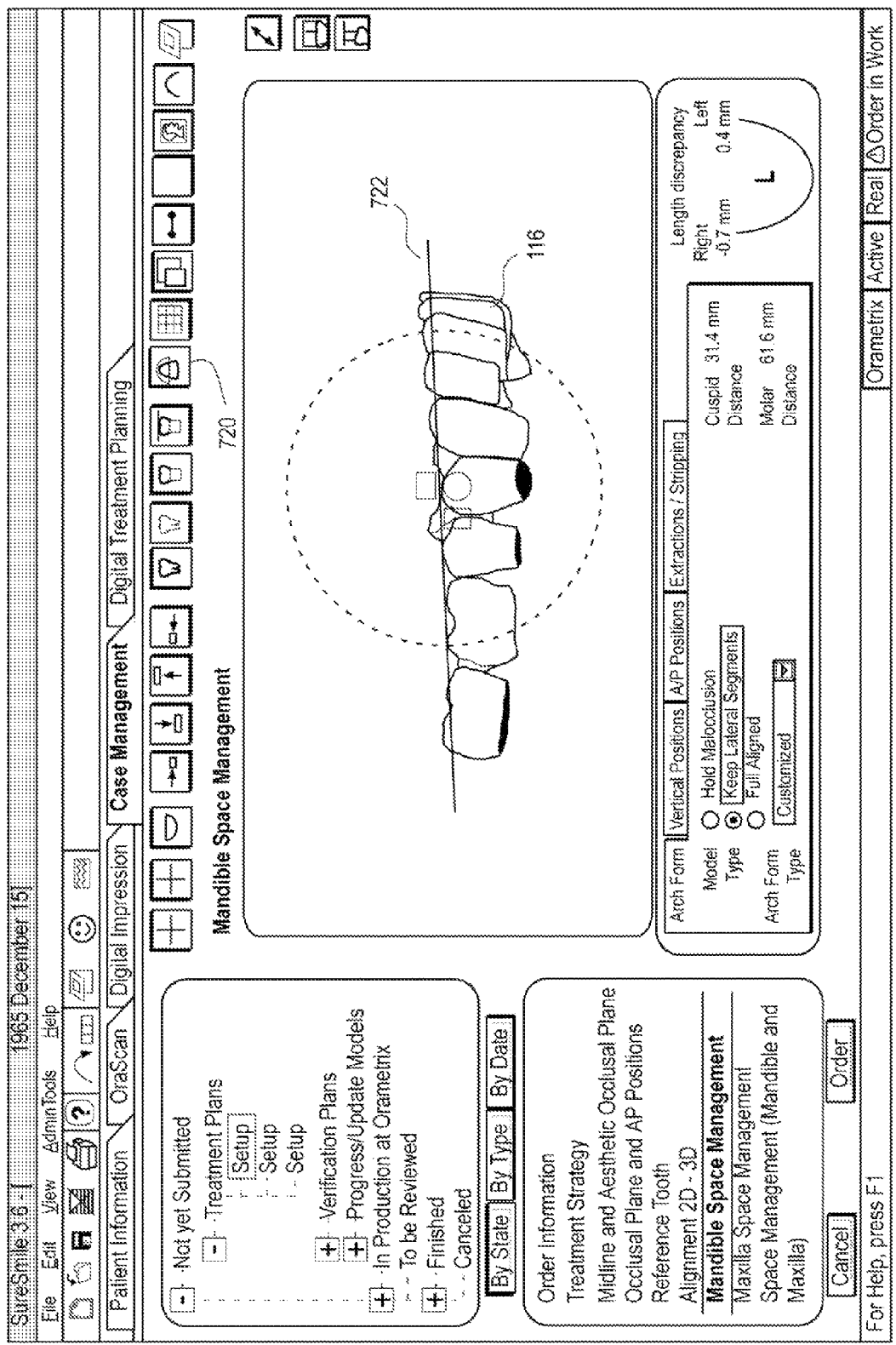

As shown in FIG. 24, the user has re-oriented the teeth to a side view and activated the icons to show both the teeth 116 and the treatment occlusal plane 722. This view gives the user a better view of the points of intersection of the occlusal plane with the teeth.

Figure 25:
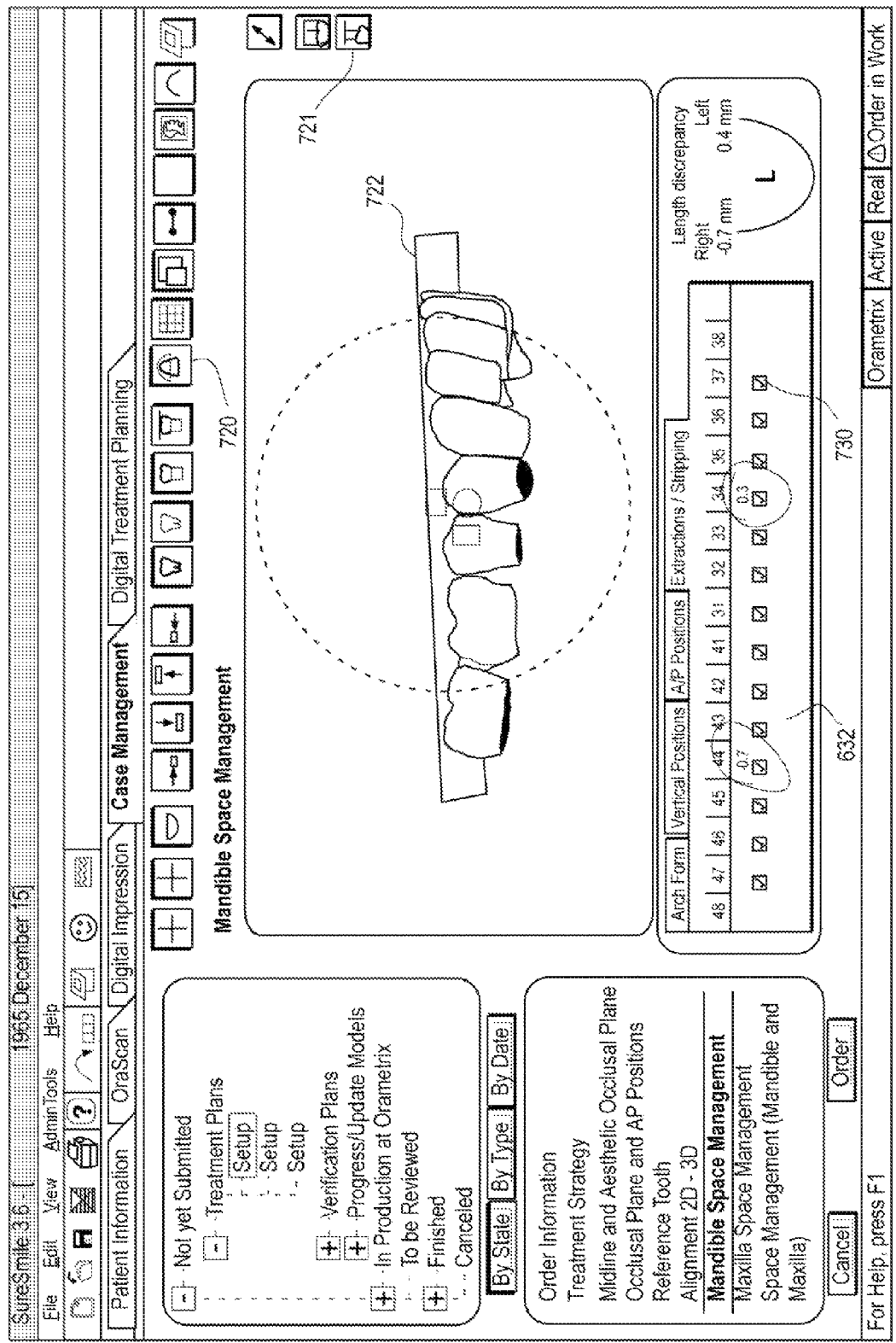

In FIG. 25, the user has activated the extractions/stripping tab 632. This causes the display to show the teeth of the lower arch, and a row of numbers corresponding to each tooth in the lower arch. The display also includes a check box 730 below each number. If the user un-checks the box 730, the corresponding tooth disappears to simulate an extraction. The numbers above the check boxes indicate the spacing needed in each half of the arch to meet the arch length requirements and reduce the arch length discrepancy to zero.

The display also includes an icon 721, which, when activated, all the teeth in the arch are moved in three dimensions such that they just touch the occlusal plane. This is an automatic function, since the location of the teeth and teeth cusps are known in three dimensions, and the treatment occlusal plane is also known in three dimensions.

Figure 26:
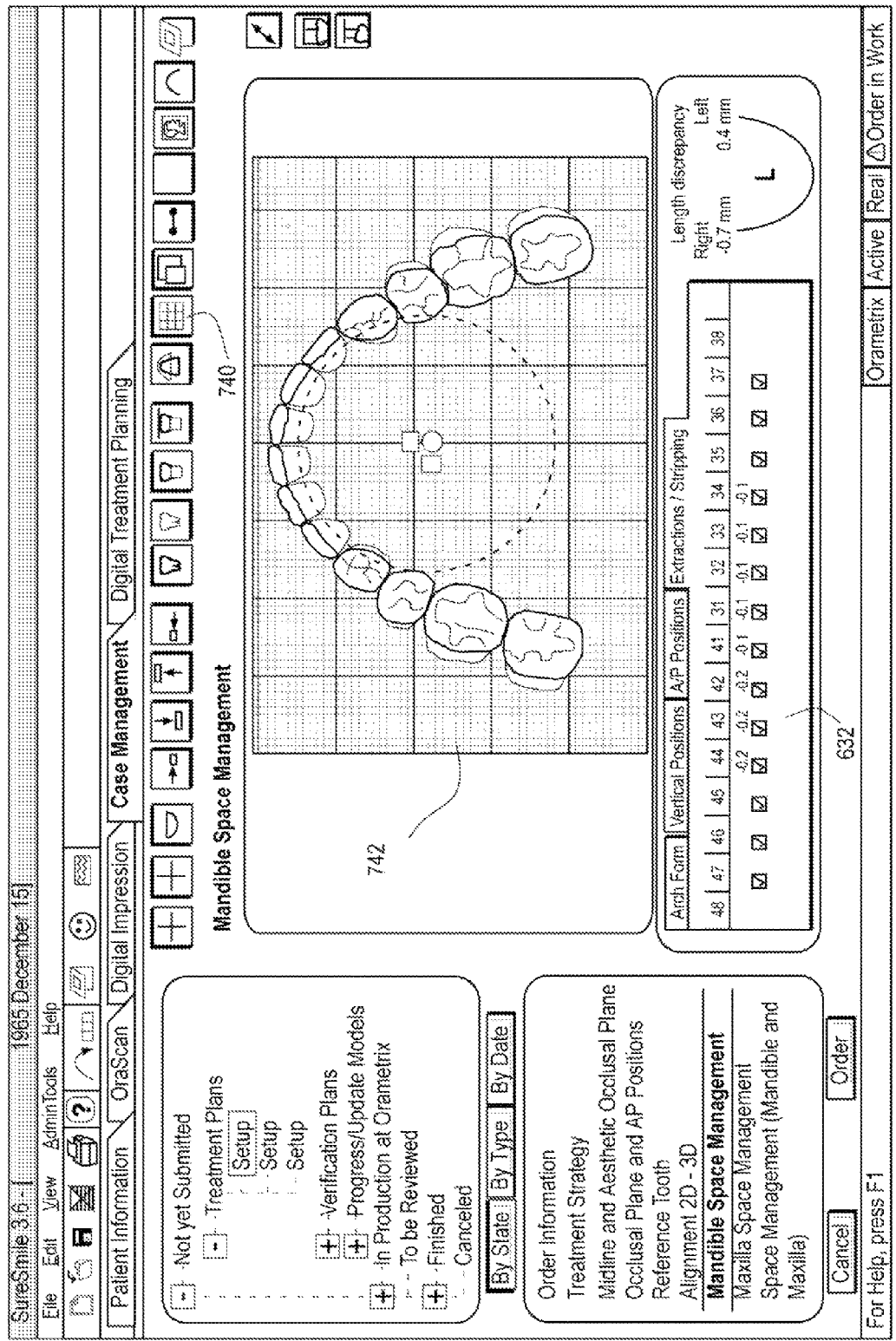
Figure 26A:
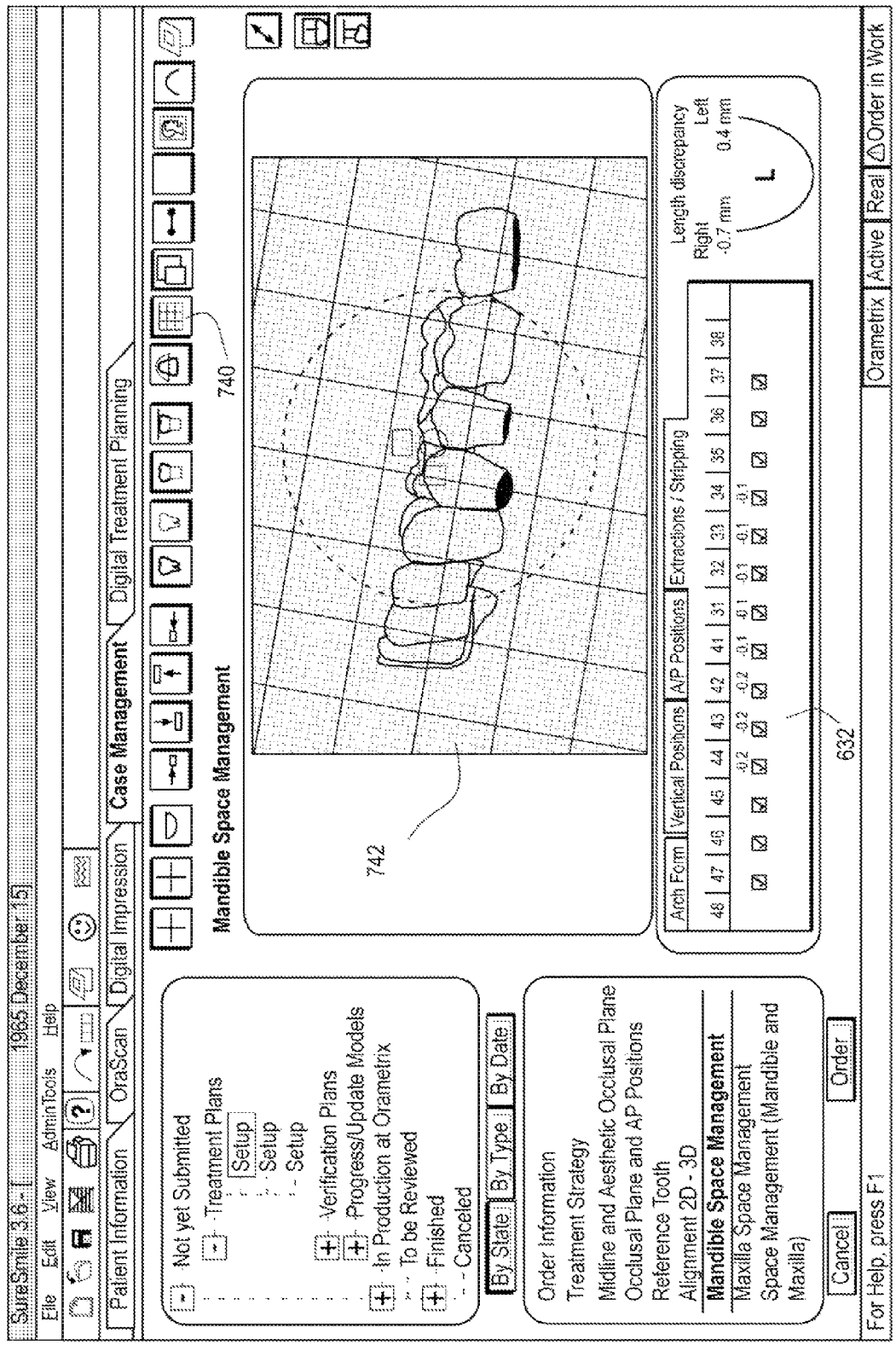

FIGS. 26 and 26A show the user activating a grid icon 740, which causes the display to show a grid 742. The grid, which is in units of millimeters, gives the user an additional tool to gauge distances between teeth (e.g., inter-molar width, intercanine width, etc.). In FIG. 26, the numbers in the field 632 above the check boxes are essentially evenly distributed among the teeth in the left hand side of the arch, and in the right hand side of the arch, indicating that the interproximal reduction is symmetrically and evenly distributed between the teeth. The teeth can be morphed accordingly to simulate the change in shape either through reduction in size or buildup in size as necessitated by the treatment. By un-checking any of the boxes in field 632, the user can simulate a tooth extraction and move teeth to manage the gap in space on a tooth by tooth basis, or have the space distributed evenly between the teeth, etc. Once the user is satisfied, they can go to the screen of FIG. 28 and see where the teeth are relevant to the bone.

Figure 27:
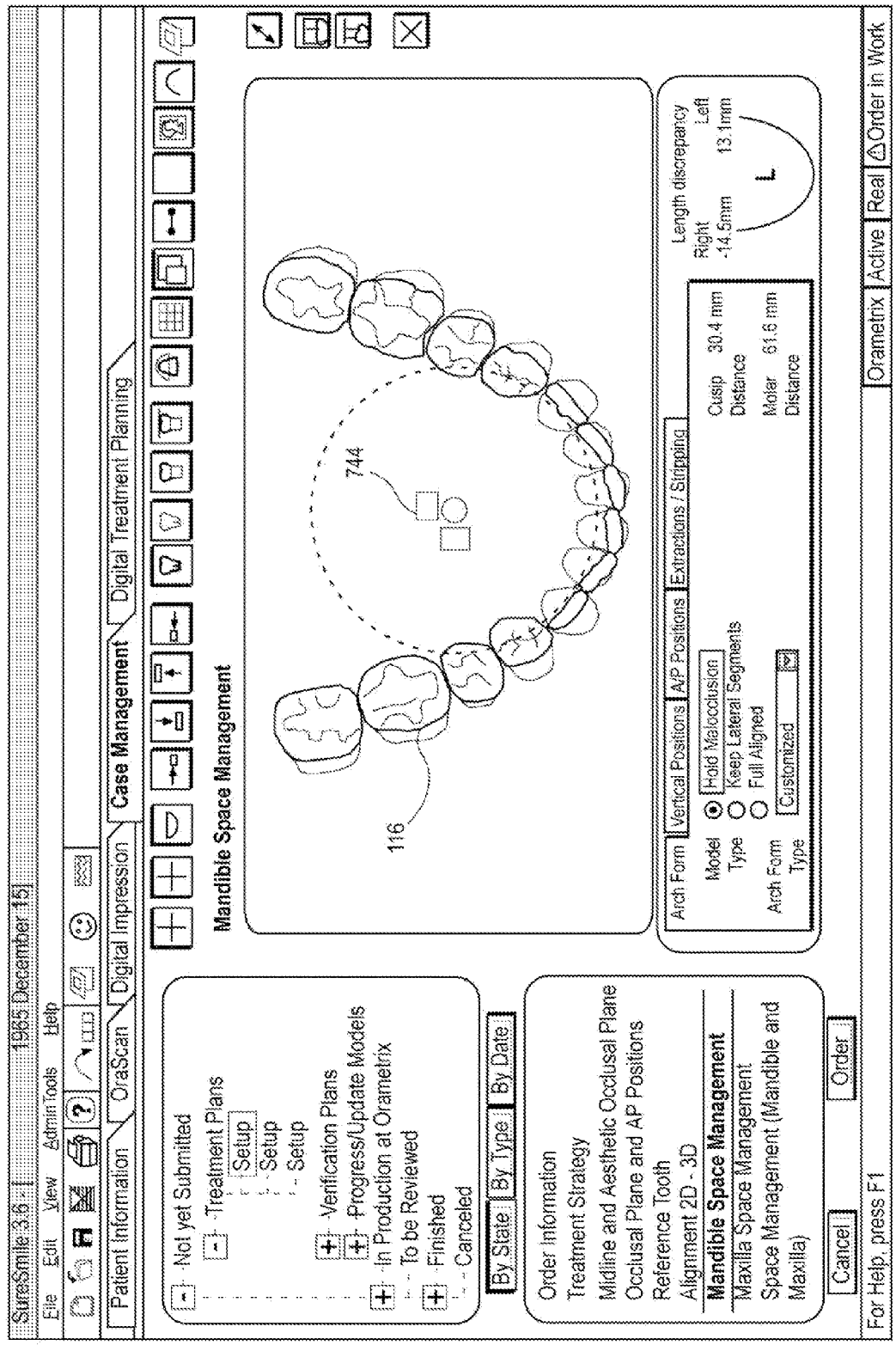

FIG. 27 shows the virtual model of the teeth of the lower jaw. Because the teeth are shown in a plan view it may be difficult for the user to see the texture and surface characteristics of the teeth. Thus, the user interface preferably includes an icon 744, which when activated allows the user to change the simulated illumination of the teeth, i.e., become brighter, or come from a different place, in order to more clearly show the surface characteristics of the teeth.

Figure 28:
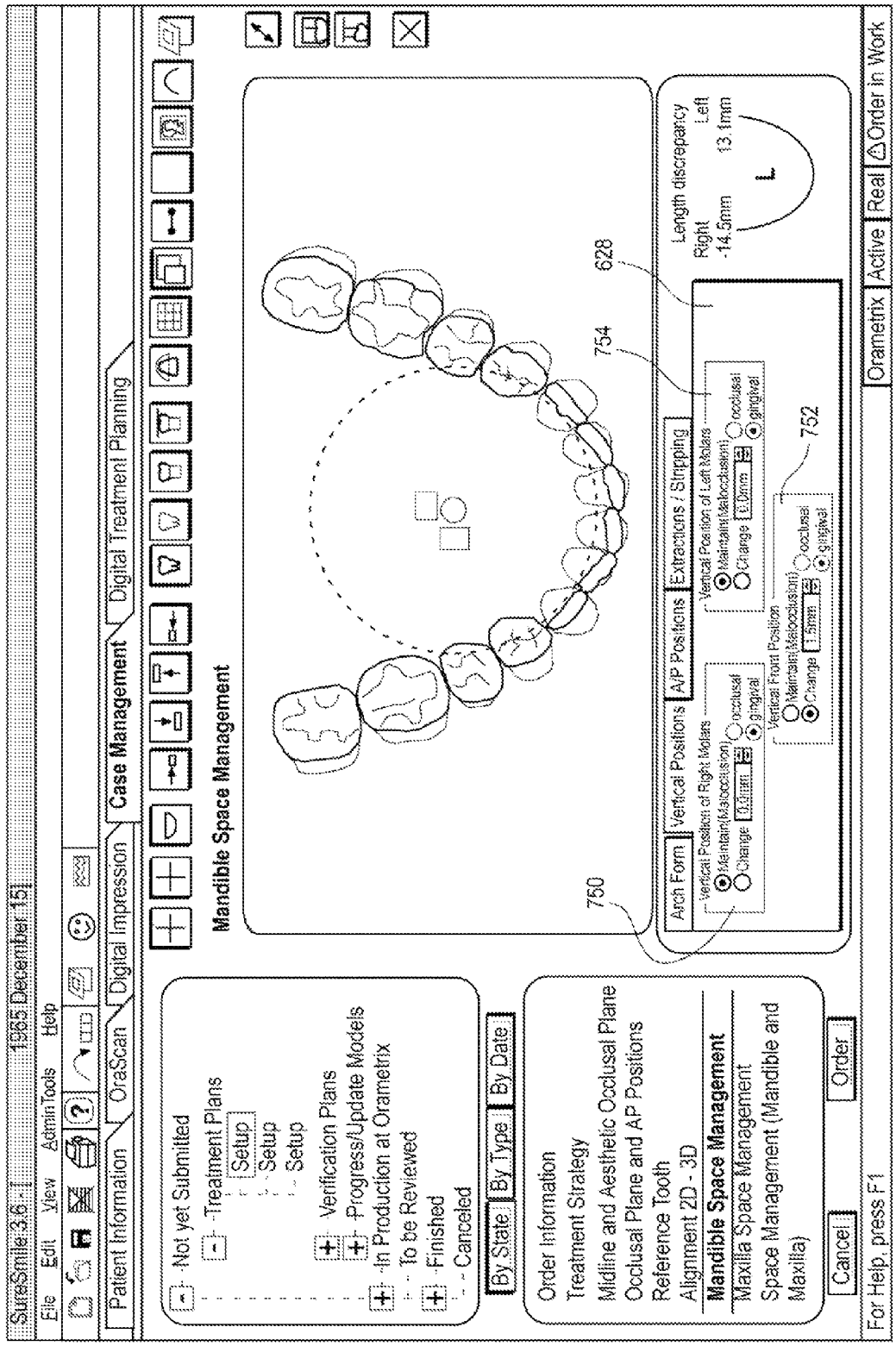

FIG. 28 shows the user activating the vertical position tab 628. This tab includes a field 750 in which the user can either maintain the malocclusion vertical position of the right molars, or change the position by any user specified amount either towards or away from the occlusal plane. Similarly, the tab includes a field 752 where the user can either maintain or change the vertical position of the front teeth. A field 754 allows the user to maintain or change the vertical position of the left molars.

Figure 29A:
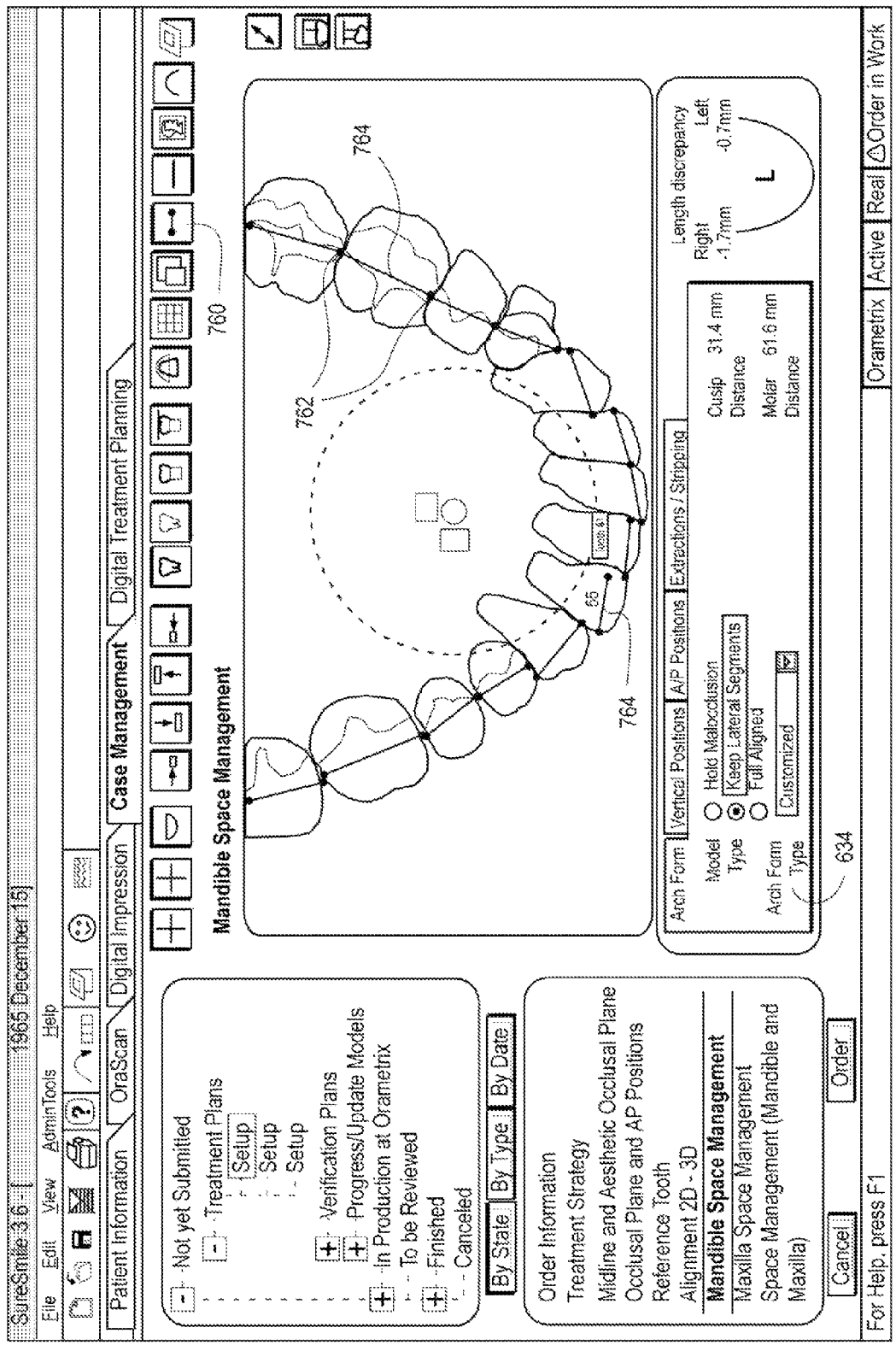

FIG. 29A shows a contact points feature that provides the user of a graphical display of the contact points between teeth. The user has activated the arch form tab 634, but the contact point function can be invoked at any time while the user is in the "Mandible Space Management" routine. The user has activated icon 760, which signifies that the user wishes to inspect and measure and the contact points between the teeth. When icon 760 is clicked, points 762 appear on the teeth, which indicate the points of contact between the teeth. The points 762 are joined by straight lines 764, which indicate the shortest distance between the points. By placing the cursor on a particular tooth, the display shows the tooth number and distance along the line in millimeters. This gives us the true measure of the widest points in the teeth. These contact points are automatically identified and the measurements are also automatic. The user can also change the location of the points to make additional measurements of the teeth. For example, for tooth 41, the distance is 5.5 mm.

Figure 29B:
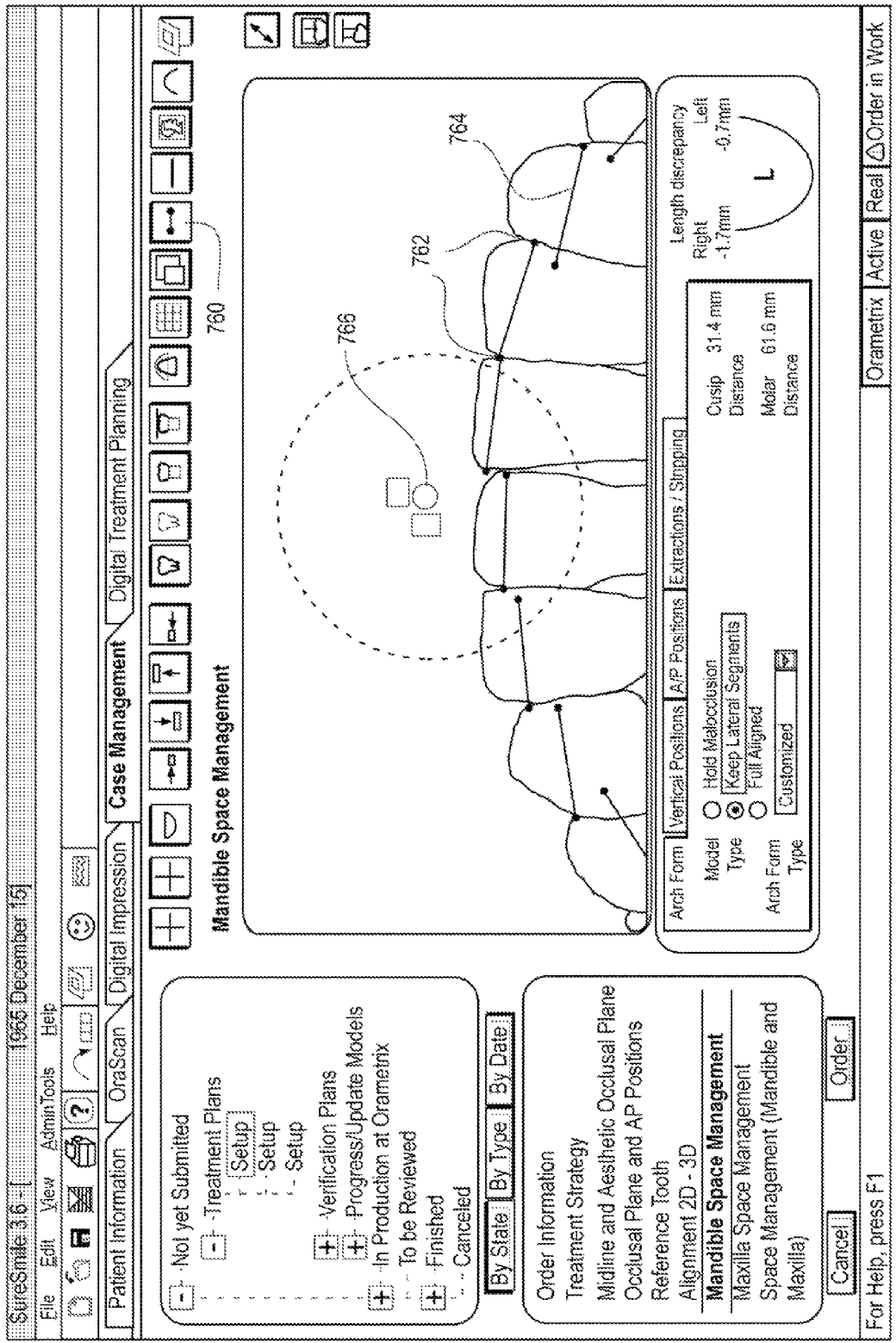

FIG. 29B shows the teeth of FIG. 29A rotated and displayed in a new orientation. By using the camera navigation icons 766, the user can zoom in or rotate the teeth to have a new viewpoint as desired. This enables the user to see more readily, in three dimensions, how the teeth are oriented.

Figure 29C:
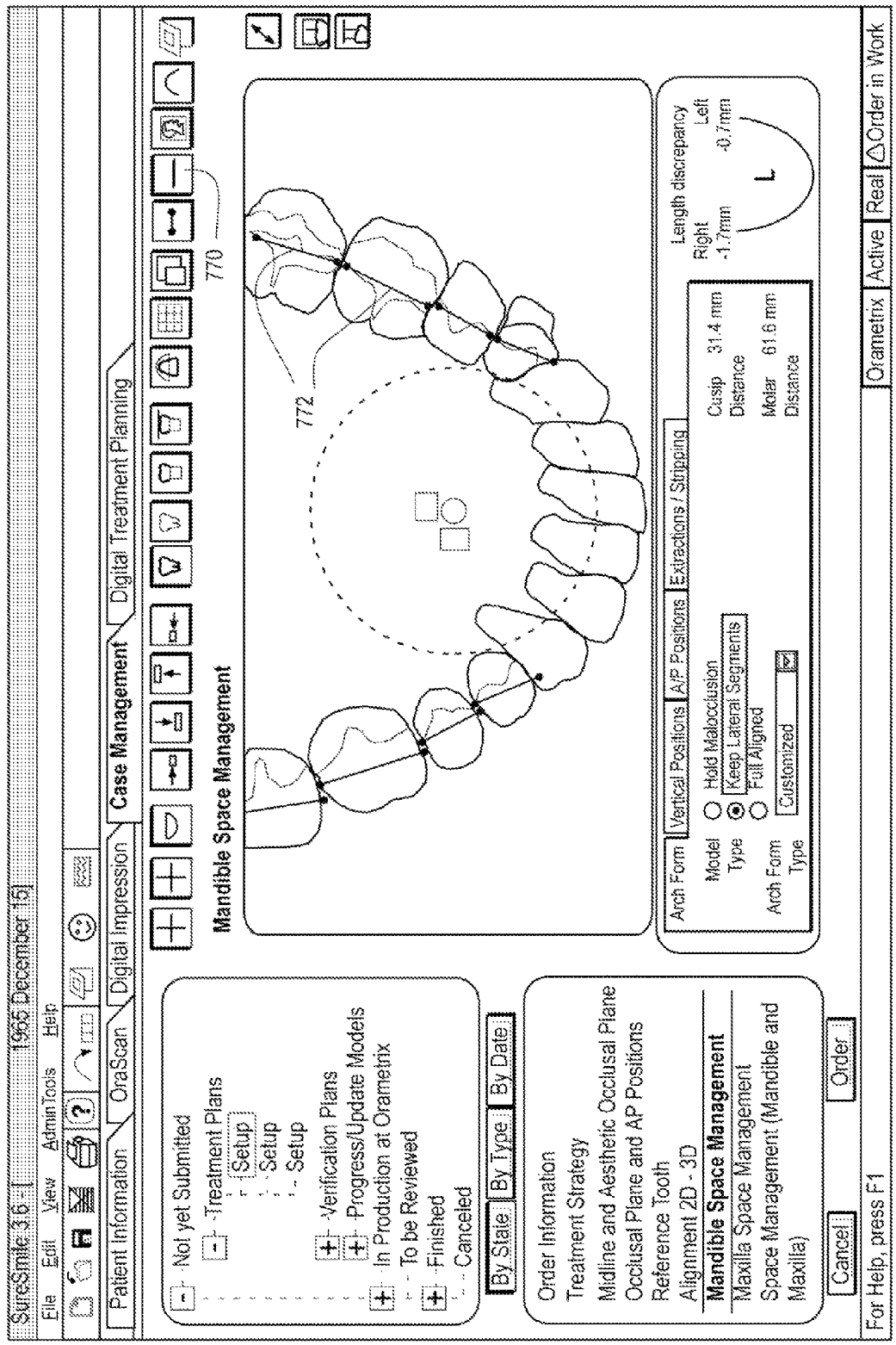

FIG. 29C shows the user activating an icon 770 which uses a feature extraction algorithm to highlight for the user the marginal ridges and indicate the distance along the marginal ridges. The marginal ridges and associated lines connecting them across the teeth are shown in FIG. 29C as lines 772. Other feature extraction tools are possible, including icons for showing cusp tips and cusp fossa.

Figure 29D:
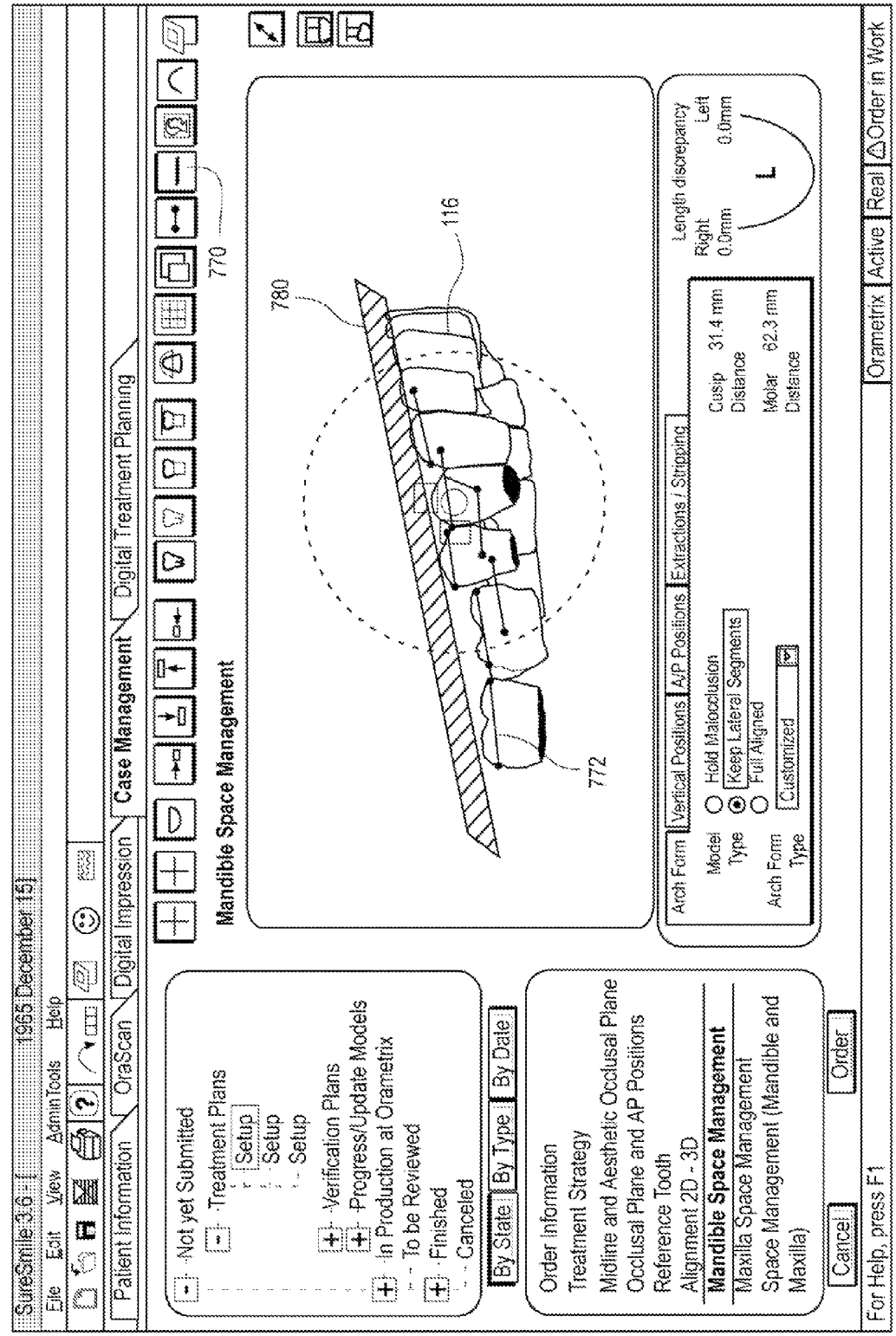
Figure 29E:
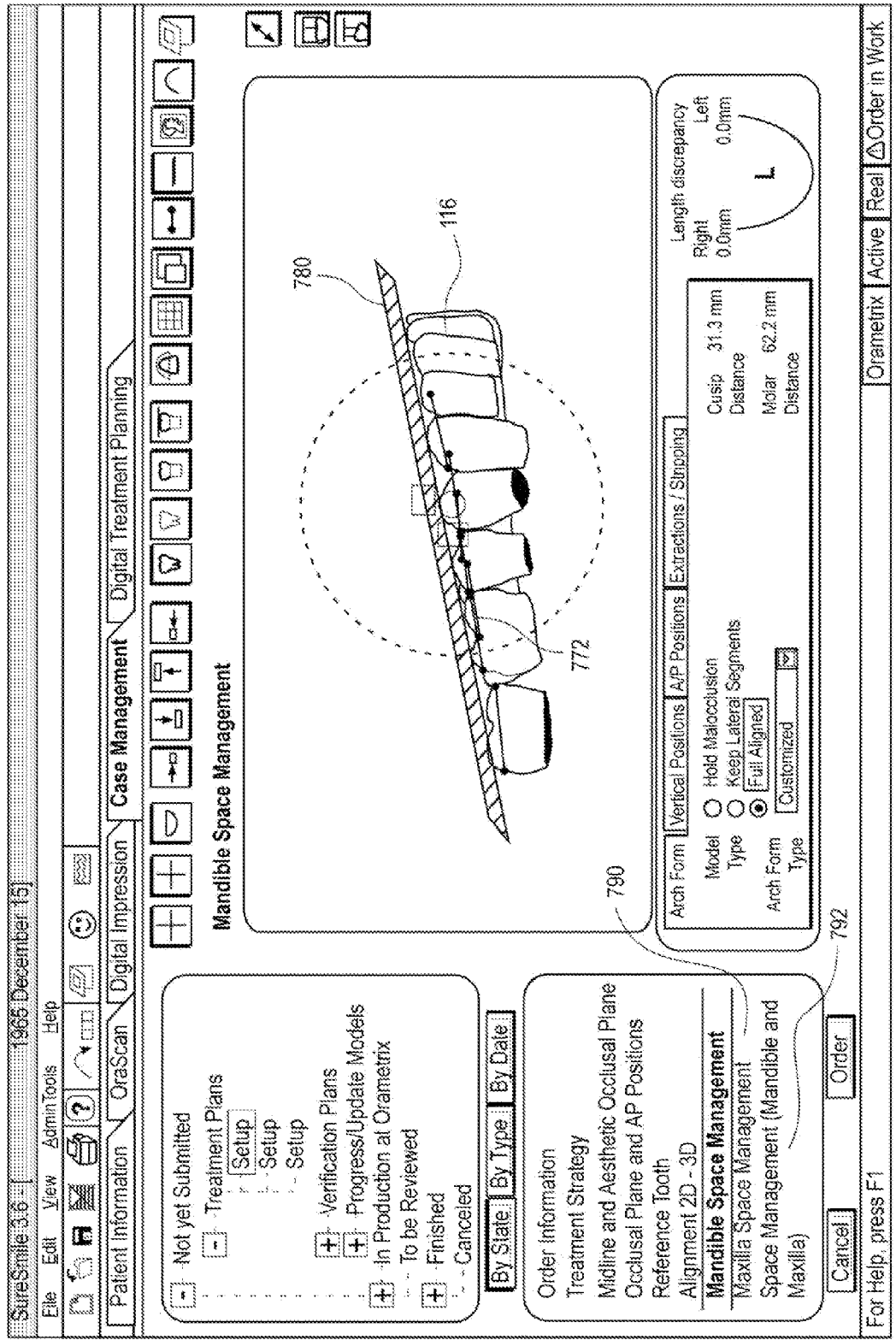

Usage of the contact points feature of FIGS. 29A and 29B is shown in FIGS. 29C and 29D. In FIG. 29D, the user has displayed the malocclusion teeth model 116 along with the lines 772 indicating the marginal ridges, together with the occlusal plane 780. Note that the lines 772 have a pronounced step relationship. In FIG. 29E, the user has interactively moved the teeth in the model 116 so that the teeth just touch the occlusal plane 780. Note that the step relationship in the lines 772 has essentially disappeared. The user can either move a tooth individually or select a group of teeth and move them as a group. Once the molars have been moved as shown in FIG. 29D the user will typically proceed to setting up the incisor position. To do this, the user may wish to invoke the clipping plane feature discussed elsewhere in this document to cut through the teeth and define the upper and lower incisor relationship in two dimensions, and then in three dimensions.

After the user has completed space management for the mandible using the tools in the previous figures, the user proceeds to maxilla space management using the tab 790. Similar screen displays as shown in the previous "Mandible Space Management" figures are provided to the user and thy perform space management tasks for the upper arch.

Figure 30:
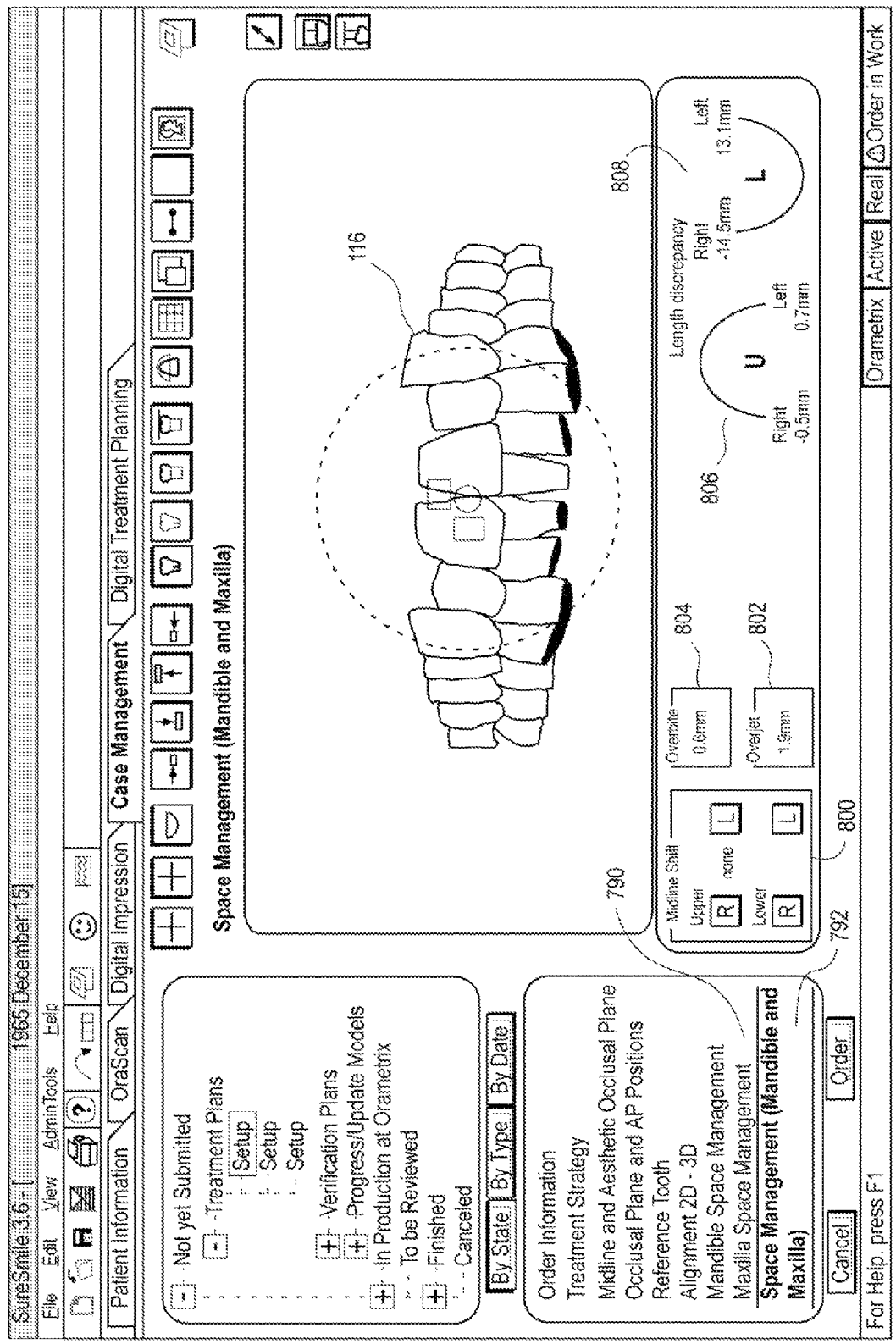
Figure 30A:
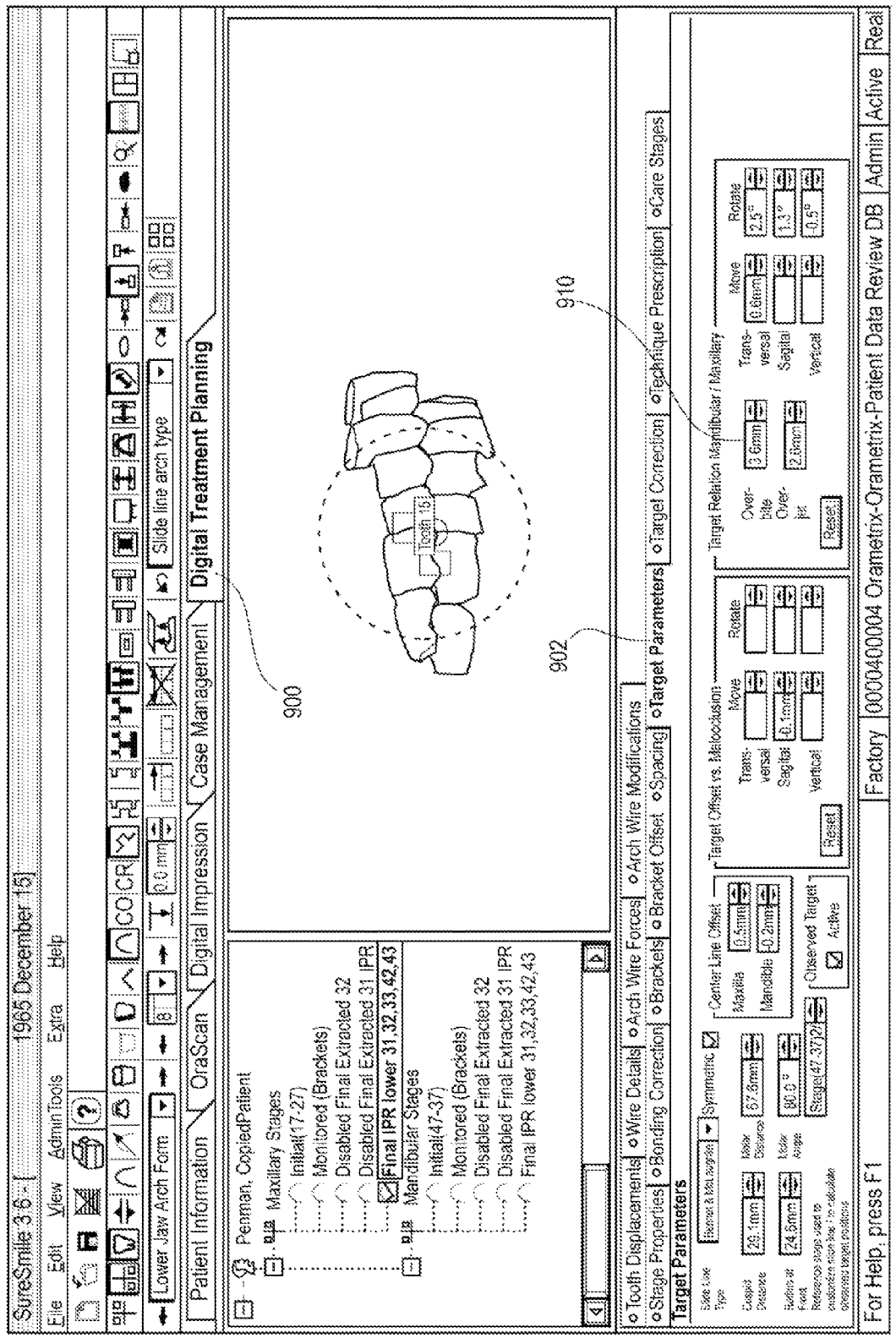
Figure 30B:
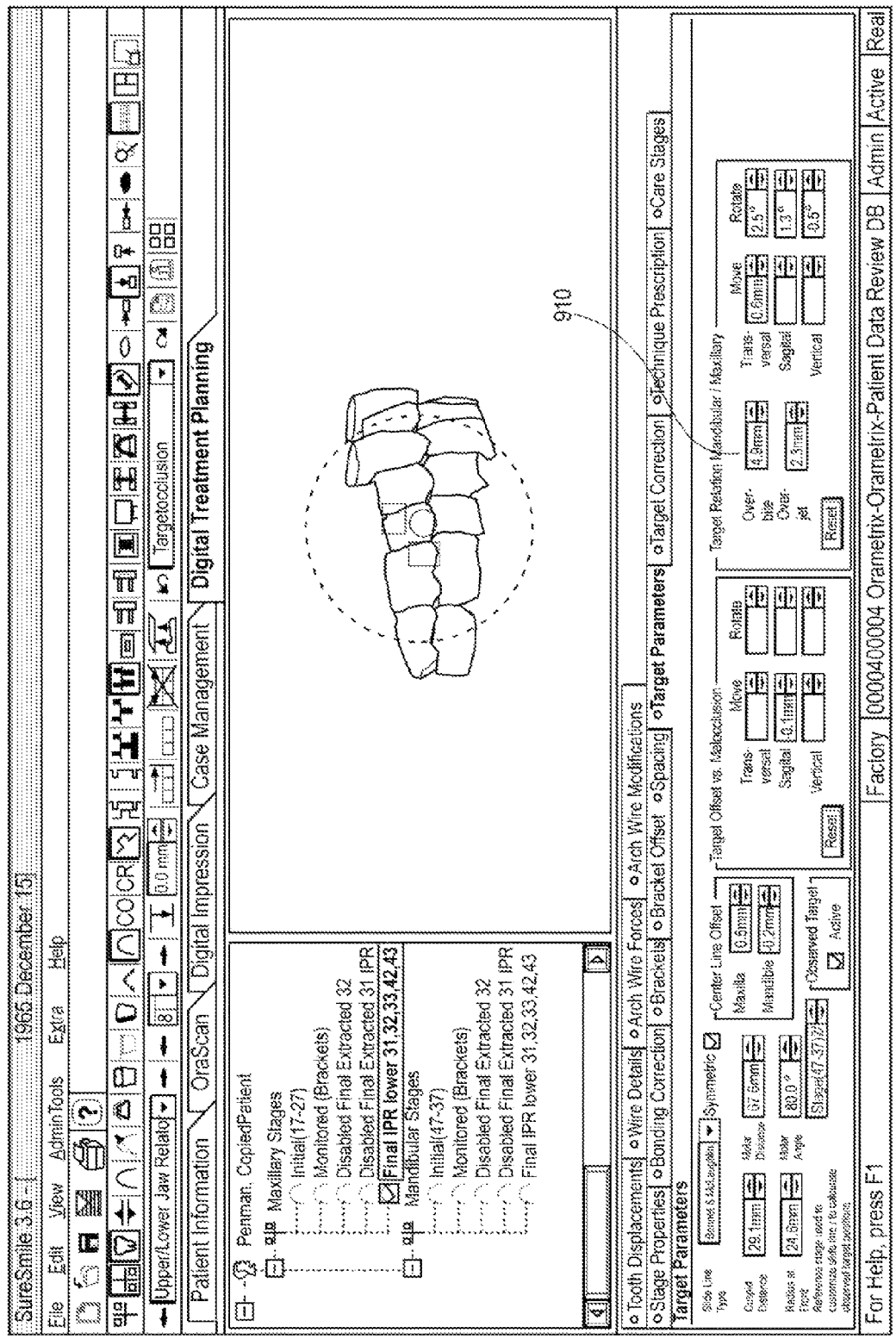

After completion of maxilla space management, the user proceeds to click on a "Space Management (Mandible and Maxilla)" icon 792, and the screen display of FIG. 30 appears. In this display, the user is provided with the same set of icons across the top of the display, allowing the user to hide or show the upper or lower arches, gingival structure, occlusal planes, contact points, X-ray or other image data, etc. Here, the user has selected for display both arches in the occluded condition and the tooth model 116 is displayed. This display includes a field 800 whereby the user can shift the midline of both the upper and lower arches right or left by pressing the R and L buttons with the mouse. The midline then shifts, with the amount of the shift indicated in numerical value. The display includes an overbite icon 804, which indicates the amount of over bite in mm. The user can user the icon to change interactively the amount of the overbite. Similarly, using icon 802 the user can change the amount of the overjet. The tools 806 and 808 provide the length discrepancy for both arches. FIGS. 30A and 30B shows similar functionality being available during activation of the "Digital Treatment Planning Icon 900 and its associated displays; in these figures the Target Parameter tab 902 is selected and the user is changing values for overbite and overjet via the numerical value entry fields 910 and the results are immediately visible on the display.

Figure 31:
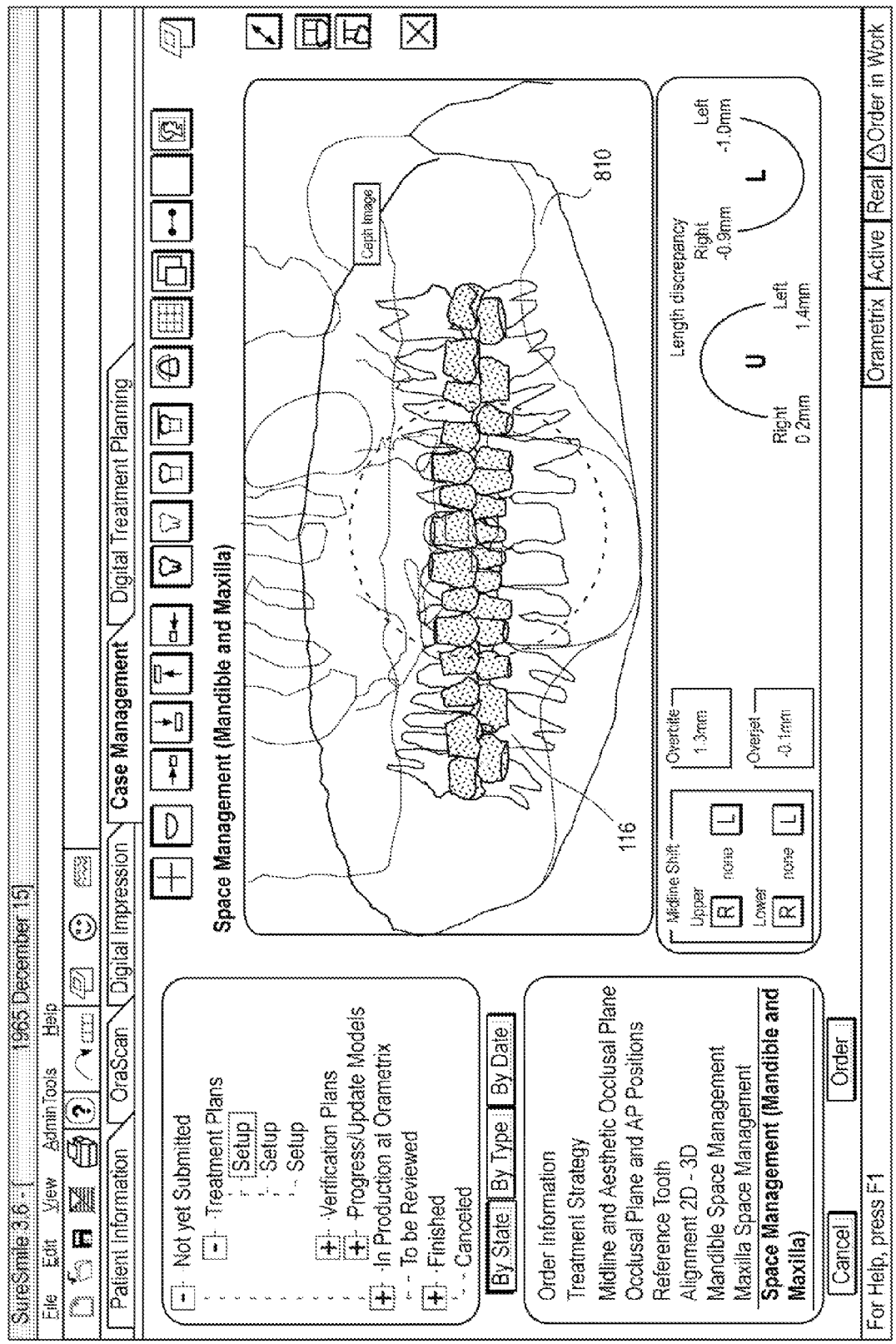
Figure 31A:
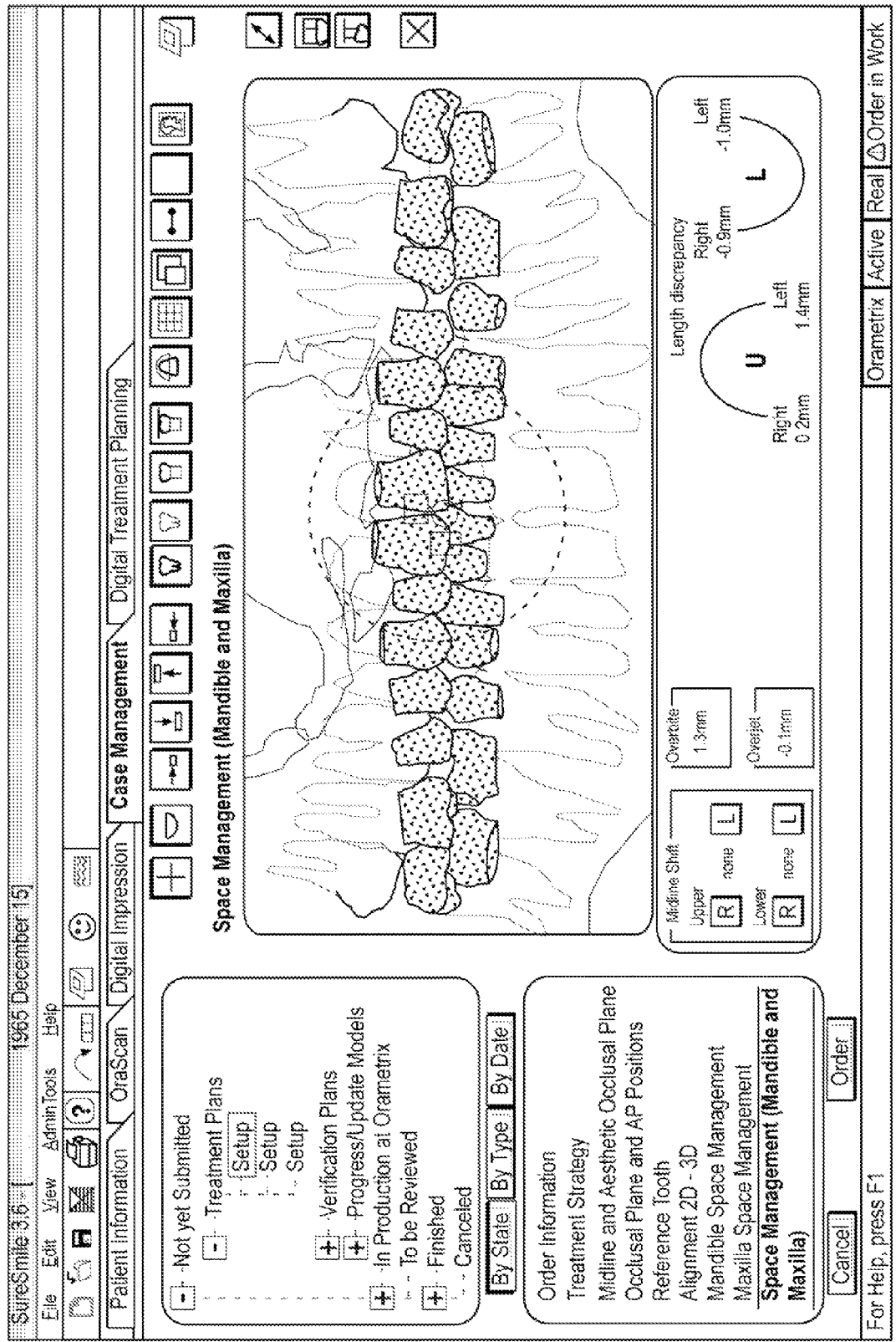
Figure 31B:
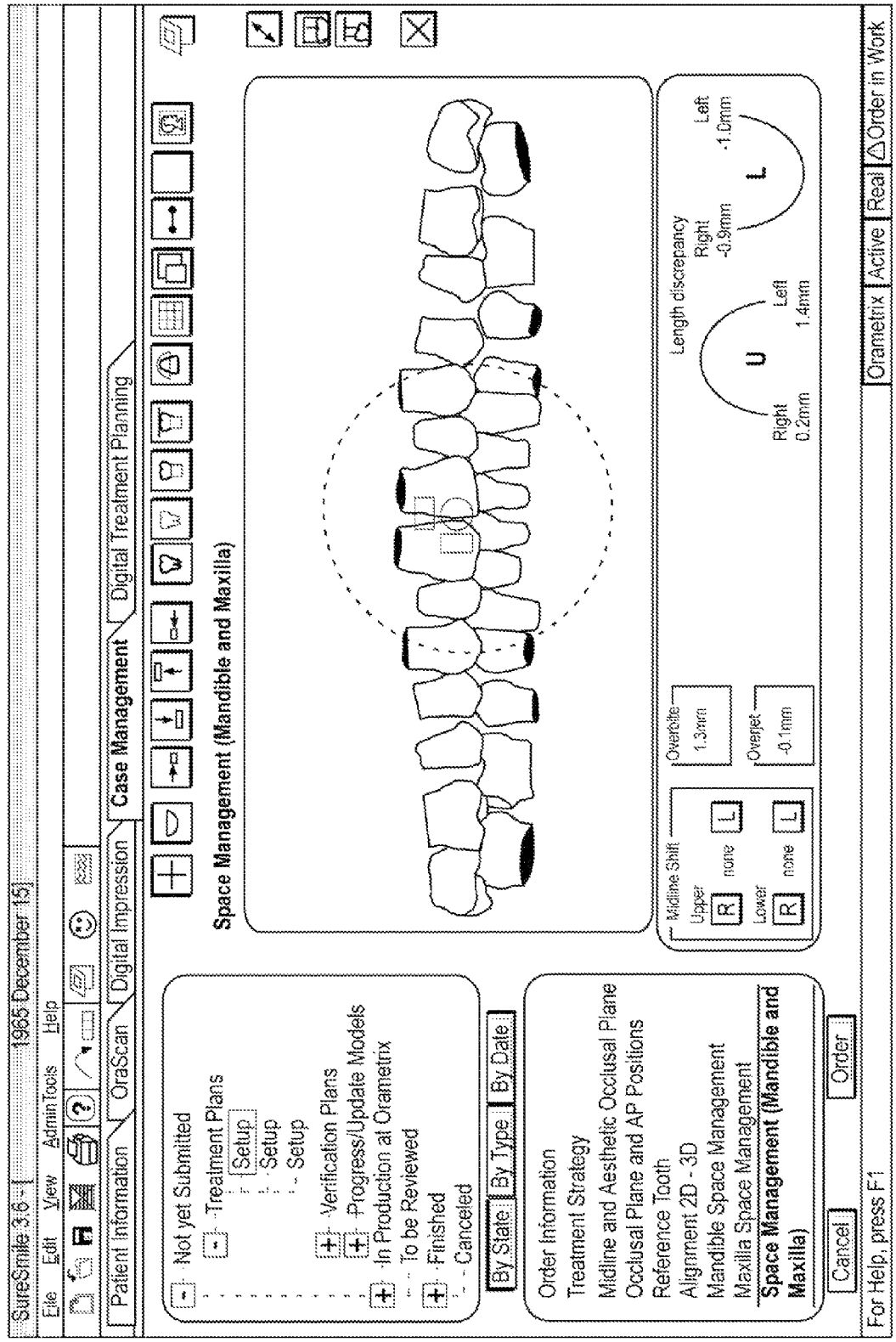

In FIGS. 31 and 31A, the user has activated the icons across the top of the display to simultaneously display both a 2D panoramic X-ray 810 of the teeth and jaw as well as the 3D model of the teeth, but with the teeth 116 spread out and represented in two dimensions in registry with the 2D panorama X-ray. The teeth models that are shown in FIG. 31 represent the tooth positions in a proposed treatment. In FIG. 31B, the user has unchecked the X-ray icon and only the teeth are displayed. In FIGS. 31, 31A and 31B, the user activates the icons to superimpose the 3D model in registry with the 2D x-ray. The user thus is able to figure out the axis inclinations of the teeth and can revisit the selection of a reference tooth (see FIG. 9) if appropriate. Any changes in tooth position and its effect on root position can be evaluated in the 2D/3D model of the panorex radiograph, CT scan, etc. plus superimposed crowns, as in FIGS. 31A and 31B. From these views, the user can quickly arrive at a proposed setup by aligning (interactively moving) the 3D teeth up and down to find the ideal position, selecting or designing an arch form and midline, and then wrapping the teeth around the desired arch form in three dimensions. When viewing the resulting proposed set up, e.g., in FIGS. 30 and 30A, the user is again given arch length inadequacy from a three dimensional model and proceed to modify the set up to eliminate the arch length inadequacy using the techniques described previously. As proposed modifications are made, the user is instantly provided with new values for arch length inadequacy, and can immediately determine whether the proposed modifications are sufficient to remove remaining arch length inadequacy.

Figure 32:
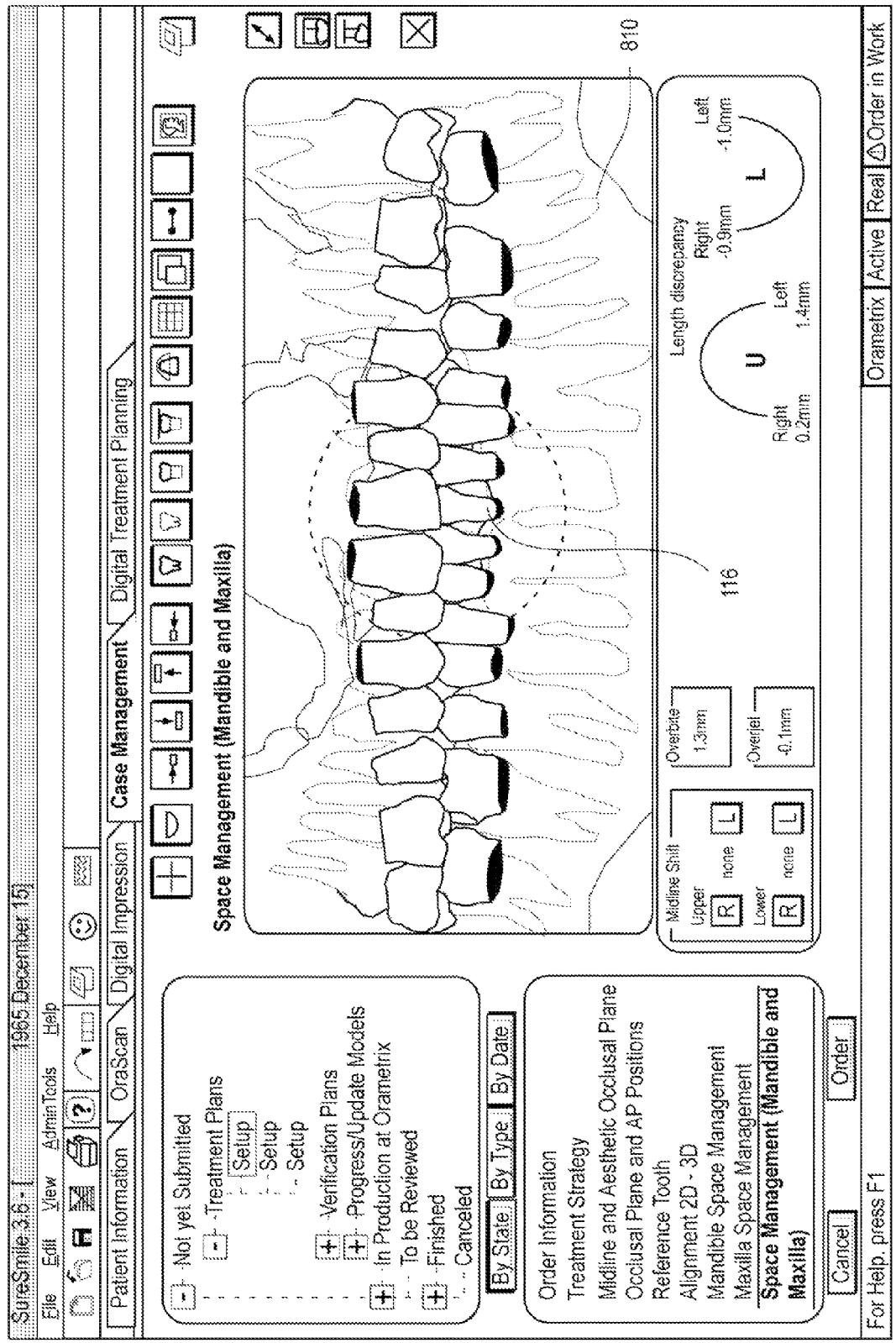

In FIG. 32 the teeth 116 that are shown are the malocclusion or original arrangement of the teeth. Thus, FIGS. 31 and 32 show that the user can toggle back and forth between initial tooth configuration and proposed treatments for the patient. Any changes in any one-environment of module changes the values in the other environments.

Figure 33:
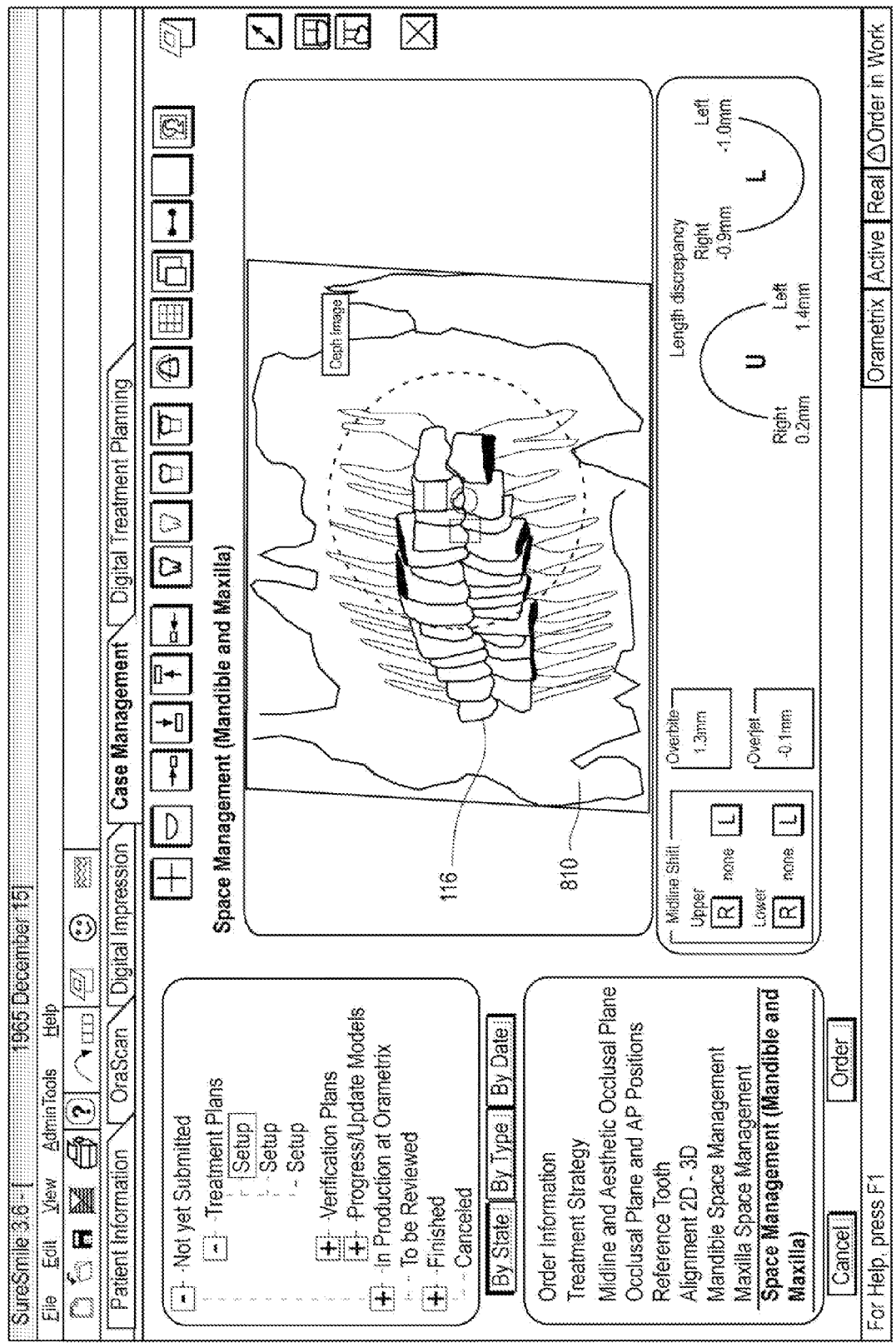
Figure 33A:
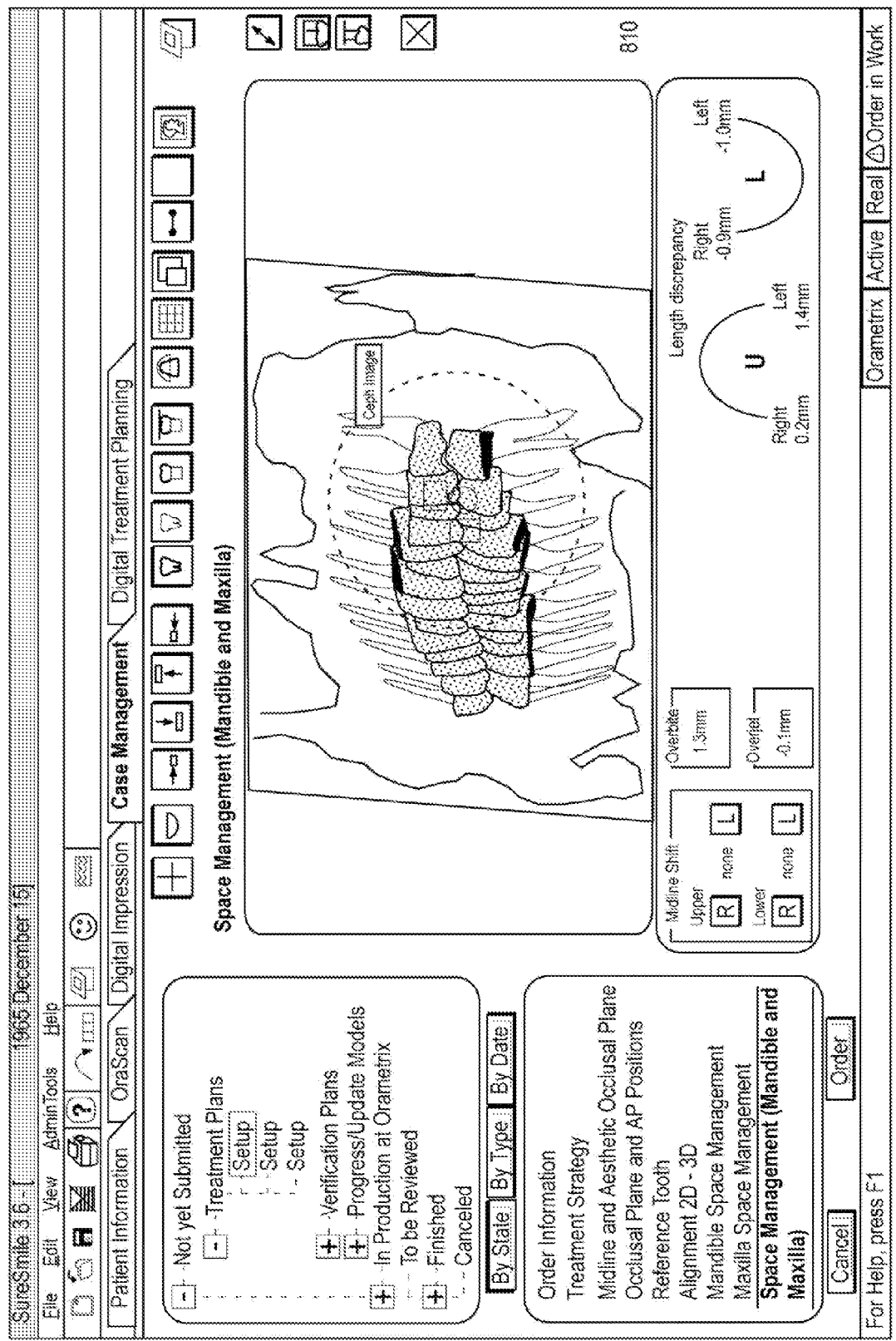

In FIG. 33 and FIG. 33A, the user has used the navigation icons to rotate the view shown in FIG. 32. The user is provided with excellent visual aids to view how the teeth line up with the tooth roots.

Figure 34:
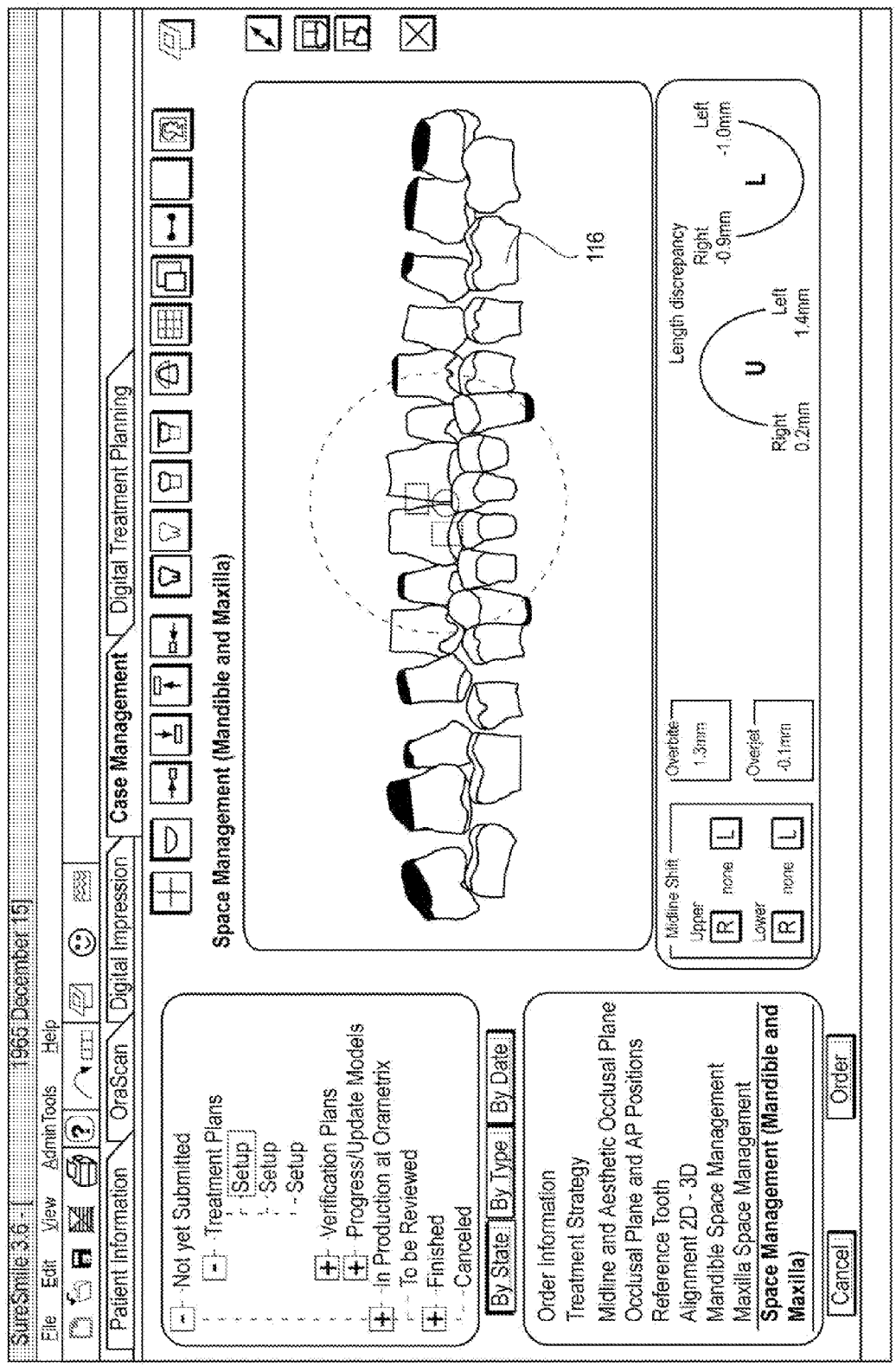
Figure 35:
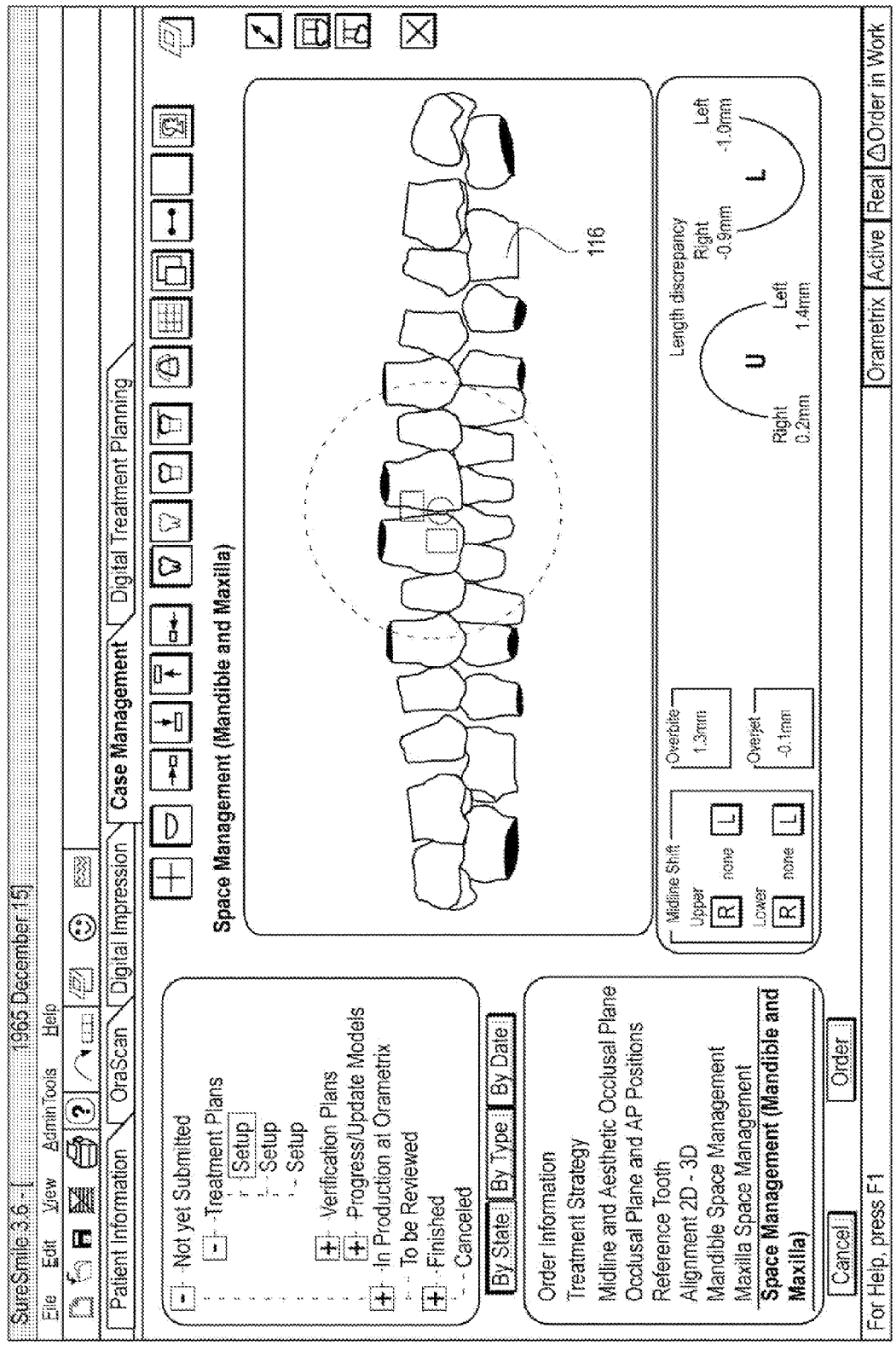

FIG. 34 illustrates that the user can unclick the icon causing the X-ray to disappear from the screen and simply perform space management for both the upper and lower arches using the virtual teeth models. As shown in FIG. 34, the teeth 116 are arranged in a line and seen from an anterior view. FIG. 35 shows the view of the teeth 113 from the opposite direction.

After the user has completed the task of managing space between the virtual teeth in the proposed arrangement; the user is able to cycle back and repeat any of the previous steps by activating the icons on the lower left portion of the display and entering into the appropriate displays and making further adjustments in the proposed arrangement.

The user can then access the rest of the treatment planning software, such as the software indicated by tab 458 (FIG. 3) and proceed with additional treatment planning procedures. Finally, when they are finished, the user selects a finalized proposed treatment plan for treating the patient. This updates the patient's prescription and is stored in the workstation. The display of FIG. 30 shows how the patient's teeth will look at the end of treatment. Adjustments in inter-arch relationships, as shown in FIGS. 10 and 11, either as a result change in overjet or overbite, or change in relationship of the jaws, are either tooth driven or jaw driven. These actions change arch length inadequacy values. These can all be simulated on the user interface.

Figure 36:
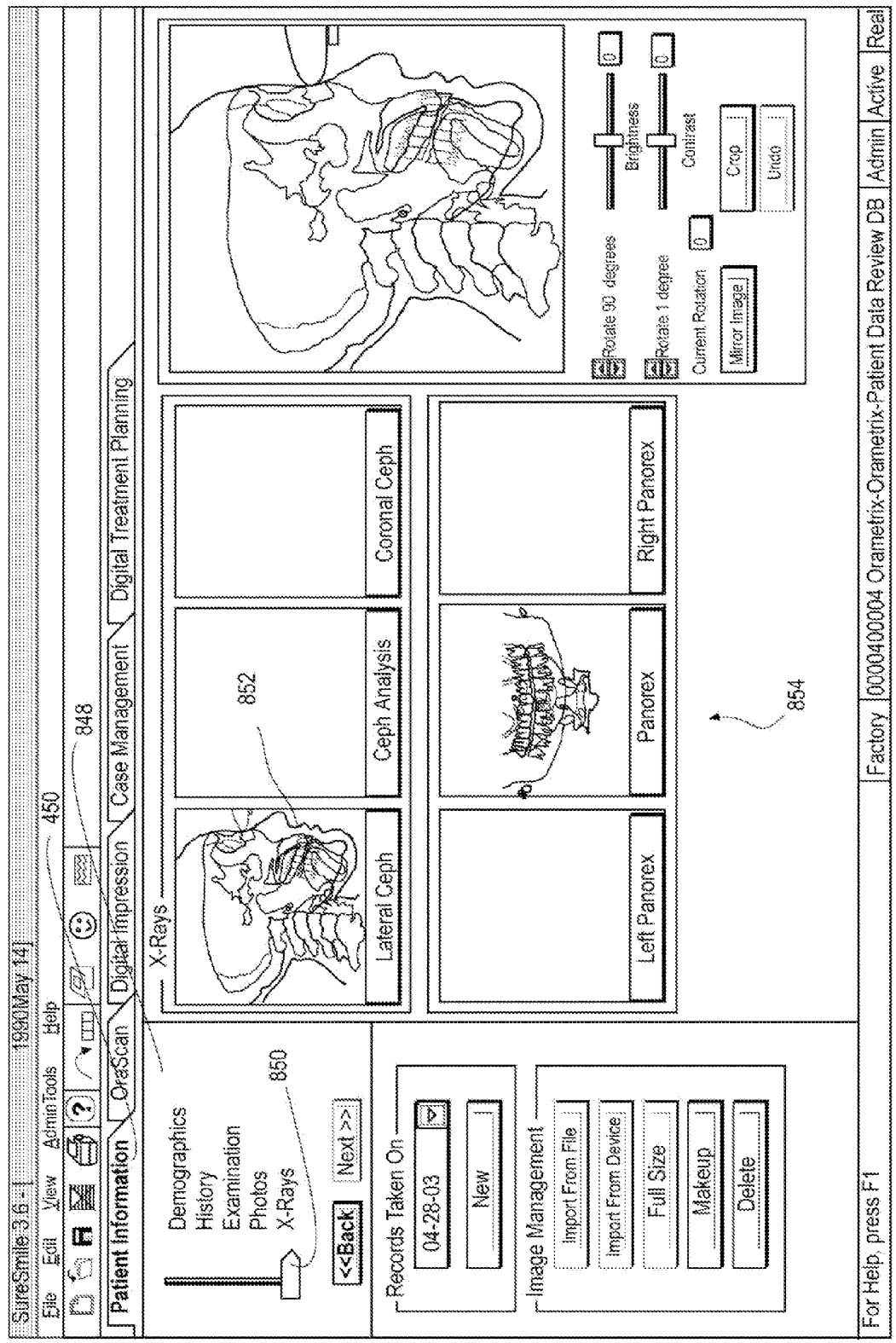

FIG. 36 shows the user entering the patient information tab 450, where the user has access to the patient's dental clinical examinations and dental radiographic examination. The upper left hand portion 848 includes a slide bar 850 that allows the user to access various fields, including demographics, patient history, examination (notes), photographs, and X-rays. Additional fields are made available by activating the "Next" icon. The user has moved the slide bar to X-rays. In the display 854, the user is provided with the X-rays that are currently stored for the patient, which include a later X-ray of the face ("Lateral Ceph"). The portion 856 of the display shows the X-ray and icons for rotation of the X-ray, changing the brightness and contrast, and displaying a mirror image of the X-ray. The user can point and click in any region of interest to access dental history or access photo image databases, radiographic images, and so forth. The navigation icons allow the user to rotate, pan, zoom all the X-rays to see them appropriately to check for pathology, etc. Also, the user can mark up the X-rays for making measurements in two dimensions, measuring angles, and entering that information into the patient database.

Figure 37:
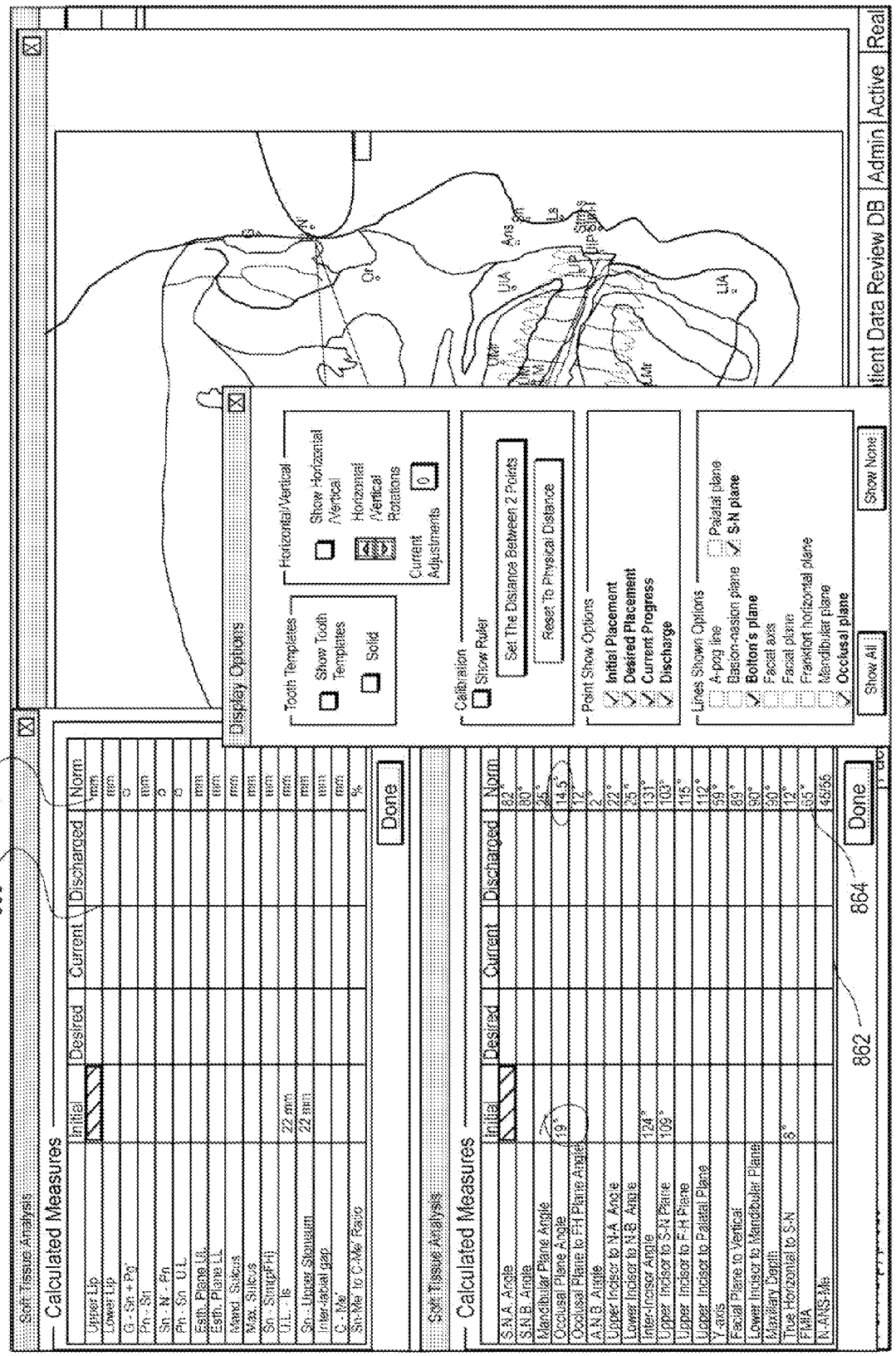

In FIG. 37, the user has navigated to a soft tissue analysis screen from the patient information window. Here, the user is allowed to enter into the workstation via field 860 specific, numerical values for initial measurements of soft tissue, desired values for these soft tissue parameters. In the field 862, the user is able to measure or calculate angles, e.g., between various teeth and various planes, angles of canting of planes that the user has specified, etc. Again, these angles are calculated by means of display on the workstation of patient's X-rays or other image data (including possibly scan data).

The workstation includes a database of "normal" or normative measurements for patients of different ages, races, and sexes, for both soft tissue measurements as well as all of the angles shown in FIG. 37. The comparison thus leads the practitioner to identify deviations from normative measurements. The display shows the normal values in the right hand column 864 of the displays 860 and 862. Thus, as the user is designing treatment and entering proposed or "desired" values for any of these biological parameters, the screen display simultaneously displays the "normal" values for a patient having the same (or approximately the same) characteristics as that of the patient.

Additional feature extraction algorithms that the workstation preferably provides besides the marginal ridge and contact points features described previously, include algorithms for identifying tooth cusps and fossa of the teeth. Such measurement tools are useful in automatically performing the Bolton tooth discrepancy level and Angel classification methods.

One of the unique features of the software is that the measurement features described herein allow the practitioner to determine the Bolton tooth size discrepancy.

Bolton Analysis

A method developed by W. Bolton (1958) for the evaluation of mesiodistal tooth size discrepancies between sets of corresponding maxillary and mandibular teeth. The analysis distinguishes between the "overall ratio," which involves all permanent teeth except the second and third molars, and the "anterior ratio," which encompasses only the six anterior teeth of each jaw. For this analysis it is assumed that the relatively smaller tooth material is the correct one. A table of standard values lists the tooth width value in the opposing arch that is ideally related to this given correct value. The difference between the ideal and actual dental width in the arch with the excess value gives an estimate in millimeters of the severity of tooth size discrepancy between the arches.

Tooth Size Discrepancy (Bolton Discrepancy)

Incongruity between the sums of the mesiodistal tooth sizes of sets of corresponding maxillary and mandibular teeth, is determined by the Bolton analysis. A discrepancy could involve the "overall ratio" (which encompasses all permanent teeth except the second and third molars) or the "anterior ratio" (which includes the six anterior teeth of each jaw) and is identified as a maxillary or mandibular excess or deficiency. Only deviations that are larger than two standard deviations are considered to be of potential clinical significance.

A tooth size discrepancy may cause difficulties in achieving an ideal overjet and overbite or arriving at a good intercuspation during the final stages of orthodontic treatment. Different ways to address such a problem include extraction of teeth in the arch with the excess tooth material (usually one mandibular incisor), interproximal stripping, compromising the angulation of some teeth so they can occupy a larger or a smaller space in the arch, or increasing the mesiodistal tooth size in the arch with the deficiency in tooth material (build-ups).

The present software provides measuring tools for measuring these parameters and conducting this analysis (using the contact points algorithm described and illustrated previously). Moreover, the workstation includes a database of normative or normal ratios for patients. The user compares the ratio for the patient, obtained directly using the measuring tools, and compares the result with the normative values from the database in the workstation. The difference is displayed for the user. The result is the Bolton tooth size discrepancy and is useful in treatment planning and allows the user to measure the total form or shape of the teeth.

Another feature provided herein is the so-called "Angle classification", which is a measure of how closely the upper and lower arches fit in an occlused condition. The classification system is as follows.

Class I Malocclusion (Neutroclusion)

A malocclusion in which the buccal groove of the mandibular first permanent molar occludes with the mesiobuccal cusp of the maxillary first permanent molar. The term "Class I" is sometimes used incorrectly as a synonym for normal occlusion, although in reality, it only signifies a normal relationship of maxillary and mandibular first molars in the sagittal plane.

Class II Malocclusion (Distoclusion, Postnormal Occlusion)

A malocclusion in which the buccal groove of the mandibular first permanent molar occludes posterior (distal) to the mesiobuccal cusp of the maxillary first permanent molar. The severity of the deviation from the Class I molar relationship usually is indicated in fractions (or multiples) of the mesiodistal width of a premolar crown ("cusp" or "unit")

Class II Malocclusion, Division I

A Class II malocclusion with proclined maxillary incisors, resulting in an increased overjet Class III Malocclusion (Mesiocclusion, Prenormal Occlusion)

A malocclusion in which the buccal groove of the mandibular first permanent molar occludes anterior (mesial) to the mesiobuccal cusp of the maxillary first permanent molar. The same conventions as described above are used to indicate the severity of deviation from a Class I molar relationship.

Angle Classification

"Subdivisions" (left or right) are used in asymmetric situations to indicate the side that deviates from a Class I molar relationship.

The workstation software features measurement tools to directly make these measurements (by measuring the distance between cusps and fossa of opposing teeth). The results can be quantified and displayed to a user, and compared to normative values in a database. Additionally, the values can be classified in accordance with the Angle classification system, e.g., Class I, Class II or Class III. The resulting display of classification is useful for interdigitation or changing the spacing between the opposing teeth.

Another feature of the software is that it allows the teeth in either or both arches to be displayed as semi-transparent objects, which allows the user to view through the teeth to see opposing teeth or adjacent teeth. Several possible method of providing semi-transparent teeth is to show fewer of the points in a point cloud of teeth or fewer triangles in a mesh or triangle surface representation of the teeth.

FIG. 38 illustrate the user has navigated to a cephalometric marking screen in the patient information tab, where the user has chosen for display a lateral ceph X-ray of the head. The user has also retrieved two dimensional template teeth 870 from a library of template teeth and superimposed the template teeth over the X-ray. The user has also activated the icons 872 and 873 which causes an occlusal plane 874 to appear on the display. By activating the icons 876 in the left hand side of the display, the user can navigate to calculations screens and associated tools, which provide the user with the ability to calculate various parameters, a soft tissue analysis screen, landmark status, display options and other tools. The user can move the teeth in two dimensions, both the upper and lower teeth. The user marks the occlusal plane, and the user is able to move the teeth relative to the occlusal plane.

Figure 39:
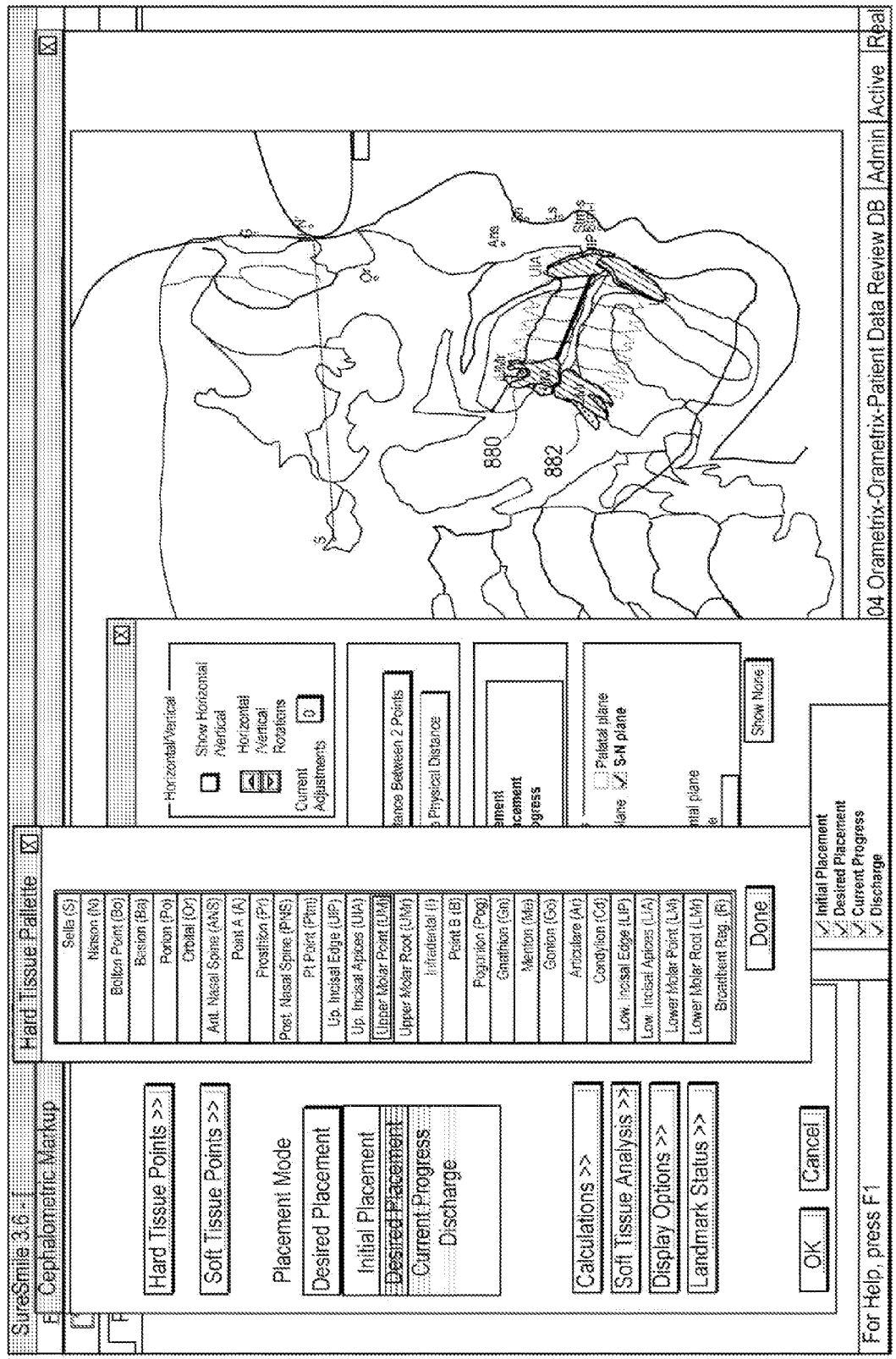
Figure 39A:
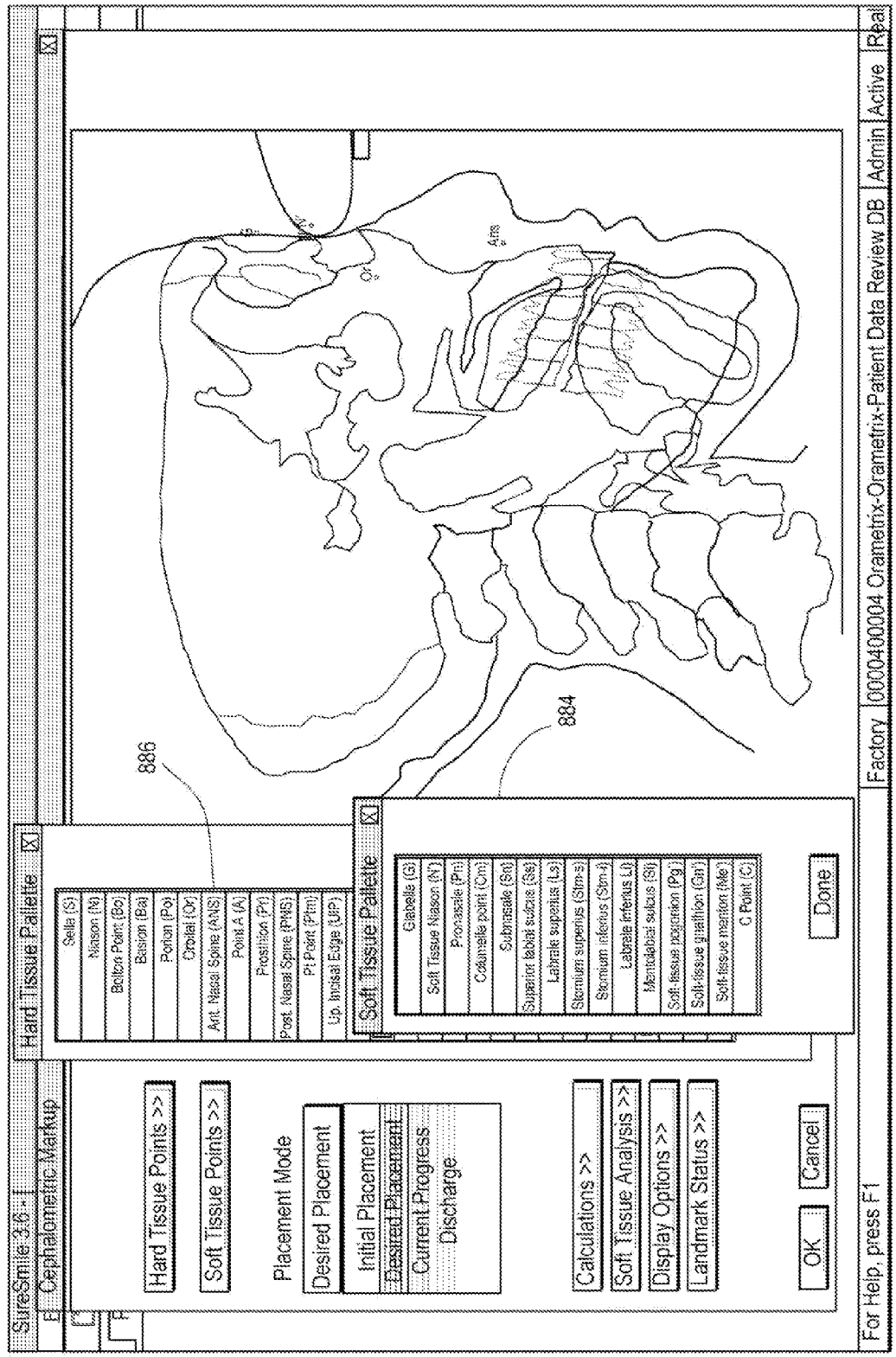

In FIG. 39, the user has navigated to a hard tissue analysis screen, wherein the user is provided with tools to mark various hard tissue anatomical locations on the X-ray image. Here, the user has activated icons to compare initial and desired tooth positions using template teeth to simulate a proposed treatment of the patient. The dark teeth 880 represent a proposed tooth position whereas the light teeth 882 represent initial tooth positions. The user can change the proposed tooth position by moving the dark teeth using the mouse by clicking and dragging.

In FIG. 39A, the user has navigated to a screen display showing both the hard and soft tissue, with the display 884 providing the user the tools to mark specific soft tissue locations on the virtual patient model, including Glabella, soft tissue Naison, subnasele, mentolabial sucus, etc. By closing out of window 884, the user accesses the window 886 where the user is able to enter hard tissue points in a similar fashion on the display. The user is again able to make measurements between any points that are marked on the screen and measure corresponding angles.

The treatment planning described in FIGS. 4-8 and 36-39A is essentially done in two dimensions. After these initial steps are taken, the software allows the user to perform more specific treatment planning operations in three dimensions using the virtual 3D model of the teeth, as described in conjunction with FIGS. 9-35. All changes to dental position or bone changes can be translated into changes in soft tissue appearance using morphing algorithms. The icons also allow for standardized views: side, planar, etc.

After the user has completed the task of managing space between the virtual teeth in the proposed arrangement, designing the desired arch form, and arriving at a proposed tooth arrangement or treatment plan, the user is able to cycle back and repeat any of the previous steps by activating the icons on the lower left portion of the display and entering into the appropriate displays and making further adjustments in the proposed arrangement.

The user can then access the rest of the treatment planning software, such as the software indicated by tab 458 (FIG. 3) and proceed with additional treatment planning procedures. Finally, when they are finished, the user selects or saves the treatment plan. The process can be repeated as often as desired and the screen displays are structured so that the user can navigate anywhere in the displays at any time, and therefore repeat, as necessary, the aligning steps, the design of the arch, enter additional patient information, access the appliance design features and change the appliance design, etc. Moreover, as the design of tooth finish position dictates or drives the prescription of the appliance, the present treatment planning techniques lead directly to appliance design parameters (bracket and wire position, or other treatment design, such as staged shell configuration) for treatment of the patient.

It will be appreciated that the comprehensive functionality provided by software described herein is fully applicable to a full range of craniofacial disorders, and while the preferred embodiment is in an orthodontic context, the invention is certainly not so limited.

It will further be noted that there may be some interdependencies between the constraints, in other words, if the user changes one constraint, e.g., occlusal plane, other constraints may also be affected (in 2 and 3 dimensions). Examples of such constraints include AP positions of the incisors and molars, intermolar width, intercanine width, amount of overjet, amount of overbite, sagittal relation of the teeth, and lip protrusion.

Proposed Treatment Evaluation

FIG. 40 shows a list of high-level criteria comprising (a) treatment efficiency 940, (b) treatment effectiveness 950, (c) patient connectedness to treatment 960, (d) timeliness of treatment 970, (e) treatment safety 980, and (f) treatment equitability 990 for a comprehensive orthodontic treatment evaluation and quality measurement process integrated into the system 100 of FIG. 1 according to the preferred embodiment of the invention. Each high level criterion may comprise plurality of sub-criteria. Basically, the evaluation process is performed as follows: Each criterion is measured and compared against a threshold in order to determine whether its performance is acceptable or not. In the event that the performance of a particular criterion is unacceptable or rejected, a root-cause analysis is performed if applicable; and the corrective actions performed accordingly. The value of a threshold can be set from experience and can be changed as additional experience is gained through treatment of new patients. The threshold can also be adjusted by a practitioner. Additionally, the threshold may be set in accordance with the patient needs.

At block 940, the treatment efficiency is evaluated while selecting the type of treatment and planning the treatment for an orthodontic patient and during the execution of the treatment. The treatment efficiency is evaluated from the perspective of (i) productivity of the people delivering the treatment, (ii) cost and availability of materials required for the treatment, (iii) suitability of the treatment method for the patient, and the estimated time duration for the treatment, (iv) reliability and cost contributions towards the treatment of the patient from the equipment necessary for creating and delivering the treatment, (v) the cost contribution and other criteria attributable to the environment in which the treatment is delivered, etc. Regarding the people planning and delivering the treatment in the field of orthodontics, they perform the tasks of scheduling patients appointments, taking photographs and x-rays of patients' faces and dentitions, scanning patients' dentitions, taking impression for preparing physical molds of patients' dentitions, placing brackets on patients' teeth and inserting archwires within the bracket slots, periodically replacing the archwires on patients' dentitions; etc. This list of tasks is simply given as an example; and it is not meant to be exhaustive. If the treatment involves aligner shells, then there are a series of tasks pertaining to that method of treatment. The productivity is measured in terms of, for example, time consumed for a patient per category of task or per appointment. The materials comprise orthodontic appliances such as brackets and archwires, and bonding agents. When applicable, aligner shells are also included in the materials category. The orthodontic treatment methods include, for example, (i) brackets and 'straight' or planar archwire, (ii) brackets and non-planar or customized archwire; and (iii) aligner shells; however, one skilled in the art would realize that other orthodontic treatment options are available. The brackets are generally customized while using a 'straight' archwire; while the brackets are generally standard while using a customized archwire. Not all treatment types can handle all classes of mal-occlusion. Furthermore, treatment times vary depending upon the treatment type. For example, the treatment using brackets and customized archwires generally takes the least amount of time to complete the treatment as compared to other treatment types. For example, the equipment comprises the equipment for manufacturing the orthodontic appliances, such as for example brackets, archwires and aligners and the appliances them selves. Mean-time-between-failures are of interest in determining the reliability of the equipment used in or related to the orthodontic treatment. The environment comprises factors such as ergonomics, chair-side utilization, mean-time-between-patients, number of staff personnel from the practitioner's clinic attending to the patient, etc.

At block 950, the treatment effectiveness is evaluated. This aspect of the preferred embodiment of the invention is discussed at length later in this specification in conjunction with FIG. 43 and supporting FIGS. 41, 42 and 44-70. Treatment effectiveness is measured against known clinical standards and benchmarks, and taking this information into account, the treatment is planned by the practitioner in accordance with the patient's needs. The treatment itself can be staged when that is a desired option.

At block 960, the patient connectedness to the treatment is evaluated. The patient connectedness criterion includes sub-criteria such as matching treatment results with the patient expectations, care of service, e.g., timeliness of response from the practice to the queries from the patient, patient comfort and patient overall satisfaction. Other factors may contribute towards a patient's connectedness towards a particular treatment.

At block 970, the timeliness of the treatment is evaluated. The timeliness criterion includes sub-criteria such as appointment intervals, length of appointments, waiting time in the reception area, difference between the estimated treatment time and the actual treatment time.

At block 980, the treatment safety is evaluated. In order to assess the safety of a treatment, it is examined against the historical database which catalogues the occurrences of the adverse events related to the treatment as well as the successful events. The adverse events are further classified according to the number of episodes causing discomfort or pain to the patient, the nature of pain, decalcification of teeth, root resorption, gingivitis, periodontitis, etc. The adverse events are also classified as follows: (a) iatrogenic event where the problem is caused by the practitioners mistake, e.g., inadvertently causing the fracture of the jaw bone of the patient; (b) idiopathic event where there is no known cause for the problem; however the patient is sensitive to the treatment; and (c) idiosyncratic event which develops a new response within the patient which was never recorded before in the history of the treatment.

At block 990, the treatment equitability is evaluated. The treatment equitability criterion comprises factors such as whether or not same standard of care is offered to all patients, matching of patient profile against the treatment needs of the patient, against established clinical pathways, and between offerings from different orthodontic practices.

According to a preferred embodiment of the invention, different ways to measure the evaluation criteria disclosed herein have been integrated into a comprehensive, unified system 100 of FIG. 1.

Furthermore, within system 100 of FIG. 1, 'alert system' is built based upon the patient's initial condition or history, whereby the alert system would raise a flag to the practitioner if a certain aspect of the treatment would be problematic to the patient, e. g., hyperterothoide can cause root resorption in a patient.

In another embodiment of the invention, system 100 of FIG. 1 is linked with other databases and key search engines such as Medline, and other resources such as doctors, hospitals and universities through Internet or other communication media. As new information is gathered from patients, the databases are updated, and the benchmarks revised accordingly.

Treatment can be planned solely in line with the practitioner's diagnosis of the patient's problems, or the patient's needs, or a combination of both.

The treatment evaluation can be performed in the beginning while planning the treatment, during the treatment and at the end of the treatment.

The system 100 of FIG. 1 is optimized to yield best clinical pathways; and it refreshes existing clinical pathways as the experience is gained from new patients.

The system 100 of FIG. 1 utilizes both internal and external data resources. The data may be image based, audio, text etc.

The measurements may be distance based or based upon volume. The measurements may be two-dimensional or three-dimensional. Three-dimensional coordinate systems providing local and global references can be used for such measurements. The evaluation process comprises analysis of 3D shapes, forms and contours of three-dimensional virtual images derived from CT scan, craneo-facial X-rays, scanning of dentition, etc. Such analysis can be used to analyze root shapes, bone structure, tissue, etc.

The measurement thresholds and grading can be set from experience; and changed as new data become available. Furthermore, the measurement thresholds and grading can be individualized as desired.

Root cause analysis depends upon the problem to be investigated. For example, if in a certain patient's case the treatment is taking longer than anticipated, a root cause analysis may reveal that one or more brackets prematurely came off from the patient's teeth due to defective base; so a proper corrective action can be undertaken.

In another embodiment of the invention, system 100 of FIG. 1 provides a closed-loop or a feedback loop for treatment planning, treatment monitoring and treatment evaluation and quality measurement.

The thresholds can be set at single or range of values.

In another embodiment of the invention, a database of cases is created to find a suitable response that would match a patient's condition.

One skilled in the art would appreciate that the treatment evaluation approach disclosed herein can also be used to evaluate denture set-ups, crowns, bridges, and in general any prosthetic or restorative dental element. The user can select the extent and type of evaluation to be performed from the types of evaluations described earlier for the orthodontic treatment.

Treatment Effectiveness

The treatment effectiveness evaluation aspect of the preferred embodiment of the invention will now be discussed in conjunction with FIG. 43 and supporting FIGS. 41, 42 and 44-70.

FIG. 41 shows a screen shot from the workstation of FIG. 1 depicting the virtual dentition model of the maxilla or the upper teeth 1002 of a patient in an initial or malocclusion state. For ease of illustration only the upper teeth are shown in FIG. 41. However, one skilled in the art would appreciate that the virtual dentition model comprises both upper and lower jaws, in this case, in the malocclusion state. The treatment is planned for this patient using the treatment planning process described earlier. FIG. 42 shows a screen shot depicting the resulting virtual dentition model of the upper teeth 1004 of the patient in the target state. Again, for ease of illustration only the upper teeth are shown in FIG. 42. After planning treatment, one skilled in the art would appreciate that the virtual dentition model comprises both upper and lower jaws in the target state.

Once the treatment is planned, the virtual dentition model of the patient in the proposed treatment set-up or the target state is evaluated using several virtual model evaluation features and criteria. FIG. 43 provides a list of the virtual model evaluation features according to the preferred embodiment of the invention. The virtual model evaluation features are: (a) alignment 1010, (b) marginal ridges 1012, (c) buccolingual inclination 1014, (d) occlusal relationship 1016, (e) occlusal contacts 1018, (f) overjet 1020, (g) interproximal contacts 1022, (h) vertical alignment of buccal cusp tips 1024, (i) vertical alignment of anterior teeth 1026, and (j) angulation of front 1028. A more detailed explanation of the virtual model evaluation features is given later on in this specification. The virtual model evaluation criteria utilize certain tooth features and distance or penetration measurements involving these tooth features for evaluating the quality of the planned treatment. Therefore, the general tooth features will now be described followed by the description of the measurement types and methods of measurements. Although some of the evaluation features and criteria are similar to those developed by ABO, the invention disclosed herein is novel and useful over the ABO approach. The invention discloses comprehensive treatment planning and evaluation process utilizing three-dimensional virtual models of patient's dentition and orthodontic structure. Whereas ABO is limited in two-dimensional measurements using a measuring gauge, the measurements disclosed herein are very versatile, complex and truly insightful to the practitioner. ABO criteria are applied to evaluate the results of a treatment once it is completed. However, the evaluation criteria disclosed herein can be used at the initial stage of planning an orthodontic treatment as well as for monitoring the progress of a treatment during the course of the treatment.

Tooth Features

The tooth features of interest according to the preferred embodiment of the invention are: (a) cusp tips, (b) marginal ridges, (c) central grooves, (d) contact points, (e) buccal grooves, and (f) crown center axis of teeth with vertical, mesial/distal and in-out orientation.

FIG. 44 shows a screen shot depicting the cusp tips 1040, shown in the form of dots, on the virtual maxilla teeth of the patient. The outer cusp tips, used for aligning the teeth, are joined by the line segments 1042. The line segments 1042 make it easier to visually check the alignment of the teeth. Although not shown in FIG. 44, one skilled in the art would appreciate that there are cusp tips associated with the virtual mandible or lower teeth of the patient as well.

Figure 45:
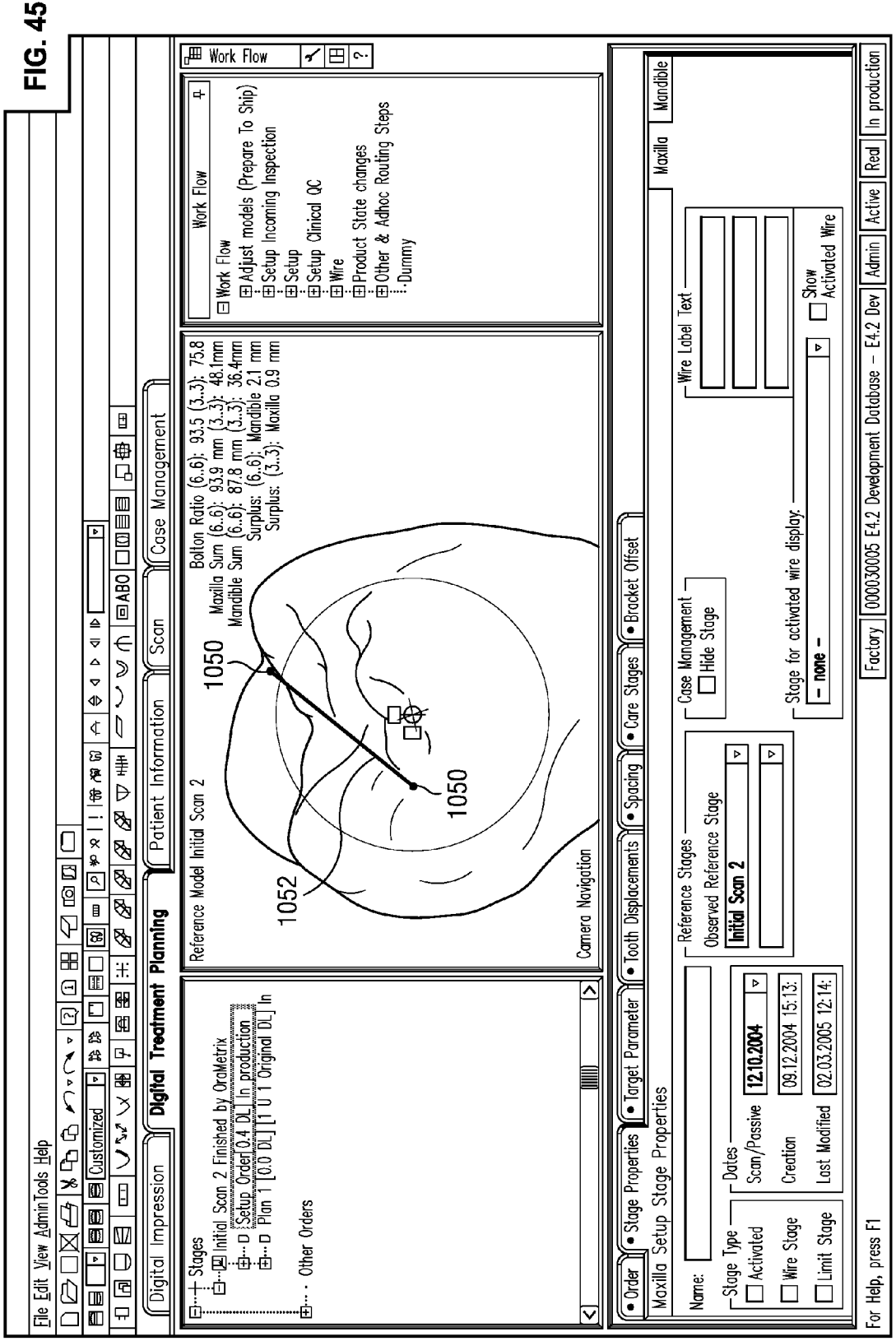
FIG. 45 shows upper posterior with marginal ridges.

FIG. 45 shows a screen shot depicting the marginal ridge 1052, shown as a line segment connecting points 1050, of an example virtual tooth of a patient. A marginal ridge is present on each of the posterior teeth such as molars and bicuspids.

Figure 46:
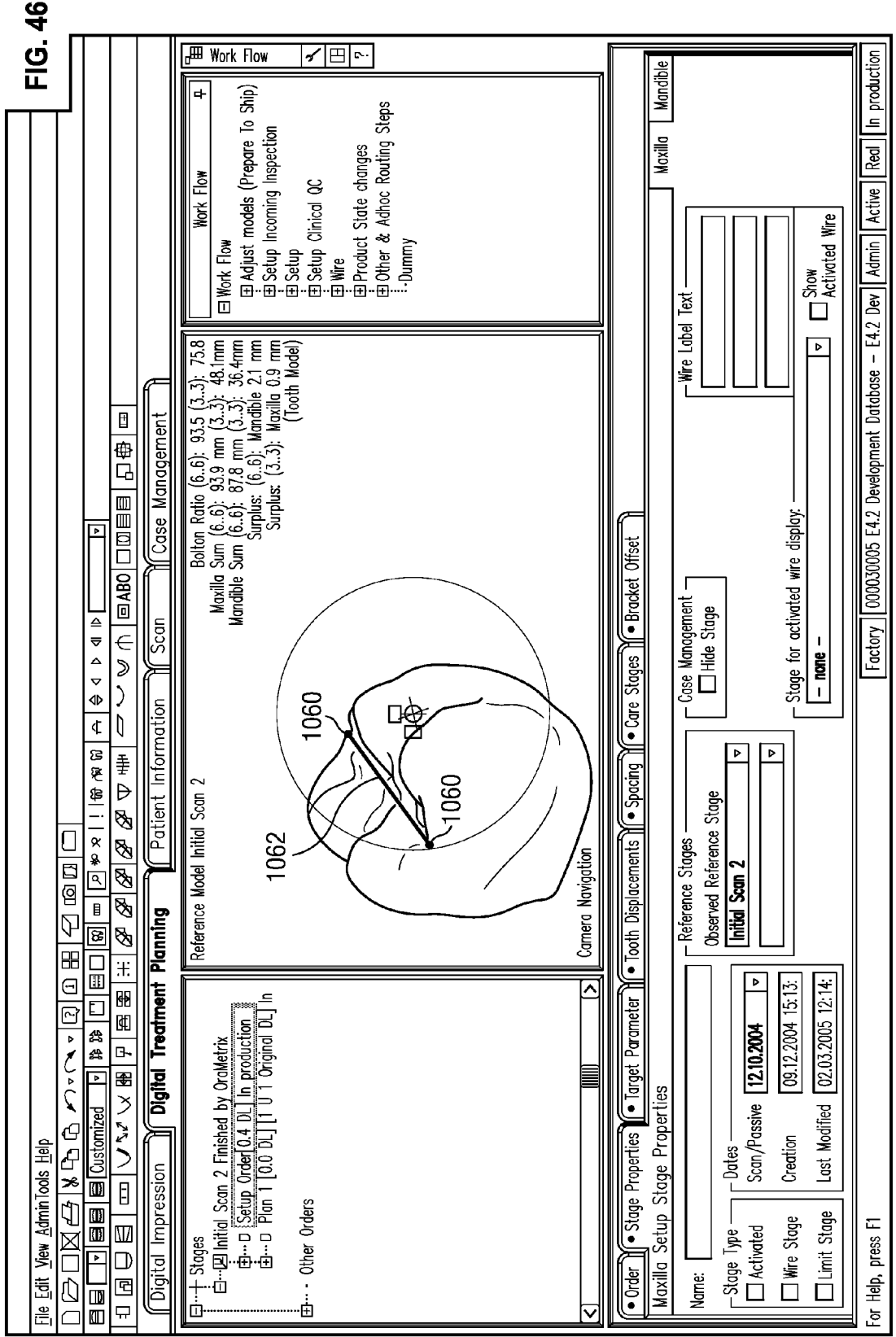
FIG. 46 shows upper posterior with central groove.
Figure 47:
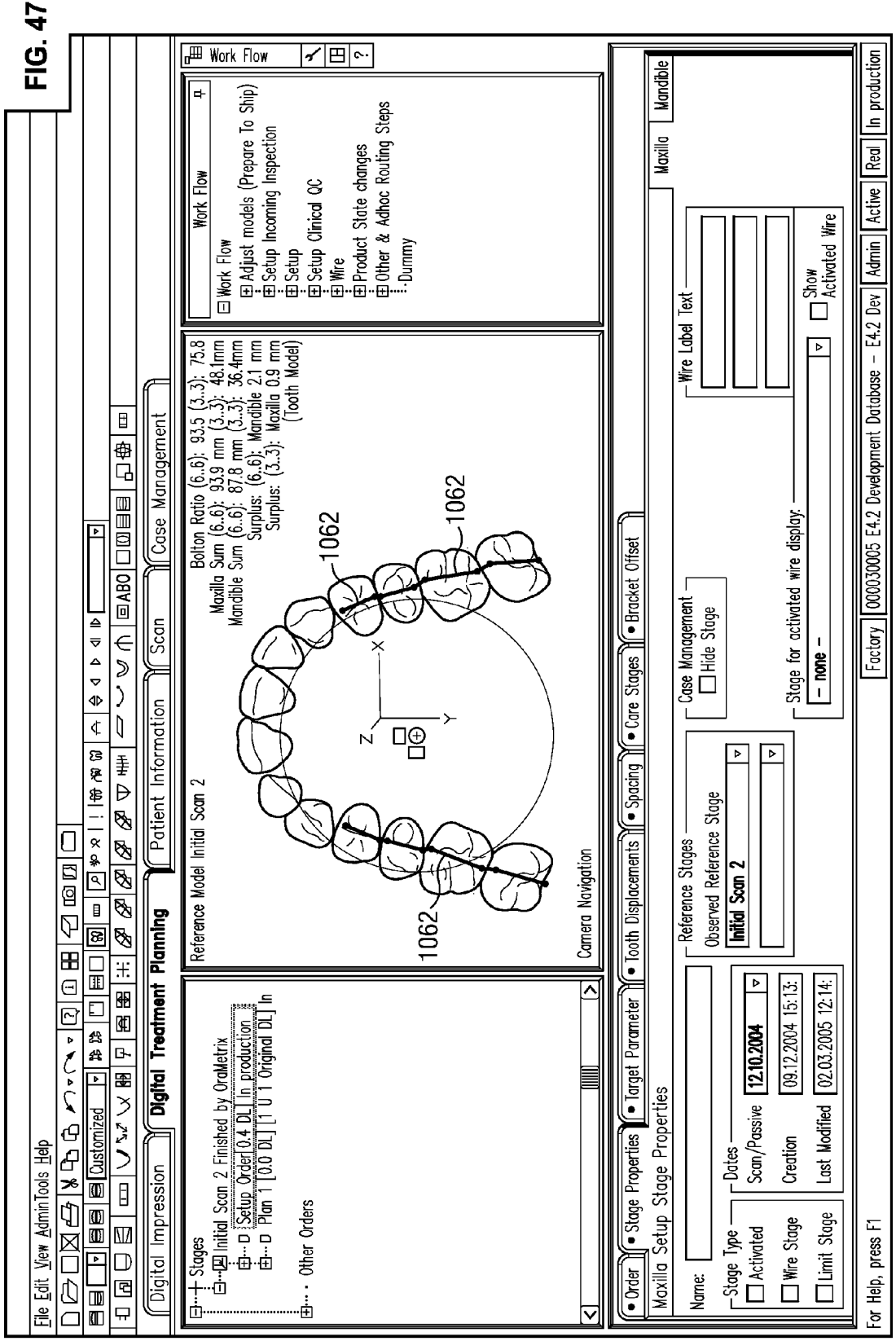
FIG. 47 shows whole upper jaw with central grooves

FIG. 46 shows a screen shot depicting the central groove 1062, shown as a line segment connecting points 1060, of an example virtual tooth of a patient. A central groove is present on each of the posterior teeth, such as molars and bicuspids, on the maxilla and the mandible. FIG. 47 shows a screen shot depicting the central groves on the posterior teeth of an upper jaw of a patient.

Figure 48:
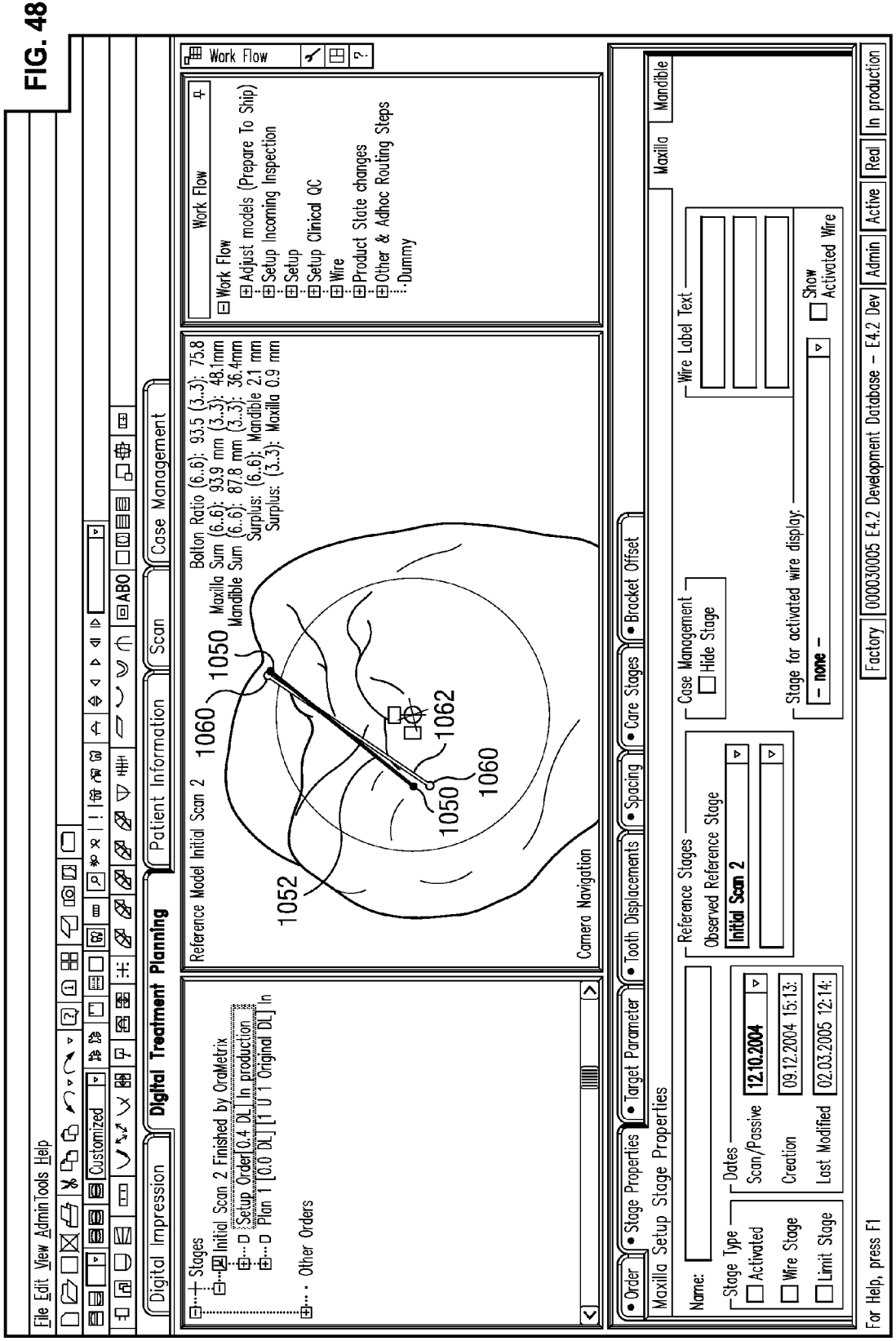
FIG. 48 shows upper posterior with central grooves and marginal ridges.

FIG. 48 shows a screen shot depicting the marginal ridge 1052, shown as a line segment connecting points 1050, super imposed on the central groove 1062, shown as a line segment connecting points 1060, of an example virtual tooth of a patient.

Figure 49:
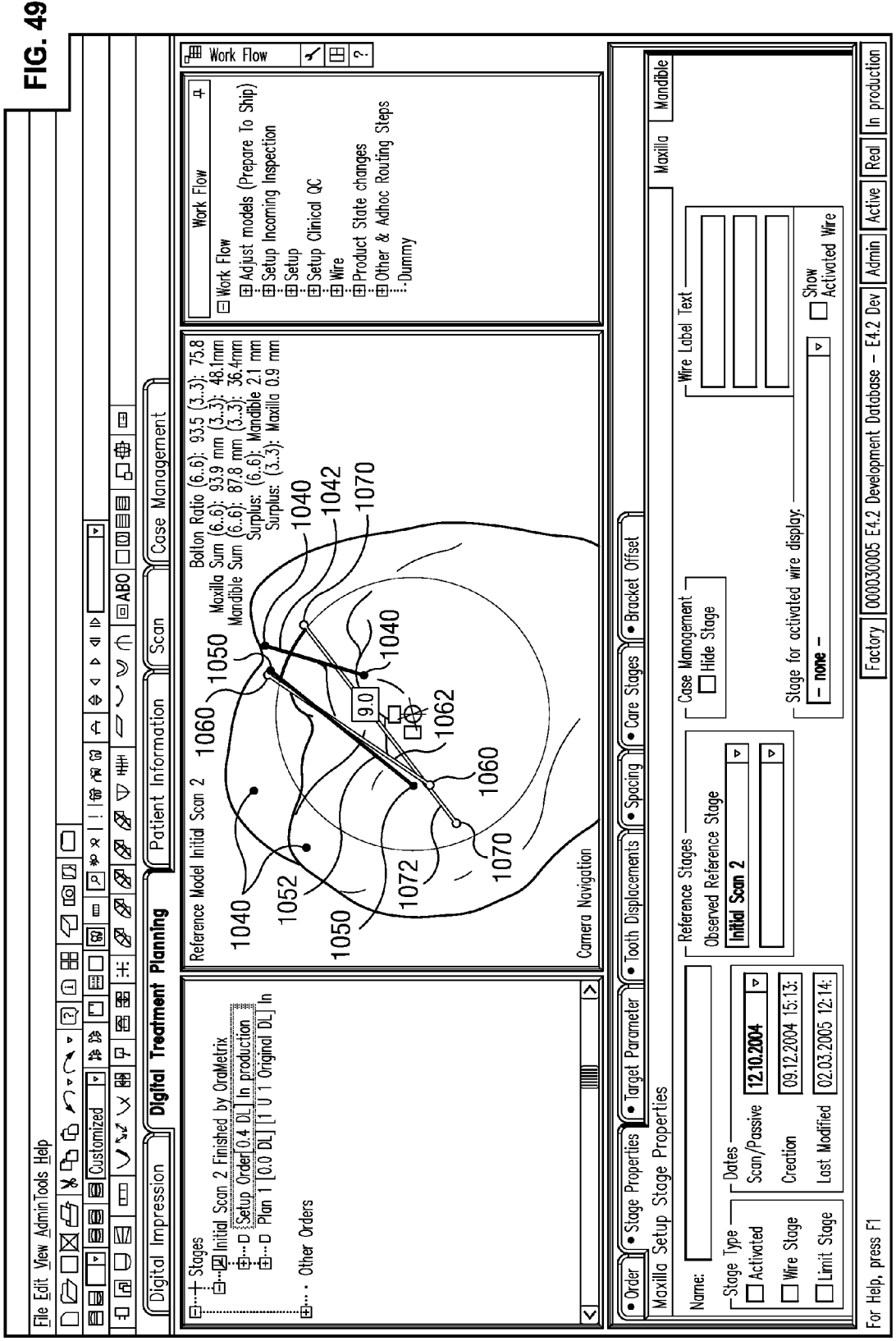
FIG. 49 shows upper posterior with central grooves, marginal ridges, contact points and cusp tips.

FIG. 49 shows a screen shot depicting the contact points 1070, connected by a line segment 1072 of an example virtual tooth of a patient. It should be pointed out that the line segment 1072, either partially or completely, might pass through the body of the tooth. However, for illustration purposes the line segment 1072 is made completely visual in FIG. 49. FIG. 49 also shows the cusp tips 1040, the line segment 1042 connecting the two outer cusp tips; the marginal ridge 1052 connecting points 1050, and the central groove 1062 connecting points 1060.

Figure 50:
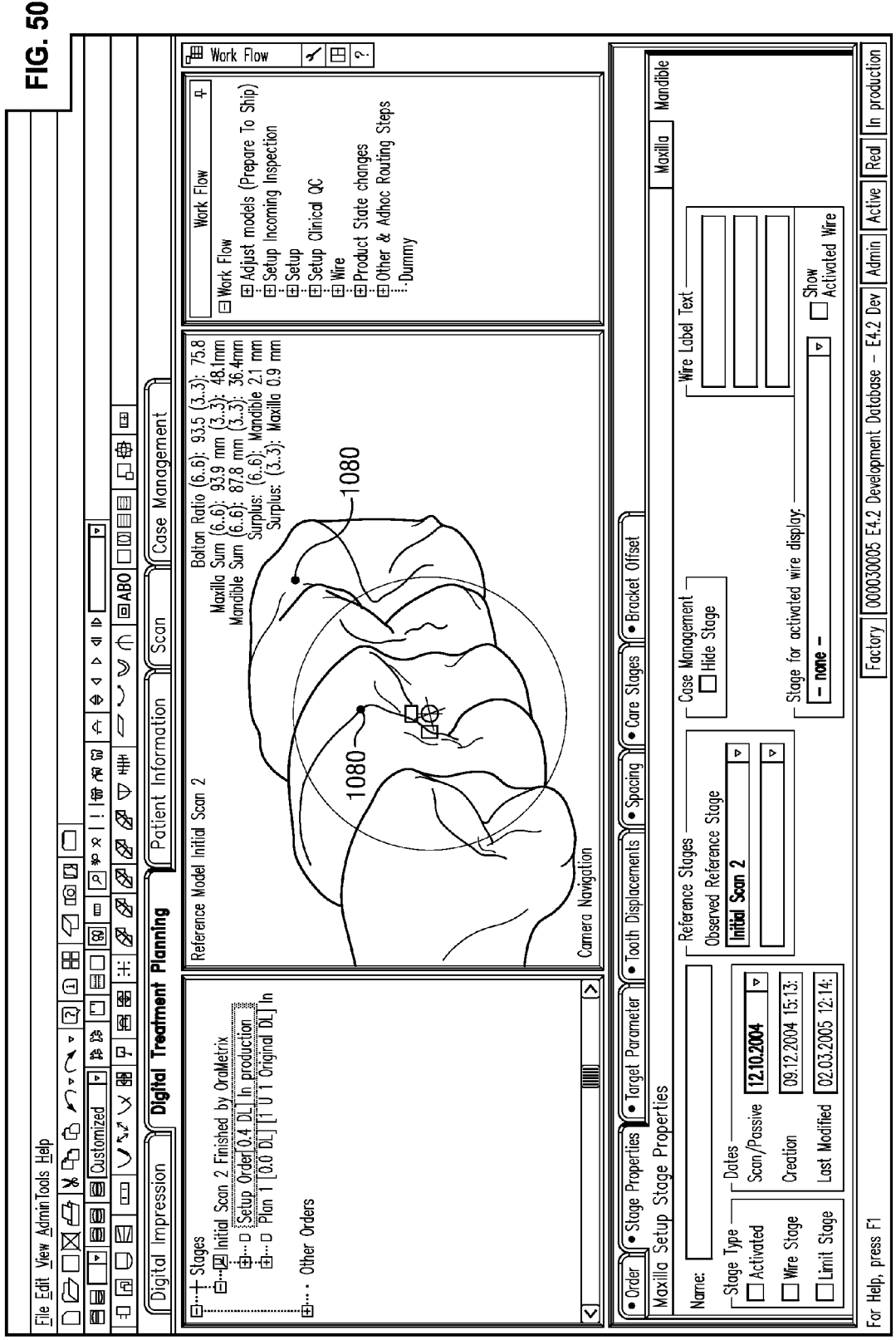
FIGS. 50 and 50A show buccal grooves.
Figure 50A:
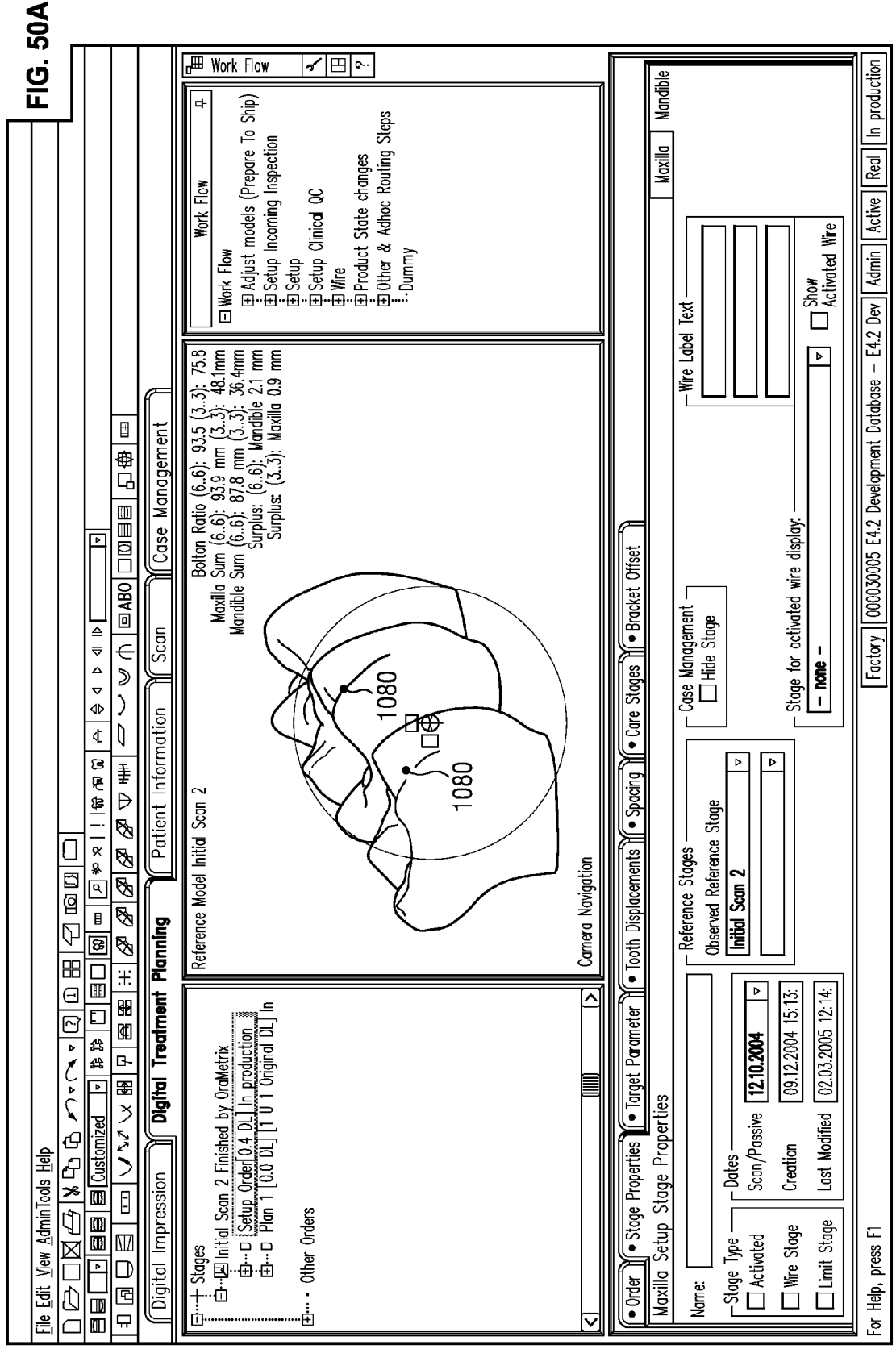

FIGS. 50 and 50A show screen shots depicting two different views of example virtual teeth with buccal grooves 1080.

Measurement Types

Figures 51, 52:
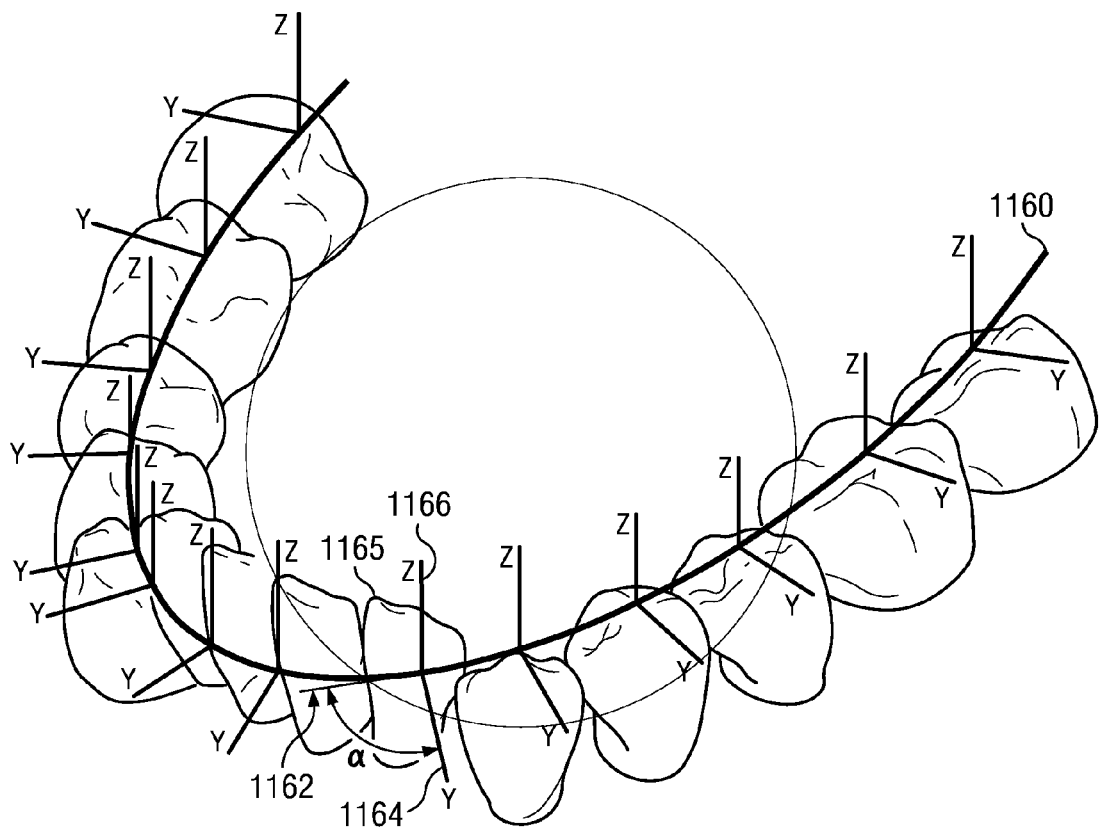
FIG. 51 provides a list of measurement types needed to support the virtual model evaluation criteria.
FIG. 52 shows an example of the orthodontic coordinate system.

Each of the virtual model evaluation features presented earlier requires some form of measurement for evaluating the proposed treatment. FIG. 51 provides a list of measurement types needed to support the virtual model evaluation features, namely, (a) distance between two points 1100, (b) distance between a point and an object 1110, (c) shortest directed distance between two objects 1120, (d) shortest distance between two objects 1130, (e) deepest penetration between two objects 1140, and (f) distance or penetration between two objects 1150. According to a preferred embodiment of the invention, an orthodontic coordinate system, as described below, is devised which enables measurement of the orthodontic parameters in a meaningful and consistent manner.

Orthodontic Coordinate System

It is a common practice with orthodontists to describe the position or the movement of a tooth or a group of teeth with the parameter values grouped as 'mbctar' (mesial, buccal, coronal, torque, angular displacement, rotation). Usually, mm and gradient are the units of measurement used to specify the parameter values. These descriptions are not unique in a mathematical sense. There are some shortcomings associated with this approach. While one can thus always describe relative translatory motion in this manner, this does not apply to rotational movements, where additionally the sequence of the movements should be specified. A further problem arises due to subjective determination of the position of the respective rotational axes by the orthodontists. This prevents the creation of reproducible tooth positions.

A novel orthodontic coordinate system is disclosed herein that obviates the shortcomings of the traditional approach discussed above. The orthodontic coordinate system provides a unique representation using the parameters familiar to the orthodontists. The orthodontic coordinate system defines and sets the respective rotational axes in such a way that their positions can be intuitively understood by the practitioners.

The orthodontic coordinate system, in principle, utilizes the central axes systems of a tooth to describe its position. The representation of the tooth axis system is done in a fixed local reference system. However, this system may not be fixed in space, as depending on the position of the tooth subjectively different rotation axes result relative to the tooth arc. Every tooth is assigned its own reference system that is applicable in any position. The position of theses reference systems coincides in any tooth position with the subjectively found rotation axes, which means buccolabial and mesiodistal alignment. The coordinate (reference) systems should be thought of as lying at the location of the tooth axis of every tooth with their origins in one plane. Within this plane a monotonously curved plane (virtual) tooth arc is defined, so that one axis of the systems coincides with the tangent at the arc at the respective position (at its origin) and one with the normal to the arc at that position. The origin of the reference systems always falls on one point of the arc. In this way rotation axes for angular displacement and torque are always in agreement with a buccolabial or a mesiodistal view of the jaw. That means the axes are oriented themselves by the jaw, not by the single tooth. An important consequence emerges regarding the tooth root movement. Due to the orientation of the axes by the tooth arc, the possible root movements are unequivocally perpendicular or parallel to the periodont, which makes them easier to direct. The virtual (tooth) arc or virtual tooth jaw (VTJ) consists of an even polynomial of higher order. That means the VTJ is symmetrical in regard of the jaw halves. The adaptation of the polynomial to the individual tooth arc is done with help of the minimum sum of distance squares between the arc points and the tooth contact points in the projection onto the aforementioned plane. FIG. 52 presents an example for an orthodontic coordinate system comprising VTJ 1160, and for the tooth 1165 a tangent 1162 to the VTJ representing the x-axis, and an axis 1164 perpendicular to the tangent, i.e. at the angel α equal to 90°, representing the y-axis. In FIG. 52, the tooth axis 1166 represents the z-axis for the tooth 1165. One skilled in the art would appreciate that orthodontic coordinate system for various teeth is shown in FIG. 52.

Measurement Methods

The virtual dentition model is first transformed into the orthodontic coordinate system so that each point of the patients' virtual dentition has the following coordinates:
x=mesio-distal (along the arch);
y=in-out (perpendicular to x, in the plane of the arch); and
z=vertical (perpendicular to x and y).

The directed distance between two points 1100 is calculated as follows:

Let $P=(P_x,P_y,P_z)$ and $Q=(Q_x,Q_y,Q_z)$ be 2 points, and $d=(d_x,d_y,d_z)$ a direction vector with length 1 (one). That is $\|d\|:=\sqrt{d_x^2+d_y^2+d_z^2}=1$).

Then, the directed distance between two points P and Q in the direction d is given by:

$$dist(P,Q,d)=|(Q-P)\cdot d|=|(Q_x-P_x)\cdot d_x+(Q_y-P_y)\cdot d_y+(Q_z-P_z)\cdot d_z|. \quad \text{Eq. (1)}$$

The directed distance between a point and an object 1110 is calculated as follows:

Let $P=(P_x,P_y,P_z)\in R^3$ be a point, $B \subset R^3$ an object (=set of points) and $d=(d_x,d_y,d_z)$ a direction vector with length 1, where R refers to the set of all real numbers.

Then, the directed distance between the point P and the object B is given by:

$$dist(P,B,d)=\min\{k\in R | P+k\cdot d\in B\}. \quad \text{Eq. (2)}$$

The shortest directed distance between two objects A and B 1120 is calculated as follows:

Let $A,B\subset R^3$ be two objects, and $d=(d_x,d_y,d_z)$ a direction vector with length 1. Then, the shortest directed distance between two objects A and B in the direction d is given by:

$$dist(A,B,d)=\min\{k\in R | \exists P\in A: P+k\cdot d\in B\}. \quad \text{Eq. (3)}$$

The shortest distance between two objects 1130 is calculated as follows:

Let $A,B\subset R^3$ be two objects.

Then the shortest distance between object A and object B is given by:

$$dist^+(A,B)=\min\{d\in R | \exists P\in A, Q\in B: \|Q-P\|=d\}. \quad \text{Eq. (4)}$$

The deepest penetration between two objects 1140 is calculated as follows:

Let $A\subset R^3$ be an object and $P\in A$ a point within this object. Then the depth of P within A is given by:

$$dist^-(P,A)=\min\{d\in R | \exists Q\in \text{Boundary}(A): \|Q-P\|=d\}.$$

Now let $A,B\subset R^3$ be two intersecting or touching objects (that means $dist(\overline{A,B})=0$ and $A\cap B\neq\{\}$, respectively).

Then the deepest penetration between A and B is given by:

$$dist^-(A,B)=\max\left\{\max_{P\in A\cap B}\{dist^-(P,A)\},\max_{P\in A\cap B}\{dist^-(P,B)\}\right\}. \quad \text{Eq. (5)}$$

The distance/penetration between two objects 1150 is calculated as follows:

The definitions of $dist^+(A,B)$ and $dist^-(A,B)$ can be combined into a new single definition as follows: Let $A,B\subset R^3$ be two objects.

Then the distance/penetration between A and B is given by:

$$dist(A,B)=\begin{cases} dist^-(A,B) & \text{for } A\cap B\neq\{\} \\ dist^+(A,B) & \text{for } A\cap B=\{\} \end{cases} \quad \text{Eq. (6)}$$

Treatment Evaluation Process

The proposed treatment plan is evaluated utilizing the virtual model evaluation features discussed earlier. The evaluation process is summarized below, and a more detailed description relevant to each criterion is subsequently given.

The alignment criterion comprises measurements involving the anterior incisor cusp tips, the anterior incisor contact points, buccal upper central groves, and buccal lower cusp tips. In this case the in-out, i.e., buccal-lingual, distance perpendicular to the mesial-distal direction in the occlusal plane is measured. The marginal ridges criterion comprises measurements involving relative vertical distance at marginal ridges. The buccolingual inclination criterion comprises measurements involving relative vertical distances of cusp tips. The occlusal relationship criterion comprises measurements involving cusp tips, actual contact points and lower buccal groove. The mesial cusp tips (maxillary) are scored in alignment to the actual contact points or the buccal groove of the opposite tooth. Class changes based on missing teeth are calculated. The occlusal contacts criterion comprises measurements involving cusp tips. Two measurements per tooth are made. For lingual cusps (maxillary) and labial cusps (mandible) the shortest vertical distance is calculated. The overjet criterion comprises measurements involving the cusp tips and central groove line. Anterior: shortest distance in in-out direction. Buccal: the alignment of the higher mandible labial cusp is calculated to the central groove of the maxilla tooth, using in-out distance. The interproximal contacts criterion comprises calculation that measures the minimum distance between two teeth. The vertical alignment of buccal cusp tips criterion comprises relative vertical distance at buccal cusp tips perpendicular to occlusal plane, done on a tooth-by-tooth basis. The vertical alignment of front criterion comprises relative vertical distance of mesial and distal incisal edges from one tooth to the neighbor. Edges are calculated from the highest point starting from the cusp tips vertically. Finally, the angulation of front criterion comprises relative distance of mesial and distal incisal edges within one tooth. Incisor edges are calculated from the highest point starting from the cusp tips vertically. A more detailed description of each of the criteria summarized above follows:

Alignment Evaluation

The alignment feature 1010 evaluation is performed by measuring the distance between:

(a) the anterior incisor cusp tips;
(b) the anterior incisor contact points;
(c) buccal upper central groves; and
(d) buccal lower cusp tips.

(a) The Anterior Incisor Cusp Tips

In this case in-out distance perpendicular to the mesial-distal direction in the occlusal plane is measured.

FIG. 53 shows a screen shot depicting the distance between the virtual maxilla incisor cusp tips. The distance is measured between the cusp tip of one tooth and the nearest cusp tip of the adjoining tooth. For example, as shown in FIG. 53, the distance between the cusp tip 1040 of the virtual tooth 1202 and the cusp tip 1040 of the adjoining virtual tooth 1204 is measured. In order to further explain this measurement, section 1210 of FIG. 53 is enlarged and shown in FIG. 53A, where the distance 1212 is measured between the cusp tips 1040. The measurement of the anterior incisor cusp tip distance is performed using the method of measuring the directed distance between two points described above and Eq. (1). Ideally, the cusp tip distance between any two adjoining anterior incisors should be less than 0.5 mm. If the anterior incisor cusp tip distance is (i) equal to or greater than 0.5 mm and less than or equal to 1.0 mm, a treatment evaluation score of −1, or (ii) greater than 1.0 mm, a treatment evaluation score of −2 is assigned to the quality of the proposed treatment for each instance of measurement of the anterior incisor cusp tip. FIG. 54 shows a screen shot depicting cusp tip distance measurements 1214 for all virtual mandible or lower teeth. Similarly, FIG. 55 shows a screen shot depicting cusp tip distance measurements 1216 for all virtual maxilla or upper teeth.

(b) The Anterior Incisor Contact Points

Figure 56:
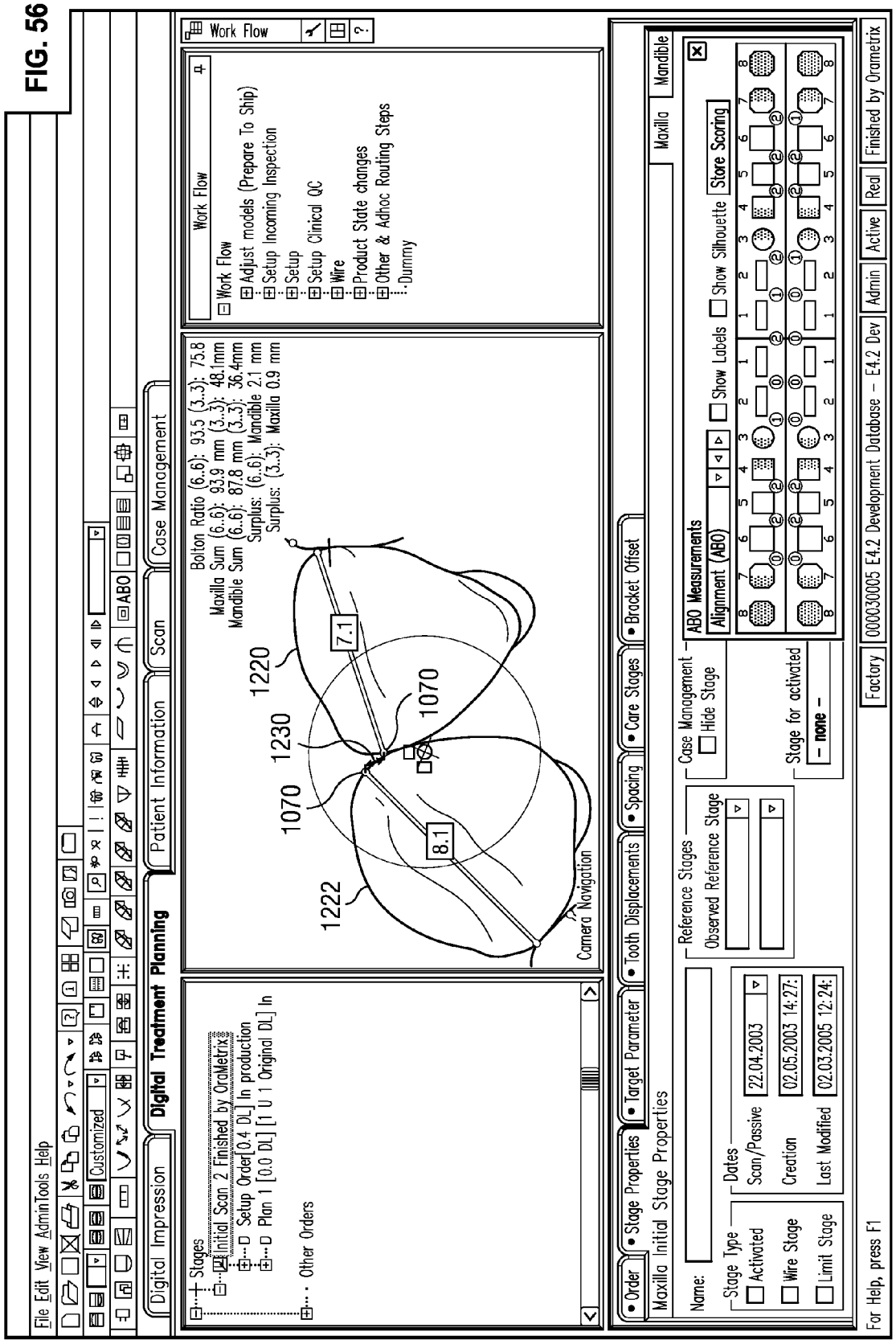
FIG. 56 shows a screen shot depicting an example of the distance between the anterior incisor contact points.
Figure 57:
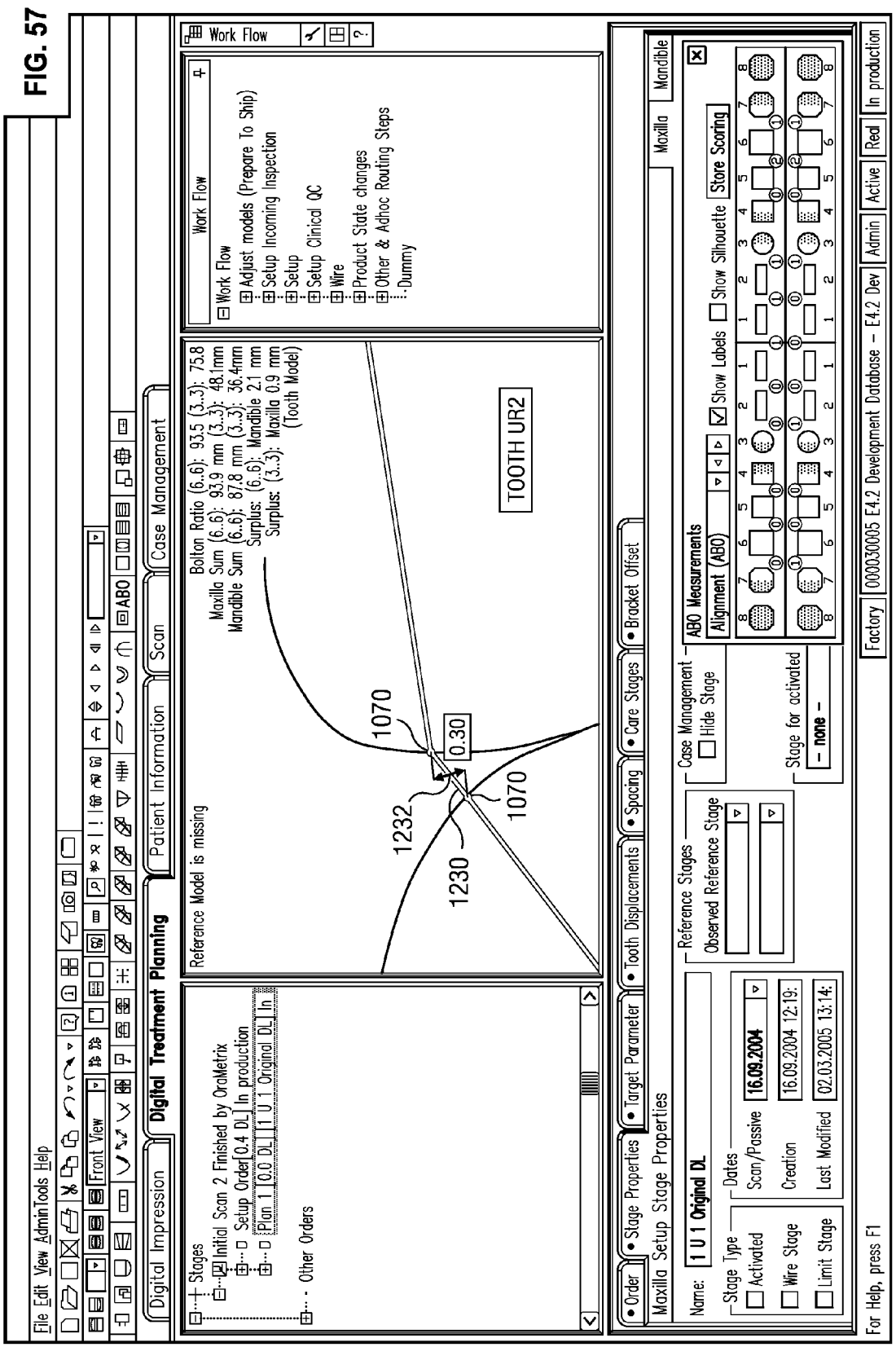
FIG. 57 shows a screen shot depicting an enlarged illustration of the distance between the anterior incisor contact points.

FIG. 56 shows a screen shot depicting an example of the distance between the anterior incisor contact points. The distance is measured between the contact point of one tooth and the contact point of the adjoining tooth. These contact points are not the actual contact points, but the ideal contact points. That means that these are not the points were the teeth touch, but were they should touch in a good setup. For example, as shown in FIG. 56, the distance between the contact point 1070 of the virtual tooth 1220 and the contact point 1070 of the adjoining virtual tooth 1222 is measured. In order to further explain this measurement, section 1230 of FIG. 56 is enlarged and shown in FIG. 57, where the distance 1232 is measured between the contact points 1070. The measurement of the anterior incisor contact point distance is performed using the method of measuring the directed distance between two points described above and Eq. (1). Ideally, the contact point distance between any two adjoining anterior incisors should be less than 0.5 mm. If the anterior incisor contact point distance is (i) equal to or greater than 0.5 mm and less than or equal to 1.9 mm, a treatment evaluation score of −1, or (ii) greater than 1.0 mm, a treatment evaluation score of −2 is assigned to the quality of the proposed treatment for each instance of measurement of the anterior incisor contact point distance.

(c) Buccal Upper Central Groves

Figure 58:
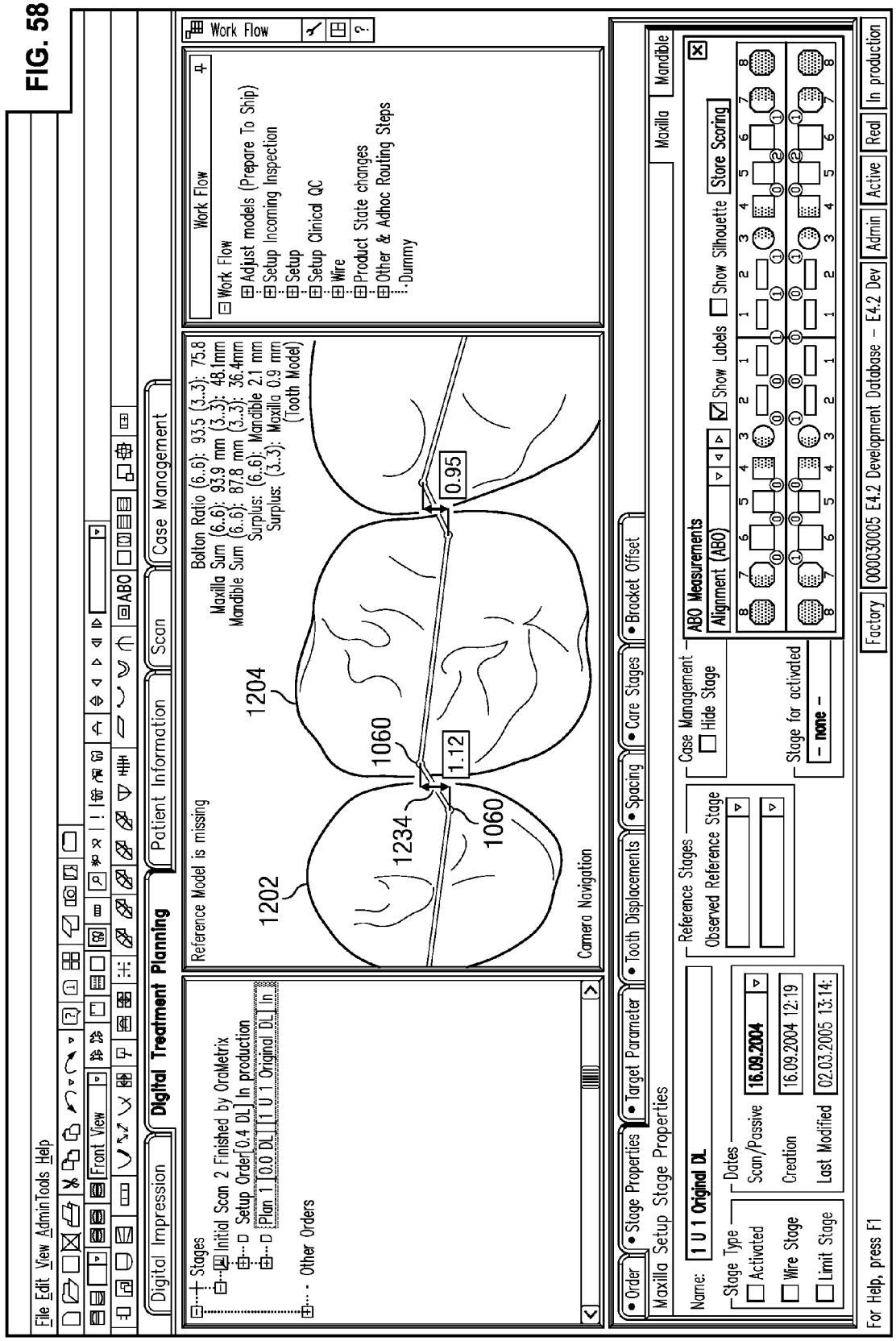
FIG. 58 shows a screen shot depicting the distance between the buccal upper central groves.

FIG. 58 shows a screen shot depicting the distance between the buccal upper central groves. The distance is measured between the central groove of one tooth and the nearest central groove of the adjoining tooth. For example, as shown in FIG. 58, the distance 1234 between the central groove 1060 of the virtual tooth 1202 and the central groove 1060 of the adjoining virtual tooth 1204 is measured. The measurement of the buccal upper central groves distance is performed using the method of measuring the directed distance between two points described above and Eq. (1). Ideally, the buccal upper central groves distance should be less than 0.5 mm. If this distance is (i) equal to or greater than 0.5 mm and less than or equal to 1.0 mm, a treatment evaluation score of −1, or (ii) greater than 1.0 mm, a treatment evaluation score of −2 is assigned to the quality of the proposed treatment for each instance.

(d) Buccal Lower Cusp Tips

As previously discussed, FIG. 54 shows a screen shot depicting cusp tip distance measurements 1214 for all virtual mandible or lower teeth. The measurement method and the evaluation criteria for the buccal lower cusp tips distances are the same as those presented earlier for the anterior incisor cusp tips.

Marginal Ridges Evaluation

Figure 59A:
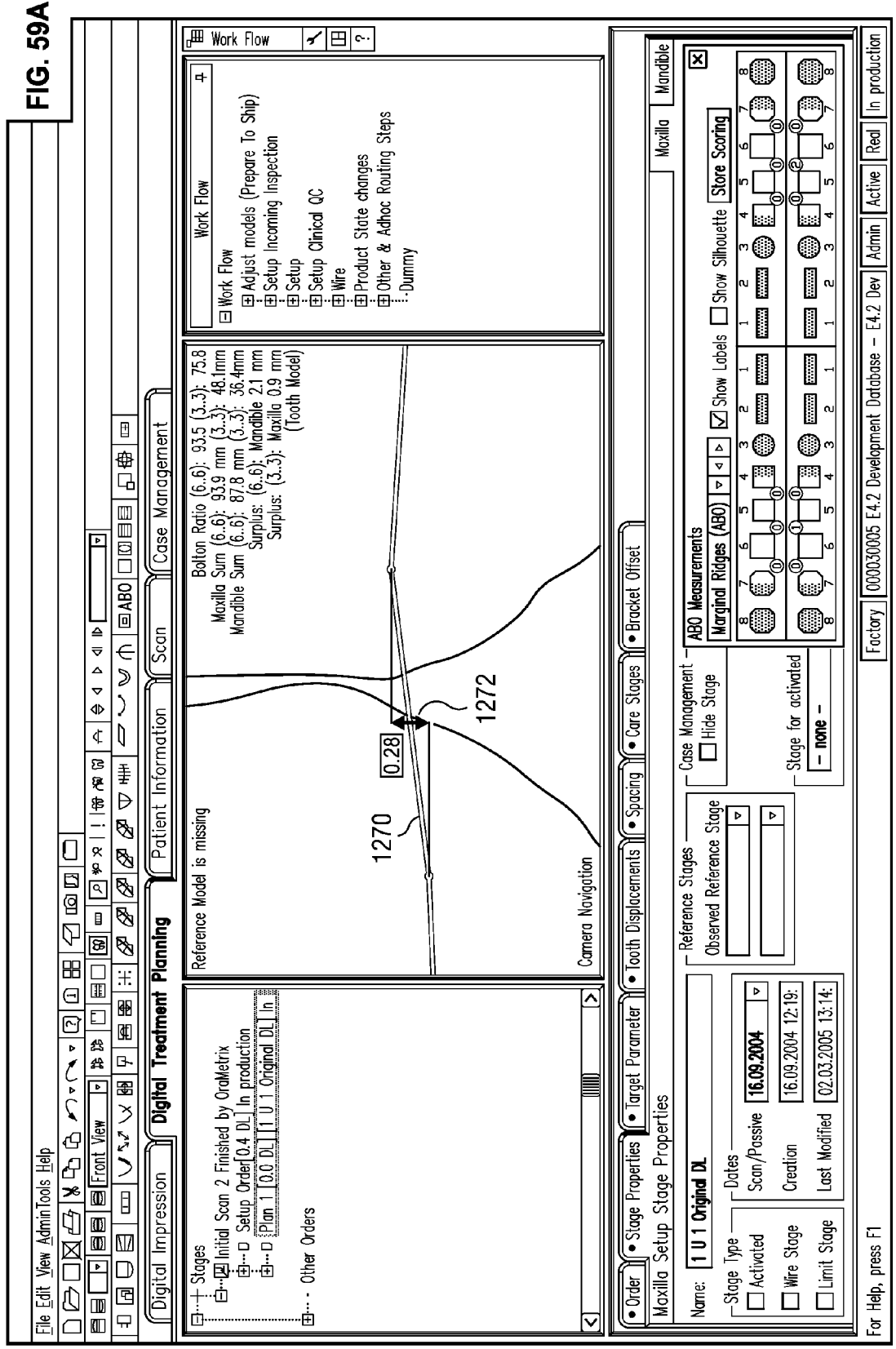
FIG. 59 shows measurement of marginal ridges.
Figure 60:
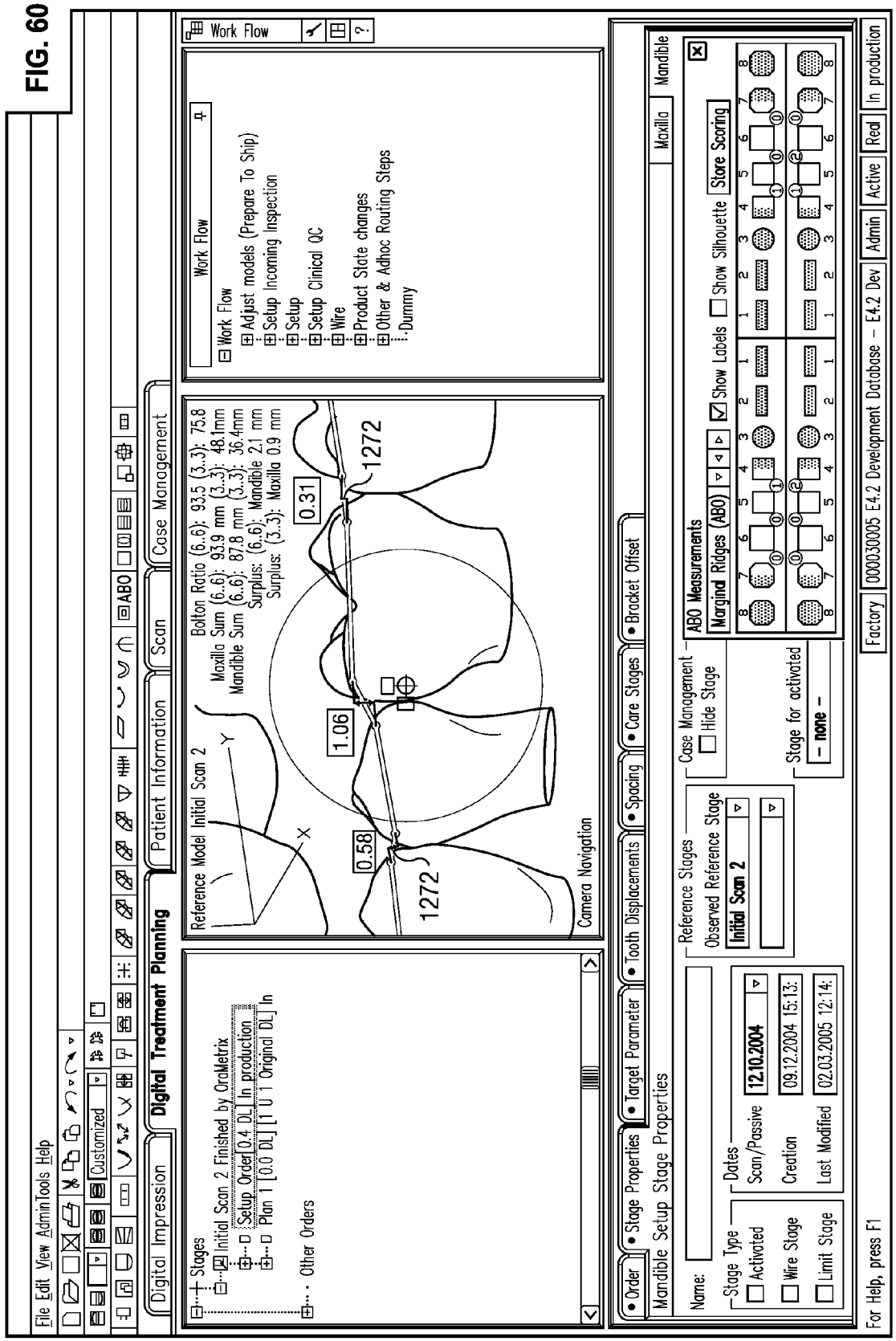
FIG. 60 shows another example of measurement of marginal ridges.

The evaluation of the proposed treatment plan or the target state using the marginal ridges feature 1012 is performed by measuring the vertical distance between the marginal ridges of the adjacent teeth. FIG. 59 shows a screen shot depicting the distance between the marginal ridges. For example, as shown in FIG. 59, the distance between the marginal ridge 1052 of the virtual tooth 1260 and the marginal ridge 1052 of the adjoining virtual tooth 1262 is measured. In order to further explain this measurement, section 1270 of FIG. 59 is enlarged and shown in FIG. 59A, where the distance 1272 illustrates the marginal ridge distance. Here again, the measurement of the marginal ridge distance is performed using the method of measuring the directed distance between two points described above and Eq. (1) Ideally, the marginal ridge distance between any two adjoining teeth should be less than 0.5 mm. If the marginal ridge distance is (i) equal to or greater than 0.5 mm and less than or equal to 1.0 mm, then a treatment evaluation score of −1, or (ii) greater than 1.0 mm, then a treatment evaluation score of −2 is assigned to the quality of the proposed treatment for each instance of measurement of the marginal ridge distance. FIG. 60 shows a screen shot depicting the marginal ridge distance measurements 1272 for several teeth.

Buccolingual Inclination Evaluation

Figure 61:
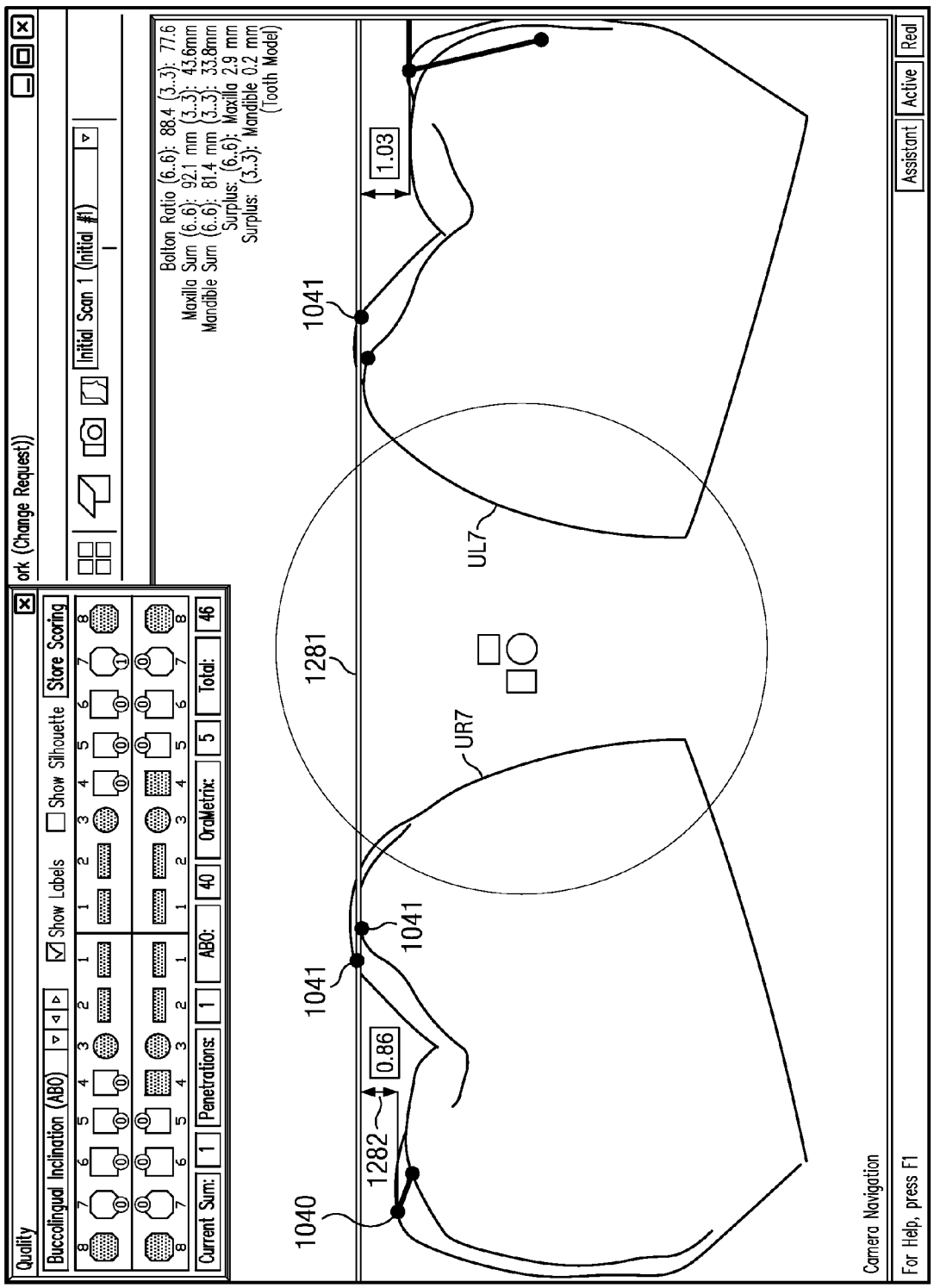
FIG. 61 shows measurement of buccolingual inclination.

The evaluation of the proposed treatment plan or the target state using the buccolingual inclination feature 1014 is performed by measuring the orthogonal distance between a plane and a cusp tip. The plane is defined by the two cusp tips most occlusal on the tooth to be measured and the most occlusal cusp tip from the same tooth-number, on the opposite side of the jaw. The cusp tip used to measure in the distance is on the tooth to be measured and is opposite the cusp tip used in defining the plane. FIG. 61 shows a screen shot depicting the buccolingual inclination measurement. For example, as shown in FIG. 61, the orthogonal distance 1282 between the mesial labial cusp tip 1040 of the virtual tooth UR7 and the plane 1281 which touches the 2 lingual cusp tips 1041 of the virtual tooth UR7 and the mesial lingual cusp tip 1041 of the virtual tooth UL7 is the buccolingual inclination measurement for the virtual tooth UR7. The algorithm always chooses the most occlusal cusp tip of the opposite virtual tooth. Ideally, the buccolingual inclination should be less than 1.0 mm. If the buccolingual inclination is (i) equal to or greater than 1.0 mm and less than or equal to 2.0 mm, then a treatment evaluation score of −1, or (ii) greater than 2.0 mm, then a treatment evaluation score of −2, is assigned to the quality of the proposed treatment plan for each instance of measurement of the buccolingual inclination.

Occlusal Relationship Evaluation

Figure 62:
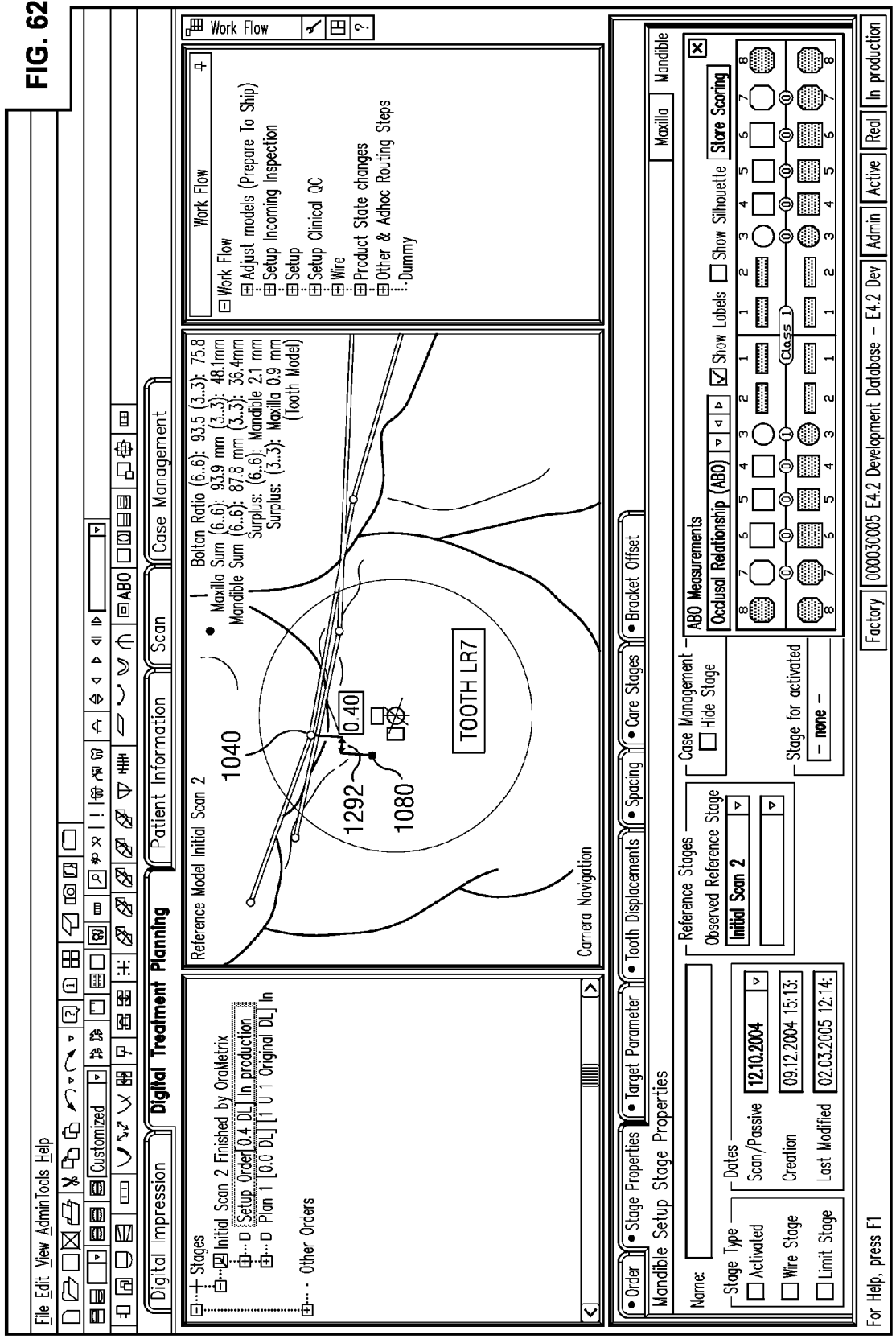
FIG. 62 shows measurement of occlusal relationship.

The evaluation of the proposed treatment plan or the target state using the occlusal relationship feature 1016 is performed by measuring the directed distance in mesio-distal direction between the mesial, labial cusp tip of the maxillary first permanent molar and the posterior buccal groove of the mandibular first permanent molar. FIG. 62 shows a screen shot depicting the occlusal relationship. For example, as shown in FIG. 62, the mesio-distal distance between the cusp tip 1040 and the buccal grove 1080 is the occlusal relationship 1292. The measurement of the occlusal relationship distance is performed using the method of measuring the directed distance between two points described above and Eq. (1). Ideally, the occlusal relationship should be less than 1.0 mm. If the occlusal relationship is (i) equal to or greater than 1.0 mm and less than or equal to 2.0 mm, then a treatment evaluation score of −1, or (ii) greater than 2.0 mm, then a treatment evaluation score of −2, is assigned to the quality of the proposed treatment plan for each instance of measurement of the occlusal relationship.

Occlusal Contacts Evaluation

Figure 63:
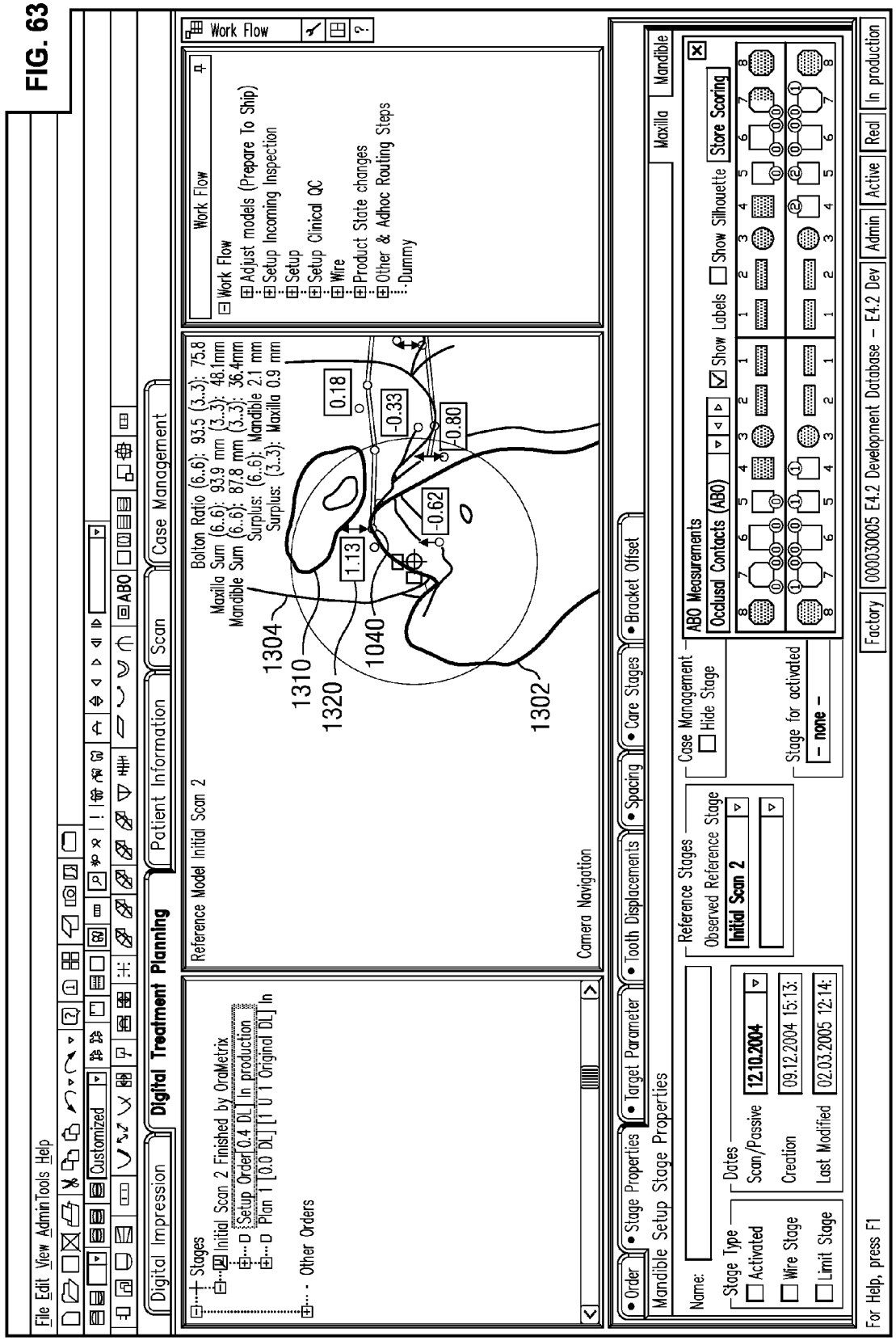
FIG. 63 shows occlusal contacts.

The evaluation of the proposed treatment plan or the target state using the occlusal contacts feature 1018 is performed by measuring the vertical distance of a cusp tip on a virtual tooth and the surface of the opposite virtual tooth. FIG. 63 shows a screen shot depicting an occlusal contact. For example, as shown in FIG. 63, the vertical distance between the cusp tip 1040 of the virtual tooth 1302 and the surface 1310 of the virtual tooth 1304 is the occlusal contact 1320. The clipping plane tool is used to slice through the virtual teeth 1302 and 1304 in order to expose the occlusal contact. The measurement of the occlusal contact is performed using the method of measuring the directed distance between a point and an object described above and Eq. (2). Ideally, the occlusal contact should be less than 0.5 mm. If the occlusal contact is (i) equal to or greater than 0.5 mm and less than or equal to 1.0 mm, then a treatment evaluation score of −1, or (ii) greater than 1.0 mm, then a treatment evaluation score of −2, is assigned to the quality of the proposed treatment plan for each instance of measurement of the occlusal contact.

Overjet Evaluation

Figure 64:
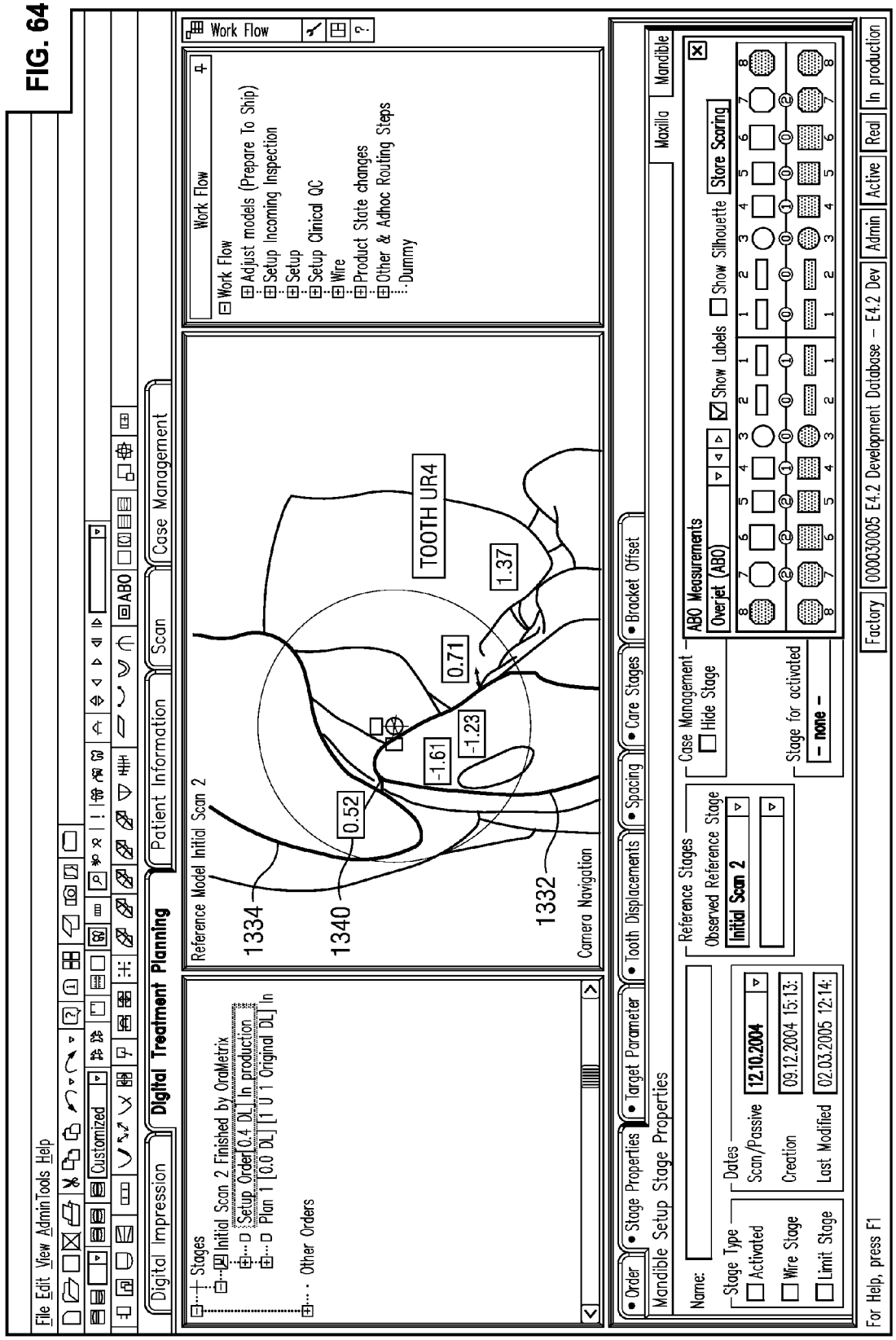
FIG. 64 shows measurement of overjet in the front area.
Figure 65:
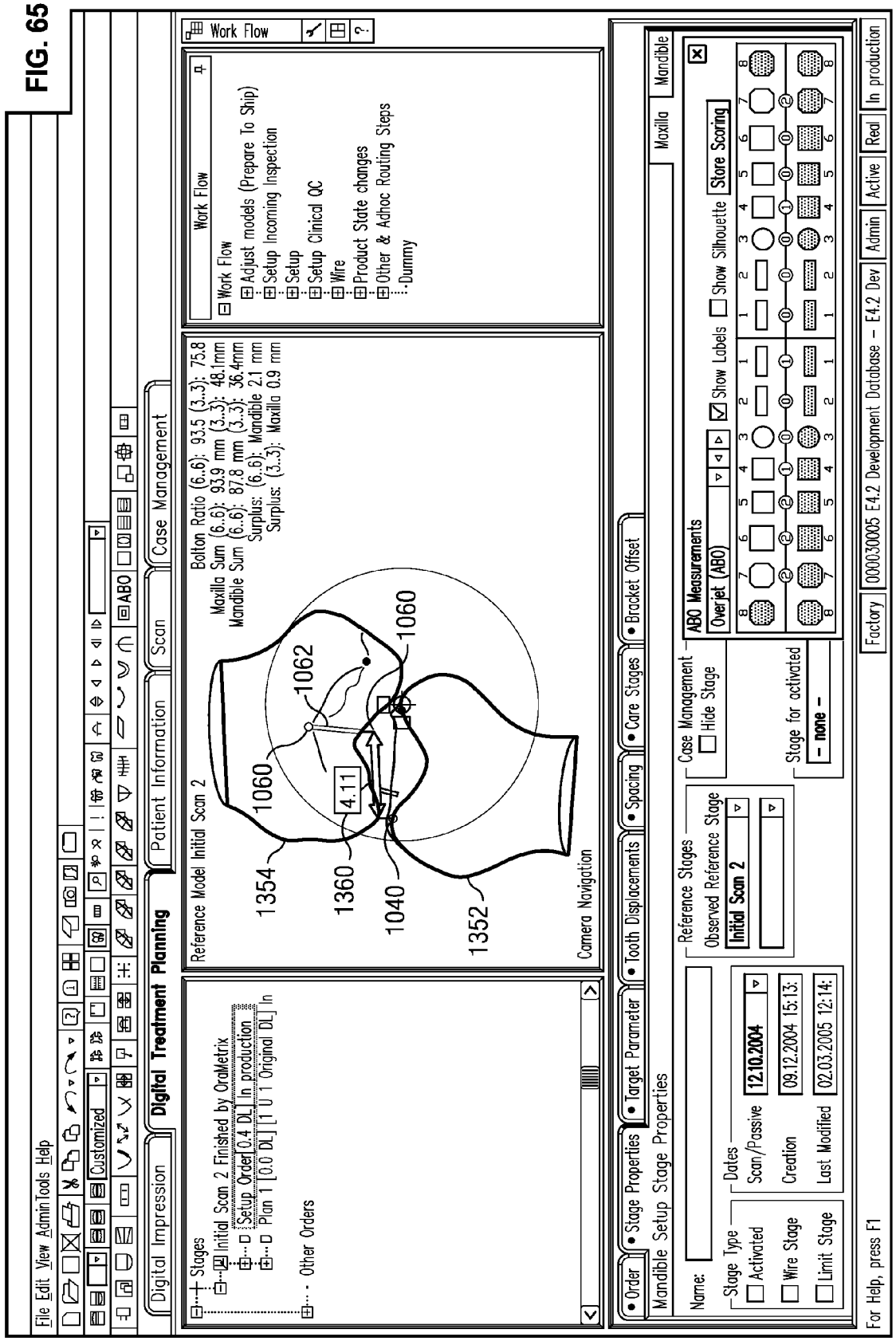
FIG. 65 shows measurement of overjet in the posterior area.

The evaluation of the proposed treatment plan or the target state using the overjet feature 1020 is performed by measuring the overjet in two different ways: (a) in the anterior area, the shortest distance in the in-out direction between the posterior of the virtual upper jaw and the anterior of the virtual lower jaw; and (b) in the posterior area, the mesio-distal distance of the lower jaw labial cusp tip and the upper jaw central groove line connecting the central groove points. FIG. 64 shows a screen shot illustrating an example of the type (a) overjet by measuring the shortest distance in the in-out direction between the posterior of the virtual upper jaw and the anterior of the virtual lower jaw. In FIG. 64, the overjet 1340 is shown between the virtual tooth 1332 and the virtual tooth 1334. The clipping plane tool is used to expose the overjet 1340. On the other hand, FIG. 65 shows a screen shot illustrating an example of the type (b) overjet. FIG. 65 depicts, with the help of the clipping plane tool, the cusp tip 1040 on the virtual tooth 1352 and the central groove line 1062 connecting the central groove points 1060 on virtual tooth 1354. In this case, the overjet 1360 is the distance between the cusp tip 1040 and the central groove line 1062. The overjet measurement in case (a) is performed using the method of measuring the shortest directed distance between two objects described above and Eq. (3); and in case (b) is performed using the method of measuring the directed distance between the lower jaw virtual tooth labial cusp tip and the plane, formed by the central groove line of the upper jaw virtual tooth central groove line and perpendicular to the occlusial plane, described above and Eq. (1). Ideally, the overjet in either case (a) or case (b) should be less than 0.5 mm. If the overjet is (i) equal to or greater than 0.5 mm and less than or equal to 1.0 mm, then a treatment evaluation score of −1, or (ii) greater than 1.0 mm, then a treatment evaluation score of −2 is assigned to the quality of the proposed treatment plan for each instance of measurement of the overjet.

Interproximal Contacts Evaluation

Figure 66:
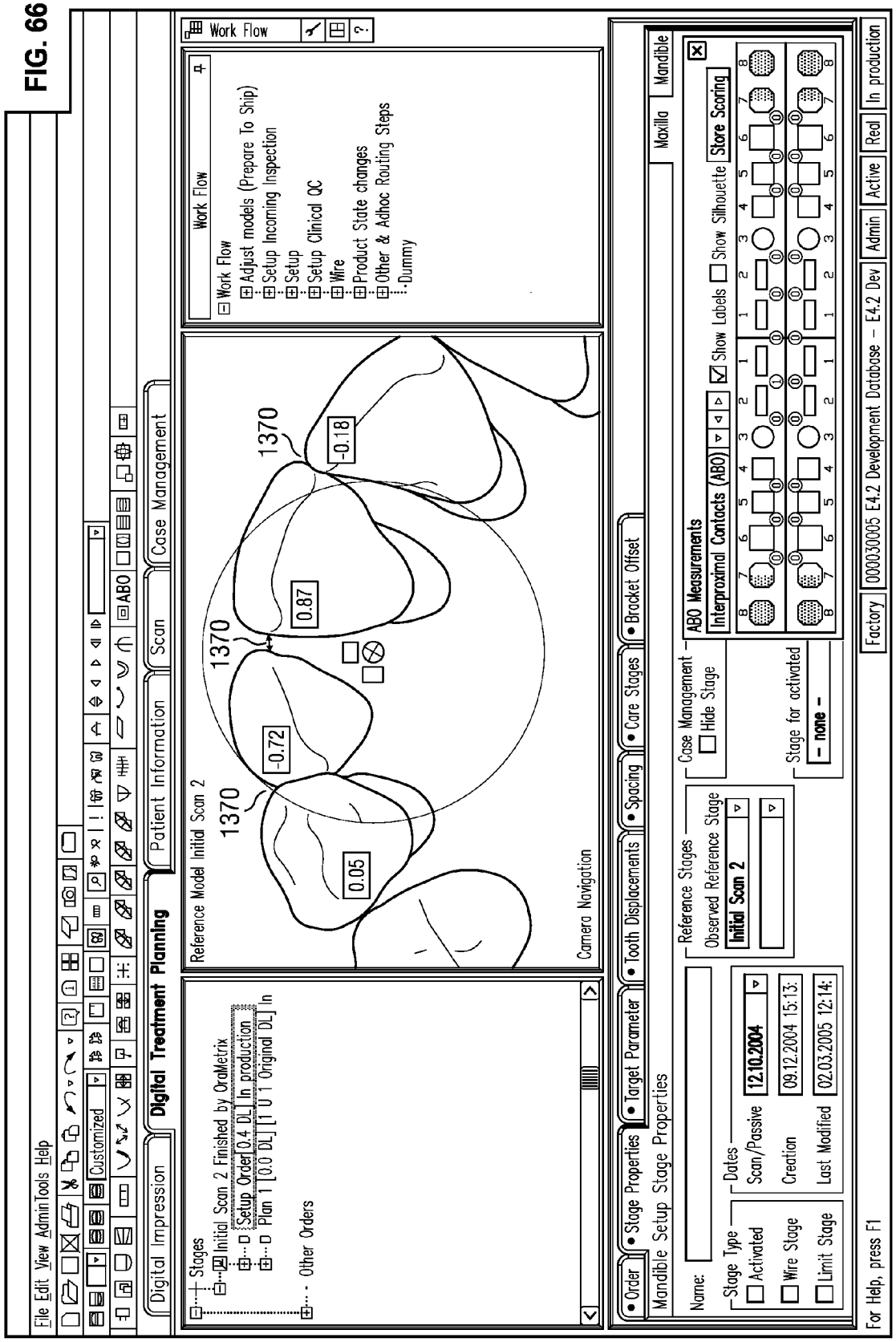
FIG. 66 shows measurement of interproximal contacts.

The evaluation of the proposed treatment plan or the target state using the interproximal contacts feature 1022 is performed by measuring the interproximal contacts between the adjoining teeth. FIG. 66 shows a screen shot illustrating an example of the interproximal contacts 1370. The interproximal contacts measurement is performed using the method of measuring the shortest distance between two objects described above and Eq. (6). Ideally, the interproximal contact should be less than 0.5 mm. If the interproximal contact is (i) equal to or greater than 0.5 mm and less than or equal to 1.0 mm, then a treatment evaluation score of −1, or (ii) greater than 1.0 mm, then a treatment evaluation score of −2, (iii) less than or equal to 0.5 mm then a treatment evaluation score of zero, is assigned to the quality of the proposed treatment plan for each instance of measurement of the interproximal contact.

Vertical Alignment of Buccal Cusp Tips Evaluation

Figure 67:
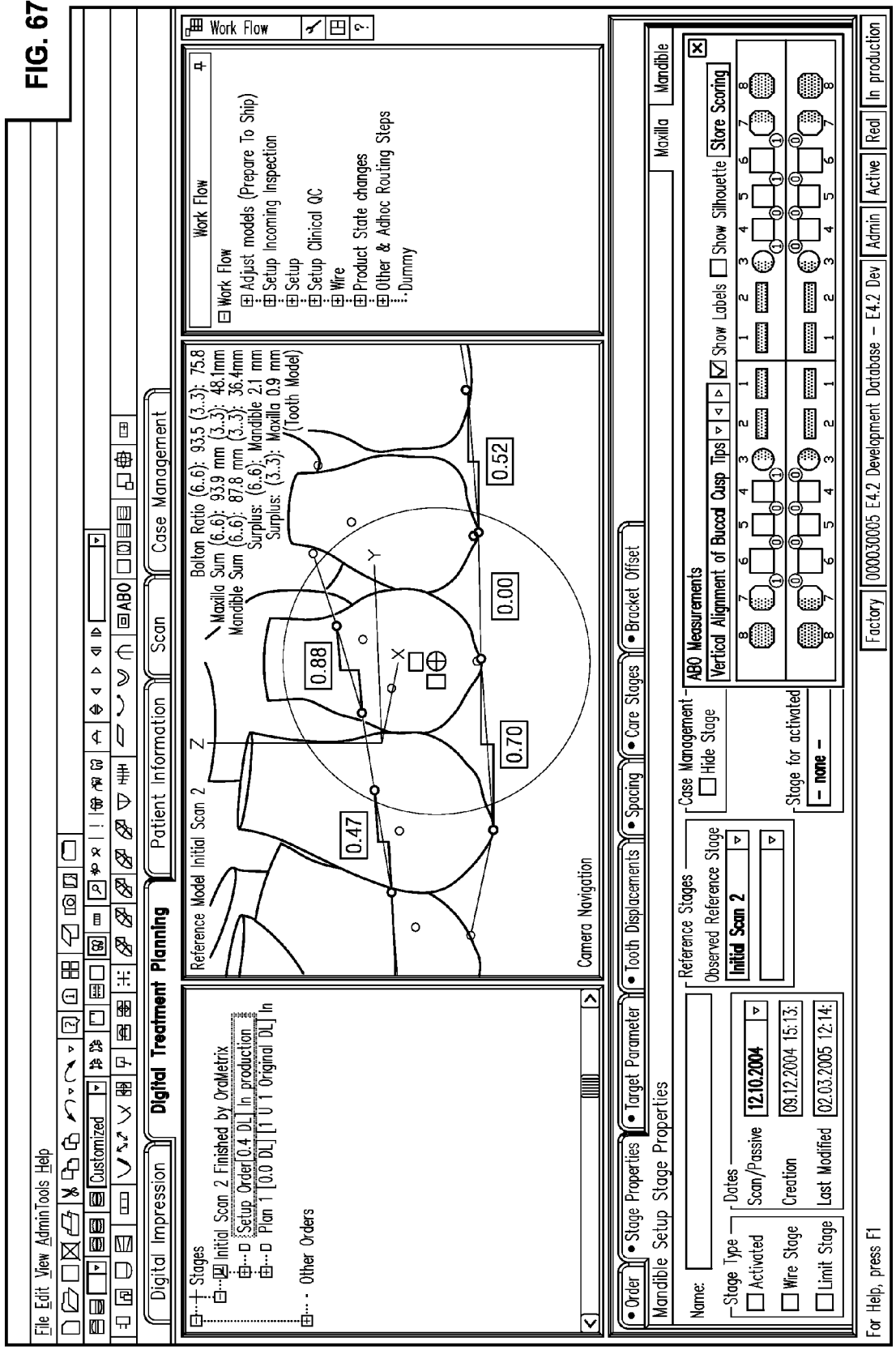
FIG. 67 shows vertical alignment of buccal cusp tips.

The evaluation of the proposed treatment plan or the target state using the vertical alignment of buccal cusp tips feature 1024 is performed by measuring the vertical distance of the buccal cusp tips of the virtual canines and the virtual posterior teeth. The vertical alignment measure is made between a plane containing the cusp tips of the virtual canines and parallel to the occlusal plane and the cusp tips of each of the virtual posterior teeth. FIG. 67 shows a screen shot illustrating an example of the vertical alignment of buccal cusp tips. The vertical alignment of buccal cusp tips measurement is performed using the method of measuring the directed distance between two points described above and Eq. (1). Ideally, the vertical alignment of buccal cusp tips distance should be less than 0.5 mm. If vertical alignment of buccal cusp tips distance is (i) equal to or greater than 0.5 mm and less than 1.0 mm, then a treatment evaluation score of −1, or (ii) greater than or equal to 1.0 mm and less than 2.0 mm, then a treatment evaluation score of −2, or (iii) greater than or equal to 2.0 mm, then a treatment evaluation score of −3 is assigned to the quality of the proposed treatment plan for each instance of measurement of the vertical alignment of buccal cusp tips.

Vertical Alignment of Front Evaluation

Figure 68:
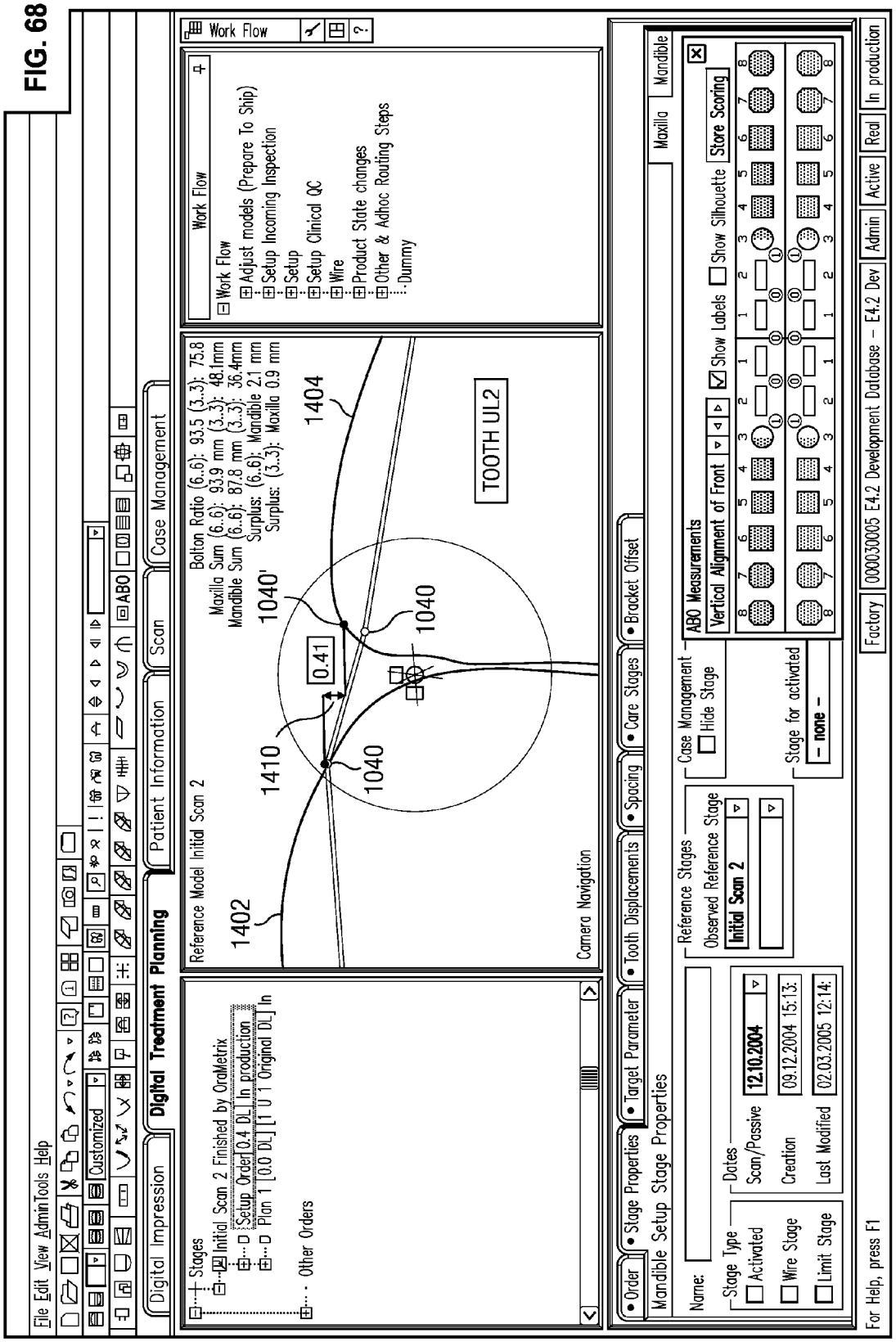

The evaluation of the proposed treatment plan or the target state using the vertical alignment of front feature 1026 is performed by measuring the vertical distance between the "corrected cusp tips" of two virtual adjacent teeth. "Corrected cusp tips" are defined as cusp tips moved to the most occlusal point of the intersection of the virtual tooth-model and a plane, which contains the cusp tip and is perpendicular to the mesio-distal direction at the cusp tip. FIG. 68 shows a screen shot illustrating an example of the vertical alignment of front. In FIG. 68, first the cusp tip 1040 of the virtual tooth 1404 is moved to the corrected cusp tip 1040' position at the edge of the virtual tooth 1404. Then the vertical alignment of front distance 1410 is the distance between the cusp tip 1040 of the virtual tooth 1402 and the corrected cusp tip 1040' of the virtual tooth 1404. FIG. 69 shows a screen shot depicting another example of the vertical alignment of front distances 1410 between adjacent virtual teeth. The vertical alignment of front measurement is performed using the method of measuring the directed distance between two points described above and Eq. (1). Ideally, the vertical alignment of "corrected cusp tips" distance should be less than 0.5 mm. If vertical alignment of "corrected cusp tips" distance is (i) equal to or greater than 0.5 mm and less than 1.0 mm, then a treatment evaluation score of −1, or (ii) greater than or equal to 1.0 mm and less than 2.0 mm, then a treatment evaluation score of −2, or (iii) greater than or equal to 2.0 mm, then a treatment evaluation score of −3, is assigned to the quality of the proposed treatment plan for each instance of measurement of the vertical alignment of front evaluation. This measurement provides an important esthetic/orthodontic criterion for the comparison of target verses another.

Angulation of Front Evaluation

The evaluation of the proposed treatment plan or the target state using the angulation of front feature 1028 is performed by measuring the vertical distance between the two "corrected cusp tips", as defined above, of the same virtual tooth. FIG. 70 shows a screen shot illustrating an example of the angulation of front. In FIG. 70, the angulation of front distance 1420 is the distance between the two "corrected cusp tips" 1040' on the same virtual tooth. The angulation of front measurement is performed using the method of measuring the directed distance between two points described above and Eq. (1). Ideally, the angulation of "corrected cusp tip" distance should be less than 0.5 mm. If vertical alignment of "corrected cusp tips" distance is (i) equal to or greater than 0.5 mm and less than 1.0 mm, then a treatment evaluation score of −1, or (ii) greater than or equal to 1.0 mm and less than 2.0 mm then a treatment evaluation score of −2, or (iii) greater than or equal to 2.0 mm, then a treatment evaluation score of −3, is assigned to the quality of the proposed treatment plan for each instance of measurement of the vertical alignment of front evaluation. This measurement provides an important esthetic/orthodontic criterion for the comparison of target verses another.

The evaluation criteria disclosed herein can be used at the initial stage of planning an orthodontic treatment as well as for monitoring the progress of a treatment during the course of the treatment. For periodically monitoring treatment progress for a patient, during the course of the treatment, a virtual model of the dentition of the patient is developed by in-vivo scanning the dentition of the patient with brackets bonded on the teeth of the patient. The treatment planning instructions and tools previously disclosed can also be used in conjunction with the virtual three-dimensional model of the dentition of the patient discussed above to evaluate progress of the treatment and plan desired corrective actions.

Although by way of examples, specific values for thresholds were disclosed above, one skilled in the art would appreciate that the thresholds can be changed and customized by the user. Examples are given above for illustrative purposes and are not intended to limit the scope of the invention disclosed herein.

Presently preferred and alternative embodiments of the invention have been set forth. Variation from the preferred and alternative embodiments may be made without departure from the scope and spirit of this invention.

We claim:

1. A system for comprehensive treatment planning, evaluation and measurement of quality of care of an orthodontic patient comprising:

a workstation having a computing platform comprising a graphical user interface, a processor and a computer storage medium; and a set of one or more reference databases accessible to said workstation;

wherein said computer storage medium contains digitized records pertaining to a patient, said digitized records including image data, text data, and a three-dimensional virtual model of said patient wherein said virtual model includes a three dimensional dentition model of said patient;

wherein said computer storage further contains a set of interactive software instructions enabling an user in planning and evaluating orthodontic treatment of said patient;

wherein said computer storage further includes software instructions providing graphical user interface tools for providing said user with access to said digitized records for planning and evaluating orthodontic treatment of said patient;

wherein said interactive software instructions allow said user to simulate various possible treatments for said patient on the workstation and visualize the results of proposed treatments on the user interface in order to arrive at a target treatment for said patient;

wherein said set of software instructions include instructions for evaluating at least one of the following criteria pertaining to orthodontic treatment:

a) treatment efficiency criterion;
b) treatment effectiveness criterion;
c) patient connectedness to treatment criterion;
d) treatment timeliness criterion;
e) treatment safety criterion; and
f) treatment equitability criterion;

wherein said computer storage further includes software instructions for designing shape and configuration of customized orthodontic appliances based upon said target treatment for said patient.

2. The system of claim 1, wherein said treatment efficiency criterion comprises at least one of the following sub-criteria (i) productivity of the people delivering the treatment, (ii) cost and availability of materials required for the treatment, (iii) suitability of the treatment method for the patient, and the estimated time duration for the treatment, (iv) reliability and cost contributions towards the treatment of the patient from the equipment necessary for creating and delivering the treatment, and (v) the cost contribution and other criteria attributable to the environment in which the treatment is delivered.

3. The system of claim 1, wherein said treatment effectiveness criterion comprises at least one of the following sub-criteria: (i) alignment, (ii) marginal ridges, (iii) buccolingual inclination, (iv) occlusal relationship, (v) occlusal contacts, (vi) overjet, (vii) interproximal contacts, (viii) vertical alignment of buccal cusp tips, (ix) vertical alignment of front, and (x) angulation of front.

4. The system of claim 1, wherein said patient connectedness to treatment criterion comprises at least one of the following sub-criteria: (i) matching treatment results with the patient expectations, (ii) care of service, (iii) patient comfort, and (iv) patient overall satisfaction.

5. The system of claim 1, wherein said treatment timeliness criterion comprises at least one of the following sub-criteria: (i) appointment intervals, (ii) length of appointments, (iii) (iv) time spent waiting in the reception area, and (v) difference between the estimated treatment time and the actual treatment time.

6. The system of claim 1, wherein said treatment safety criterion comprises at least one of the following sub-criteria: (i) the number of episodes causing discomfort or pain to the patient, (ii) the nature of pain, (iii) decalcification of teeth, (iv) root resorption, (v) gingivitis, (vi) periodontitis, (vii) iatrogenic event where the problem is caused by the practitioner's mistake, (viii) idiopathic event where there is no known cause for the problem; however the patient is sensitive to the treatment; and (ix) idiosyncratic event which develops a new response within the patient which was never recorded before in the history of the treatment.

7. The system of claim 1, wherein said treatment equitability criterion comprises at least one of the following sub-criteria: (i) whether or not same standard of care is offered to all patients, and (ii) matching of patient profile against the treatment needs of the patient, against established clinical pathways, and between offerings from different orthodontic practices.

8. The system of claim 1, wherein said reference databases include a normative database.

9. The system of claim 8, wherein said normative database enables said user to compare an initial dentition state and a treatment set-up state against normative data.

10. The system of claim 1, wherein said digitized records further comprise a library of virtual bracket sets enabling said user in evaluating a prescription for said treatment set-up state and said evaluation tools enabling said practitioner to make adjustments to said prescription by choosing an appropriate bracket from said library and/or changing the position of said bracket relative to a tooth.

11. The system of claim 1, wherein said evaluation tools enable comparisons of tooth positions in said patient's initial state relative to tooth positions in the proposed treatment set-up state.

12. The system of claim 11, wherein said comparisons of tooth positions are done by viewing said initial state and said proposed treatment set-up side-by-side.

13. The system of claim 11, wherein said comparisons are done by superimposition of said states and providing visual indicia of the change of position from said initial state and said proposed treatment set-up state.

14. The system of claim 11, wherein said comparisons of tooth positions are done automatically.

* * * * *